United States Patent
Ma et al.

(10) Patent No.: US 12,264,161 B2
(45) Date of Patent: *Apr. 1, 2025

(54) HETEROCYCLIC ADENOSINE RECEPTOR ANTAGONISTS

(71) Applicant: Exelixis, Inc., Alameda, CA (US)

(72) Inventors: Sunghoon Ma, Foster City, CA (US); Yong Wang, South San Francisco, CA (US); Wei Xu, Danville, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/323,510

(22) Filed: May 25, 2023

(65) Prior Publication Data

US 2023/0382917 A1    Nov. 30, 2023

Related U.S. Application Data

(63) Continuation of application No. 17/201,380, filed on Mar. 15, 2021, now Pat. No. 11,718,622.

(60) Provisional application No. 62/990,105, filed on Mar. 16, 2020.

(51) Int. Cl.
| | |
|---|---|
| *C07D 487/04* | (2006.01) |
| *A61K 31/4985* | (2006.01) |
| *A61K 31/519* | (2006.01) |
| *A61P 9/00* | (2006.01) |
| *A61P 25/00* | (2006.01) |
| *A61P 29/00* | (2006.01) |
| *A61P 35/00* | (2006.01) |
| *C07D 487/14* | (2006.01) |
| *C07D 513/14* | (2006.01) |

(52) U.S. Cl.
CPC ......... *C07D 487/04* (2013.01); *C07D 487/14* (2013.01); *C07D 513/14* (2013.01)

(58) Field of Classification Search
CPC ............... C07D 487/04; C07D 487/14; C07D 513/14; A61K 31/4985; A61K 31/519; A61P 9/00; A61P 25/00; A61P 29/00; A61P 35/00
See application file for complete search history.

(56) References Cited

U.S. PATENT DOCUMENTS

2012/0149708 A1    6/2012    Kashanchi

FOREIGN PATENT DOCUMENTS

| | | |
|---|---|---|
| JP | 2004238296 A | 8/2004 |
| WO | 1996034866 A1 | 11/1996 |
| WO | 1999051606 A1 | 10/1999 |
| WO | 2002006286 A2 | 1/2002 |
| WO | 2002062801 A1 | 8/2002 |
| WO | 2005018532 A2 | 3/2005 |
| WO | 2005120513 A1 | 12/2005 |
| WO | 2009047514 A1 | 4/2009 |
| WO | 2010059836 A1 | 5/2010 |
| WO | 2010068684 A2 | 6/2010 |
| WO | 2010119264 A1 | 10/2010 |
| WO | 2011068881 A1 | 6/2011 |
| WO | 2011089400 A1 | 7/2011 |
| WO | 2011112687 A2 | 9/2011 |
| WO | 2011113606 A1 | 9/2011 |
| WO | 2012054233 A1 | 4/2012 |
| WO | 2012088411 A1 | 6/2012 |
| WO | 2013048214 A2 | 4/2013 |
| WO | 2016148306 A1 | 9/2016 |

OTHER PUBLICATIONS

Allard, Bertrand et al., Current Opinion Pharmacology, 2016, 29, pp. 7-16.
Blay, Jonathan et al., Cancer Research, 1997, 57, pp. 2602-2605.
Borea, Pier Andrea et al., Physiol Rev., 2018. 98, pp. 1591-1625.
Hammami, Akil et al., Seminars in Immunology, 2019, 42, 101304.
Leone, Robert D. et al., Cancer Immunology, Immunotherapy, 2018, 67, pp. 1271-1284.
Livingston, Mark et al., Inflammation Research, 2004, 53, pp. 171-178.
Okamura, Takashi et al., 1,2,4-Triazolo[5,1-i]purine derivatives as highly potent and selective human adenosine A(3) receptor ligands, Journal of Medicinal Chemistry. 2002, 45(17), pp. 3703-3708.
Roy, Kunal et al. QSAR of adenosine receptor antagonists. Part 3: Exploring physicochemical requirements for selective binding of 1,2,4-triazolo[5,1-i]purine derivatives with human adenosine A3 receptor subtype. Bioorg Med Chem Lett. 2004;14(14):3705-3709. doi: 10.1016/j.bmcl.2004.05.007.
Burbiel, et al. 2-Amino[1,2,4]triazolo[1,5-c]quinazolines and Derived Novel Heterocycles: Syntheses and Structure-Activity Relationships of Potent Adenosine Receptor Antagonists, CHEMMEDCHEM, vol. 11, No. 20, pp. 2272-2286 (2016).
CAS Printout of Bowie, et al., Ring Transformations Involving Chloro Heterocycles. I. Reaction of Chloronaphthyridines With Hydrazine Hydrate, Journal of the Chemical Society, Perkin Transactions 1; Organic and Bio-Organic Chemistry, Vo. 8, pp. 1106-1108 (1972).
CAS printout of compounds of Aurora Fine Chemicals with Reg. No. 1501248-39-0, 1501125-59-2, 1501076-01-2, 1500815-50-8. 1500284-35-4, 1499985-28-2, 1499796-34-7, 1499384-08-5, 1499305-74-6, 1499290-32-2, 1498961-09-3, 15040153-11-0, 1503252-73-0, 1503033-61-1, 1502755-89-6, 1502509-72-9, etc. (2013).

*Primary Examiner* — Brenda L Coleman
(74) *Attorney, Agent, or Firm* — Honigman LLP; Heidi M. Berven; Andrew S. Chipouras

(57) ABSTRACT

Heterocyclic compounds useful as antagonists of adenosine receptors, and methods of treatment of diseases using antagonists of adenosine receptors are disclosed herein. Also disclosed herein are pharmaceutical compositions and methods of administration of heterocyclic antagonists of adenosine receptors and processes for producing heterocyclic antagonists of adenosine receptors.

20 Claims, No Drawings

HETEROCYCLIC ADENOSINE RECEPTOR ANTAGONISTS

CROSS-REFERENCE TO RELATED APPLICATIONS

This application is a continuation of U.S. application Ser. No. 17/201,380 filed on Mar. 15, 2021, which claims the benefit of priority to U.S. Provisional Application No. 62/990,105, filed Mar. 16, 2020, the entire contents of which are incorporated herein by reference.

FIELD OF THE INVENTION

The present invention relates to heterocyclic compounds useful as antagonists of adenosine receptors, and further relates to methods of treatment of diseases using antagonists of adenosine receptors. The invention also relates to pharmaceutical compositions and methods of administration of heterocyclic antagonists of adenosine receptors. The invention also relates to processes for producing heterocyclic antagonists of adenosine receptors.

BACKGROUND OF THE INVENTION

Adenosine, an endogenous nucleoside that exists both intracellularly and extracellularly, regulates numerous important physiological functions such as the maintenance of cellular and tissue homeostasis (Borea, P. A. et al., *Physiol Rev.*, 2018, 98, 1591-1625). In humans, four subtypes of adenosine receptors have been described: A1 (also known as ADORA1A), A2A (also known as ADORA2A), A2B (also known as ADORA2B), and A3 (also known as ADORA3). Whereas A1 and A2A are high affinity receptors for adenosine, A2B and A3 function as low affinity receptors. Through differential binding to specific receptors localized on the plasma membrane, adenosine can elicit varying pharmacological effects in different tissue systems.

In the immune system, adenosine signaling normally functions to limit inflammation and dampen the immune response, thus protecting tissues against excessive immune reactions (Allard, B. et al., *Curr. Opin. Pharmacol.*, 2016, 29, 7-16). Many immune cell types express adenosine receptors and hence are directly regulated by adenosine. A2A adenosine receptor is primarily expressed on lymphoid-derived cells, including T effector cells, regulatory T cells, and natural killer cells. A2B adenosine receptor, in contrast, is primarily expressed on monocyte-derived cells, including myeloid-derived suppressor cells, tumor-associated macrophages, and dendritic cells. Binding of adenosine to A2A or A2B receptors on immune cells results in activation of adenylate cyclase, which catalyzes the production of intracellular cyclic AMP (cAMP). This increased intracellular cAMP in turn blocks the activation of immune effector cells and increases the number of immunosuppressive cells, thus suppressing the overall immune response (Livingstone, M. et al., *Inflamm. Res.*, 2004, 53, 171-178).

Within the tumor microenvironment, adenosine levels are maintained at unusually high levels compared to normal physiological conditions (Blay, J. et al., *Cancer Res.*, 1997, 57, 2602-2605). High adenosine levels function to suppress the anti-tumor immune response, thus promoting cancer progression. Enhanced production of adenosine within the tumor is primarily achieved via the overexpression of CD39 and CD73, two cell surface ectoenzymes that catalyze the breakdown of extracellular ATP to adenosine (Hammami, A. et al., *Semin Immunol.*, 2019, 42, 101304). Many cell types within the tumor can express CD39 and CD73, including tumor cells, endothelial cells, mesenchymal stem cells, cancer-associated fibroblasts, T effector cells, regulatory T cells, tumor-associated macrophages, and myeloid-derived suppressor cells. Moreover, conditions inherent to a tumor such as hypoxia and inflammation can further upregulate the expression of CD39 and CD73, thus effectively sustaining adenosine production.

Given the importance of adenosine in creating and maintaining an immunosuppressive tumor microenvironment, inhibition of adenosine receptor signaling may be a viable anti-cancer strategy (Leone, R. D. et al., *Cancer Immunol. Immunother.*, 2018, 67, 1271-1284). Indeed, targeted inhibition of A2A receptor has been shown to downregulate immunosuppressive signals that inactivate T effector cells, resulting in enhanced anti-tumor immune responses with subsequent tumor regression. Similarly, targeted inhibition of A2B receptor has been shown to enhance tumor antigen presentation, resulting in suppressed primary tumor growth and inhibited metastasis. That A2A and A2B receptor knockout mice are viable and fertile with no apparent growth abnormalities (Allard, B. et al., *Curr. Opin. Pharmacol.*, 2016, 29, 7-16) suggests that pharmacological inhibition of either or both adenosine receptors may be a tolerable approach to restoring anti-cancer immunity.

SUMMARY OF THE INVENTION

In one aspect, the present invention provides a compound of formula I:

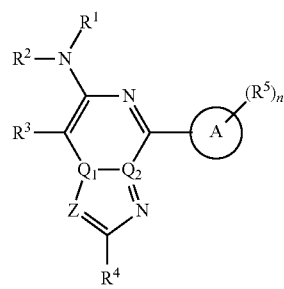

or a pharmaceutically acceptable salt thereof, wherein:

Ring A is heteroaryl or aryl;

$R^1$ is H or alkyl optionally substituted with 1, 2, 3, or 4 independently selected $R^a$ substituents;

$R^2$ is H, alkyl, —COR''', —CONR'R'', —COOR', —SO$_2$R', —SO$_2$NR'R'', or —SO$_2$OR', wherein the alkyl of $R^2$ is optionally substituted with 1, 2, 3, or 4 independently selected $R^a$ substituents;

$R^3$ is H, alkyl, halo, —CN, or —CONR'R'', wherein the alkyl of $R^3$ is optionally substituted with 1, 2, 3, or 4 independently selected $R^a$ substituents;

or $R^2$ and $R^3$ together form 5-6 membered heterocycloalkyl or 5-6 membered heteroaryl, each of which is optionally substituted with 1, 2, 3, 4, or 5 independently selected $R^7$ substituents, and wherein when $R^2$ and $R^3$ together form 6-membered heteroaryl, then $R^1$ is absent;

$R^4$ is H, alkyl, halo, haloalkyl, —NR'R", —COR', —CONR'R", —COOR', —SO$_2$R', —SO$_2$NR'R", —SO$_2$OR', cycloalkyl, heterocycloalkyl, aryl, heteroaryl, or —C$_{1-4}$ alkylene-R$^b$, wherein R$^b$ is cycloalkyl, heterocycloalkyl, aryl or heteroaryl, and wherein the alkyl, cycloalkyl, heterocycloalkyl, aryl, heteroaryl, or —C$_{1-4}$ alkylene-R$^b$ of $R^4$ is optionally substituted with 1, 2, 3, or 4 independently selected R$^a$ substituents;

each $R^5$ is independently H, alkyl, halo, haloalkyl, alkoxy, —CN, —COR', —CONR'R", —COOR', —SO$_2$R', —SO$_2$NR'R", —SO$_2$OR', cycloalkyl, heterocycloalkyl, aryl, or heteroaryl wherein the alkyl, alkoxy, cycloalkyl, heterocycloalkyl, aryl, or heteroaryl of $R^5$ is optionally substituted with 1, 2, 3, or 4 independently selected R$^a$ substituents;

n is 0, 1, 2, 3, 4, or 5;

one of Q$_1$ and Q$_2$ is N and the other is C;

Z is N or CR$^6$;

$R^6$ is H or alkyl, wherein the alkyl of $R^6$ is optionally substituted with 1, 2, 3, or 4 independently selected R$^a$ substituents;

each $R^7$ is independently oxo, alkyl, halo, haloalkyl, hydroxy, alkoxy, hydroxyalkyl, cycloalkyl, or heterocycloalkyl, wherein each cycloalkyl and heterocycloalkyl of $R^7$ is optionally and independently further substituted with 1, 2, or 3 of C$_{1-4}$ alkyl, halo, C$_{1-4}$ haloalkyl, hydroxy, or C$_{1-4}$ alkoxy;

R' and R" are each independently H or alkyl, wherein each alkyl of R' and R" is optionally substituted with 1, 2, 3, or 4 independently selected R$^a$ substituents;

R'" is alkyl, haloalkyl, cycloalkyl, or heterocycloalkyl, wherein the alkyl, cycloalkyl or heterocycloalkyl of R'" is optionally substituted with 1, 2, 3, or 4 independently selected R$^a$ substituents; and each R$^a$ is independently alkyl, halo, haloalkyl, hydroxy, alkoxy, hydroxyalkyl, cycloalkyl, or heterocycloalkyl, wherein each cycloalkyl and heterocycloalkyl of R$^a$ is optionally and independently further substituted with 1, 2, or 3 of C$_{1-4}$ alkyl, halo, C$_{1-4}$ haloalkyl, hydroxy, or C$_{1-4}$ alkoxy;

wherein when $R^4$ is H, aryl, or heteroaryl, then Ring A is furanyl.

Another aspect provides a pharmaceutical composition comprising a compound or a pharmaceutically acceptable salt thereof as described herein, and a pharmaceutically acceptable carrier or excipient.

Another aspect provides a method of inhibiting an activity of an adenosine receptor, comprising contacting the receptor with a compound or a pharmaceutically acceptable salt thereof as described herein.

Another aspect provides a method of treating a disease or disorder in a patient, wherein the disease or disorder is associated with abnormal expression of A2A or A2B receptors, the method comprising administering to the patient a therapeutically effective amount of a compound or a pharmaceutically acceptable salt thereof, or a pharmaceutical composition, as described herein.

Another aspect provides processes for producing a compound or a pharmaceutically acceptable salt thereof as described herein (e.g., compounds of formula I).

DETAILED DESCRIPTION OF THE INVENTION

Abbreviations and Definitions

The following abbreviations and terms have the indicated meanings throughout:

| Abbreviation | Meaning |
| --- | --- |
| Ac | Acetyl |
| anhyd | Anhydrous |
| Aq | Aqueous |
| Ar | Aryl |
| Boc | Tert-butoxy carbonyl |
| ° C. | Degrees Celsius |
| c- | Cyclo |
| calcd | Calculated |
| DBU | 1,8 Diazabicyclo[5.4.0]undec-7-ene |
| DCM | Dichloromethane |
| DIEA | N,N-Diisopropylethylamine (Hünig's base) |
| DMF | N,N-Dimethyl formamide |
| DMSO | Dimethyl sulfoxide |
| EI | Electron Impactionization |
| eq or equiv | Equivalent |
| EtOAc | Ethyl acetate |
| Fmoc | Fluorenylmethyloxycarbonyl |
| g | Gram(s) |
| h or hr | Hour(s) |
| HPLC | High pressure liquid chromatography |
| Abbreviation | Meaning |
| H$_2$ | Hydrogen |
| L | Liter(s) |
| M | Molar or molarity |
| MHz | Megahertz (frequency) |
| Min | Minute(s) |
| mL | Milliliter(s) |
| Mp | Melting point |
| μl | Microliter(s) |
| Mol | Mole(s) |
| MS | Mass spectral analysis |
| N$_2$ | Nitrogen |
| N | Normal or normality |
| nM | Nanomolar |
| NMR | Nuclear magnetic resonance spectroscopy |
| Pd/C | Palladium on carbon |
| RT | Room temperature |
| soln | Solution |
| THF | Tetrahydrofuran |

The symbol "—" means a single bond, and "=" means a double bond.

As used herein, the singular forms "a," "an," and "the" include plural reference unless the context clearly dictates otherwise.

When a variable is defined generically, with a number of possible substituents, each individual radical can be defined with our without the bond. For example, if R$^z$ can be hydrogen, this can be indicated as "—H" or "H" in the definition of R$^z$.

When chemical structures are depicted or described, unless explicitly stated otherwise, all carbons are assumed to have hydrogen substitution to conform to a valence of four. For example, in the structure on the left-hand side of the schematic below, there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

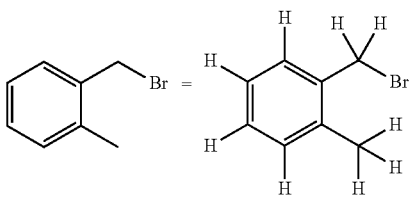

As used herein, a wavy line, ⌇, can indicate the attachment point of a chemical moiety. For example, in the structure,

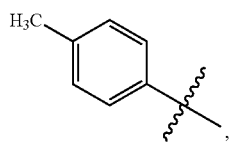 [SMILES: *c1ccc(C)cc1]

the phenyl group is attached to the rest of the molecule at the position para to the methyl group.

If a group "R" is depicted as "floating" on a ring system, as for example in the formula:

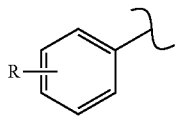

then, unless otherwise defined, a substituent "R" may reside on any atom of the ring system, assuming replacement of a depicted, implied, or expressly defined hydrogen from one of the ring atoms, so long as a stable structure is formed.

When a group "R" is depicted as existing on a ring system containing saturated carbons, for example in the formula:

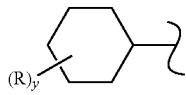

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group, there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

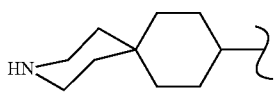

"Halogen" or "halo" refers to fluorine, chlorine, bromine, or iodine.

The term "$C_{n-m}$" or "$C_n$-$C_m$" indicates a range which includes the endpoints, wherein n and m are integers and indicate the number of carbons. Examples include $C_{1-4}$, $C_1$-$C_4$, $C_{1-6}$, $C_1$-$C_6$, and the like.

"Alkyl" refers to a branched or straight hydrocarbon chain of one to eight carbon atoms, such as methyl, ethyl, n-propyl, isopropyl, n-butyl, isobutyl, sec-butyl, t-butyl, pentyl, hexyl, and heptyl. The term "$C_{n-m}$ alkyl" or ($C_n$-$C_m$) alkyl, refers to an alkyl group having n to m carbon atoms.

"Alkylene" refers to an optionally substituted bivalent saturated aliphatic radical having from 1 to 10 carbon atoms, 1 to 8 carbon atoms, 1 to 6 carbon atoms, 1 to 4 carbon atoms, or 1 to 2 carbon atoms. The term "$C_{n-m}$ alkylene" refers to an alkylene group having n to m carbon atoms. Examples of alkylene groups include, but are not limited to, methylene, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

As used herein, an "alkoxy" group refers to an alkyl-O— group where "alkyl" has been defined previously.

As used herein, "heterocycloalkyl" or "heterocyclo" refer to a non-aromatic ring or ring system, which may optionally contain one or more alkenylene groups as part of the ring structure, which has at least one heteroatom ring member independently selected from boron, nitrogen, sulfur, oxygen, and phosphorus, and which has 4-14 ring members, 4-10 ring members, 4-7 ring members, or 4-6 ring members. Included within the term "heterocycloalkyl" are monocyclic 4-, 5-, 6-, and 7-membered heterocycloalkyl groups. Heterocycloalkyl groups can include mono- or bicyclic or polycyclic (for example, having two or three fused or bridged rings) ring systems or spirocycles. In some embodiments, the heterocycloalkyl group is a monocyclic group having 1, 2, or 3 heteroatoms independently selected from nitrogen, sulfur, and oxygen. Ring-forming carbon atoms and heteroatoms of a heterocycloalkyl group can be optionally oxidized to form an oxo or sulfido group or other oxidized linkage (for example, C(O), S(O), C(S), S(O)$_2$, N-oxide, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, for example, benzo or thienyl derivatives of piperidine, morpholine, azepine, etc. A heterocycloalkyl group containing a fused aromatic ring can be attached through any ring-forming atom, including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 4,5,6,7-tetrahydrothiazolo[5,4-c]pyridinyl, and thiomorpholino.

The term "heteroatom" used herein is meant to include boron, phosphorus, sulfur, oxygen, and nitrogen.

The term "haloalkyl" as used herein refers to an alkyl group in which one or more of the hydrogen atoms has been replaced by a halogen atom. The term "$C_{n-m}$ haloalkyl" or ($C_n$-$C_m$) haloalkyl refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" or ($C_n$-$C_m$) haloalkoxy refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

"Aryl" means a monovalent six- to fourteen-membered, mono- or bi-carbocyclic ring (e.g., having two fused rings), wherein the monocyclic ring is aromatic and at least one of the rings in the bicyclic ring is aromatic. The term "$C_{n-m}$ aryl" or "($C_n$-$C_m$) aryl" refers to an aryl group having from n to m ring carbon atoms. In some embodiments, aryl groups have from 6 to about 10 carbon atoms. In some embodiments aryl groups have 6 carbon atoms. In some embodiments aryl groups have 10 carbon atoms. Unless stated otherwise, the valency of the group may be located on any atom of any ring within the radical, valency rules permitting. Representative examples include phenyl, naphthyl, and indanyl, and the like.

"Cycloalkyl" refers to a non-aromatic hydrocarbon ring system (monocyclic, bicyclic, or polycyclic), including cyclized alkyl and alkenyl groups. The term "$C_{n-m}$ cycloalkyl" or "($C_n$-$C_m$) cycloalkyl" refers to a cycloalkyl that has n to m ring member carbon atoms. Cycloalkyl groups can include mono- or polycyclic (e.g., having 2, 3, or 4 fused rings) groups and spirocycles. Cycloalkyl groups can have 3, 4, 5, 6, 7, 8, 9, 10, 11, 12, 13, or 14 ring-forming carbons ($C_{3-14}$). In some embodiments, the cycloalkyl group has 3 to 14 members, 3 to 10 members, 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl, or cyclohexyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl. In some embodiments, cycloalkyl includes a single saturated carbocyclic ring of three to eight ring carbons, such as cyclopropyl, cyclobutyl, cyclopentyl, and cyclohexyl.

"Heteroaryl" means a monocyclic, fused bicyclic, or fused tricyclic, monovalent radical of 5 to 14 ring atoms containing one or more, preferably one, two, three, or four ring heteroatoms independently selected from —O—, —S(O)$_n$— (n is 0, 1, or 2), —N—, and —N(R')—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(=NH)— group. R' is hydrogen, alkyl, hydroxy, alkoxy, acyl, or alkylsulfonyl. Unless stated otherwise, the valency may be located on any atom of any ring of the heteroaryl group, valency rules permitting. In particular, when the point of valency is located on the nitrogen, an additional nitrogen substituent is not present. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, and N-oxide or a protected derivative thereof.

A five-membered heteroaryl ring is a heteroaryl group having five ring atoms wherein one or more (e.g., 1, 2, 3, or 4) ring atoms are independently selected from N, O, and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl group having six ring atoms wherein one or more (e.g., 1, 2, 3, or 4) ring atoms are independently selected from N, O, and S. Exemplary six-membered ring heteroaryls are pyridyl, pyrazinyl, pyrimidinyl, triazinyl, and pyridazinyl.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (for example, chloro, bromo, iodo), —OR$^{LG}$ (when the O atom is attached to a carbonyl group), —O(C=O)R$^{LG}$, or —O(SO)$_2$R$^{LG}$ (for example, tosyl, mesyl, besyl), wherein R$^{LG}$ is optionally substituted alkyl, optionally substituted aryl, or optionally substituted heteroaryl. In certain embodiments, the leaving group is a halogen.

"Yield" for each of the reactions described herein is expressed as a percentage of the theoretical yield.

"Patient" for the purposes of the present invention includes humans and any other animals, particularly mammals, and other organisms. Thus the methods are applicable to both human therapy and veterinary applications. In a preferred embodiment the patient is a mammal, and in a most preferred embodiment the patient is human. Examples of the preferred mammals include mice, rats, other rodents, rabbits, dogs, cats, swine, cattle, sheep, horses, and primates.

"Therapeutically effective amount" is an amount of a compound of the invention that, when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Head and neck: squamous cell carcinomas of the head and neck, laryngeal and hypopharyngeal cancer, nasal cavity and paranasal sinus cancer, nasopharyngeal cancer, salivary gland cancer, oral and orppharyngeal cancer; Lung: bronchogenic carcinoma (squamous cell, undifferentiated small cell, undifferentiated large cell, adenocarcinoma, non-small cell lung cancer), alveolar (bronchiolar) carcinoma, bronchial adenoma, sarcoma, lymphoma, chondromatous hamartoma, mesothelioma; Colon: colorectal cancer, adenocarcinoma, gastrointestinal stromal tumors, lymphoma, carcinoids, Turcot Syndrome; Gastrointestinal: gastric cancer, gastroesophageal junction adenocarcinoma, esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Breast: metastatic breast cancer, ductal carcinoma in situ, invasive ductal carcinoma, tubular carcinoma, medullary carcinoma, mucinous carcinoma, lobular carcinoma in situ, triple negative breast cancer; Genitourinary tract: kidney (adenocarcinoma, Wilm's tumor [nephroblastoma], lymphoma, leukemia, renal cell carcinoma), bladder and urethra (squamous cell carcinoma, transitional cell carcinoma, adenocarcinoma, urothelial carcinoma), prostate (adenocarcinoma, sarcoma, castrate resistant prostate cancer), testis (seminoma, teratoma, embryonal carcinoma, teratocarcinoma, choriocarcinoma, sarcoma, interstitial cell carcinoma, fibroma, fibroadenoma, adenomatoid tumors, lipoma), clear cell carcinoma, papillary carcinoma; Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma, and giant cell tumors; Thyroid: medullary thyroid cancer, differentiated thyroid cancer, papillary thyroid cancer, follicular thyroid cancer, hurthle cell cancer, and anaplastic thyroid cancer; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial cancer), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable salts" includes "pharmaceutically acceptable acid addition salts" and "pharmaceutically acceptable base addition salts." "Pharmaceutically acceptable acid addition salts" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salts" include those derived from inorganic bases such as sodium, potassium, lithium, ammonium, calcium, magnesium, iron, zinc, copper, manganese, aluminum salts, and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

The term, "compound," as used herein is meant to include all stereoisomers, geometric isomers, tautomers, and isotopes of the structures depicted. The term is also meant to refer to compounds of the inventions, regardless of how they are prepared, for example, synthetically, through biological process (for example, metabolism or enzyme conversion), or a combination thereof.

Compounds of the invention can also include all isotopes of atoms occurring in the intermediates or final compounds. Isotopes include those atoms having the same atomic number but different mass numbers. For example, isotopes of hydrogen include tritium and deuterium.

Any one of the process steps or sequences disclosed and/or claimed herein can be performed under an inert gas atmosphere, more particularly under argon or nitrogen. In addition, the methods of the present invention may be carried out as semi-continuous or continuous processes, more preferably as continuous processes.

Moreover, many of the process steps and sequences that are described herein can be telescoped.

In general, the nomenclature used in this Application is based on naming conventions adopted by the International Union of Pure and Applied Chemistry (IUPAC). Chemical structures shown herein were prepared using CHEMDRAW®. Any open valency appearing on a carbon, oxygen, or nitrogen atom in the structures herein indicates the presence of a hydrogen atom.

EMBODIMENTS OF THE INVENTION

One aspect provides a compound of formula I:

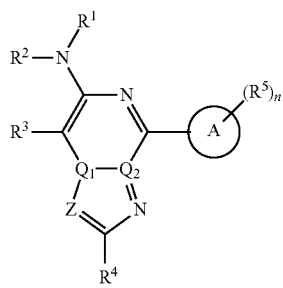

I or a pharmaceutically acceptable salt thereof, wherein:
Ring A is heteroaryl or aryl;
$R^1$ is H or alkyl optionally substituted with 1, 2, 3, or 4 independently selected $R^a$ substituents;
$R^2$ is H, alkyl, —COR''', —CONR'R'', —COOR', —SO$_2$R', —SO$_2$NR'R'', or —SO$_2$OR', wherein the alkyl of $R^2$ is optionally substituted with 1, 2, 3, or 4 independently selected $R^a$ substituents;
$R^3$ is H, alkyl, halo, —CN, or —CONR'R'', wherein the alkyl of $R^3$ is optionally substituted with 1, 2, 3, or 4 independently selected $R^a$ substituents;
or $R^2$ and $R^3$ together form 5-6 membered heterocycloalkyl or 5-6 membered heteroaryl, each of which is optionally substituted with 1, 2, 3, 4, or 5 independently selected $R^7$ substituents, and wherein when $R^2$ and $R^3$ together form 6-membered heteroaryl, then $R^1$ is absent;
$R^4$ is H, alkyl, halo, haloalkyl, —NR'R'', —COR', —CONR'R'', —COOR', SO$_2$R', —SO$_2$NR'R'', —SO$_2$OR', cycloalkyl, heterocycloalkyl, aryl, heteroaryl, or —C$_{1-4}$ alkylene-R$^b$, wherein R$^b$ is cycloalkyl, heterocycloalkyl, aryl or heteroaryl, and wherein the alkyl, cycloalkyl, heterocycloalkyl, aryl, heteroaryl, or —C$_{1-4}$ alkylene-R$^b$ of $R^4$ is optionally substituted with 1, 2, 3, or 4 independently selected $R^a$ substituents;
each $R^5$ is independently H, alkyl, halo, haloalkyl, alkoxy, —CN, —COR', —CONR'R'', —COOR', —SO$_2$R', —SO$_2$NR'R'', —SO$_2$OR', cycloalkyl, heterocycloalkyl, aryl, or heteroaryl wherein the alkyl, alkoxy, cycloalkyl, heterocycloalkyl, aryl, or heteroaryl of $R^5$ is optionally substituted with 1, 2, 3, or 4 independently selected $R^a$ substituents;
n is 0, 1, 2, 3, 4, or 5;
one of $Q_1$ and $Q_2$ is N and the other is C;
Z is N or CR$^6$;

$R^6$ is H or alkyl, wherein the alkyl of $R^6$ is optionally substituted with 1, 2, 3, or 4 independently selected $R^a$ substituents;
each $R^7$ is independently oxo, alkyl, halo, haloalkyl, hydroxy, alkoxy, hydroxyalkyl, cycloalkyl, or heterocycloalkyl, wherein each cycloalkyl and heterocycloalkyl of $R^7$ is optionally and independently further substituted with 1, 2, or 3 of C$_{1-4}$ alkyl, halo, C$_{1-4}$ haloalkyl, hydroxy, or C$_{1-4}$ alkoxy;
R' and R'' are each independently H or alkyl, wherein each alkyl of R' and R'' is optionally substituted with 1, 2, 3, or 4 independently selected $R^a$ substituents;
R''' is alkyl, haloalkyl, cycloalkyl, or heterocycloalkyl, wherein the alkyl, cycloalkyl or heterocycloalkyl of R''' is optionally substituted with 1, 2, 3, or 4 independently selected $R^a$ substituents; and
each $R^a$ is independently alkyl, halo, haloalkyl, hydroxy, alkoxy, hydroxyalkyl, cycloalkyl, or heterocycloalkyl, wherein each cycloalkyl and heterocycloalkyl of $R^a$ is optionally and independently further substituted with 1, 2, or 3 of C$_{1-4}$ alkyl, halo, C$_{1-4}$ haloalkyl, hydroxy, or C$_{1-4}$ alkoxy;
wherein when $R^4$ is H, aryl, or heteroaryl, then Ring A is furanyl.

In some embodiments of this aspect, Ring A is monocyclic heteroaryl or monocyclic aryl. In some embodiments, Ring A is phenyl or 5-6 membered heteroaryl. In some embodiments, ring A is a 5-6 membered heteroaryl ring. In some embodiments, ring A is a 6-membered heteroaryl selected from pyridyl, pyrimidyl, and pyrazyl. In other embodiments, ring A is selected from a 5-membered heteroaryl ring selected from furanyl, pyrrolyl, pyrazyl, immidazolyl, triazolyl, tetrazolyl, thiophenyl, oxazolyl, isoxazolyl, thiazolyl, isothiazolyl, oxadiazolyl, and thiadiazolyl. In some embodiments, Ring A is phenyl, furanyl, thiophenyl, oxazolyl, pyrazolyl, or pyridinyl. In some embodiments, ring A is furanyl. In other embodiments, Ring A is phenyl.

In some embodiments of this aspect, $R^1$ is H or C$_{1-4}$ alkyl. In some embodiments, $R^1$ is H.

In some embodiments of this aspect, $R^2$ is H, C$_{1-4}$ alkyl, —C(O)—C$_{1-4}$ alkyl, —C(O)—C$_{1-4}$ haloalkyl —C(O)-cycloalkyl, —C(O)-heterocycloalkyl, —CONH$_2$, —CONH—C$_{1-4}$ alkyl, —COO—C$_{1-4}$ alkyl, —SO$_2$-C$_{1-6}$ alkyl or —CONH—C$_{1-4}$ alkylene-heterocycloalkyl, and $R^2$ is optionally substituted with 1 or 2 independently selected $R^a$ substituents. In some embodiments, $R^2$ is H or methyl. In other embodiments, $R^2$ is acetyl or —C(O)-cyclopropyl.

In some embodiments of this aspect, $R^3$ is H, C$_{1-4}$ alkyl, halo, —CN, or —CONH$_2$. In some embodiments, $R^3$ is H, methyl, halo, or —CN.

In other embodiments of this aspect, $R^2$ and $R^3$ together form 5-6 membered heterocycloalkyl or 5-6 membered heteroaryl, wherein the heterocycloalkyl or heteroaryl of $R^2$ and $R^3$ is optionally substituted with 1, 2, 3, or 4 independently selected $R^7$ substituents, wherein each $R^7$ is independently oxo, C$_{1-4}$ alkyl, C$_{1-4}$ hydroxyalkyl, or C$_{1-4}$ haloalkyl. In some embodiments, $R^2$ and $R^3$ together form 5-6 membered heterocycloalkyl having 1 or 2 nitrogen atoms as ring members or 5-6 membered heteroaryl having 1 or 2 nitrogen atoms as ring members.

In some embodiments of this aspect, $R^4$ is H, C$_{1-4}$ alkyl, C$_{1-4}$ hydroxymethyl, halo, C$_{1-4}$ haloalkyl, —NH$_2$, —COOH, or —COO—C$_{1-4}$ alkyl. In some embodiments, $R^4$ is C$_{1-4}$ alkyl. In other embodiments, $R^4$ is benzyl, heterocycloalkyl, heteroaryl, or cycloalkyl, wherein the benzyl, heterocycloalkyl, heteroaryl, or cycloalkyl are optionally substituted with 1, 2 or 3 substituents independently selected from $C_{1-4}$ alkyl, halo, $C_{1-4}$ haloalkyl, hydroxy, and $C_{1-4}$ alkoxy.

In some embodiments of this aspect, n is 0, 1, or 2 and each $R^5$ is independently H, $C_{1-4}$ alkyl, halo, $C_{1-4}$ haloalkyl, $C_{1-4}$ alkoxy, —CN, acetyl, $SO_2NH_2$, $SO_2N(CH_3)_2$, $SO_2OH$, or $SO_2CH_3$. In some embodiments, n is 0, 1, or 2, and each $R^5$ is independently H, methyl, halo, $CF_3$, methoxy, or —CN.

In some embodiments of this aspect, $R^6$ is H or methyl.

In some embodiments of this aspect, R' and R" are each independently H or $C_{1-4}$ alkyl.

In some embodiments of this aspect, $Q_1$ is N, and Z is N or $CR^6$; or $Q_2$ is N, and Z is N.

In some embodiments of this aspect, $Q_1$ is N and Z is N.

In some embodiments of this aspect, $Q_1$ is N and Z is $CR^6$.

In some embodiments of this aspect, $Q_2$ is N and Z is N.

In some embodiments of this aspect, the compound of formula I is a compound of formula II:

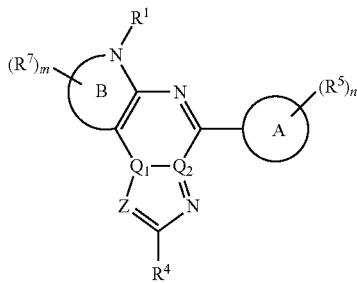

II or a pharmaceutically acceptable salt thereof, wherein
Ring A, $R^1$, $R^4$, $R^5$, $R^7$, $Q_1$, $Q_2$, Z and n are as defined in any of the embodiments of formula I and wherein:
Ring B is 5-6 membered heteroaryl or 5-6 membered heterocycloalkyl; and
m is 0, 1, 2, 3 or 4.

In some embodiments, $R^7$ is oxo, $C_{1-4}$ alkyl, halo, $C_{1-4}$ haloalkyl, hydroxy, $C_{1-4}$ alkoxy, or $C_{1-4}$ hydroxyalkyl, and m is 0, 1, or 2.

In some embodiments of this aspect, the compound of formula I is a compound of formula III:

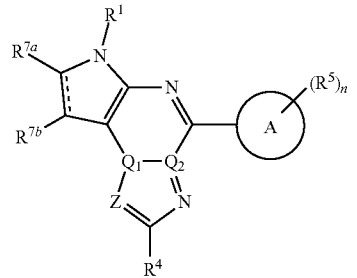

III or a pharmaceutically acceptable salt thereof, wherein
Ring A, $R^1$, $R^4$, $R^5$, $Q_1$, $Q_2$, Z and n are as defined in any of the embodiments of formula I and wherein:
$R^{7a}$ and $R^{7b}$ are each independently H, oxo, $C_{1-4}$ alkyl, halo, $C_{1-4}$ haloalkyl, hydroxy, $C_{1-4}$ alkoxy, or $C_{1-4}$ hydroxyalkyl; and
---- represents a single or double bond.

In some embodiments, Ring A is furanyl.

In some embodiments, $R^4$ is $C_{1-4}$ alkyl or $C_{1-4}$ haloalkyl.

In some embodiments of this aspect, the compound of formula I is a compound of formula IV:

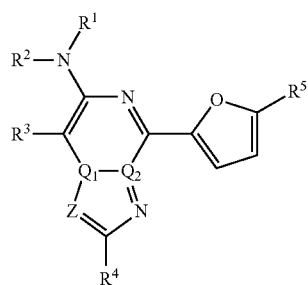

IV or a pharmaceutically acceptable salt thereof, wherein $R^1$, $R^2$, $R^3$, $R^4$, $R^5$, $Q_1$, $Q_2$ and Z are as defined in any of the embodiments of formula I.

In some embodiments, $R^5$ is H, $C_{1-4}$ alkyl, halo, $C_{1-4}$ haloalkyl, or cycloalkyl.

In some embodiments of this aspect, the compound of formula I is a compound of formula V:

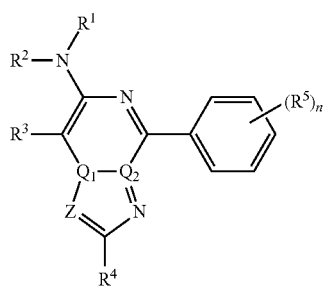

V or a pharmaceutically acceptable salt thereof, wherein $R^1$, $R^2$, $R^3$, $R^4$, $R^5$, $Q_1$, $Q_2$, Z and n are as defined in any of the embodiments of formula I.

In some embodiments, $R^5$ is independently H, $C_{1-4}$ alkyl, halo, —CN, acetyl, —$SO_2CH_3$, $C_{1-4}$ alkoxy, $SO_2NH_2$, $SO_2OH$, or $SO_2N(CH_3)_2$.

In some embodiments, $R^2$ is H or —COR'''.

In some embodiments, $R^4$ is $C_{1-4}$ alkyl, $C_{1-4}$ hydroxyalkyl, halo, $C_{1-4}$ haloalkyl, —$NH_2$, —COOH, or —COO—$C_{1-4}$ alkyl.

In some embodiments of this aspect, the compound of formula I is a compound of formula IA, IB, or IC:

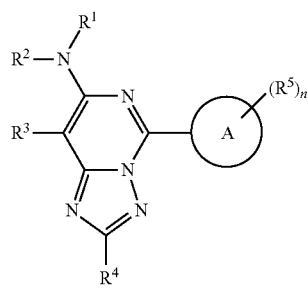

IA

-continued

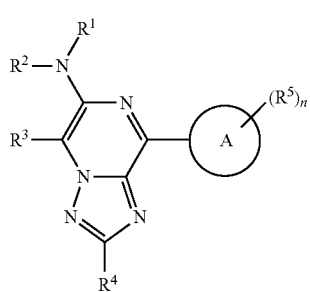

IB

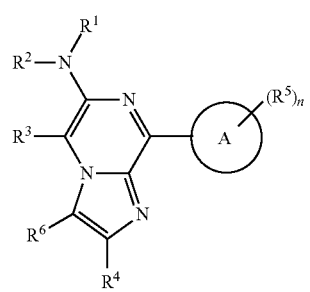

IC or a pharmaceutically acceptable salt thereof, wherein Ring A, $R^1$, $R^2$, $R^3$, $R^4$, $R^5$, $R^6$ and n are as defined in any of the embodiments of formula I.

In some embodiments, the compound of formula I is a compound of formula IA or a pharmaceutically acceptable salt thereof.

In some embodiments, the compound of formula I is a compound of formula IB or a pharmaceutically acceptable salt thereof.

In some embodiments, the compound of formula I is a compound of formula IC or a pharmaceutically acceptable salt thereof.

In some embodiments, the compound of formula I is a compound of formula IA, wherein Ring A is phenyl, furanyl, thiophenyl, oxazolyl, pyrazolyl, or pyridinyl.

In some embodiments, the compound of formula I is a compound of formula IA, wherein $R^2$ is H, methyl, acetyl or —C(O)-cyclopropyl.

In some embodiments, the compound of formula I is a compound of formula IA, wherein $R^4$ is $C_{1-4}$ alkyl, haloalkyl, cycloalkyl or heterocycloalkyl.

In some embodiments, the compound of formula I is a compound of formula IB, wherein Ring A is furanyl or phenyl.

In some embodiments, the compound of formula I is a compound of formula IB, wherein $R^2$ is H, acetyl or —C(O)-cyclopropyl.

In some embodiments, the compound of formula I is a compound of formula IB, wherein $R^4$ is $C_{1-4}$ alkyl, haloalkyl, halo or amino.

In some embodiments, the compound of formula I is a compound of formula IC, wherein Ring A is furanyl or phenyl.

In some embodiments, the compound of formula I is a compound of formula IC, wherein $R^2$ is H or —C(O)-cyclopropyl.

In some embodiments, the compound of formula I is a compound of formula IC, wherein one of $R^4$ and $R^6$ is H and the other is $C_{1-4}$ alkyl.

In some embodiments of this aspect, the compound of formula I is a compound of formula IIA, IIB, or IIC:

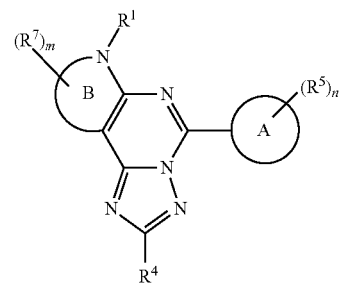

IIA

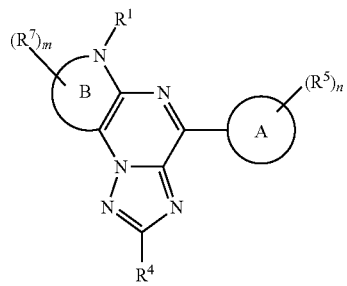

IIB

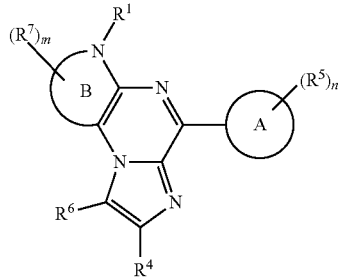

IIC or a pharmaceutically acceptable salt thereof, wherein Ring A, Ring B, $R^1$, $R^4$, $R^5$, $R^6$, $R^7$, m and n are as defined in any of the embodiments of formula I or II.

In some embodiments, the compound of formula I is a compound of formula IIA or a pharmaceutically acceptable salt thereof.

In some embodiments, the compound of formula I is a compound of formula IIB or a pharmaceutically acceptable salt thereof.

In some embodiments, the compound of formula I is a compound of formula IIC or a pharmaceutically acceptable salt thereof.

In some embodiments, the compound of formula I is a compound of formula IIA, wherein $R^7$ is oxo, $C_{1-4}$ alkyl, halo, $C_{1-4}$ haloalkyl, hydroxy, $C_{1-4}$ alkoxy, or $C_{1-4}$ hydroxyalkyl, and m is 0, 1 or 2.

In some embodiments of this aspect, the compound of formula I is a compound of IIIA, IIIB, or IIIC:

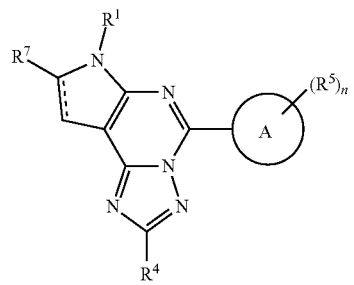

IIIA

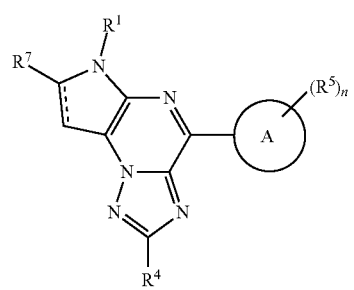

IIIB

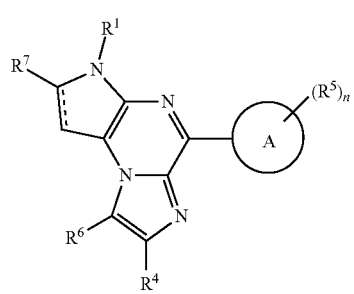

IIIC or a pharmaceutically acceptable salt thereof, wherein Ring A, $R^1$, $R^4$, $R^5$, $R^6$, $R^7$ and n are as defined in any of the embodiments of formula I or III.

In some embodiments, the compound of formula I is a compound of formula IIIA or a pharmaceutically acceptable salt thereof.

In some embodiments, the compound of formula I is a compound of formula IIIB or a pharmaceutically acceptable salt thereof.

In some embodiments, the compound of formula I is a compound of formula IIIC or a pharmaceutically acceptable salt thereof.

In some embodiments, the compound of formula I is a compound of formula IIA or IIIA, wherein Ring A is furanyl.

In some embodiments, the compound of formula I is a compound of formula IIA or IIIA, wherein $R^4$ is $C_{1-4}$ alkyl or $C_{1-4}$ haloalkyl.

In some embodiments of this aspect, the compound of formula I is a compound of formula IVA, IVB, or IVC:

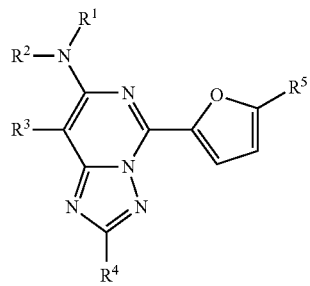

IVA

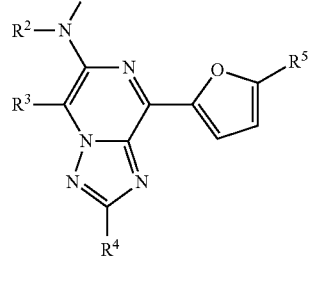

IVB

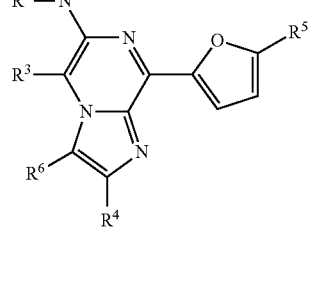

IVC or a pharmaceutically acceptable salt thereof, wherein $R^1$, $R^2$, $R^3$, $R^4$, $R^5$ and $R^6$ are as defined in any of the embodiments of formula I or IV.

In some embodiments, the compound of formula I is a compound of formula IVA or a pharmaceutically acceptable salt thereof.

In some embodiments, the compound of formula I is a compound of formula IVB or a pharmaceutically acceptable salt thereof.

In some embodiments, the compound of formula I is a compound of formula IVC or a pharmaceutically acceptable salt thereof.

In some embodiments, $R^5$ is H, $C_{1-4}$ alkyl, halo, $C_{1-4}$ haloalkyl, or cycloalkyl.

In some embodiments, $R^5$ is H or methyl.

In some embodiments of this aspect, the compound of formula I is a compound of formula VA, VB, or VC:

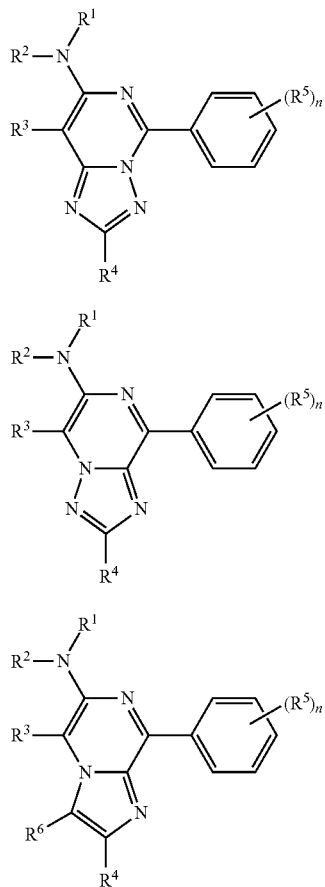

or a pharmaceutically acceptable salt thereof, wherein $R^1$, $R^2$, $R^3$, $R^4$, $R^5$, $R^6$ and n are as defined in any of the embodiments of formula I or V.

In some embodiments, the compound of formula I is a compound of formula VA or a pharmaceutically acceptable salt thereof.

In some embodiments, the compound of formula I is a compound of formula VB or a pharmaceutically acceptable salt thereof.

In some embodiments, the compound of formula I is a compound of formula VC or a pharmaceutically acceptable salt thereof.

In some embodiments, n is 0, 1 or 2 and each $R^5$ is independently H, $C_{1-4}$ alkyl, halo, —CN, acetyl, —$SO_2CH_3$, $C_{1-4}$ alkoxy, $SO_2NH_2$, $SO_2OH$, or $SO_2N(CH_3)_2$.

In some embodiments, $R^2$ is H or —COR'''.

In some embodiments, the compound of formula I is a compound of Table 1, Table 2, or Table 3 or a pharmaceutically acceptable salt thereof.

One aspect provides a pharmaceutical composition comprising a compound or a pharmaceutically acceptable salt thereof as described herein, and a pharmaceutically acceptable carrier or excipient.

Another aspect provides a method of inhibiting an activity of an adenosine receptor, comprising contacting the receptor with a compound or a pharmaceutically acceptable salt thereof as described herein.

Another aspect provides a method of treating a disease or disorder in a patient, wherein the disease or disorder is associated with abnormal expression of A2A or A2B receptors, the method comprising administering to the patient a therapeutically effective amount of a compound or a pharmaceutically acceptable salt thereof, or a pharmaceutical composition as described herein.

In some embodiments of this aspect, the disease or disorder is cancer, an inflammatory disease, a cardiovascular disease, or a neurodegenerative disease.

In some embodiments, the cancer is lung cancer, non-small cell lung cancer, melanoma, malignant melanoma, renal cell cancer, triple negative breast cancer, colorectal cancer, bladder cancer, metastatic castration resistant prostate, cervical cancer, ovarian cancer, colorectal cancer, pancreatic cancer, esophageal cancer, prostate cancer, kidney cancer, skin cancer, thyroid cancer, liver cancer, or uterine cancer.

In some embodiments, the inflammatory disease is a respiratory disorder, sepsis, reperfusion injury, or thrombosis.

In some embodiments, the cardiovascular disease is coronary artery-disease, cerebrovascular disease, peripheral artery disease, aortic atherosclerosis, or aneurysm.

In some embodiments, the neurodegenerative disease is Parkinson's disease.

One aspect provides a process for producing a compound of formula I

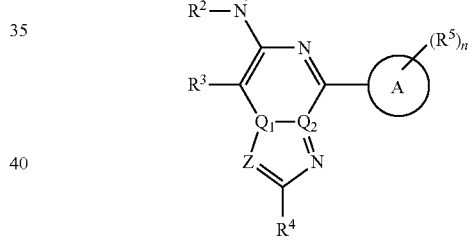

or a pharmaceutically acceptable salt thereof, comprising contacting a compound of formula G-1

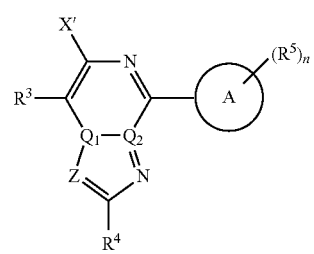

with a compound of formula G-2

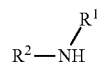

in the presence of a palladium catalyst, a solvent, and a base, wherein X' is a leaving group selected from halogen or a sulfonate derivative, such as methanesulfonate, p-toluenesulfonate, or trifluoromethanesulfonate, and Ring A, $R^1$, $R^2$, $R^3$, $R^4$, $R^5$, $Q_1$, $Q_2$, Z and n are as defined in an embodiment described herein.

In some embodiments of this aspect, the compound of formula G-2 is PG-NH$_2$, wherein PG is an amino protecting group. In some embodiments, PG is selected from t-butylcarboxy (BOC), carboxybenzyl (Cbz), benzyl, benzoyl, acetyl, trifluoroacetyl, phthalimide, p-toluenesulfonyl, methanesulfonyl, and trifluoromethanesulfonyl. In a further embodiment, PG is BOC.

In some embodiments, the compound of formula G-2 is R'''—C(O)NH$_2$, R''—NHC(O)NH$_2$, or R'—OC(O)NH$_2$, wherein R''', R'', and R' are defined herein.

In some embodiments of this aspect, the solvent is an organic solvent. In some embodiments, the solvent is a polar aprotic solvent. In some embodiments, the solvent is DMF, DMSO, THF, or 1,4-dioxane.

One aspect provides a process for producing a compound of formula II

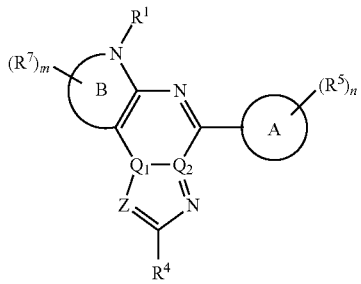

or a pharmaceutically acceptable salt thereof, comprising contacting a compound of formula G-3

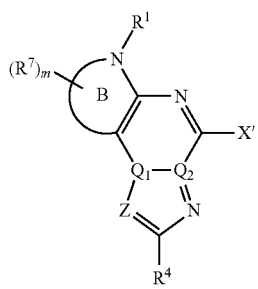

with a compound of formula G-4

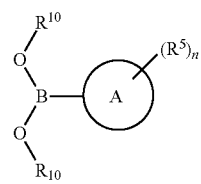

in the presence of a palladium catalyst, a solvent, and a base, wherein each $R^{10}$ is a $C_{1-6}$ alkyl group, or both $R^{10}$ substituents, together with the atoms to which they are attached, form a 5-6 membered ring, and Ring A, Ring B, X', $R^1$, $R^4$, $R^5$, $R^7$, $Q_1$, $Q_2$, Z, m and n are as defined in an embodiment described herein.

In some embodiments of this aspect, ring A is heteroaryl or aryl. In some embodiments, ring A is a 5-6 membered heteroaryl ring. In some embodiments, ring A is a 6-membered heteroaryl selected from pyridyl, pyrimidyl, and pyrazyl. In other embodiments, ring A is a 5-membered heteroaryl ring selected from furanyl, pyrrolyl, pyrazyl, immidazolyl, triazolyl, tetrazolyl, thiophenyl, oxazolyl, isoxazolyl, thiazolyl, isothiazolyl, oxadiazolyl, and thiadiazolyl. In some embodiments, ring A is furanyl. In other embodiments, ring A is phenyl.

In some embodiments of this aspect, both $R^{10}$ substituents, together with the atoms to which they are attached, form a 5-membered ring. In some embodiments,

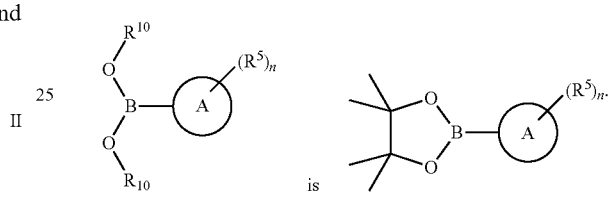

In some embodiments of this aspect, the solvent is an organic solvent. In some embodiments, the solvent is a polar aprotic solvent. In some embodiments, the solvent is DMF, DMSO, THF, or 1,4-dioxane.

Another aspect provides a process for producing a compound of formula IIA

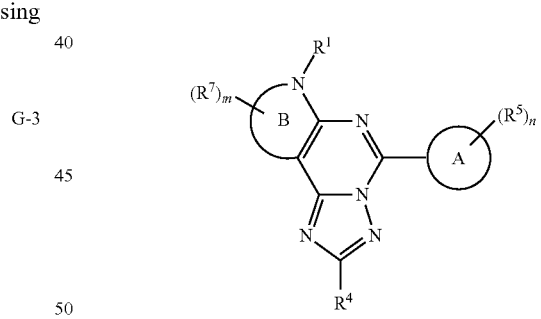

or a pharmaceutically acceptable salt thereof, comprising contacting a compound of formula G-5

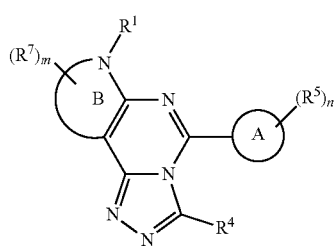

with a base in the presence of an alcoholic solvent at elevated temperature, wherein Ring A, Ring B, $R^1$, $R^4$, $R^5$, $R^7$, m and n are as defined in an embodiment described herein.

In some embodiments of this aspect, the alcohol is methanol or ethanol.

In some embodiments of this aspect, the base is an amine base. In some embodiments, the base is selected from triethylamine, DIEA, DBU, and N-methylpiperidine.

In some embodiments, the base is an inorganic base. In some embodiments, the base is selected from hydroxide bases, such as NaOH and KOK, and carbonate bases such as $Na_2CO_3$, and $K_2CO_3$.

Another aspect provides a process for producing a compound of formula G-6

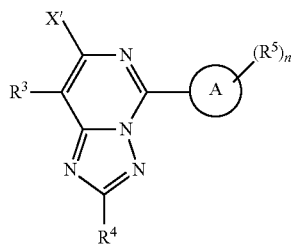

G-6 or a pharmaceutically acceptable salt thereof, comprising contacting a compound of formula G-7

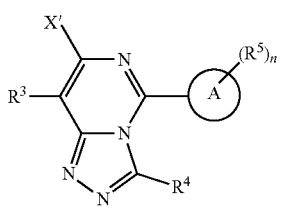

G-7 with a base in the presence of an alcoholic solvent at elevated temperature, wherein Ring A, X', $R^3$, $R^4$, $R^5$ and n are as defined herein.

In some embodiments of this aspect, the alcohol is methanol or ethanol.

In some embodiments of this aspect, the base is an amine base. In some embodiments, the base is selected from triethylamine, DIEA, DBU, and N-methylpiperidine.

In some embodiments, the base is an inorganic base. In some embodiments, the base is selected from hydroxide bases, such as NaOH and KOK, and carbonate bases such as $Na_2CO_3$, and $K_2CO_3$.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as, for example, tablets, suppositories, pills, soft elastic and hard gelatin capsules, powders, solutions, suspensions, aerosols, and the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, and the like. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate, and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, and the like.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, and the like, a compound(s) of the invention, or a pharmaceutically acceptable salt thereof, and optional pharmaceutical adjuvants in a carrier, such as, for example, water, saline, aqueous dextrose, glycerol, ethanol, and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, and dimethylformamide; oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol, and sorbitan esters, microcrystalline cellulose, aluminum metahydroxide, bentonite, agar-agar, and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol, or a suppository wax, which are solid at ordinary temperatures but liquid at body temperature and therefore melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode, and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Synthesis

Compounds of this invention can be made by the synthetic procedures described below. The starting materials and reagents used in preparing these compounds are either available from commercial suppliers such as Sigma Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, $4^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure and over a temperature range from about −78° C. to about 150° C., more preferably from about 0° C. to about 125° C., and most preferably at about room (or ambient) temperature, e.g., about 20° C. Unless otherwise stated (as in the case of a hydrogenation), all reactions are performed under an atmosphere of nitrogen.

The compounds disclosed and claimed herein have asymmetric carbon atoms or quaternized nitrogen atoms in their structure and may be prepared through the through syntheses described herein as single stereoisomers, racemates, and as mixtures of enantiomers and diastereomers. The compounds may also exist as geometric isomers. All such single stereoisomers, racemates, and mixtures thereof, and geometric isomers are intended to be within the scope of this invention.

Some of the compounds of the invention may exist as tautomers. For example, where a ketone or aldehyde is present, the molecule may exist in the enol form; where an amide is present, the molecule may exist as the imidic acid;

and where an enamine is present, the molecule may exist as an imine. All such tautomers are within the scope of the invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereomeric salts or complexes which may be separated, for example, by crystallization; via formation of diastereomeric derivatives which may be separated, for example, by crystallization; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomers may be synthesized by asymmetric synthesis using optically active reagents, substrates, catalysts or solvents or by converting an enantiomer to the other by asymmetric transformation. For a mixture of enantiomers, enriched in a particular enantiomer, the major component enantiomer may be further enriched (with concomitant loss in yield) by recrystallization.

The starting materials and reagents, which do not have their synthetic route explicitly disclosed herein, are generally available from commercial sources or are readily prepared using methods well known to the person skilled in the art.

In general, the nomenclature used in this Application is based on the computerized naming system in CHEMDRAW®. Chemical structures shown herein were prepared using CHEMDRAW®. Any open valency appearing on a carbon, oxygen or nitrogen atom in the structures herein indicates the presence of a hydrogen atom.

The following examples are provided for the purpose of further illustration and are not intended to limit the scope of the claimed invention.

General Synthetic Strategies

The Schemes below provide general guidance in connection with preparing compounds of the invention. One skilled in the art would understand that the preparations shown in the Schemes can be modified or optimized using general knowledge of organic chemistry to make various compounds of the invention.

Compounds as claimed and described herein can be prepared in accordance with the synthetic routes set forth in Schemes 1-7.

Scheme 1

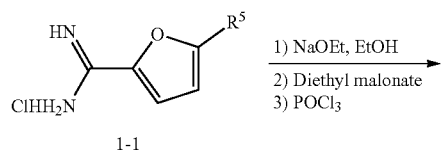

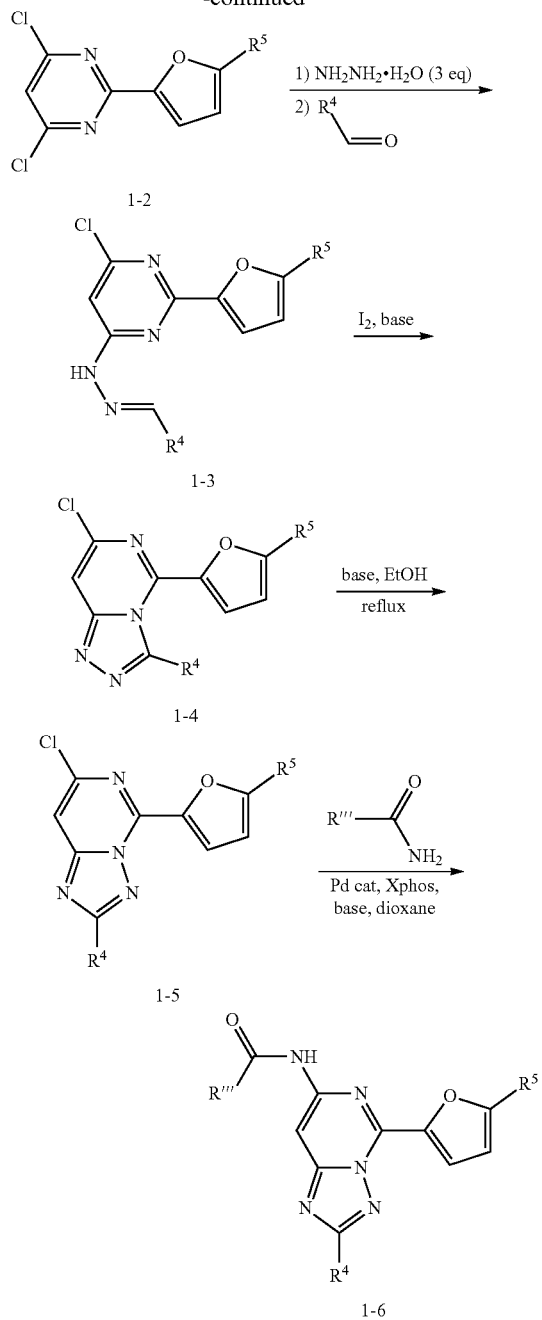

Cyclization of unsubstituted ($R^5$=H) or substituted ($R^5$=alkyl) furan-2-caroximidamide (1-1) can be achieved by reacting compound 1-1 with diethylmalonate in the presence of a base such as NaOEt in a solvent at reflux temperature to generate a pyrimidine intermediate, which can be converted to dichloropyrimidine compound 1-2 by reacting with phosphoryl chloride. Compounds of formula 1-3 can be prepared by coupling compound 1-2 with hydrazine hydrate followed by reacting with an appropriate aldehyde reagent ($R^4$CH(=O)), in which $R^4$ is as defined herein, for example, $R^4$ can be methyl, ethyl, isopropyl, cycloalkyl, cyclic ethers, cyclic amines, fluoromethyl, trifluoromethyl, or furanyl. Compounds of formula 1-4 can be prepared by reacting with iodine or trifluoromethanesulfonic anhydride or iodosobenzene diacetate mediated cyclization under basic conditions. Compounds of formula 1-5 can be prepared under Dimroth rearrangement conditions at an elevated temperature. Compounds of formula 1-6, triazlopyrimidine scaffold compounds, can be prepared by reacting a compound of formula 1-5 with an appropriately substituted amide (R'''—C(O)NH$_2$) under palladium-catalyzed C—N cross coupling reaction conditions, wherein R''' can be an alkyl (such as methyl, ethyl, or t-butyl), cyclic alkyl, aliphatic amine, cyclic amine, carbamate, or carbonate group.

Scheme 2 outlines the synthesis of compounds of formula 2-5. Compounds of formula 2-2, triazlopyrimidine scaffold compounds, can be prepared from compounds of formula 2-1 under Suzuki cross-coupling conditions (e.g. in the presence of a palladium catalyst and a suitable base) with an appropriately substituted phenyl boronic acid, in which R$^5$ is a halide such as F, Cl, Br or I. Compounds of formula 2-3 can then be prepared by coupling compounds of formula 2-2 with a protected amine, such as tert-butyl carbamate, in the presence of a palladium catalyst, a phosphine ligand such as 2-dicyclohexylphosphino-2',4',6'-triisopropylbiphenyl (XPhos), and a suitable base. Compounds of formula 2-4 can be obtained after removing the amine protecting group of compounds of formula 2-3. Compounds of formula 2-4 can be halogenated using an appropriate reagent such as N-chlorosuccinimide (NCS), N-bromosuccinimide (NBS), or N-iodosuccinimide (NIS) to afford compounds of formula 2-5.

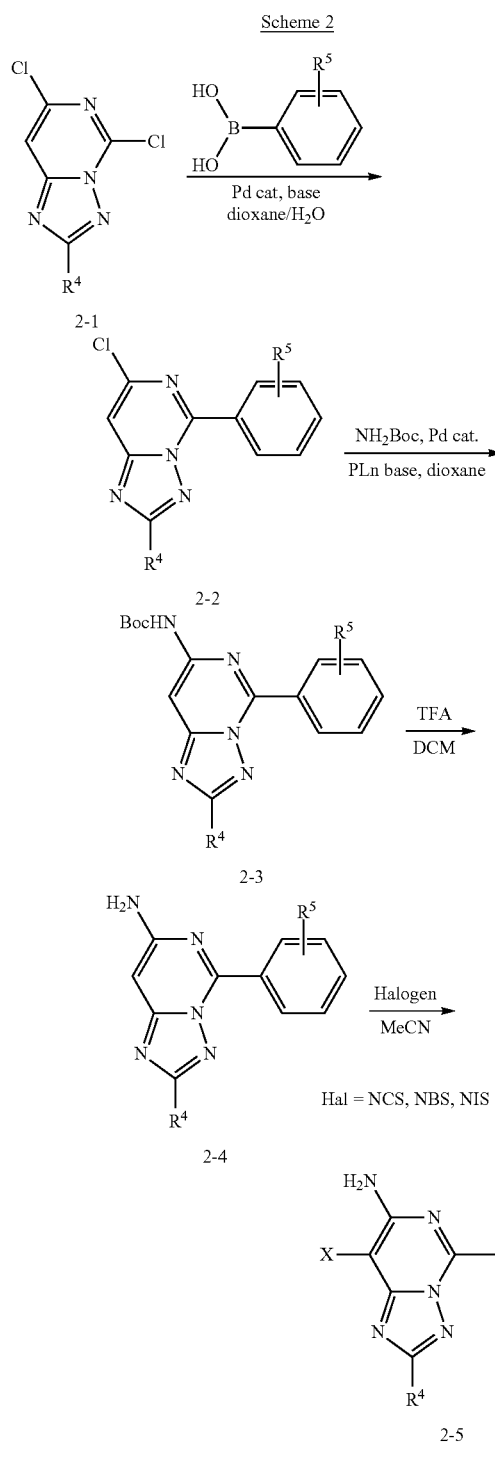

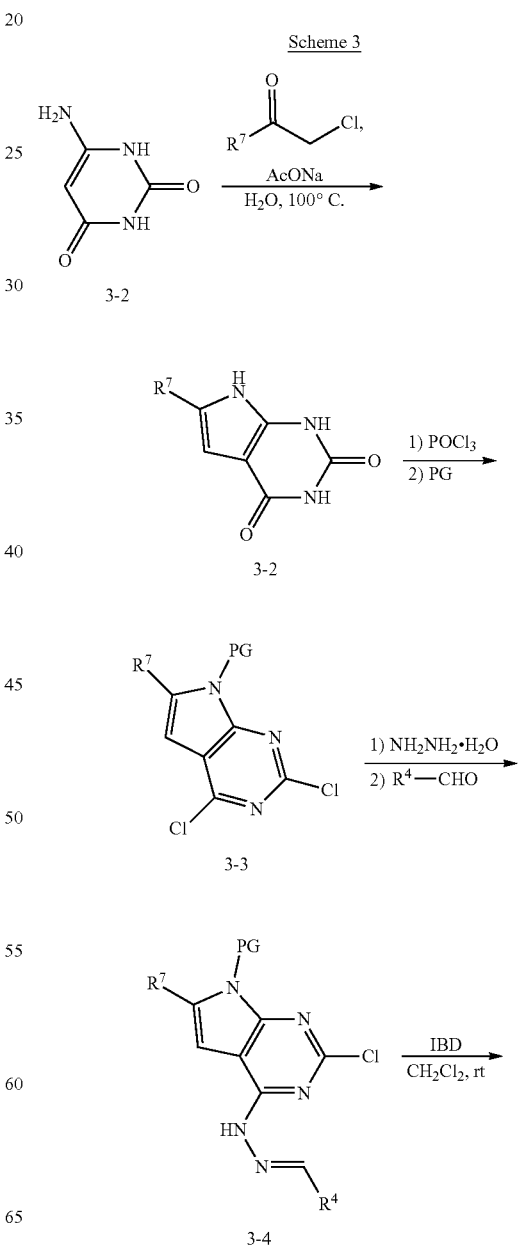

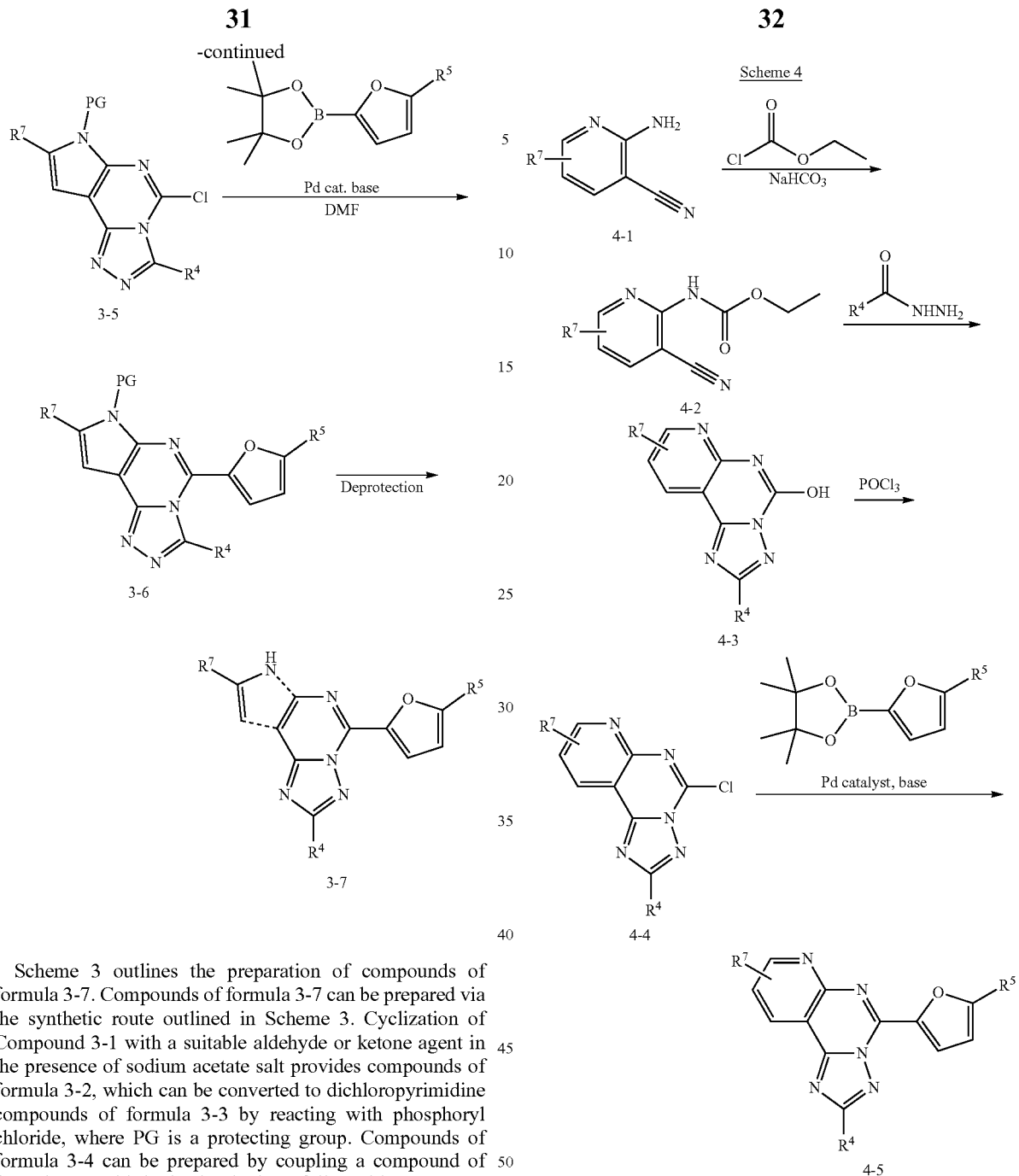

Scheme 3 outlines the preparation of compounds of formula 3-7. Compounds of formula 3-7 can be prepared via the synthetic route outlined in Scheme 3. Cyclization of Compound 3-1 with a suitable aldehyde or ketone agent in the presence of sodium acetate salt provides compounds of formula 3-2, which can be converted to dichloropyrimidine compounds of formula 3-3 by reacting with phosphoryl chloride, where PG is a protecting group. Compounds of formula 3-4 can be prepared by coupling a compound of formula 3-3 with hydrazine hydrate followed by treatment with an appropriate aldehyde reagent, $R^4$—CHO, in which $R^4$ can be an alkyl (such as methyl, ethyl, or isopropyl), cycloalkyl, cyclic ethers, cyclic amines, fluoromethyl, trifluoromethyl, or furanyl. Compounds of formula 3-5 can be prepared by iodine, trifluoromethanesulfonic anhydride, or iodosobenzen diacetate (IBD) mediated cyclization under basic conditions. Compounds of formula 3-6 can be prepared from compounds of formula 3-5 under the standard Suzuki cross-coupling condition (e.g., in the presence of a palladium catalyst and a suitable base). Removal of the amino protecting group from a compound of formula 3-6 under appropriate conditions, such as in the presence of aqueous sodium hydroxide or potassium hydroxide at elevated temperature (removal by hydrolysis) or anhydrous acid conditions (acid labile protecting groups) gives triazlopyrimidine compounds of formula 3-7.

Scheme 4 outlines the preparation of compounds of formula 4-5. Compound of formula 4-5 can be prepared via the synthetic route outlined in Scheme 4. Reacting of a compound of formula 4-1 with an acyl halide agent under basic conditions yields a compound of formula 4-2, in which $R^7$ is an aliphatic alkyl group, F, Cl, Br or I. The compound of formula 4-2 is then cyclized at an elevated temperature in the presence of an appropriate hydrazide agent, $R^4C(O)NHNH_2$ (wherein $R^4$ is defined above) under suitable conditions to afford 4-3. Chlorination of a compound of formula 4-3 using a suitable reagent (e.g. phosphorus oxychloride) gives a compound of formula 4-4. Compounds of formula 4-4 can be coupled to an appropriate boronic acid or a boronic ester under standard Suzuki cross-coupling conditions (e.g., in the presence of a palladium catalyst and a suitable base) to yield compounds of formula 4-5.

Scheme 5

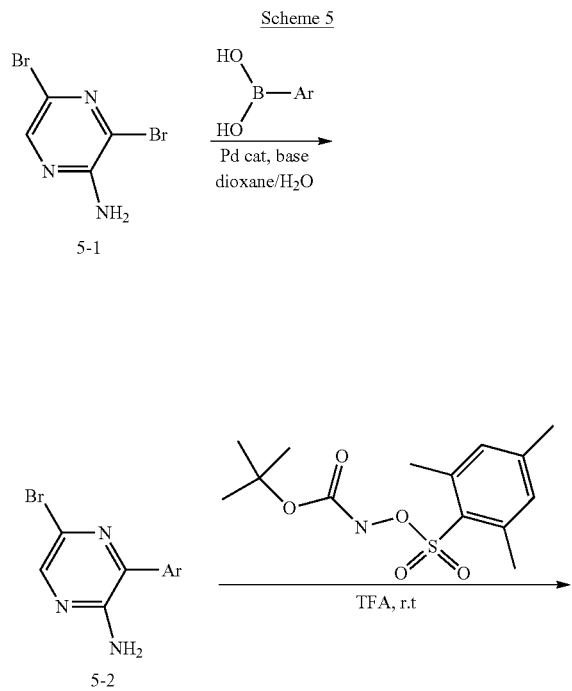

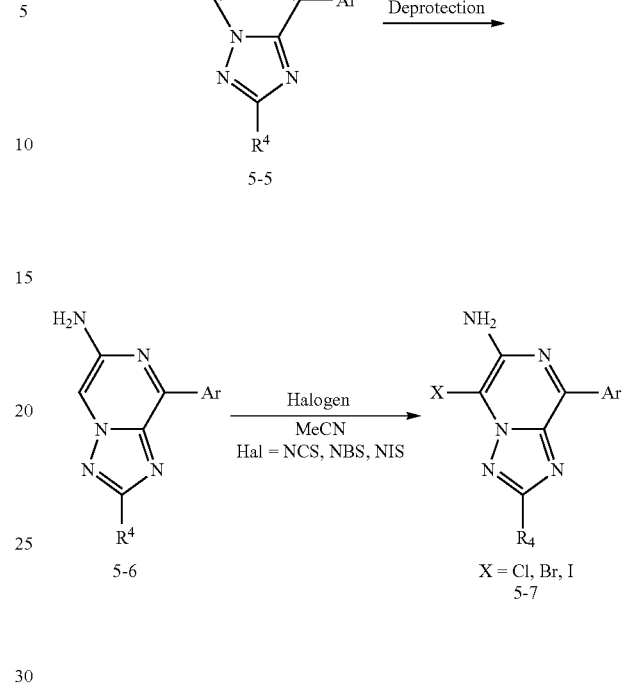

Scheme 5 outlines the preparation of compounds of formula 5-7. Compounds of formula 5-2 can be prepared from compounds of formula 5-1 by reaction with an appropriate aromatic boronic acid or aromatic boronic ester agent under standard Suzuki cross-coupling conditions (e.g., in the presence of a palladium catalyst and a suitable base). The amination of a compound of formula 5-2 with N-tert-butoxycarbonyl-O-(mesitylsulfonyl) hydroxylamine produces a compound of formula 5-3, which can be cyclized at an elevated temperature in the presence of an appropriate aldehyde, $R^4$—CHO, where $R^4$ is as defined herein. Compounds of formula 5-5 can then be prepared by coupling an appropriately protected amine in the presence of a palladium catalyst, a phosphine ligand such as XPhos, and a suitable base. A compound of formula 5-7 can be prepared by deprotecting or removing the protecting group in the compound of formula 5-5 to form a compound of formula 5-6 and then halogenating the compound of formula 5-6 using an appropriate halogenating reagent, such as N-chlorosuccinimide (NCS), N-bromosuccinimide (NBS), or N-iodosuccinimide (NIS).

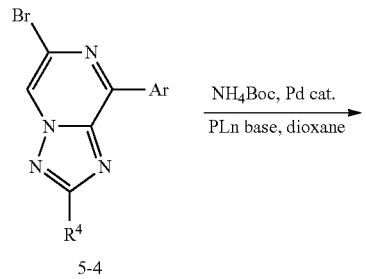

Scheme 6

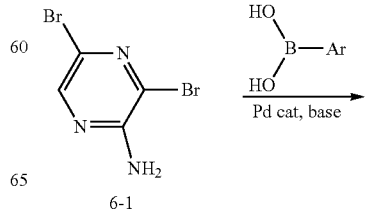

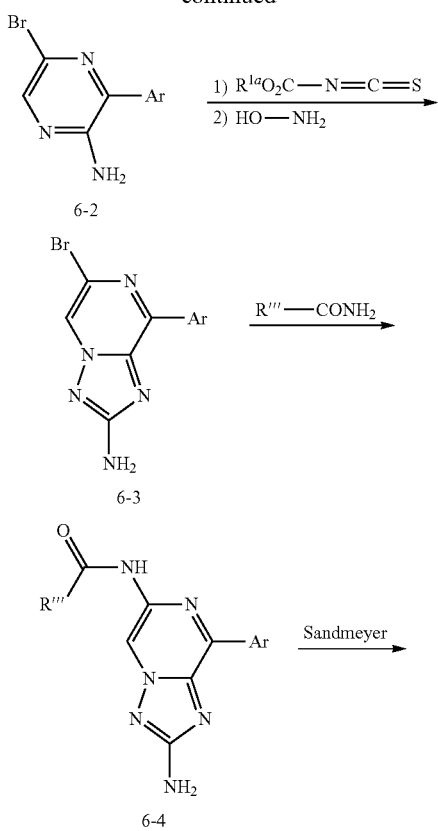

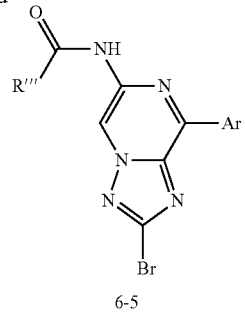

Scheme 6 outlines the preparation of compounds of formula 6-5. Compounds of formula 6-2 can be prepared by reacting an appropriate aromatic boronic acid or aromatic boronic ester with compound 6-1 under standard Suzuki cross-coupling conditions (e.g., in the presence of a palladium catalyst and a suitable base). Compounds of formula 6-3 can be produced by reacting compounds of formula 6-2 with a compound represented by the formula, $R^{1a}O_2C\!=\!N\!=\!C\!=\!S$, wherein $R^{1a}$ is a $C_{1-6}$ alkyl, to yield the corresponding thiourea intermediate, which is reacted with hydroxylamine in the presence of a suitable base. Compounds of formula 6-4 can be prepared by reacting with an appropriately substituted amide $(R'''\!-\!C(O)NH_2)$ under a palladium-catalyzed C—N cross coupling conditions, where R''' can be methyl, ethyl, t-butyl, cyclic alkyl, aliphatic amine, cyclic amine, carbamate, carbonate group. Compounds of formula 6-5 can be prepared by reacting a compound of formula 6-4 with an aryl diazonium salt under Sandmeyer conditions using copper salts of a chloride, bromide or iodide as reagents or catalysts.

Scheme 7

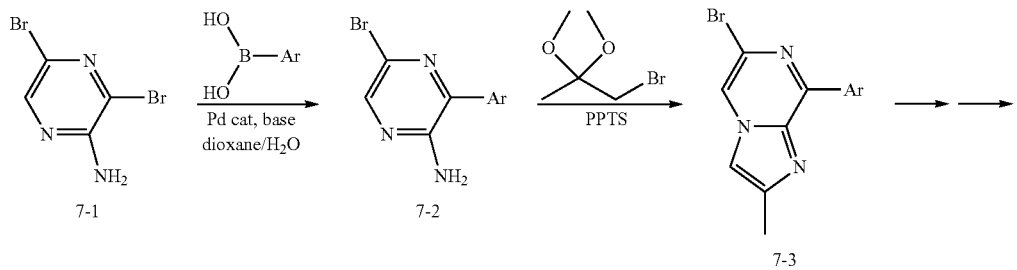

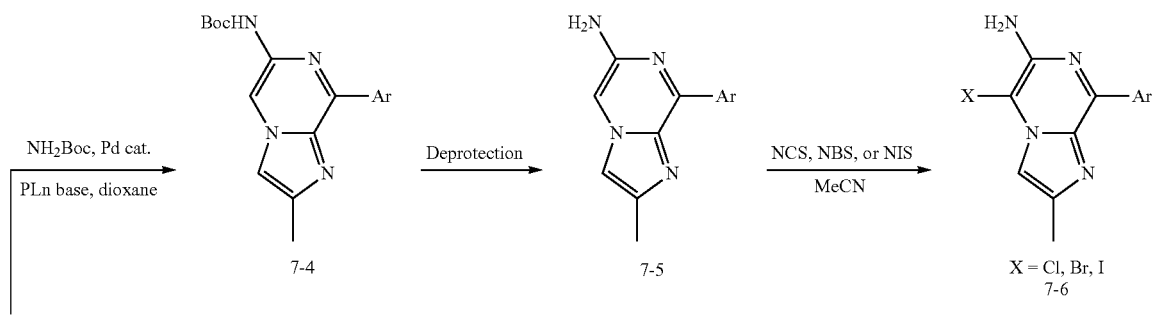

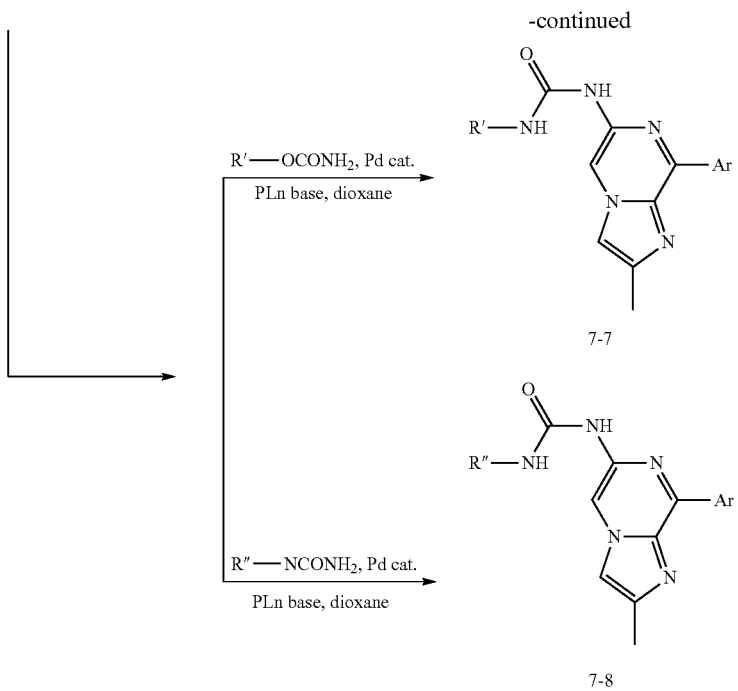

Scheme 7 outlines the preparation of compounds of formula 7-6. 7-7, and 7-8. Compounds of formula 7-6, 7-7 and 7-8 can be prepared from Compound 7-1 by reaction with an appropriate aromatic boronic acid or an aromatic boronic ester under standard Suzuki cross-coupling conditions (e.g., in the presence of a palladium catalyst and a suitable base). Reacting a compound of formula 7-2 with bromoacetone dimethyl acetal in the presence of a catalytic amount of pyridinium p-toluenesulfonate (PPTS) affords a compound of formula 7-3. Compounds of formula 7-4 can be prepared by coupling a compound of formula 7-3 with an appropriate protected amine in the presence of a palladium catalyst, a phosphine ligand such as XPhos and a suitable base. Removing the protecting group in intermediate 7-4 affords a compound of formula 7-5. Halogenation of intermediate 7-5 using an appropriate reagent, such as N-chlorosuccinimide (NCS), N-bromosuccinimide (NBS) or N-iodosuccinimide (NIS) gives a compound of formula 7-6. Compounds of formula 7-7 can be prepared by coupling a compound of formula 7-3 with an appropriate carbamate, R'OCONH$_2$ in the presence of a palladium catalyst, a phosphine ligand such as XPhos and a suitable base, where R' can be methyl, ethyl, isopropyl, cycloalkyl, cyclic ethers, cyclic amines, fluoromethyl, or trifluoromethyl. Compound of formula 7-8 can be prepared by coupling a compound of formula 7-3 with an appropriate urea, R"—NCONH$_2$ in the presence of a palladium catalyst, a phosphine ligand such as XPhos and a suitable base, where R" can be methyl, ethyl, isopropyl, cycloalkyl, cyclic ethers, cyclic amines, fluoromethyl, or trifluoromethyl.

EXAMPLES

The following examples are provided for illustrative purposes only and not to limit the scope of the claims provided herein. In the following examples, Scaffold 1 is the triazolopyrimidine scaffold, Scaffold 2 is the triazolopyrazine scaffold, and Scaffold 3 is the imidazolopyrazine scaffold.

Part I: Preparation of Triazolopyrimidine Adenosine Antagonists

Example 1: Preparation of N-(2-methyl-5-(5-methylfuran-2-yl)-[1,2,4]triazolo[1,5-c]pyrimidin-7-yl)cyclopropanecarboxamide (2)

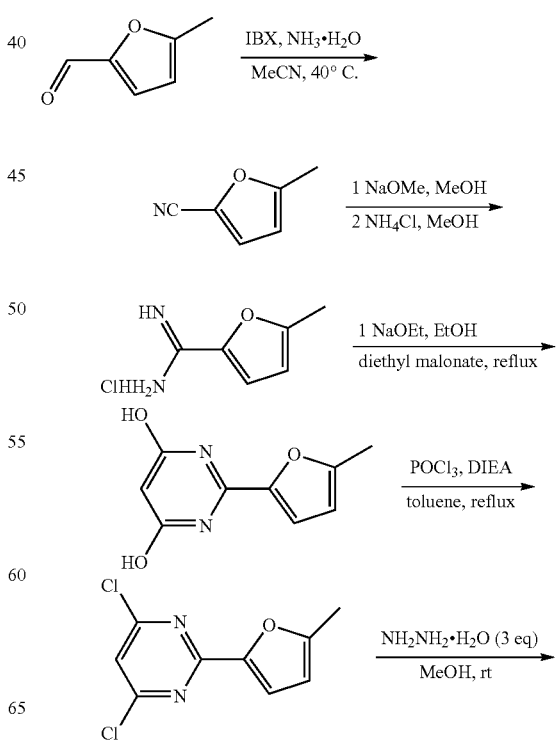

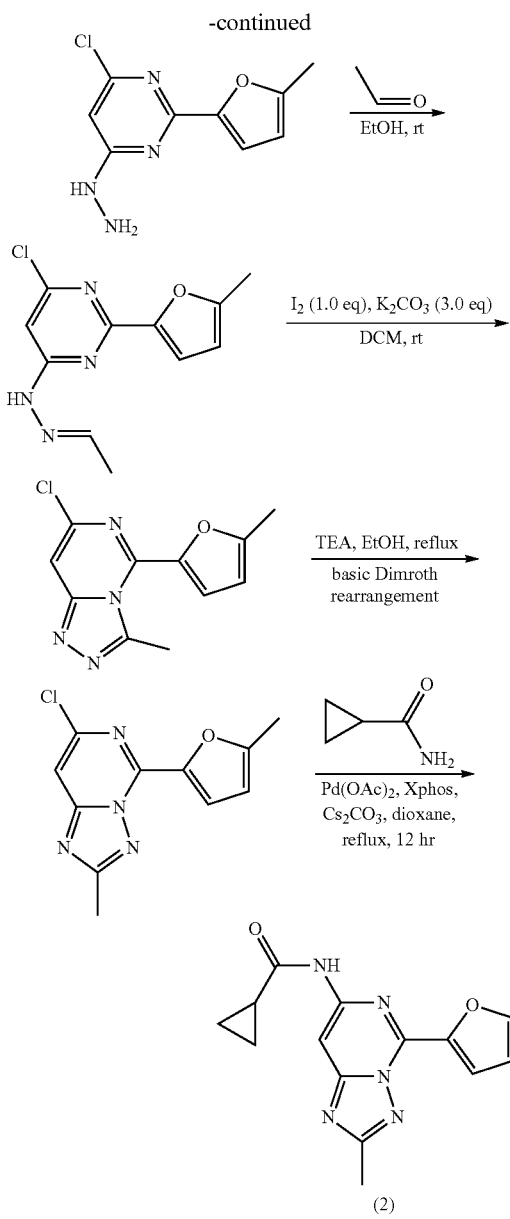

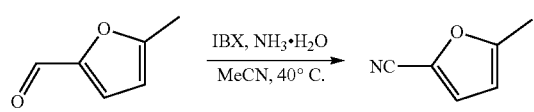

Step 1: Preparation of 5-methylfuran-2-carbonitrile

5-Methylfuran-2-carbaldehyde (50 g, 454.09 mmol, 1 eq.) was added to a stirred solution of 2-iodoxybenzoic acid (190.73 g, 681.13 mmol, 1.5 eq.) in NH$_3$·H$_2$O (500 mL, 28% purity) and CH$_3$CN (150 mL) at 25° C. and the reaction mixture was stirred at 40° C. for 2 h. TLC (Petroleum ether/EtOAc=10/1, R$_f$=0.45) indicated the reactant was consumed completely and one new spot formed. The reaction mixture was diluted with water and extracted with petroleum ether (500 mL×3). The combined organic layer was washed with water (200 mL), and brine (180 mL), dried over sodium sulfate and concentrated under vacuo to afford practically pure nitrile. The product was used in the next step without further purification. Compound 5-methylfuran-2-carbonitrile (36 g, 71.0% yield) was obtained as a yellow oil; $^1$HNMR (CDCl$_3$ 400 MHz) δ 7.01 (d, J=3.2 Hz, 1H), 6.13 (d, J=3.6 Hz, 1H), 2.38 (s, 3H).

Step 2: Preparation of 5-methylfuran-2-carboxamidine hydrochloride

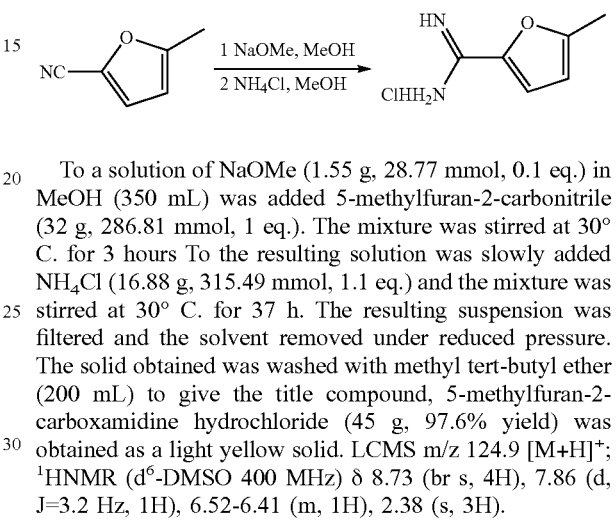

To a solution of NaOMe (1.55 g, 28.77 mmol, 0.1 eq.) in MeOH (350 mL) was added 5-methylfuran-2-carbonitrile (32 g, 286.81 mmol, 1 eq.). The mixture was stirred at 30° C. for 3 hours To the resulting solution was slowly added NH$_4$Cl (16.88 g, 315.49 mmol, 1.1 eq.) and the mixture was stirred at 30° C. for 37 h. The resulting suspension was filtered and the solvent removed under reduced pressure. The solid obtained was washed with methyl tert-butyl ether (200 mL) to give the title compound, 5-methylfuran-2-carboxamidine hydrochloride (45 g, 97.6% yield) was obtained as a light yellow solid. LCMS m/z 124.9 [M+H]$^+$; $^1$HNMR (d$^6$-DMSO 400 MHz) δ 8.73 (br s, 4H), 7.86 (d, J=3.2 Hz, 1H), 6.52-6.41 (m, 1H), 2.38 (s, 3H).

Step 3: Preparation of 2-(5-methyl-2-furyl)pyrimidine-4,6-diol

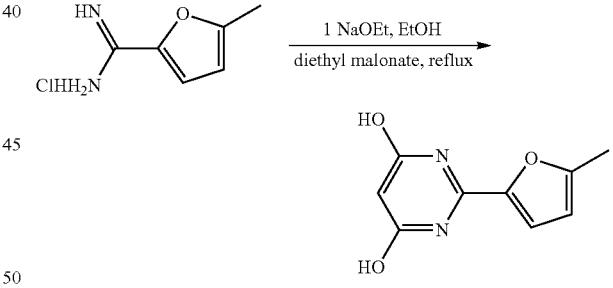

To a solution of EtONa (95.34 g, 1.40 mol, 5 eq.) in EtOH (900 mL) was slowly added 5-methylfuran-2-carboxamidine hydrochloride (45 g, 280.20 mmol, 1 eq.). The mixture was stirred at 30° C. for 30 minutes and then diethyl malonate (67.32 g, 420.30 mmol, 1.5 eq.) was added. The suspension was stirred at 78° C. for 24 h. The solvent was removed under reduced pressure. The residue was suspended in water (450 mL) and acidified to pH=6 with 5 N hydrochloric acid. The resulting solid was filtered and washed with water (300 mL), ethanol/methyl tert-butyl ether (4:1, 250 mL), methyl tert-butyl ether (200 mL×2) to give a 2-(5-methyl-2-furyl)pyrimidine-4,6-diol (41 g, 76.1% yield) was obtained as a light yellow solid. LCMS m/z 192.9 [M+H]$^+$; $^1$HNMR (d$^6$-DMSO 400 MHz) δ 11.84 (br s, 2H), 7.46 (d, J=3.2 Hz, 1H), 6.35 (d, J=2.8 Hz, 1H), 5.22 (s, 1H), 2.35 (s, 3H).

Step 4: Preparation of 4,6-dichloro-2-(5-methyl-2-furyl)pyrimidine

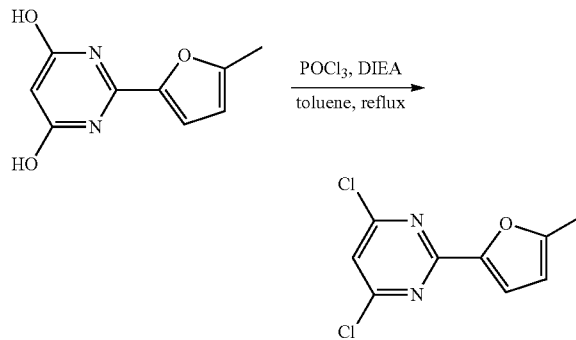

To a mixture of 2-(5-methyl-2-furyl)pyrimidine-4,6-diol (24 g, 124.89 mmol, 1 eq.) and DIEA (29.68 g, 229.64 mmol, 40 mL, 1.84 eq.) in toluene (40 mL) and then POCl$_3$ (66.63 g, 434.55 mmol, 40.38 mL, 3.48 eq.) was dropwise added. The mixture was stirred at 110° C. for 2 h, and then the solvent was removed under reduced pressure. CH$_2$Cl$_2$ (300 mL) and ice water (200 mL) were slowly added to the residue. The resulting mixture was washed with water (100 mL×2), saturated sodium bicarbonate (100 mL×2), brine, dried over Na$_2$SO$_4$, filtered and concentrated. The solvent was removed under reduced pressure to give the product (26 g, 90.8% yield) as a black-brown solid. The crude compound was used without further purification. LCMS m/z 229.2 [M+H]$^+$; $^1$HNMR (CDCl$_3$ 400 MHz) δ 7.36-7.35 (d, J=3.2 Hz, 1H), 7.12 (s, 1H), 6.21-6.20 (dd, J$_1$=3.6 Hz, J$_2$=3.2 Hz, 1H), 2.45 (s, 3H).

Step 5: Preparation of [6-chloro-2-(5-methyl-2-furyl)pyrimidin-4-yl]hydrazine

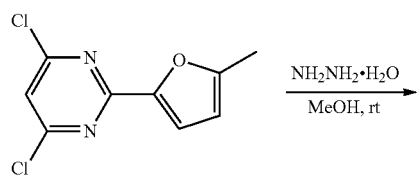

A mixture of 4,6-dichloro-2-(5-methyl-2-furyl)pyrimidine (20 g, 87.31 mmol, 1 eq.) and NH$_2$NH$_2$·H$_2$O (13.39 g, 267.48 mmol, 13 mL, 3.06 eq.) in MeOH (150 mL) was stirred at 28-30° C. for 3 hours. The solvent was partially removed under reduced pressure. The resulting solid was filtered, washed with water (150 mL), methyl tert-butyl ether (50 mL×2), and dried. The solvent was removed under reduced pressure to give [6-chloro-2-(5-methyl-2-furyl)pyrimidin-4-yl]hydrazine (19 g, 96.8%) as an off-white solid. LCMS m/z 225.2 [M+H]$^+$; $^1$HNMR (d$^6$-DMSO 400 MHz) δ 8.92 (br s, 1H), 7.05 (br s, 1H), 6.62 (br s, 1H), 6.27-6.26 (d, J=2.4 Hz, 1H), 4.52 (br s, 2H), 2.34 (s, 3H).

Step 6: Preparation of 6-chloro-N-[(E)-ethylideneamino]-2-(5-methyl-2-furyl)pyrimidin-4-amine

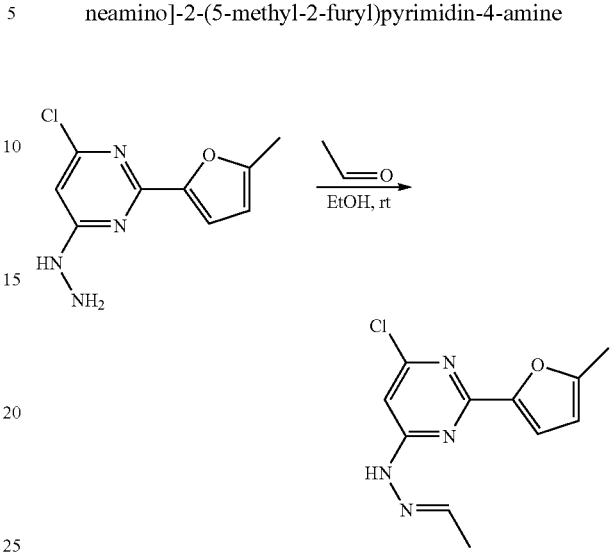

To the suspension of [6-chloro-2-(5-methyl-2-furyl)pyrimidin-4-yl]hydrazine (3.4 g, 15.13 mmol, 1 eq.) in EtOH (30 mL) was added dropwise with vigorous stirring acetaldehyde (800.07 mg, 18.16 mmol, 1.02 mL, 1.2 eq.) at 30° C. The reaction mixture was stirred at 30° C. for 0.5 hours. The solvent was removed under reduced pressure to afford 6-chloro-N-[(E)-ethylideneamino]-2-(5-methyl-2-furyl)pyrimidin-4-amine (3.4 g, 89.6% yield) as a yellow solid. The crude product was used in the next step without further purification. LCMS m/z 251.3 [M+H]$^+$; HNMR (CDCl$_3$ 400 MHz) δ 9.27-9.22 (m, 0.7H), 8.57 (s, 0.3H), 7.23-7.22 (d, J=3.2 Hz, 0.3H), 7.19-7.18 (d, J=3.6 Hz, 0.7H), 7.09-7.05 (m, 0.7H), 6.98 (s, 0.3H), 6.95 (s, 0.7H), 6.85-6.81 (m, 0.3H), 6.16-6.13 (m, 1H), 2.42 (s, 1H), 2.38 (s, 2H), 1.96-1.94 (m, 2H), 1.89-1.87 (m, 1H).

Step 7: Preparation of 7-chloro-3-methyl-5-(5-methyl-2-furyl)-[1,2,4]triazolo[4,3-c]pyrimidine F

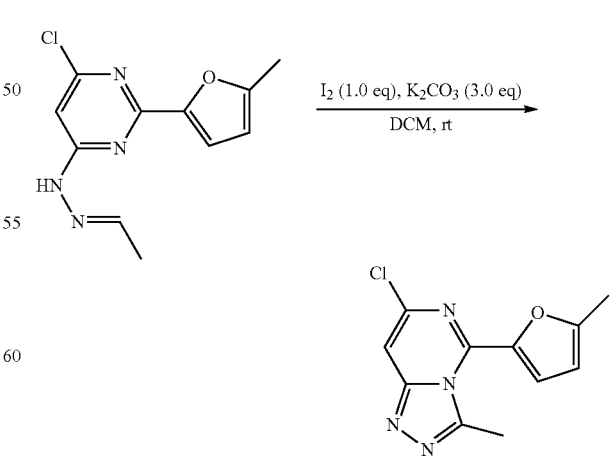

To the suspension of 6-chloro-N-[(E)-ethylideneamino]-2-(5-methyl-2-furyl)pyrimidin-4-amine (3.4 g, 13.56 mmol, 1 eq.) in CH₂Cl₂ (50 mL) was followed by the sequential addition of K₂CO₃ (5.62 g, 40.69 mmol, 3 eq.) and I₂ (3.44 g, 13.56 mmol, 1 eq.). The reaction mixture was stirred at 30° C. for 12 hours. The reaction mixture was quenched with 5% Na₂S₂O₃ (300 mL), and then extracted with CH₂C₂ (200 mL×3). The combined organic layer was washed with brine (100 mL), dried over anhydrous Na₂SO₄, filtration and concentrated to give 7-chloro-3-methyl-5-(5-methyl-2-furyl)-[1,2,4]triazolo[4,3-c]pyrimidine (3.2 g, crude) as a black-brown solid. The crude product was used in the next step without further purification. LCMS m/z 249.2 [M+H]⁺.

Step 8: Preparation of 7-chloro-2-methyl-5-(5-methyl-2-furyl)-[1,2,4]triazolo[1,5-c]pyrimidine

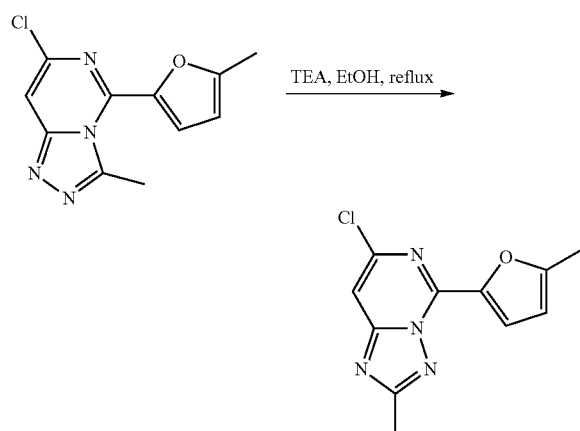

To a solution of 7-chloro-3-methyl-5-(5-methyl-2-furyl)-[1,2,4]triazolo[4,3-c]pyrimidine (3.2 g, 12.87 mmol, 1 eq.) in EtOH (30 mL) was added triethylamine (1.30 g, 12.87 mmol, 1.79 mL, 1 eq.) and the reaction mixture was stirred and heated at 80° C. for 12 hours TLC (Petroleum ether/Ethyl acetate=4/1, R_f=0.6) indicated reactant was consumed completely. The mixture was evaporated in vacuo to give the crude product. The crude product was re-slurried with EtOH (50 mL) and filtered to afford 7-chloro-2-methyl-5-(5-methyl-2-furyl)-[1,2,4]triazolo[1,5-c]pyrimidine as a yellow solid (2 g, 62.50% yield). LCMS m/z 248.9 [M+H]⁺; ¹HNMR (CDCl₃, 400 MHz) δ 8.24-8.23 (d, J=3.6 Hz, 1H), 7.40 (s, 1H), 6.35-6.34 (d, J=3.2 Hz, 1H), 2.64 (s, 3H), 2.52 (s, 3H).

Step 9: Preparation of N-[2-methyl-5-(5-methyl-2-furyl)-[1,2,4]triazolo[1,5-c]pyrimidin-7-yl]cyclopropanecarboxamide (2)

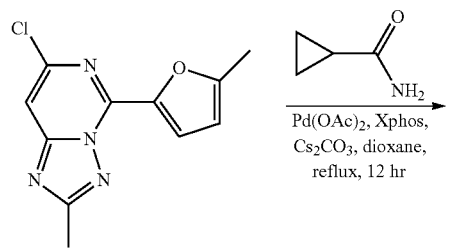

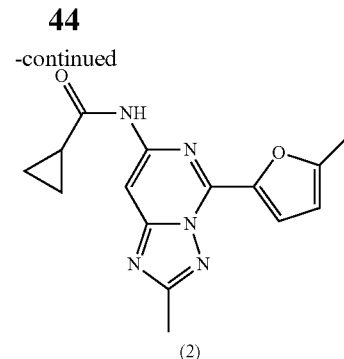

(2)

7-chloro-2-methyl-5-(5-methyl-2-furyl)-[1,2,4]triazolo[1,5-c]pyrimidine (2 g, 8.04 mmol, 1 eq.), cyclopropanecarboxamide (2.06 g, 24.21 mmol, 3.01 eq.), XPhos (384.00 mg, 805.51 μmol, 0.1 eq.), Pd(OAc)₂ (100.00 mg, 445.42 μmol, 0.0554 eq.) and Cs₂CO₃ (3.94 g, 12.09 mmol, 1.5 eq.) in dioxane (10 mL) was de-gassed and then the mixture was heated to 100° C. for 2 hours under N₂. The reaction mixture was partitioned between water (80 mL) and ethyl acetate (100 mL×2). The organic phase was separated, washed with brine (20 mL), dried with anhydrous Na₂SO₄, filtered and concentrated. The residue was purified by flash silica gel chromatography and then the mixture was washed by 10% ethyl acetate/petroleum ether and lyophilized to yield N-[2-methyl-5-(5-methyl-2-furyl)-[1,2,4]triazolo[1,5-c]pyrimidin-7-yl]cyclopropanecarboxamide (1.64 g, 68.5% yield) was obtained as a brown solid. LCMS m/z 298.1 [M+H]⁺; ¹HNMR (CDCl₃, 400 MHz) δ 8.50 (s, 1H), 8.25 (s, 1H), 8.24 (s, 1H), 6.36-6.35 (m, 1H), 2.63 (s, 3H), 2.52 (s, 3H), 1.59-1.53 (m, 1H), 1.17-1.13 (m, 2H), 0.94-0.89 (m, 2H).

Example 2: Preparation of 8-chloro-2-methyl-5-phenyl-[1,2,4]triazolo[1,5-c]pyrimidin-7-amine (33)

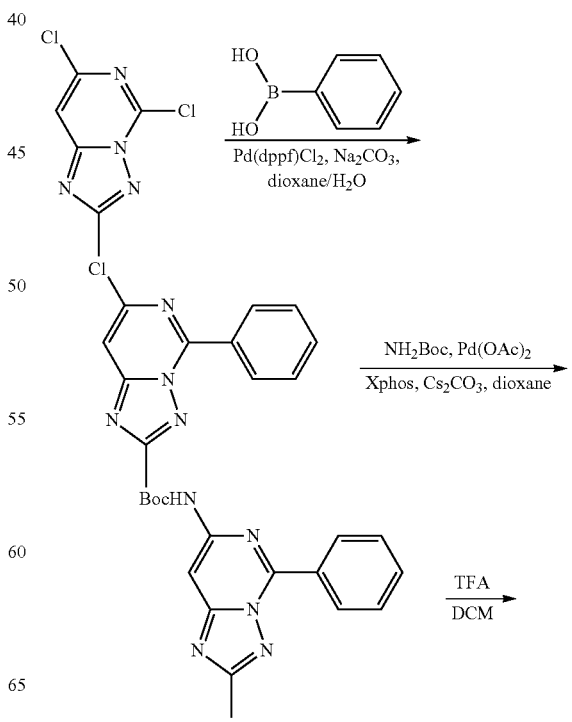

-continued

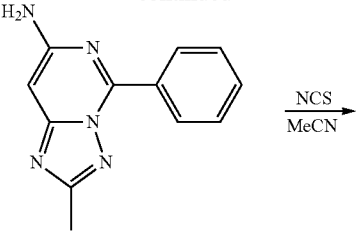

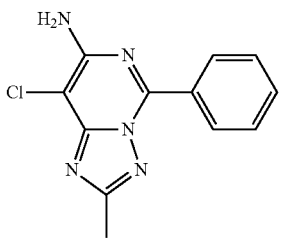

(33)

Step 1: Preparation of 7-chloro-3-methyl-5-phenyl-[1,2,4]triazolo[4,3-c]pyrimidine

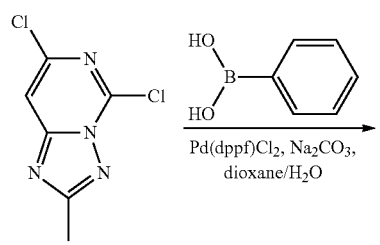

A mixture of 5,7-dichloro-3-methyl-[1,2,4]triazolo[4,3-c]pyrimidine (800 mg, 3.94 mmol, 1 eq.), phenylboronic acid (576.53 mg, 4.73 mmol, 1.2 eq.), Na$_2$CO$_3$ (835.27 mg, 7.88 mmol, 2 eq.), in dioxane (12 mL) and H$_2$O (2 mL), Pd(dppf)Cl$_2$ (144.16 mg, 197.02 μmol, 0.05 eq.) was added. The mixture was stirred at 80° C. for 20 hours under N$_2$ atmosphere. LC-MS showed the starting material was consumed completed. The reaction mixture filtered and concentrated under reduced pressure and was purified by column chromatography to afford a 7-chloro-3-methyl-5-phenyl-[1,2,4]triazolo[4,3-c]pyrimidine (410 mg, 1.68 mmol, 42.5% yield) as a white solid. LCMS m/z 244.9 [M+H]$^+$.

Step 2: Preparation of tert-butyl N-(3-methyl-5-phenyl-[1,2,4]triazolo[4,3-c]pyrimidin-7-yl)carbamate

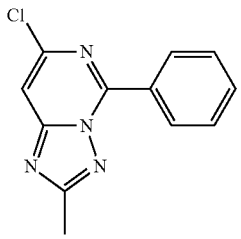

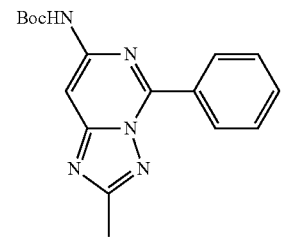

A mixture of 7-chloro-3-methyl-5-phenyl-[1,2,4]triazolo[4,3-c]pyrimidine (410 mg, 1.68 mmol, 1 eq.), NH$_2$Boc (392.61 mg, 3.35 mmol, 2.0 eq.), Cs$_2$CO$_3$ (818.95 mg, 2.51 mmol, 1.5 eq.) in dioxane (8 mL). The mixture was degassed and purged with N$_2$ for 3 min, then Pd(OAc)$_2$ (18.81 mg, 83.78 μmol, 0.05 eq.) and XPhos (78.18 mg, 164.00 μmol, 0.079e eq.) was added. The black mixture was stirred at 105° C. for 20 hours under N$_2$ atmosphere. LC-MS showed a starting material was consumed completed and showed a desired compound was formed. The reaction mixture was filtered and concentrated under reduced pressure to give a residue. The residue was purified by flash column chromatography to afford tert-butyl N-(3-methyl-5-phenyl-[1,2,4]triazolo[4,3-c]pyrimidin-7-yl)carbamate (545 mg, 1.68 mmol, 99.96% yield) as yellow oil. LCMS m/z 325.9 [M+H]$^+$.

Step 3: Preparation of 2-methyl-5-phenyl-[1,2,4]triazolo[1,5-c]pyrimidin-7-amine

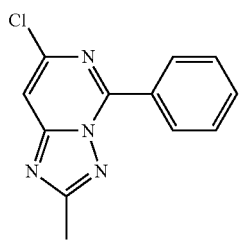

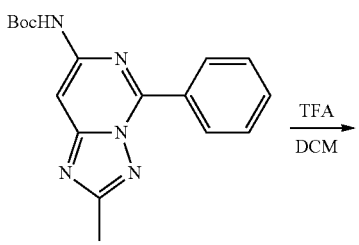

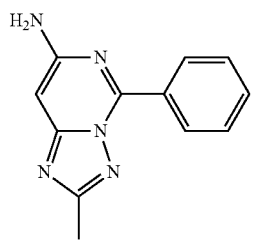

A mixture of tert-butyl N-(2-methyl-5-phenyl-[1,2,4]triazolo[1,5-c]pyrimidin-7-yl)carbamate (545 mg, 1.68 mmol, 1 eq.) in dichloromethane (8 mL) was added trifluoroacetic acid (2 mL). The yellow solution was degassed and purged with N₂ for 3 times, and then the mixture was stirred at 30° C. for 2 hours under N₂ atmosphere. The mixture was concentrated under reduced pressure and the residue was diluted with water (80 mL) and basified with sodium NaHCO₃ solution to pH=7-8. The aqueous layer was extracted with ethyl acetate (80 mL×3). The combined organic layers were washed with brine (80 mL), dried over Na₂SO₄ filtered and concentrated under reduced pressure to give 2-methyl-5-phenyl-[1,2,4]triazolo[1,5-c]pyrimidin-7-amine (377 mg, 1.67 mmol) as a white solid, which was used for next step directly without further purification. LCMS m/z 226.1 [M+H]⁺.

Step 4: Preparation of 8-chloro-2-methyl-5-phenyl-[1,2,4]triazolo[1,5-c]pyrimidin-7-amine (33)

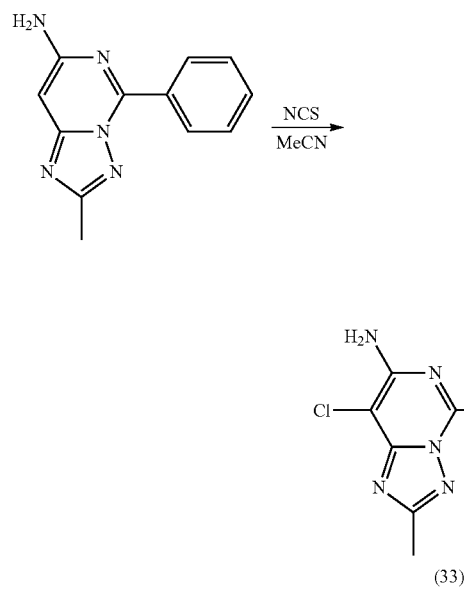

A mixture of 2-methyl-5-phenyl-[1,2,4]triazolo[1,5-c]pyrimidin-7-amine (377 mg, 1.67 mmol, 1 eq.), NCS (245.84 mg, 1.84 mmol, 1.1 eq.) in acetonitrile (3 mL), and then the mixture was stirred at 30° C. for 2 hours under N₂ atmosphere. The reaction mixture was basified with sodium NaHCO₃ solution until pH=7-8 was attained, and then diluted with water (50 mL) and extracted with EtOAc (50 mL×3). The combined organic layers were washed with brine (50 mL), dried over Na₂SO₄ filtered and concentrated under reduced to give a residue. The residue was purified by flash silica gel chromatography to afford 8-chloro-2-methyl-5-phenyl-[1,2,4]triazolo[1,5-c]pyrimidin-7-amine (290.9 mg, 1.12 mmol, 66.9% yield, 100% purity) as an off-white solid. LCMS m/z 260.1 [M+H]⁺; ¹H NMR (400 MHz, DMSO-d₆) δ 8.42-8.35 (dd, J=8.0, J=1.6 Hz, 2H), 7.66-7.55 (m, 3H), 7.1 (s, 2H), 2.40 (s, 3H)

Example 3: Preparation of N-(2-methyl-5-(oxazol-5-yl)-[1,2,4]triazolo[1,5-c]pyrimidin-7-yl)acetamide (51)

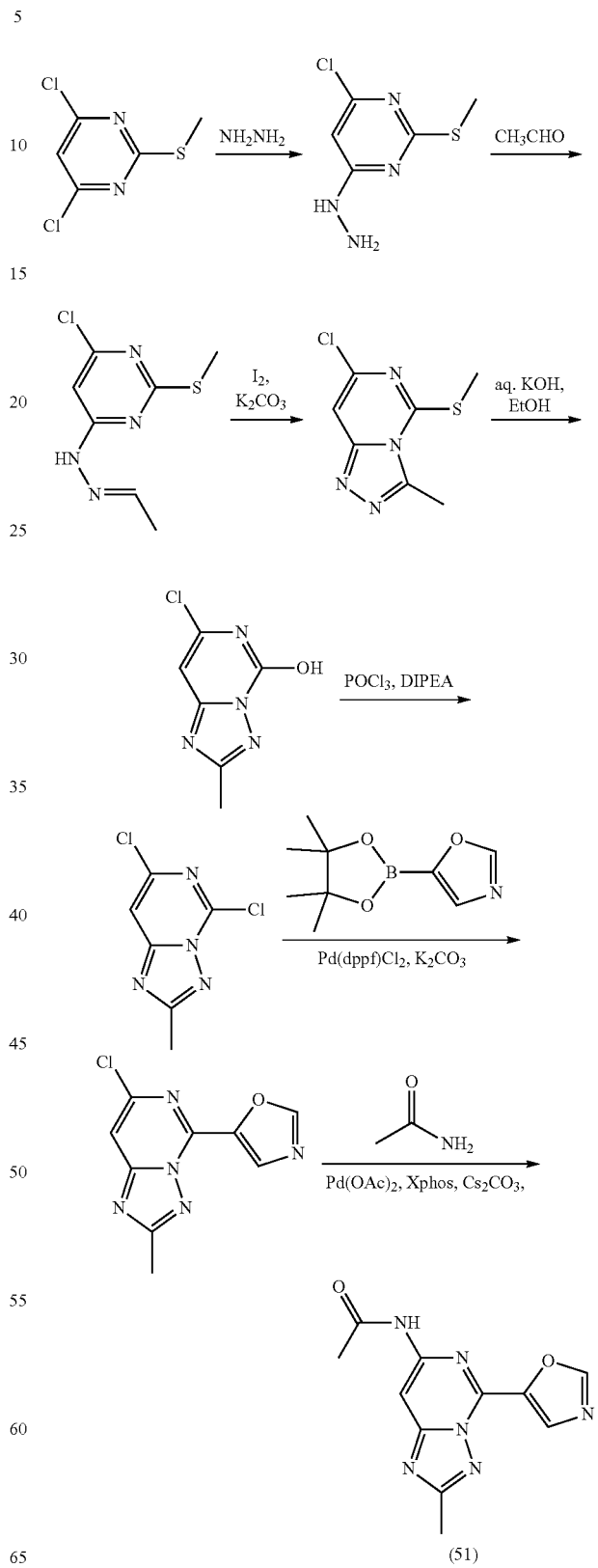

Step 1: Preparation of (6-chloro-2-methylthio-pyrimidin-4-yl)hydrazine

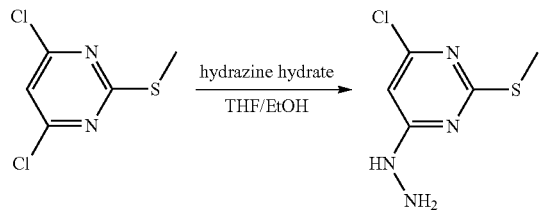

To a solution of 4,6-dichloro-2-methylthio-pyrimidine (40.50 g, 197.24 mmol, 1.0 eq.) in anhydrous tetrahydrofuran (250 mL) was dropwise a solution of hydrazine hydrate (16.32 g, 98% purity, 319.52 mmol, 1.62 eq.) in anhydrous tetrahydrofuran (150 mL) and anhydrous ethanol (50 mL) at below −10° C. within 1 hour. The resulting solution was allowed to warm to 0° C. and stirring was maintained for 3 hours to form a yellow suspension with lots of precipitates. After TLC (acidic silica gel, petroleum ether/ethyl acetate=3/1) confirmed reaction completion, the reaction mixture was concentrated to remove most of volatiles and then stirred in water (90 mL) for 15 minutes. The precipitate was collected by filtration and washed with water (10 mL×3) and triturated with petroleum ether/ethyl acetate (100 mL, v/v=19/1) for 30 minutes. The insoluble solid was collected by filtration, washed with petroleum ether (10 mL×2) and then dried over vacuum to afford (6-chloro-2-methylthio-pyrimidin-4-yl)hydrazine (29.60 g, 155.26 mmol, 78.7% yield) as an off-white solid. LCMS m/z 190.9 [M+H]$^+$; $^1$H NMR (DMSO-d$_6$ 400 MHz) δ 8.82 (s, 1H), 6.63-5.97 (m, 1H), 4.49 (s, 2H), 2.41 (s, 3H).

Step 2: Preparation of 6-chloro-N-ethylideneamino]-2-methylthio-pyrimidin-4-amine

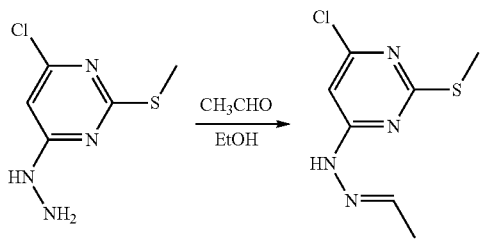

To a suspension of (6-chloro-2-methylthio-pyrimidin-4-yl)hydrazine (29.60 g, 155.26 mmol, 1.0 eq.) in anhydrous ethanol (450 mL) was added dropwise, acetaldehyde (14.70 mL, 259.28 mmol, 1.67 eq.). The resulting mixture was maintained stirring at 25° C. for 2 hours to provide a yellow suspension. After TLC (acidic silica gel, petroleum ether/Ethyl acetate=2/1) confirmed the completion, the reaction mixture was concentrated under reduced pressure to remove most of volatiles. The residue was dried over vacuum to afford 6-chloro-N-ethylideneamino]-2-methylthio-pyrimidin-4-amine (32.55 g mixture of (Z) and (E) isomers, 150.21 mmol, 96.75% yield) as a light yellow solid, which was used directly in the next step without further purification. $^1$H NMR (CDCl$_3$ 400 MHz) δ 8.16 (brs, 1H), 7.19 (q, J=5.6 Hz, 1H), 6.82 (s, 1H), 2.50 (s, 3H), 2.02 (d, J=5.2 Hz, 3H). (The major isomer), δ 8.10 (s, 1H), 6.86 (s, 1H), 6.83 (q, J=5.6 Hz, 1H), 2.53 (s, 3H), 1.90 (d, J=5.2 Hz, 3H). (The minor isomer)

Step 3: Preparation of 7-chloro-3-methyl-5-methylthio-[1,2,4]triazolo[4,3-c]pyrimidine

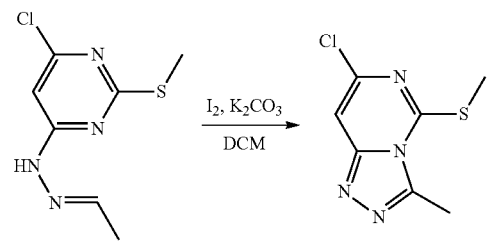

To a stirring solution of 6-chloro-N-ethylideneamino-2-methylthio-pyrimidin-4-amine (32.13 g mixture of (Z) and (E) isomers, 148.28 mmol, 1.0 eq.) in anhydrous dichloromethane (1000 mL) were added K$_2$CO$_3$ (62.30 g, 450.76 mmol, 3.04 eq.) and iodine (44.78 g, 176.45 mmol, 1.19 eq.). The resulted dark-red solution was maintained stirring at 25° C. for 60 hours to provide a dark-red suspension. After TLC (acidic silica gel, petroleum ether/Ethyl acetate=1/1) confirmed near completion, the reaction mixture was filtered to remove the insoluble solid. The filtrate was concentrated under reduced pressure. The residue was purified by column chromatograph to afford 7-chloro-3-methyl-5-methylthio-[1,2,4]triazolo[4,3-c]pyrimidine (18.44 g, 83.19 mmol) as a yellow solid. LCMS m/z 214.9 [M+H]$^+$; $^1$H NMR (Acetonitrile-d$_3$ 400 MHz) δ 7.30 (s, 1H), 2.98 (s, 3H), 2.68 (s, 3H).

Step 4: Preparation of 7-chloro-2-methyl-[1,2,4]triazolo[1,5-c]pyrimidin-5-ol

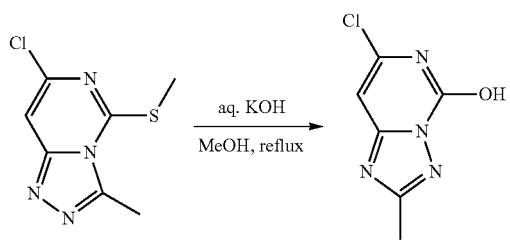

To a solution of 7-chloro-3-methyl-5-methylthio-[1,2,4]triazolo[4,3-c]pyrimidine (18.40 g, 83.01 mmol, 1.0 eq.) in methanol (750 mL) was added dropwise a solution of KOH (13.97 g, 249.02 mmol, 3.00 eq.) in water (125 mL). The resulted mixture was heated to 65° C. and maintained stirring for 4 hours to provide a red solution. After TLC confirmed the completion, the reaction mixture was concentrated to remove most of methanol and was neutralized with 6 N HCl solution. The formed precipitate was collected by filtration, washed with water and dried over high vacuum to give 7-chloro-2-methyl-[1,2,4]triazolo[1,5-c]pyrimidin-5-ol (9.66 g, 52.33 mmol, 63.0% yield) as an off-white solid. LCMS m/z 184.9 [M+H]$^+$; $^1$H NMR (DMSO-d$_6$ 400 MHz) δ 6.17 (s, 1H), 2.26 (s, 3H);

Step 5: Preparation of 5,7-dichloro-2-methyl-[1,2,4]triazolo[1,5-c]pyrimidine

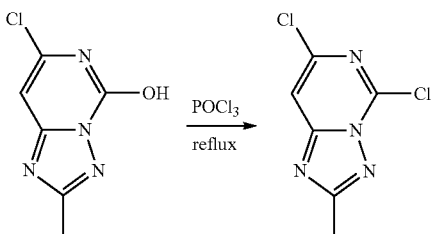

7-chloro-2-methyl-[1,2,4]triazolo[1,5-c]pyrimidin-5-ol (9.66 g, 52.33 mmol, 1.0 eq.) was suspended in phosphorus oxychloride (102.90 mL, 1.11 mol, 21.16 eq.) under nitrogen. The resulted mixture was heated to 117° C. and maintained stirring for 10 hours to provide a red solution. After LCMS confirmed the completion, the reaction mixture was cooled and concentrated to remove most of the volatiles, co-evaporated with toluene (120 mL) twice, and then suspended in water (250 mL) and dichloromethane (300 mL). The resulted suspension was neutralized with $NaHCO_3$ powder to pH=7 under vigorously stirring. The organic phase was separated and the aqueous phase was extracted with dichloromethane (150 mL×2). The combined organic extracts were washed with brine (250 mL), dried over anhydrous $Na_2SO_4$, filtered and concentrated over vacuum to give 5,7-dichloro-2-methyl-[1,2,4]triazolo[1,5-c]pyrimidine (7.90 g, 38.91 mmol, 74.3% yield) as a light red solid, which was used directly in the next step without further purifications. LCMS m/z 202.9 [M+H]+; 1H NMR (CDCl3 400 MHz) δ 7.56 (s, 1H), 2.66 (s, 3H).

Step 6: Preparation of 5-(7-chloro-2-methyl-[1,2,4]triazolo[1,5-c]pyrimidin-5-yl)oxazole

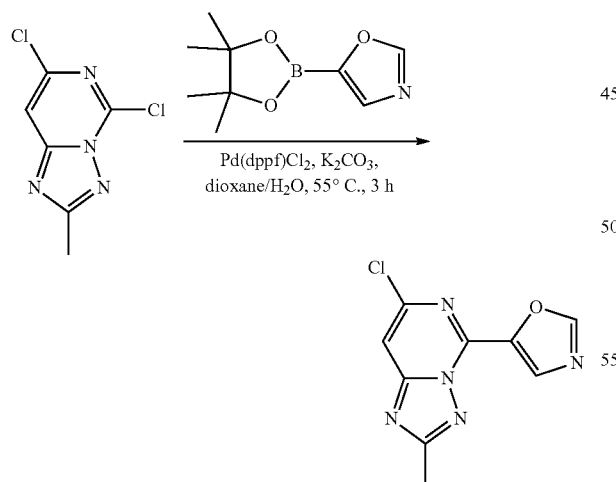

To a solution of 5,7-dichloro-2-methyl-[1,2,4]triazolo[1,5-c]pyrimidine (60 mg, 295.52 μmol, 1 eq.) and 5-(4,4,5,5-tetramethyl-1,3,2-dioxaborolan-2-yl)oxazole (57.63 mg, 295.52 μmol, 1 eq.) in dioxane (2 mL) and $H_2O$ (0.4 mL) were added $K_2CO_3$ (102.11 mg, 738.81 μmol, 2.5 eq.) and Pd(dppf)Cl2 (21.62 mg, 29.55 μmol, 0.1 eq.) under N2 atmosphere. The resulting solution was heated to 55° C. for 12 hours and added water (20 mL). The mixture was extracted with EtOAc (25 mL×3) and the combined organic layers were dried over anhydrous sodium sulfate, concentrated in vacuum to give the residue. The residue was purified by column chromatography to give the title compound, 5-(7-chloro-2-methyl-[1,2,4]triazolo[1,5-c]pyrimidin-5-yl)oxazole (20 mg, 25.85% yield, 90% purity) was obtained as an off-white solid. LCMS m/z 236 [M+H]+

Step 7: Preparation of N-(2-methyl-5-(oxazol-5-yl)-[1,2,4]triazolo[1,5-c]pyrimidin-7-yl)acetamide (51)

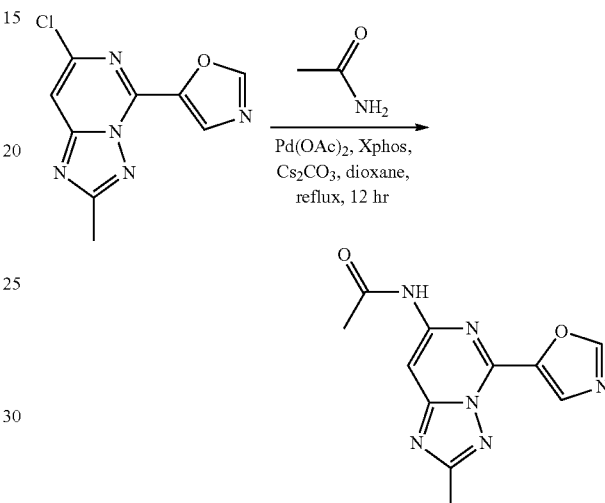

5-(7-chloro-2-methyl-[1,2,4]triazolo[1,5-c]pyrimidin-5-yl)oxazole (20 mg, 0.848 mmol, 1 eq.), acetoamide (15.04 mg, 2.546 mmol, 3.01 eq.), XPhos (8.09 mg, 805.51 μmol, 0.2 eq.), Pd(OAc)2 (1.91 mg, 8.49 μmol, 0.1 eq.) and $Cs_2CO_3$ (69.14 mg, 0.212 mmol, 2.5 eq.) in dioxane (2 mL) was de-gassed and then the mixture was heated to 100° C. for 4 hours under N2. The reaction mixture was partitioned between water (20 mL) and ethyl acetate (25 mL×2). The organic phase was separated, washed with brine (20 mL), dried with anhydrous $Na_2SO_4$ followed by filtered and concentrated. The residue was purified by flash silica gel chromatography to yield N-(2-methyl-5-oxazol-5-yl-[1,2,4]triazolo[1,5-c]pyrimidin-7-yl)acetamide (5.1 mg, 17.77 μmol, 20.9% yield) as yellow solid. LCMS m/z 259.1 [M+H]+; 1HNMR (CDCl3, 400 MHz) δ=11.13 (s, 1H), 8.89 (s, 1H), 8.63 (s, 1H), 8.19 (s, 1H), 2.68 (s, 3H), 2.18 (s, 3H)

Example 4: Preparation of 2-isopropyl-8-methyl-5-(5-methylfuran-2-yl)-7H-pyrrolo[3,2-e][1,2,4]triazolo[1,5-c]pyrimidine (75)

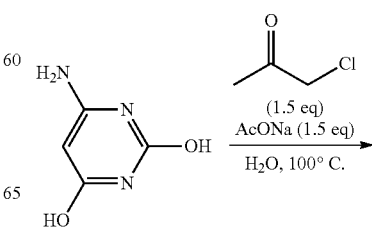

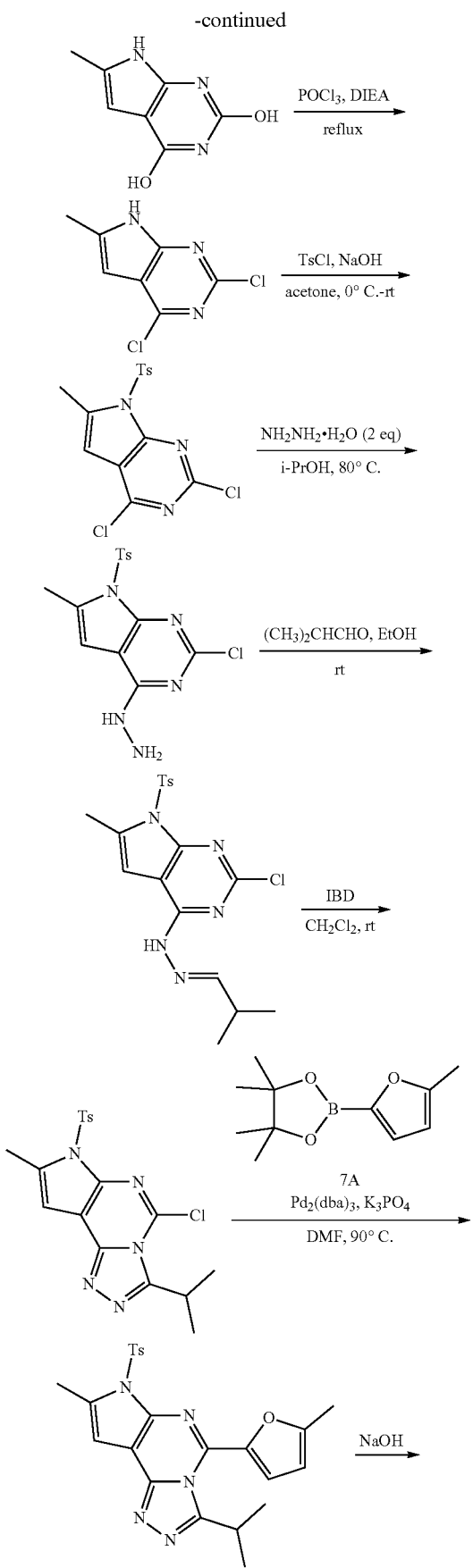

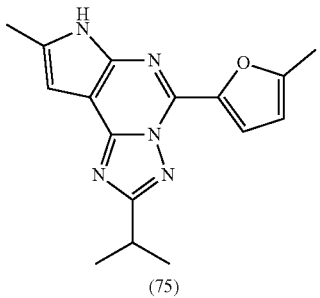

(75)

Step 1: Preparation of 6-methyl-7H-pyrrolo[2,3-d]pyrimidine-2,4-diol

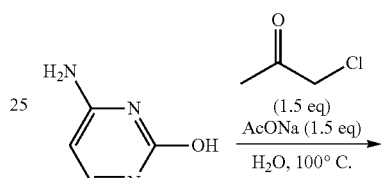

A solution of 6-amino-1H-pyrimidine-2,4-dione (45 g, 354.05 mmol, 1 eq.) was treated at 30° C. with AcONa (45.00 g, 548.55 mmol, 1.55 eq.) dissolved in H₂O (1800 mL). After the mixture was stirred for 30 min at 30° C., 1-chloropropan-2-one (49.50 g, 535.00 mmol, 45.00 mL, 1.51 eq.) was added, and the solution was heated to 100° C. for 72 h. The reaction was cooled and filtered to yield compound. The crude product was used in the next step without further purification. 6-methyl-7H-pyrrolo[2,3-d]pyrimidine-2,4-diol (28 g, 47.89% yield) was obtained as a yellow solid; ¹HNMR (DMSO-d₆ 400 MHz) δ 11.66-10.75 (m, 2H), 10.37 (br s, 1H), 5.87 (s, 1H), 2.13 (s, 3H).

Step 2: Preparation of 2,4-dichloro-6-methyl-7H-pyrrolo[2,3-d]pyrimidine

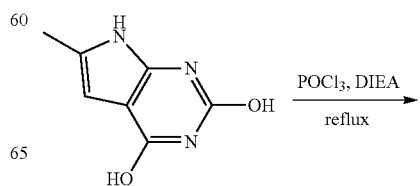

-continued

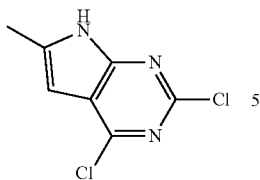

A mixture of 6-methyl-7H-pyrrolo[2,3-d]pyrimidine-2,4-diol (15 g, 90.83 mmol, 1 eq.) and DIEA (28.48 mL, 163.49 mmol, 1.8 eq.) in POCl₃ (100 mL, 1.08 mol, 11.85 eq.) was stirred at 110° C. for 36 hours. The solvent was removed under pressure, and CH₂Cl₂ (600 mL.) and ice water (400 mL) were slowly added, washed with water (150 mL×2), saturated solution of sodium bicarbonate (150 mL×2), brine, and dried over Na₂SO₄, filtered and concentrated to afford 2,4-dichloro-6-methyl-7H-pyrrolo[2,3-d]pyrimidine (10 g, 54.4% yield) as a yellow solid. The crude product was used into the next step without further purification. LCMS m/z 202.3 [M+H]⁺

Step 3: Preparation of 2,4-dichloro-6-methyl-7-(p-tolylsulfonyl)pyrrolo[2,3-d]pyrimidine

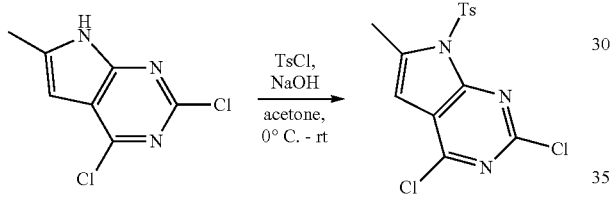

Sodium hydroxide (5.35 g, 133.64 mmol, 3 eq.) was added to a solution of 2,4-dichloro-6-methyl-7H-pyrrolo[2,3-d]pyrimidine (9 g, 44.55 mmol, 1 eq.) in acetone (100 mL) at 0° C. Then a solution of 4-methylbenzenesulfonyl chloride (10.19 g, 53.45 mmol, 1.2 eq.) in acetone (50 mL) was added dropwise to the above solution at 0° C. The reaction mixture was stirred at 16° C. for 3 h. The desired mass was detected by LCMS. The reaction mixture was filtered upon addition of water (150 mL). The filter cake washed with H₂O/acetone (100 mL/50 mL) to give a 2,4-dichloro-6-methyl-7-(p-tolylsulfonyl)pyrrolo[2,3-d]pyrimidine (12.9 g, 81.29% yield) as a yellow solid. LCMS m/z 356.3 [M+H]⁺; ¹HNMR (CDCl₃ 400 MHz) δ 8.09 (d, J=8.3 Hz, 2H), 7.36 (d, J=8.0 Hz, 2H), 6.37 (d, J=1.0 Hz, 1H), 2.76 (s, 3H), 2.43 (s, 3H).

Step 4: Preparation of [2-chloro-6-methyl-7-(p-tolylsulfonyl)pyrrolo[2,3-d]pyrimidin-4-yl]hydrazine

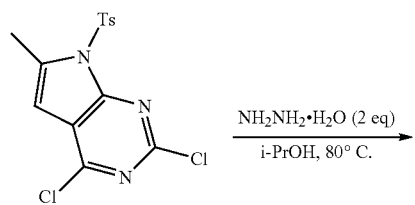

-continued

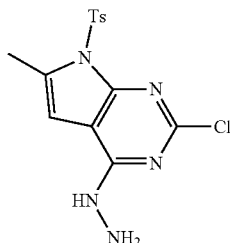

A solution of 2,4-dichloro-6-methyl-7-(p-tolylsulfonyl) pyrrolo[2,3-d]pyrimidine (12 g, 33.69 mmol, 1 eq.) and NH₂NH₂·H₂O (3.37 g, 67.37 mmol, 2 eq.) in i-PrOH (150 mL) was stirred at 80° C. for 2 hours. After completion, the solvent was partially removed under reduced pressure. The resulting solid was filtered, washed with water (50 mL), methyl tertiary butyl ether (50 mL) and dried to afford[2-chloro-6-methyl-7-(p-tolylsulfonyl)pyrrolo[2,3-d]pyrimidin-4-yl]hydrazine (11 g, 92.82% yield) as a yellow solid. LCMS m/z 352.4 [M+H]⁺; ¹HNMR (CDCl₃ 400 MHz) δ 8.06 (br d, J=8.4 Hz, 2H), 7.31 (br d, J=8.0 Hz, 2H), 6.67 (br s, 1H), 6.38 (br s, 1H), 4.03 (br s, 2H), 2.66 (s, 3H), 2.41 (s, 3H).

Step 5: Preparation of 2-chloro-6-methyl-N-[(E)-2-methylpropylideneamino]-7-(p-tolylsulfonyl) pyrrolo[2,3-d]pyrimidin-4-amine

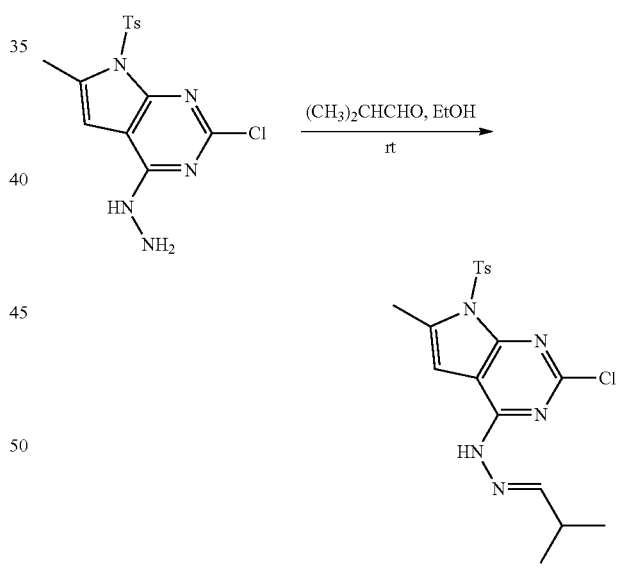

To the suspension of [2-chloro-6-methyl-7-(p-tolylsulfonyl)pyrrolo[2,3-d]pyrimidin-4-yl]hydrazine (2.5 g, 7.11 mmol, 1 eq.) in EtOH (20 mL) was added dropwise with vigorous stirring 2-methylpropanal (614.87 mg, 8.53 mmol, 1.2 eq.) at 16° C. The reaction mixture was stirred at 16° C. for 1 hour. The solvent was removed under reduced pressure to afford the crude product, 2-chloro-6-methyl-N-[(E)-2-methylpropylideneamino]-7-(p-tolylsulfonyl)pyrrolo[2,3-d] pyrimidin-4-amine (2.8 g, 97.07% yield) as a yellow solid. The crude product was used in the next step without further purification. LCMS m/z 406.4 [M+H]⁺

Step 6: Preparation of 5-chloro-3-isopropyl-8-methyl-7-tosyl-7H-pyrrolo[3,2-e][1,2,4]triazolo[4,3-c]pyrimidine

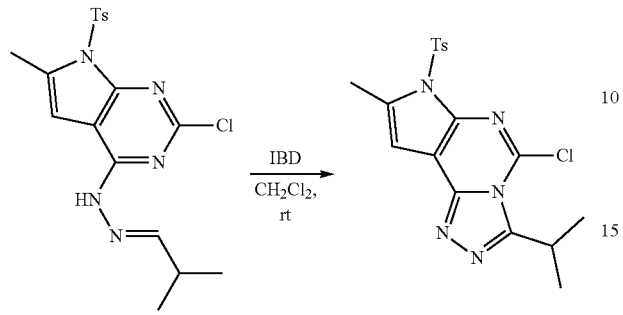

Iodosobenzene diacetate (2.89 g, 8.97 mmol, 1.3 eq.) was added to a suspension of 2-chloro-6-methyl-N-[(E)-2-methylpropylideneamino]-7-(p-tolylsulfonyl)pyrrolo[2,3-d]pyrimidin-4-amine (2.8 g, 6.90 mmol, 1 eq.) in $CH_2Cl_2$ (50 mL) and the mixture was stirred at 30° C. for 2 hours. The reaction mixture was concentrated under reduce pressure and was purified by flash silica gel chromatography to afford 5-chloro-3-isopropyl-8-methyl-7-tosyl-7H-pyrrolo[3,2-e][1,2,4]triazolo[4,3-c]pyrimidine (1.5 g, 53.84% yield) as a yellow solid. LCMS m/z 404.4 [M+H]$^+$; $^1$HNMR (CDCl$_3$, 400 MHz) δ 8.04 (d, J=8.4 Hz, 2H), 7.35 (d, J=8.0 Hz, 2H), 6.77 (d, J=0.8 Hz, 1H), 4.03 (spt, J=6.8 Hz, 1H), 2.75 (s, 3H), 2.42 (s, 3H), 1.55 (d, J=6.8 Hz, 6H).

Step 7: Preparation of 3-isopropyl-8-methyl-5-(5-methylfuran-2-yl)-7-tosyl-7H-pyrrolo[3,2-e][1,2,4]triazolo[4,3-c]pyrimidine

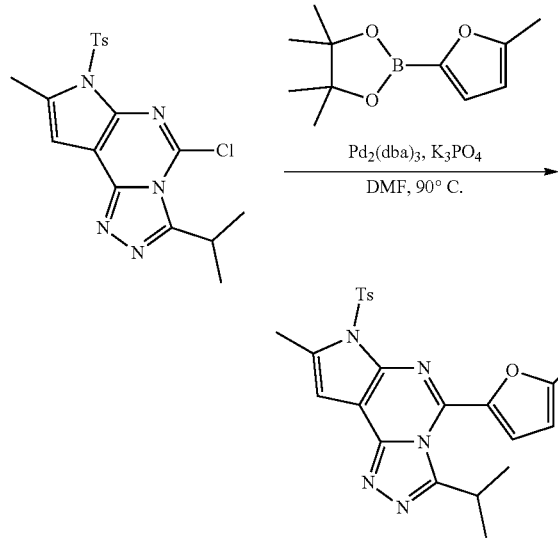

A mixture of 5-chloro-3-isopropyl-8-methyl-7-tosyl-7H-pyrrolo[3,2-e][1,2,4]triazolo[4,3-c]pyrimidine (350 mg, 866.58 µmol, 1 eq.), 4,4,5,5-tetramethyl-2-(5-methyl-2-furyl)-1,3,2-dioxaborolane (540.91 mg, 2.60 mmol, 3 eq.), $K_3PO_4$ (367.90 mg, 1.73 mmol, 2 eq.) and Pd$_2$(dba)$_3$ (39.68 mg, 43.33 µmol, 0.05 eq.) in DMF (10 mL) was stirred at 90° C. for 2 h under N$_2$. The resulting solution was heated to 85° C. for 12 hours. The reaction mixture was added water (20 mL) and was extracted with EtOAc (25 mL×3). The combined organic layers were dried over anhydrous sodium sulfate, concentrated in vacuum to give a crude product, 3-isopropyl-8-methyl-5-(5-methylfuran-2-yl)-7-tosyl-7H-pyrrolo[3,2-e][1,2,4]triazolo[4,3-c]pyrimidine (300 mg, 77.01% yield), which was used into the next step without further purification. LCMS m/z 450.0 [M+H]$^+$

Step 8: Preparation of 2-isopropyl-8-methyl-5-(5-methylfuran-2-yl)-7H-pyrrolo[3,2-e][1,2,4]triazolo[1,5-c]pyrimidine (75)

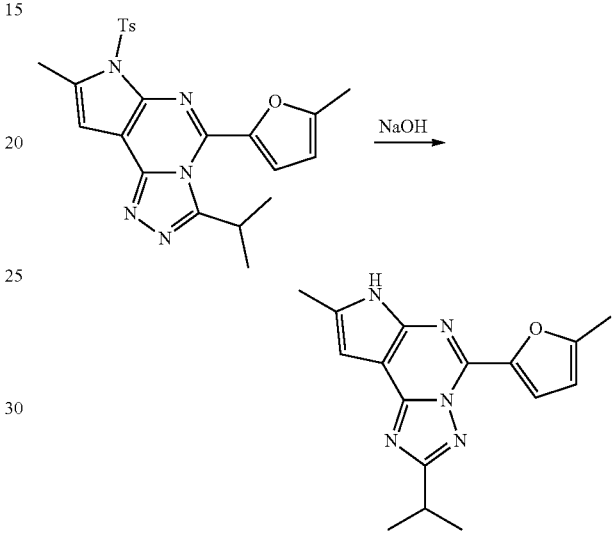

A 3-isopropyl-8-methyl-5-(5-methylfuran-2-yl)-7-tosyl-7H-pyrrolo[3,2-e][1,2,4]triazolo[4,3-c]pyrimidine (290 mg, 645.13 µmol, 1 eq.) and NaOH (51.61 mg, 1.29 mmol, 2 eq.) in EtOH (20 mL) was stirred at 60° C. for 2 hours. The reaction mixture was concentrated under reduced pressure and was purified by flash silica gel chromatography to give a 2-isopropyl-8-methyl-5-(5-methylfuran-2-yl)-7H-pyrrolo[3,2-e][1,2,4]triazolo[1,5-c]pyrimidine (57.9 mg, 29.56% yield) was obtained as a yellow solid. LCMS m/z 296.1 [M+H]$^+$; $^1$HNMR (CDCl$_3$, 400 MHz) δ 8.97 (br s, 1H), 8.17 (d, J=3.6 Hz, 1H), 6.66 (d, J=1.2 Hz, 1H), 6.32 (dd, J=0.8, 3.6 Hz, 1H), 3.35 (spt, J=6.8 Hz, 1H), 2.52 (s, 3H), 2.50 (s, 3H), 1.52 (d, J=7.2 Hz, 6H).

Example 5: Preparation of 2-methyl-5-(5-methylfuran-2-yl)-7,9-dihydro-8H-pyrrolo[3,2-e][1,2,4]triazolo[1,5-c]pyrimidin-8-one (97)

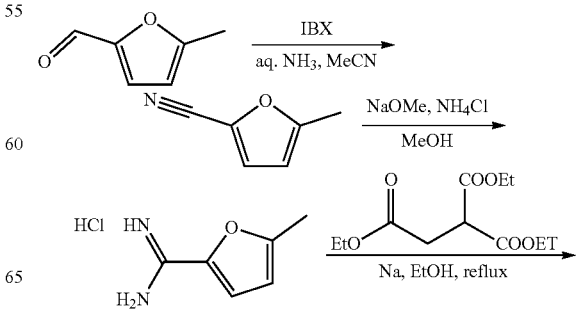

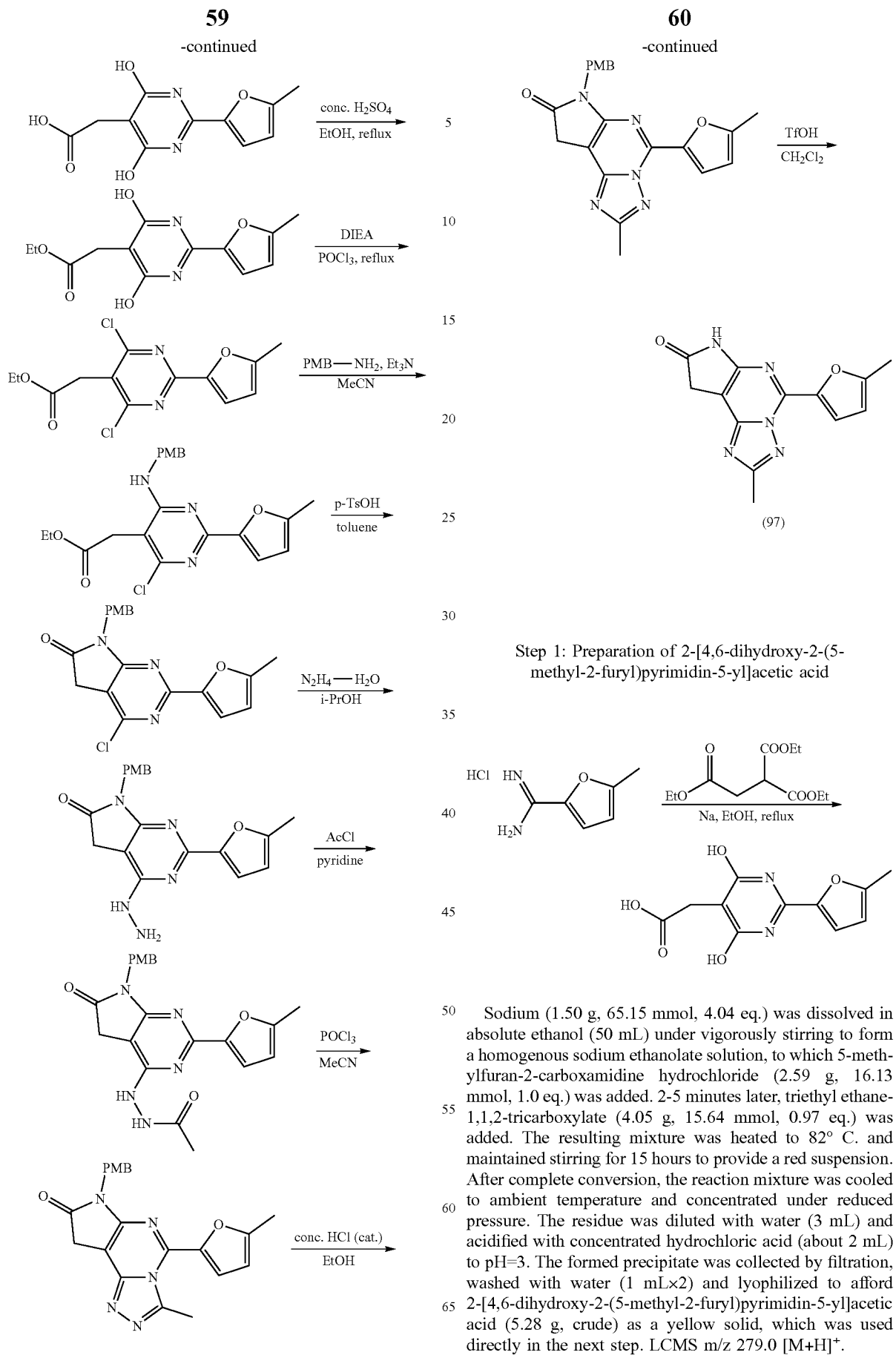

Step 1: Preparation of 2-[4,6-dihydroxy-2-(5-methyl-2-furyl)pyrimidin-5-yl]acetic acid Sodium (1.50 g, 65.15 mmol, 4.04 eq.) was dissolved in absolute ethanol (50 mL) under vigorously stirring to form a homogenous sodium ethanolate solution, to which 5-methylfuran-2-carboxamidine hydrochloride (2.59 g, 16.13 mmol, 1.0 eq.) was added. 2-5 minutes later, triethyl ethane-1,1,2-tricarboxylate (4.05 g, 15.64 mmol, 0.97 eq.) was added. The resulting mixture was heated to 82° C. and maintained stirring for 15 hours to provide a red suspension. After complete conversion, the reaction mixture was cooled to ambient temperature and concentrated under reduced pressure. The residue was diluted with water (3 mL) and acidified with concentrated hydrochloric acid (about 2 mL) to pH=3. The formed precipitate was collected by filtration, washed with water (1 mL×2) and lyophilized to afford 2-[4,6-dihydroxy-2-(5-methyl-2-furyl)pyrimidin-5-yl]acetic acid (5.28 g, crude) as a yellow solid, which was used directly in the next step. LCMS m/z 279.0 [M+H]$^+$.

Step 2: Preparation of ethyl 2-[4,6-dihydroxy-2-(5-methyl-2-furyl)pyrimidin-5-yl]acetate

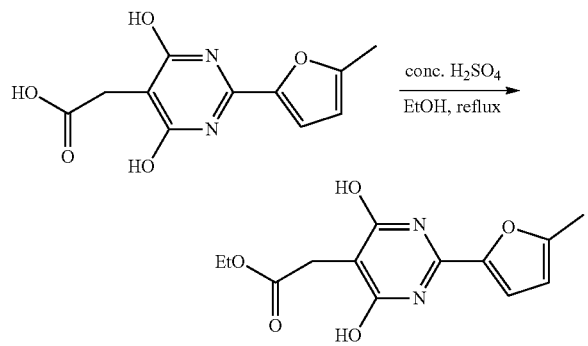

To a suspension of 2-[4,6-dihydroxy-2-(5-methyl-2-furyl) pyrimidin-5-yl]acetic acid (5.28 g, crude) in anhydrous ethanol (40 mL) was added sulfuric acid (188 mg, 98%, 1.88 mmol). The resulting mixture was heated to 85° C. and maintained stirring for 18 hours to provide a yellow suspension. The reaction mixture was cooled to ambient temperature and concentrated. The residue was then triturated with water (30 mL). The resulted solid was washed with water (10 mL×2) and cold ethanol (5 mL×2), then dried over high vacuum to afford ethyl 2-[4,6-dihydroxy-2-(5-methyl-2-furyl)pyrimidin-5-yl]acetate (3.29 g, 11.82 mmol, 56.3% yield) as a light yellow solid. LCMS m/z 279.1 [M+H]$^+$; $^1$H NMR (DMSO-d$_6$ 400 MHz) δ 12.00 (brs, 2H), 7.49 (d, J=3.6 Hz, 1H), 6.36 (d, J=2.8 Hz, 1H), 4.04 (q, J=7.2 Hz, 2H), 3.27 (s, 2H), 2.36 (s, 3H), 1.17 (t, J=7.2 Hz, 3H).

Step 3: Preparation of ethyl 2-[4,6-dichloro-2-(5-methyl-2-furyl)pyrimidin-5-yl]acetate

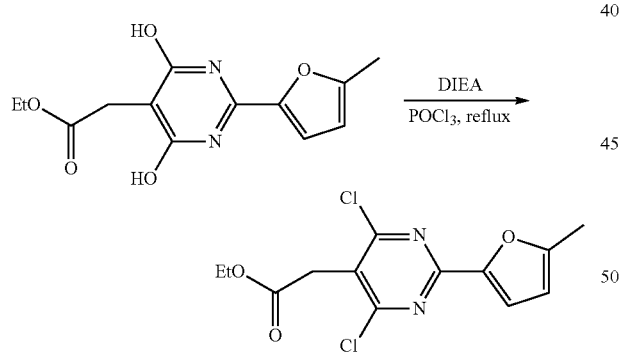

A mixture of ethyl 2-[4,6-dihydroxy-2-(5-methyl-2-furyl) pyrimidin-5-yl]acetate (3.29 g, 11.82 mmol, 1.0 eq.) and DIEA (2.23 g, 17.22 mmol, 3.0 mL, 1.46 eq.) in phosphorus oxychloride (18 mL) was heated to 108° C. and maintained stirring for 3 hours to provide a dark red solid. After complete conversion, the reaction mixture was cooled to ambient temperature and concentrated. The residue was suspended in dichloromethane (20 mL) and basified with saturated NaHCO$_3$ solution (50 mL) to pH=7, then extracted with dichloromethane (30 mL×3). The combined organic layers were washed with brine (40 mL), dried over anhydrous Na$_2$SO$_4$, filtered and concentrated under reduced pressure to afford ethyl 2-[4,6-dichloro-2-(5-methyl-2-furyl) pyrimidin-5-yl]acetate (3.27 g, 9.27 mmol, 78.4% yield) as a dark brown solid, which was used directly in the next step without further purifications. LCMS m/z 315.0 [M+H]$^+$.

Step 4: Preparation of ethyl 2-[4-chloro-6-(4-methoxybenzylamino)-2-(5-methyl-2-furyl)pyrimidin-5-yl]acetate

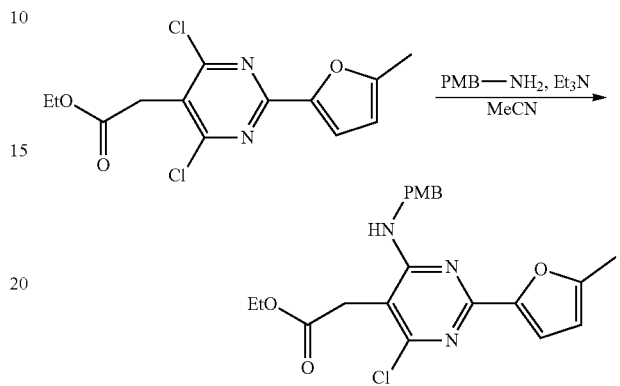

To a solution of ethyl 2-[4,6-dichloro-2-(5-methyl-2-furyl)pyrimidin-5-yl]acetate (3.27 g, 9.27 mmol, 1.0 eq.) in acetonitrile (50 mL) were added 4-methoxybenzylamine (1.50 g, 10.39 mmol, 1.12 eq.) and triethylamine (1.17 g, 11.59 mmol, 1.25 eq.). The resulting mixture was heated to 80° C. and maintained stirring for 12 hours to provide a red solution. The reaction mixture was cooled to ambient temperature and suspended in ethyl acetate (300 mL), then washed with water (100 mL×2) and brine (120 mL), dried over anhydrous Na$_2$SO$_4$, filtered and concentrated under reduced pressure to afford ethyl 2-[4-chloro-6-(4-methoxybenzylamino)-2-(5-methyl-2-furyl)pyrimidin-5-yl]acetate (3.86 g, quantitative yield) as a red solid, which was used directly in the next step. LCMS m/z 416.1 [M+H]$^+$; $^1$H NMR (CDCl$_3$ 400 MHz) 37.30 (d, J=8.8 Hz, 2H), 7.16 (d, J=3.2 Hz, 1H), 6.92-6.81 (m, 2H), 6.12 (d, J=3.6 Hz, 1H), 5.87 (t, J=4.8 Hz, 1H), 4.68 (d, J=5.6 Hz, 2H), 4.06 (q, J=4.0 Hz, 2H), 3.79 (s, 3H), 3.63 (s, 2H), 2.41 (s, 3H), 1.19 (t, J=7.2 Hz, 3H).

Step 5: Preparation of 4-chloro-7-(4-methoxybenzyl)-2-(5-methyl-2-furyl)-5H-pyrrolo[2,3-d]pyrimidin-6-one

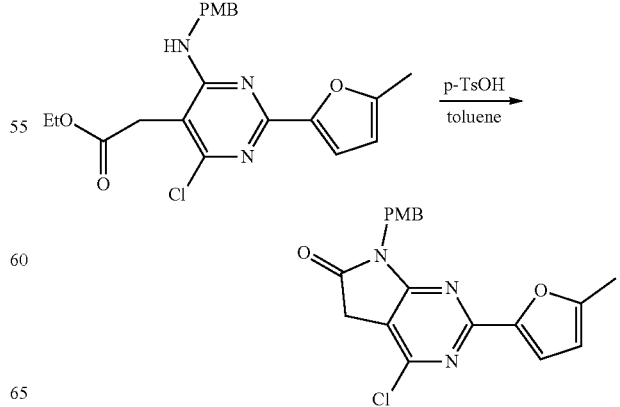

A solution of ethyl 2-[4-chloro-6-(4-methoxybenzylamino)-2-(5-methyl-2-furyl)pyrimidin-5-yl]acetate (3.86 g, 9.28 mmol, 1.0 eq.) and p-toluenesulfonic acid monohydrate (399 mg, 2.10 mmol, 0.226 eq.) in anhydrous toluene (260 mL) was heated to 120° C. under nitrogen atmosphere and maintained stirring for 18 hours to provide a dark red solution. The reaction mixture was dissolved in ethyl acetate/methanol (1.05 L, v/v=20/1). The resulting solution was washed with saturated NaHCO₃ solution (200 mL), water (200 mL) and brine (300 mL), dried over anhydrous Na₂SO₄, filtered and concentrated under reduced pressure to afford 4-chloro-7-(4-methoxybenzyl)-2-(5-methyl-2-furyl)-5H-pyrrolo[2,3-d]pyrimidin-6-one (3.61 g, 93.8% yield) as a brown solid, which was used directly in the next step. LCMS m/z 370.0 [M+H]⁺; ¹H NMR (CDCl₃ 400 MHz) 37.47 (d, J=8.8 Hz, 2H), 7.32 (d, J=3.2 Hz, 1H), 6.84 (d, J=8.4 Hz, 2H), 6.21 (d, J=2.8 Hz, 1H), 4.91 (s, 2H), 3.77 (s, 3H), 3.55 (s, 2H), 2.47 (s, 3H).

Step 6: Preparation of 4-hydrazino-7-(4-methoxybenzyl-2-(5-methyl-2-furyl)-5H-pyrrolo[2,3-d]pyrimidin-6-one

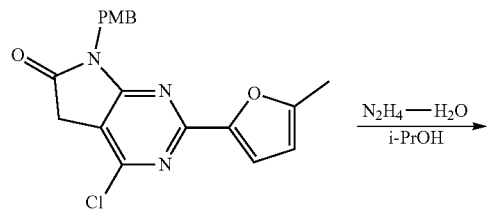

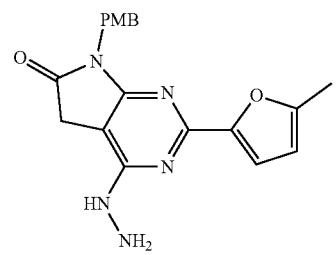

To a solution of 4-chloro-7-(4-methoxybenzyl)-2-(5-methyl-2-furyl)-5H-pyrrolo[2,3-d]pyrimidin-6-one (3.61 g, 2.22 mmol, 1.0 eq.) in 2-propanol (23 mL) was added hydrazine hydrate (382 mg, 98%, 7.48 mmol, 3.37 eq.). The resulting mixture was heated to 98° C. under nitrogen atmosphere and maintained stirring for 17 hours to provide a yellow green solution. The reaction mixture was cooled to ambient temperature and concentrated under reduced pressure to remove most of volatiles, then suspended in water (20 mL). The resulted precipitate was collected by filtration, washed with water (5 mL×2) and then dried over vacuum to afford 4-hydrazino-7-(4-methoxybenzyl-2-(5-methyl-2-furyl)-5H-pyrrolo[2,3-d]pyrimidin-6-one (791 mg, 2.16 mmol, 97.56% yield) as a brown solid, which was used directly in the next step. LCMS m/z 366.1 [M+H]⁺; ¹H NMR (DMSO-d₆ 400 MHz) δ 8.29 (s, 1H), 7.31 (d, J=8.4 Hz, 2H), 7.07 (d, J=3.6 Hz, 1H), 6.86 (d, J=8.4 Hz, 2H), 6.25 (d, J=2.4 Hz, 1H), 4.75 (s, 2H), 4.44 (brs, 2H), 3.70 (s, 3H), 3.66 (s, 2H), 2.35 (s, 3H).

Step 7: Preparation of N'-[7-(4-methoxybenzyl)-2-(5-methyl-2-furyl)-6-oxo-5H-pyrrolo[2,3-d]pyrimidin-4-yl]acetohydrazide

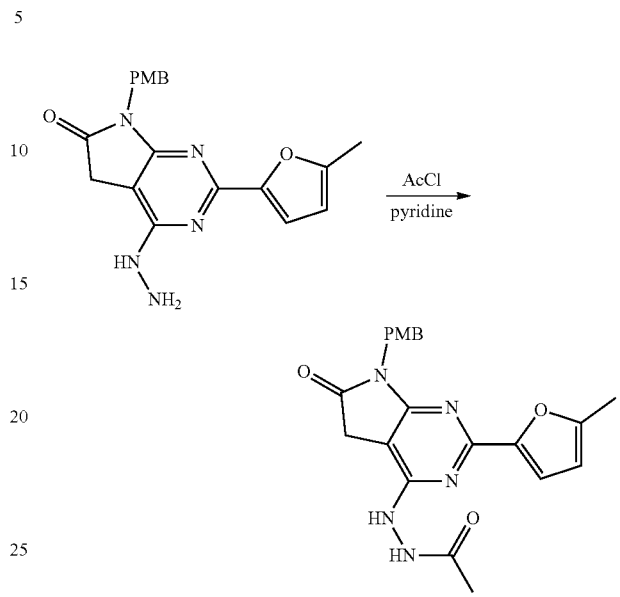

To a suspension of 4-hydrazino-7-(4-methoxybenzyl-2-(5-methyl-2-furyl)-5H-pyrrolo[2,3-d]pyrimidin-6-one (580 mg, 1.59 mmol, 1.0 eq.) in pyridine (2.4 mL) was added acetyl chloride (136 mg, 95% purity, 1.65 mmol, 1.04 eq.) at 0° C. The resulting mixture was turned to homogenous gradually, which was allowed to warm to 10° C. and maintained stirring for 2 hours to form a dark brown solution. The reaction mixture was diluted with water (15 mL). The formed precipitate was collected by filtration, washed with 0.1 N hydrochloric acid (3 mL) and water (3 mL), then lyophilized overnight to afford N'-[7-(4-methoxybenzyl)-2-(5-methyl-2-furyl)-6-oxo-5H-pyrrolo[2,3-d]pyrimidin-4-yl]acetohydrazide (541 mg, 100% purity, 1.33 mmol, 83.6% yield) as a green-brown solid, which was used directly in the next step. LCMS m/z 408.0 [M+H]⁺; ¹H NMR (CDCl₃ 400 MHz) δ 7.59 (brs, 1H), 7.46 (d, J=8.4 Hz, 2H), 7.20 (d, J=3.2 Hz, 1H), 6.89 (brs, 1H), 6.83 (d, J=8.8 Hz, 2H), 6.16 (d, J=2.8 Hz, 1H), 4.86 (s, 2H), 3.76 (s, 3H), 3.41 (s, 2H), 2.43 (s, 3H), 2.09 (s, 3H).

Step 8: Preparation of 7-(4-methoxybenzyl)-3-methyl-5-(5-methylfuran-2-yl)-7,9-dihydro-8H-pyrrolo[3,2-e][1,2,4]triazolo[4,3-c]pyrimidin-8-one

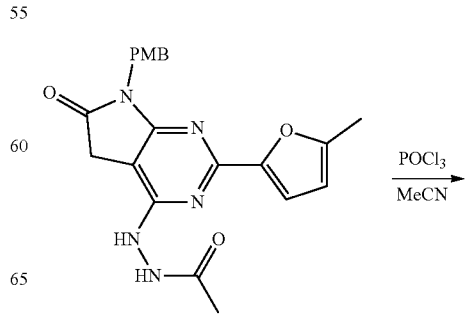

-continued

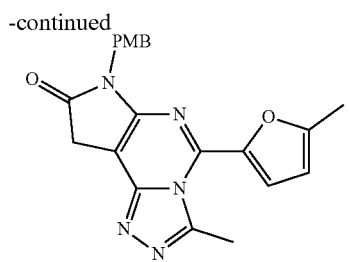

To a suspension of N'-[7-(4-methoxybenzyl)-2-(5-methyl-2-furyl)-6-oxo-5H-pyrrolo[2,3-d]pyrimidin-4-yl]acetohydrazide (541 mg, 1.33 mmol, 1.0 eq.) in anhydrous acetonitrile (10 mL) was added dropwise phosphorus oxychloride (271 mg, 1.77 mmol, 1.33 eq.). The resulting mixture was heated to 80° C. and maintained stirring for 22 hours to form a dark brown solution. After the complete conversion as confirmed by LCMS, the reaction mixture was diluted with ethyl acetate (150 mL) and then quenched by saturated NaHCO$_3$ solution (50 mL). The organic phase was collected, washed with water (50 mL) and brine (60 mL), dried over anhydrous Na$_2$SO$_4$, filtered and concentrated under reduced pressure to afford 7-(4-methoxybenzyl)-3-methyl-5-(5-methylfuran-2-yl)-7,9-dihydro-8H-pyrrolo[3,2-e][1,2,4]triazolo[4,3-c]pyrimidin-8-one (510 mg, 61.9% yield) as dark-red gum, which was used directly in the next step without further purifications. LCMS m/z 534.0 [M+H]$^+$.

Step 9: Preparation of 7-(4-methoxybenzyl)-2-methyl-5-(5-methylfuran-2-yl)-7,9-dihydro-8H-pyrrolo[3,2-e][1,2,4]triazolo[1,5-c]pyrimidin-8-one

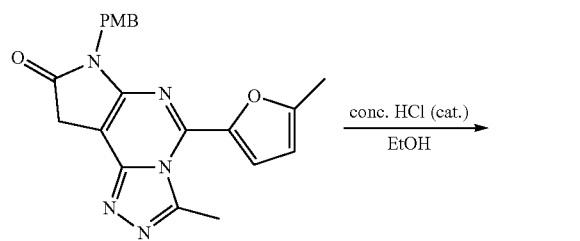

To a solution of 7-(4-methoxybenzyl)-3-methyl-5-(5-methylfuran-2-yl)-7,9-dihydro-8H-pyrrolo[3,2-e][1,2,4]triazolo[4,3-c]pyrimidin-8-one (510 mg, 62.80% purity, 822.43 μmol, 1.0 eq.) in ethanol (21 mL) was added hydrochloric acid (36.5 mg, 37% aqueous, 370.40 μmol, 0.45 eq.). The resulting mixture was heated to 88° C. and continued stirring for 16 hours to form a dark red solution. The reaction mixture was diluted with ethyl acetate (120 mL) and then quenched by saturated NaHCO$_3$ solution (30 mL). The organic phase was collected, washed with water (30 mL) and brine (40 mL), dried over anhydrous Na$_2$SO$_4$, filtered and concentrated under reduced pressure. The residue (520 mg) was purified by column chromatography to afford 7-(4-methoxybenzyl)-2-methyl-5-(5-methylfuran-2-yl)-7,9-dihydro-8H-pyrrolo[3,2-e][1,2,4]triazolo[1,5-c]pyrimidin-8-one (151 mg, 38.4% yield) as a light brown solid. LCMS m/z 390.1 [M+H]$^+$; $^1$H NMR (CDCl$_3$, 400 MHz) δ 8.21 (d, J=3.2 Hz, 1H), 7.57 (d, J=8.8 Hz, 2H), 6.84 (d, J=8.4 Hz, 2H), 6.37 (d, J=2.4 Hz, 1H), 5.03 (s, 2H), 3.83 (s, 2H), 3.76 (s, 3H), 2.61 (s, 3H), 2.57 (s, 3H).

Step 10: Preparation of 2-methyl-5-(5-methylfuran-2-yl)-7,9-dihydro-8H-pyrrolo[3,2-e][1,2,4]triazolo[1,5-c]pyrimidin-8-one (97)

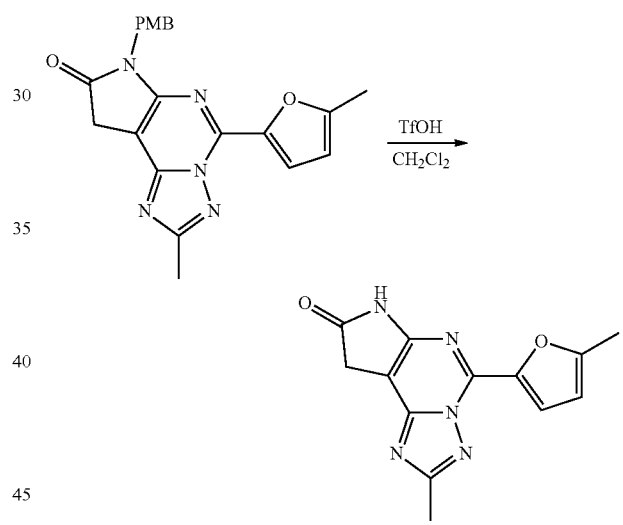

7-(4-methoxybenzyl)-2-methyl-5-(5-methylfuran-2-yl)-7,9-dihydro-8H-pyrrolo[3,2e][1,2,4]triazolo[1,5-c]pyrimidin-8-one (151 mg, 305.70 μmol, 1.0 eq.) was dissolved in anhydrous dichloromethane (3.0 mL), to which trifluoromethanesulfonic acid (750 μL, 8.07 mmol, 26.40 eq.) was added dropwise. The mixture was maintained at 10° C. with stirring for 1 hour to form a dark-red solution. After complete conversion by LCMS, the reaction mixture was quenched by saturated aqueous NaHCO$_3$ solution (15 mL) and extracted with dichloromethane (10 mL×3). The combined extracts were washed with brine (12 mL), dried over anhydrous Na$_2$SO$_4$, filtered and concentrated under reduced pressure. The residue was purified by preparative HPLC to afford 2-methyl-5-(5-methylfuran-2-yl)-7,9-dihydro-8H-pyrrolo[3,2-e][1,2,4]triazolo[1,5-c]pyrimidin-8-one (8.9 mg, 10.8% yield) as a light yellow solid. LCMS m/z 270.0 [M+H]$^+$; $^1$H NMR (DMSO-d$_6$ 400 MHz) δ 11.41 (brs, 1H), 8.10 (d, J=3.2 Hz, 1H), 6.54 (d, J=2.8 Hz, 1H), 3.81 (s, 2H), 2.54 (s, 3H), 2.46 (s, 3H).

Example 6: Preparation of 2-methyl-5-(5-methyl-furan-2-yl)-7H-pyrazolo[4,3-e][1,2,4]triazolo[1,5-c]pyrimidine (102)

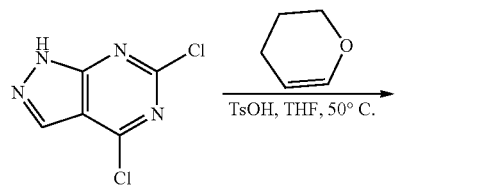

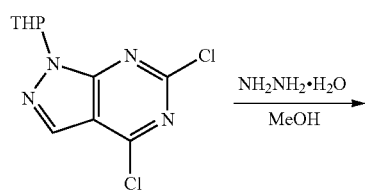

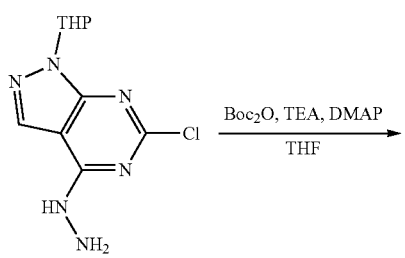

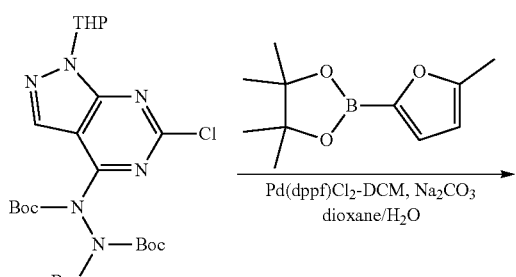

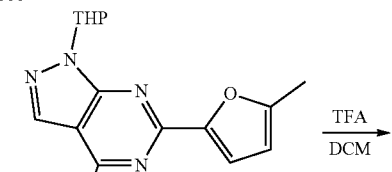

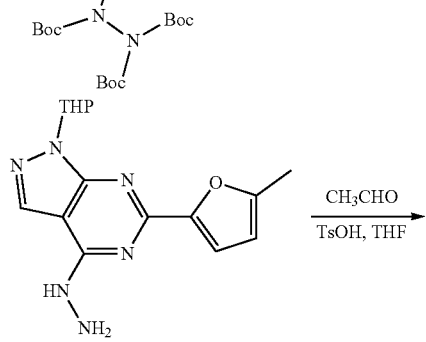

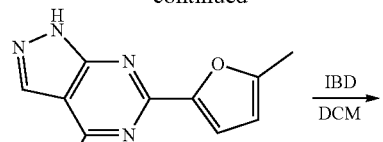

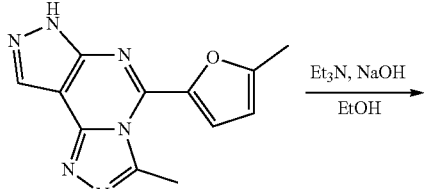

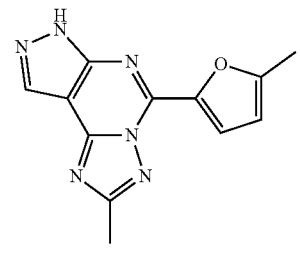

(102)

Step 1: Preparation of 4,6-dichloro-1-(tetrahydro-2H-pyran-2-yl)-1H-pyrazolo[3,4-d]pyrimidine

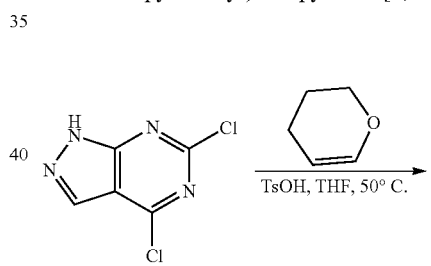

A mixture of 4,6-dichloro-1H-pyrazolo[3,4-d]pyrimidine (5 g, 26.45 mmol, 1 eq.), 3,4-dihydro-2H-pyran (4.45 g, 52.90 mmol, 2.0 eq.) and TsOH hydrate (250 mg, 1.31 mmol, 0.05 eq.) in THF (50 mL) was stirred at 50° C. for 3 hours. The solvent was evaporated and the residue was diluted with petroleum ether (100 mL). The mixture was filtered and the filter cake was washed with petroleum ether (50 mL×2). The solid was collected and dried to afford 4,6-dichloro-1-tetrahydropyran-2-yl-pyrazolo[3,4-d]pyrimidine (5.5 g, 72.3% yield) as an off-white solid. LCMS m/z 273.0 [M+H]$^+$; $^1$HNMR (CDCl$_3$ 400 MHz) δ 8.21 (s, 1H), 6.01 (dd, J 2.4, 10.4 Hz, 1H), 4.19-4.06 (m, 1H), 3.88-3.76 (m, 1H), 2.64-2.50 (m, 1H), 2.21-2.09 (m, 1H), 1.99-1.90 (m, 1H), 1.86-1.72 (m, 2H), 1.71-1.61 (m, 1H).

Step 2: Preparation of 6-chloro-4-hydrazineyl-1-(tetrahydro-2H-pyran-2-yl)-1H-pyrazolo[3,4-d]pyrimidine

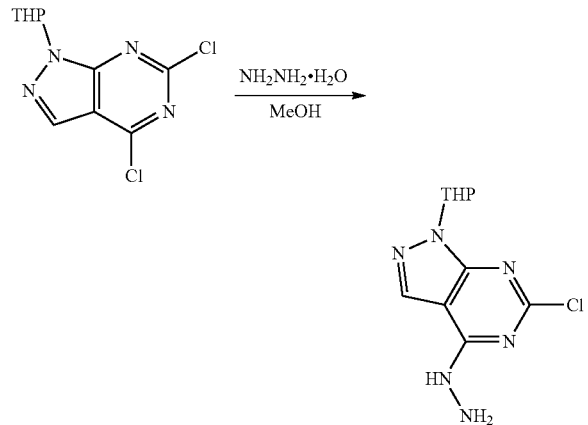

To a solution of 4,6-dichloro-1-tetrahydropyran-2-yl-pyrazolo[3,4-d]pyrimidine (5.50 g, 20.14 mmol, 1 eq.) in MeOH (50 mL) was added hydrazine hydrate (2.0 mL, 40.91 mmol, 2.03 eq.) at 10-15° C. The reaction was stirred at 10-15° C. for 30 min. After the reaction completion was confirmed by LCMS, the solvent was evaporated. The residue was diluted with petroleum ether (50 mL) and the resulting mixture was filtered, followed by wash with petroleum ether (30 mL×2). The solid was collected and dried to afford 6-chloro-1-tetrahydropyran-2-yl-pyrazolo[3,4-d]pyrimidin-4-yl)hydrazine (5.15 g, 90.4% yield) as a white solid. LCMS m/z 269.1 [M+H]$^+$; $^1$HNMR (CDCl$_3$ 400 MHz) δ 9.20 (s, 1H), 8.45 (s, 1H), 5.92 (dd, J=2.0, 10.8 Hz, 1H), 4.20 (br s, 2H), 4.15-4.06 (m, 1H), 3.86-3.73 (m, 1H), 2.60-2.46 (m, 1H), 2.16-2.04 (m, 1H), 1.95-1.87 (m, 1H), 1.79-1.71 (m, 2H), 1.64-1.57 (m, 1H).

Step 3: Preparation of tert-butyl N-[bis(tert-butoxycarbonyl)amino]-N-(6-chloro-1-tetrahydropyran-2-yl-pyrazolo[3,4-d]pyrimidin-4-yl)carbamate

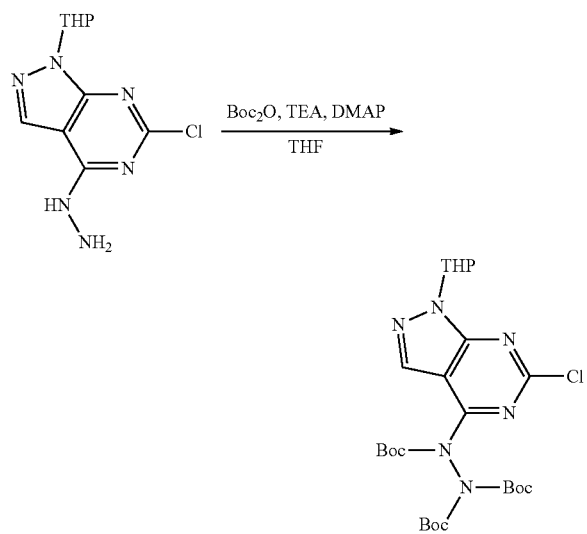

To a mixture of (6-chloro-1-tetrahydropyran-2-yl-pyrazolo[3,4-d]pyrimidin-4-yl)hydrazine (800 mg, 2.98 mmol, 1 eq.) and Et$_3$N (1.28 mL, 9.20 mmol, 3.09 eq.) in THF (10 mL) was added Boc$_2$O (2.26 mL, 9.82 mmol, 3.3 eq.) and DMAP (40 mg, 327.42 μmol, 0.11 eq.) at 5-10° C. The reaction was stirred at 5-10° C. for 1 hour. The mixture was diluted with 1.0 M HCl solution (30 mL) and the mixture was extracted with EtOAc (30 mL×3). The combined organic layers were washed with brine (50 mL), dried over Na$_2$SO$_4$, filtered and concentrated to give tert-butyl N-[bis(tert-butoxycarbonyl)amino]-N-(6-chloro-1-tetrahydropyran-2-yl-pyrazolo[3,4-d]pyrimidin-4-yl)carbamate (1.99 g) as light yellow oil, which was used in the next step directly without further purification. LCMS m/z 569.2 [M+H]$^+$.

Step 4: Preparation of tert-butyl N-[bis(tert-butoxycarbonyl)amino]-N-[6-(5-methyl-2-furyl)-1-tetrahydropyran-2-yl-pyrazolo[3,4-d]pyrimidin-4-yl]carbamate

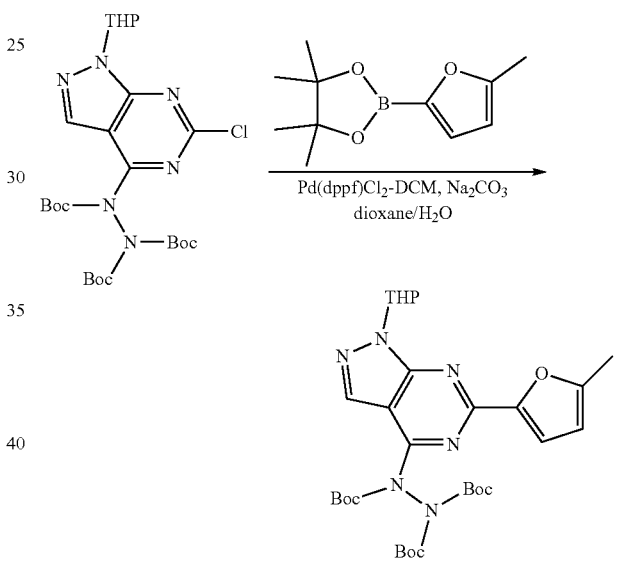

To a mixture of tert-butyl N-[bis(tert-butoxycarbonyl)amino]-N-(6-chloro-1-tetrahydropyran-2-yl-pyrazolo[3,4-d]pyrimidin-4-yl)carbamate (1.90 g, 2.84 mmol, 1 eq.), 4,4,5,5-tetramethyl-2-(5-methyl-2-furyl)-1,3,2-dioxaborolane (860 mg, 4.13 mmol, 1.46 eq.), Na$_2$CO$_3$ (670 mg, 6.32 mmol, 2.23 eq.) in dioxane (20 mL) and water (2 mL) was added Pd(dppf)Cl$_2$·CH$_2$Cl$_2$ (250 mg, 306.13 μmol, 0.108 eq.) under nitrogen. The reaction was stirred at 90° C. for 1.5 hours and cooled to room temperature. The mixture was diluted with EtOAc (30 mL) and the solid was filtered off. The filtrate was diluted with water (30 mL) and extracted with EtOAc (30 mL×3). The combined organic layers were washed with brine (50 mL), dried over Na$_2$SO$_4$, filtered and concentrated. The residue was purified by column chromatography to afford tert-butyl N-[bis(tert-butoxycarbonyl)amino]-N-[6-(5-methyl-2-furyl)-1-tetrahydropyran-2-yl-pyrazolo[3,4-d]pyrimidin-4-yl]carbamate (1.1 g, 63.0% yield for 2 steps) as dark green oil. LCMS m/z 615.3 [M+H]$^+$; $^1$HNMR (CDCl$_3$ 400 MHz) δ 8.23 (s, 1H), 7.24 (d, J 3.2 Hz, 1H), 6.20 (dd, J 2.8, 10.8 Hz, 1H), 6.14 (d, J 2.8 Hz, 1H), 4.18-4.13 (m, 1H), 3.93-3.82 (m, 1H), 2.65-2.51

(m, 1H), 2.46 (s, 3H), 2.19-2.09 (m, 1H), 2.01-1.89 (m, 1H), 1.87-1.75 (m, 2H), 1.67-1.62 (m, 1H), 1.60 (s, 9H), 1.42 (s, 9H), 1.39 (s, 9H).

Step 5: Preparation of [6-(5-methyl-2-furyl)-1-tetrahydropyran-2-yl-pyrazolo[3,4-d]pyrimidin-4-yl]hydrazine

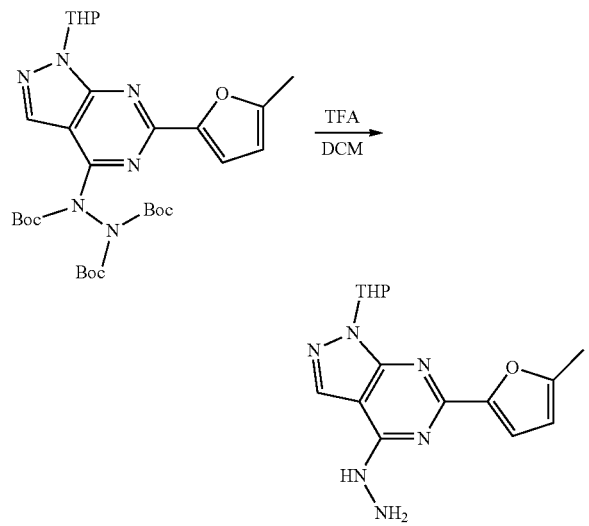

To a solution of tert-butyl N-[bis(tert-butoxycarbonyl)amino]-N-[6-(5-methyl-2-furyl)-1-tetrahydropyran-2-yl-pyrazolo[3,4-d]pyrimidin-4-yl]carbamate (1.1 g, 1.79 mmol, 1 eq.) in DCM (10 mL) was added TFA (3 mL) at 0-5° C. The reaction was stirred at 0-5° C. for 3 hours. The solvent was evaporated and the residue was diluted with EtOH (10 mL). To the resulting mixture was added $K_2CO_3$ (500 mg) and the mixture was stirred for 30 min. The solid was filtered off and the filtrate was evaporated. The resulting residue was diluted with water (30 mL) and the mixture was filtered. The filter cake was washed with water (20 mL×2) and dried to afford [6-(5-methyl-2-furyl)-1-tetrahydropyran-2-yl-pyrazolo[3,4-d]pyrimidin-4-yl]hydrazine (520 mg, 92.4% yield) as an off-white solid, which was used in the next step directly without further purification. LCMS m/z 315.1 [M+H]$^+$; $^1$HNMR (DMSO-d$_6$ 400 MHz) δ 13.42 (br s, 1H), 11.77 (br s, 1H), 8.17 (s, 1H), 7.60 (t, J 5.2 Hz, 1H), 7.05 (d, J 3.2 Hz, 1H), 6.28 (d, J 2.4 Hz, 1H), 4.43 (t, J=5.6 Hz, 1H), 3.52-3.40 (m, 2H), 2.39-2.34 (m, 5H), 1.66-1.55 (m, 2H), 1.55-1.45 (m, 2H).

Step 6: Preparation of N-[(E)-ethylideneamino]-6-(5-methyl-2-furyl)-1H-pyrazolo[3,4-d]pyrimidin-4-amine

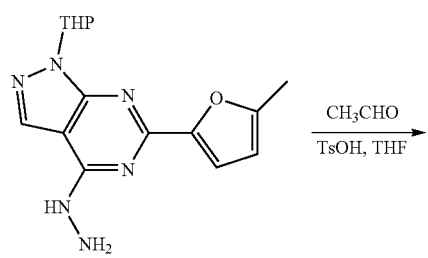

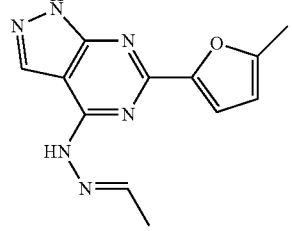

To a mixture of [6-(5-methyl-2-furyl)-1-tetrahydropyran-2-yl-pyrazolo[3,4-d]pyrimidin-4-yl]hydrazine (240 mg, 763.50 μmol, 1 eq.) and acetaldehyde (50 μL, 890.98 μmol, 1.17 eq.) in THF (5 mL) was added TsOH hydrate (15 mg, 78.86 μmol, 0.103 eq.) at 5-10° C. The reaction was stirred at 50° C. for 12 hours Additional acetaldehyde (50 μL, 890.98 μmol, 1.17 eq.) was added and the reaction was stirred at 50° C. for another 5 hours. The mixture was diluted with water (20 mL) and extracted with EtOAc (20 mL×3). The combined organic layers were washed with brine (30 mL), dried over $Na_2SO_4$, filtered and concentrated. The residue was purified by flash silica gel chromatography to afford N-[(E)-ethylideneamino]-6-(5-methyl-2-furyl)-1H-pyrazolo[3,4-d]pyrimidin-4-amine (75 mg, 38.3% yield) as a white solid. LCMS m/z 257.1 [M+H]$^+$; $^1$HNMR (DMSO-d$_6$ 400 MHz) δ 13.40 (s, 1H), 11.76 (s, 1H), 8.20 (d, J 1.2 Hz, 1H), 7.59 (q, J 5.6 Hz, 1H), 7.05 (d, J 3.2 Hz, 1H), 6.28 (d, J 2.8 Hz, 1H), 2.36 (s, 3H), 2.02 (d, J 5.2 Hz, 3H).

Step 7: Preparation of 3-methyl-5-(5-methylfuran-2-yl)-7H-pyrazolo[4,3-e][1,2,4]triazolo[4,3-c]pyrimidine

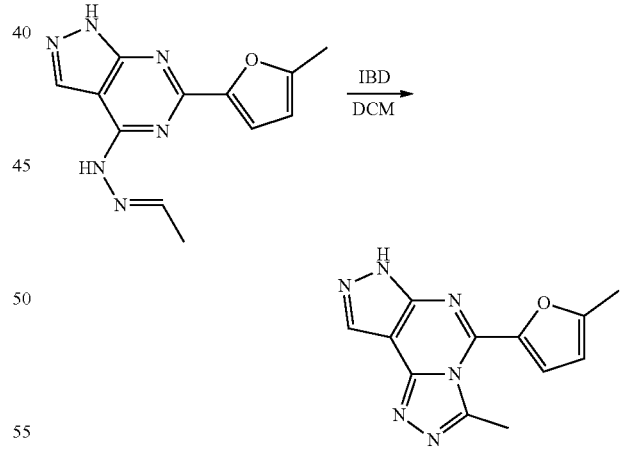

A mixture of N-[(E)-ethylideneamino]-6-(5-methyl-2-furyl)-1H-pyrazolo[3,4-d]pyrimidin-4-amine (75 mg, 292.67 μmol, 1 eq.) and [acetoxy(phenyl)-iodanyl] acetate (120 mg, 372.56 μmol, 1.27 eq.) in DCM (4 mL) was stirred at 0-5° C. for 4 hours. The reaction was stirred at 35° C. for 12 hours. The mixture was diluted with water (20 mL) and extracted with DCM (20 mL×3). The combined organic layers were washed with brine (30 mL), dried over $Na_2SO_4$, filtered and concentrated. The residue was purified by flash silica gel chromatography to afford 3-methyl-5-(5-methylfuran-2-yl)-7H-pyrazolo[4,3-e][1,2,4]triazolo[4,3-c]pyrimidine (50 mg, 67.20% yield) as an off-white solid. LCMS m/z 255.1 [M+H]+.

Step 8: Preparation of 2-methyl-5-(5-methylfuran-2-yl)-7H-pyrazolo[4,3-e][1,2,4]triazolo[1,5-c]pyrimidine (102)

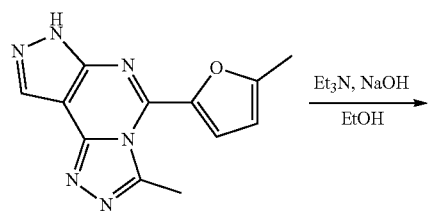

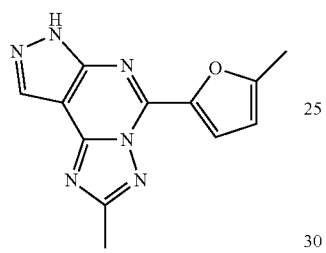

A mixture of 3-methyl-5-(5-methylfuran-2-yl)-7H-pyrazolo[4,3-e][1,2,4]triazolo[4,3-c]pyrimidine (50 mg, 196.66 μmol, 1 eq.) and triethylamine (100 μL, 717.81 μmol, 3.65 eq.) in EtOH (2 mL) was stirred at 80° C. for 12 hours. NaOH (25 mg, 625.05 μmol, 3.18 eq.) was added and the reaction was stirred at 80° C. for another 1.5 hours. The mixture was cooled to 5-10° C. and adjusted to pH=6-7 with 1.0 M HCl solution. The mixture was extracted with DCM (20 mL×3). The combined organic layers were washed with brine (20 mL), dried over Na$_2$SO$_4$, filtered and concentrated. The residue was diluted with DMF (10 mL) and poured into water (50 mL). The mixture was filtered and the filter cake was washed with water (20 mL×3) and MeCN (20 mL×2). The resulting solid was lyophilized to afford 2-methyl-5-(5-methylfuran-2-yl)-7H-pyrazolo[4,3-e][1,2,4]triazolo[1,5-c]pyrimidine (14.6 mg, 29.20% yield) as a yellow solid. LCMS m/z 255.1 [M+H]+; $^1$HNMR (DMSO-d$_6$ 400 MHz) δ 8.44 (br s, 1H), 8.13 (d, J 3.2 Hz, 1H), 6.52 (d, J 3.6 Hz, 1H), 2.57 (s, 3H), 2.47 (s, 3H).

Example 7: Preparation of 2-(2-methyl-5-(5-methylfuran-2-yl)-7H-pyrrolo[3,2-e][1,2,4]triazolo[1,5-c]pyrimidin-8-yl)propan-2-ol (134)

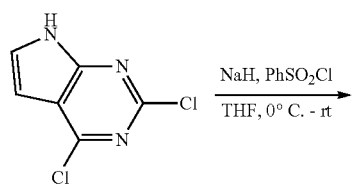

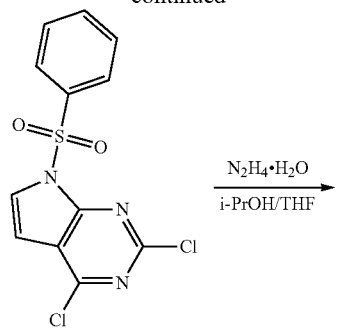

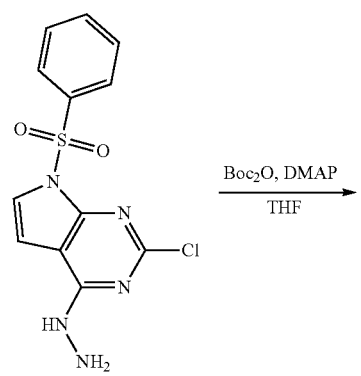

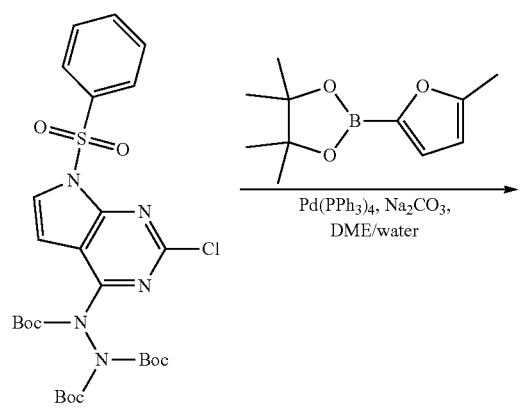

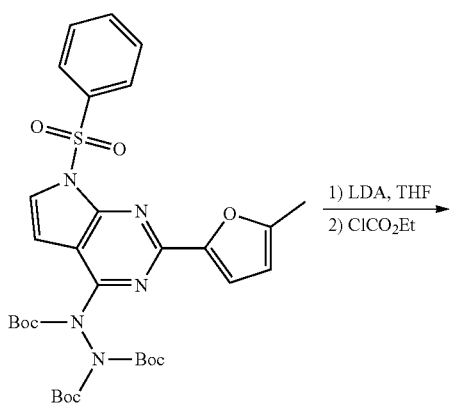

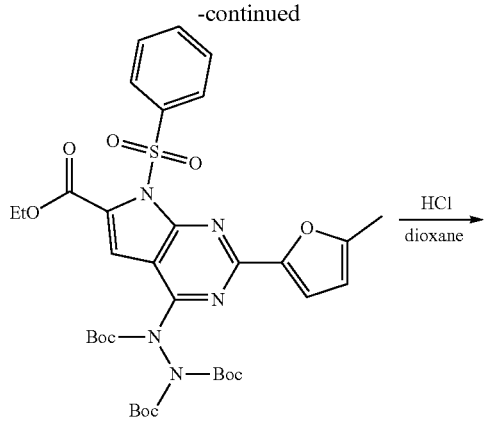

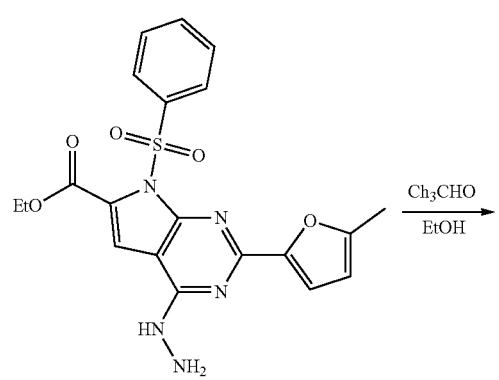

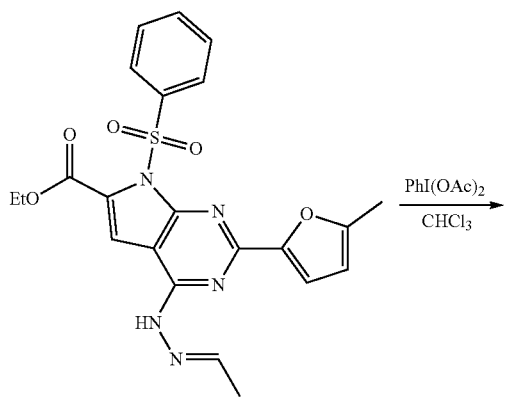

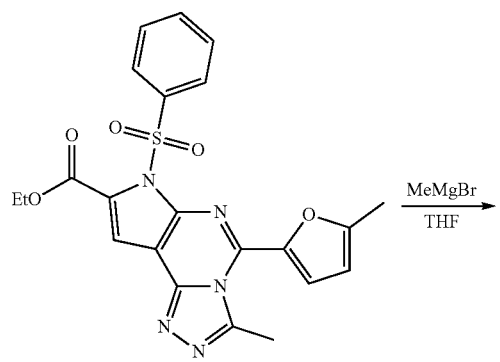

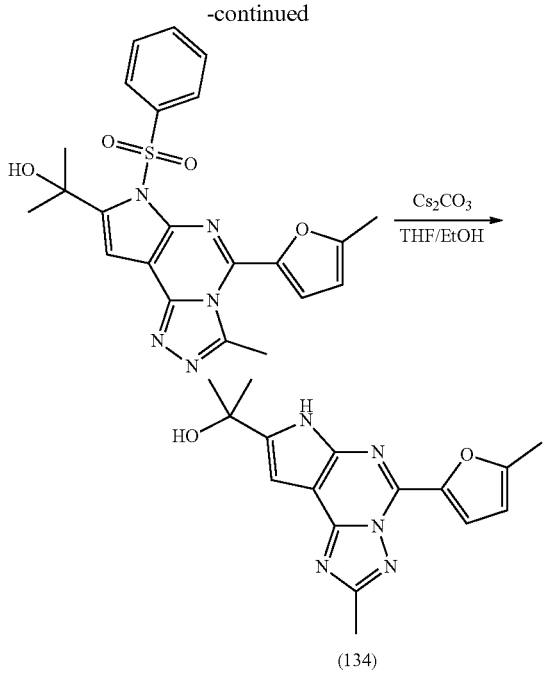

(134)

Step 1: Preparation of 7-(benzenesulfonyl)-2,4-dichloro-pyrrolo[2,3-d]pyrimidine

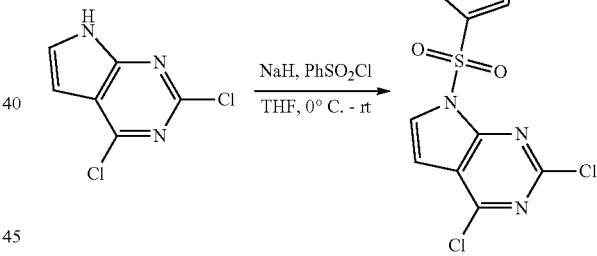

To a solution of 2,4-dichloro-7H-pyrrolo[2,3-d]pyrimidine (6.40 g, 95%, 32.34 mmol, 1.0 eq.) in anhydrous tetrahydrofuran (65 mL) was added sodium hydride (1.97 g, 49.15 mmol, 60% dispersion in oil, 1.52 eq.) in portions at 0° C. After stirring for 50 minutes, the above mixture was treated with benzenesulfonyl chloride (7.58 g, 95%, 40.75 mmol, 1.26 eq.). The resulting mixture was allowed to warm to 15° C. slowly and maintained stirring for 2 hours to form a brown suspension. After TLC confirmed the complete conversion, the reaction mixture was quenched by saturated ammonium chloride solution (30 mL) and diluted with water (30 mL), then extracted with ethyl acetate (60 mL×2). The combined organic extracts were washed with water (60 mL) and brine (60 mL), dried over anhydrous $Na_2SO_4$, filtered and concentrated under reduced pressure. The residue (11.60 g) was purified by column chromatography. Pure fractions were combined and concentrated under reduced pressure to afford 7-(benzenesulfonyl)-2,4-dichloro-pyrrolo[2,3-d]pyrimidine (10.60 g, 32.30 mmol, 99.88% yield) as an off-white solid. LCMS m/z 327.9 [M+H]$^+$; $^1$H NMR (CDCl$_3$ 400 MHz) δ 8.29-8.19 (m, 2H), 7.76 (d, J=4.0 Hz, 1H), 7.72-7.64 (m, 1H), 7.62-7.53 (m, 2H), 6.69 (d, J=4.1 Hz, 1H).

Step 2: Preparation of [7-(benzenesulfonyl)-2-chloro-pyrrolo[2,3-d]pyrimidin-4-yl]Hydrazine

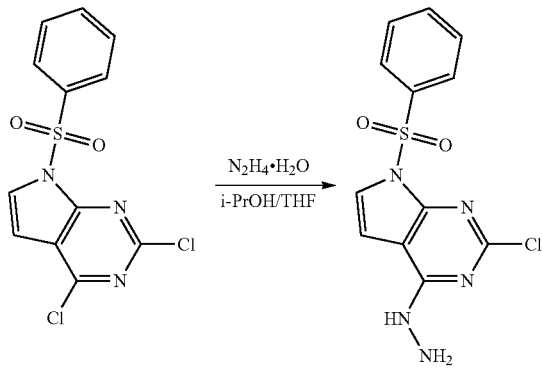

To a solution of 7-(benzenesulfonyl)-2,4-dichloro-pyrrolo[2,3-d]pyrimidine (9.77 g, 29.77 mmol, 1.0 eq.) in anhydrous tetrahydrofuran (120 mL) was added dropwise a solution of hydrazine hydrate (3.15 g, 98%, 61.63 mmol, 2.07 eq.) in 2-propanol (6 mL) at 0° C. The resulting mixture was allowed to warm to 10° C. gradually and maintained stirring for 2.5 hours to provide a white suspension. After the complete conversion was confirmed by LCMS, the reaction mixture was concentrated under reduced pressure to remove most of volatiles, then suspended in water (100 mL). The resultant suspension was filtered to collect the insoluble solid, which was then washed with water (25 mL×2). The above filter cake was dried over vacuum to afford[7-(benzenesulfonyl)-2-chloro-pyrrolo[2,3-d]pyrimidin-4-yl]hydrazine (9.55 g, 29.50 mmol, 99.1% yield) as an off-white solid, which was used in the next step without further purification. LCMS m/z 324.0 [M+H]$^+$; $^1$H NMR (DMSO-d$_6$ 400 MHz) δ 9.61-9.22 (m, 1H), 8.11-7.98 (m, 2H), 7.81-7.73 (m, 1H), 7.70-7.61 (m, 2H), 7.60-7.46 (m, 1H), 7.25-6.73 (m, 1H), 4.97-4.39 (m, 2H).

Step 3: Preparation of N-[7-(benzenesulfonyl)-2-chloro-pyrrolo[2,3-d]pyrimidin-4-yl]-N-[bis(tert-butoxycarbonyl)amino]carbamate

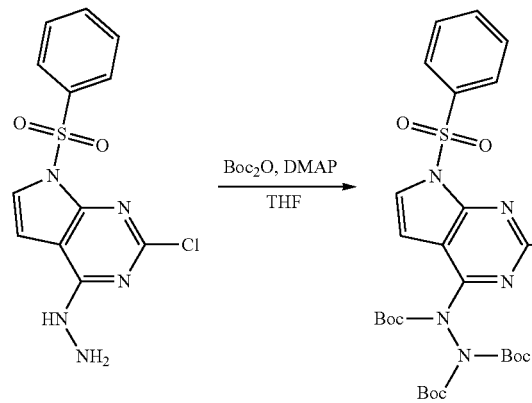

To a solution of [7-(benzenesulfonyl)-2-chloro-pyrrolo[2,3-d]pyrimidin-4-yl]hydrazine (9.55 g, 29.50 mmol, 1.0 eq.) in anhydrous tetrahydrofuran (195 mL) were added DMAP (504.5 mg, 4.13 mmol, 0.14 eq.) and Boc$_2$O (22.0 g, 95%, 95.76 mmol, 23.16 mL, 3.25 eq.). The resulting mixture was heated to 65° C. and maintained stirring for 2.5 hours to provide a yellow suspension. The complete conversion, the reaction mixture was cooled to ambient temperature and concentrated under reduced pressure to remove most of volatiles, then suspended in ethyl acetate (400 mL). The resultant solution was washed with 0.3 M hydrochloric acid (300 mL), saturated NaHCO$_3$ solution (300 mL), water (300 mL) and brine (300 mL), dried over anhydrous Na$_2$SO$_4$, filtered and concentrated under reduced pressure to afford tert-butyl N-[7-(benzenesulfonyl)-2-chloro-pyrrolo[2,3-d]pyrimidin-4-yl]-N-[bis(tert-butoxycarbonyl)amino]carbamate (17.17 g, 27.51 mmol, 93.2% yield) as a yellow solid, which was used directly in the next step. LCMS m/z 624.2 [M+H]$^+$; $^1$H NMR (CDCl$_3$ 400 MHz) b 8.27-8.19 (m, 2H), 7.70-7.64 (m, 1H), 7.63 (d, J=4.0 Hz, 1H), 7.60-7.51 (m, 2H), 6.62 (d, J=4.0 Hz, 1H), 1.54 (s, 9H), 1.45 (s, 18H).

Step 4: Preparation of tert-butyl N-[7-(benzenesulfonyl)-2-(5-methyl-2-furyl)pyrrolo[2,3-d]pyrimidin-4-yl]-N-[bis(tert-butoxycarbonyl)amino]carbamate

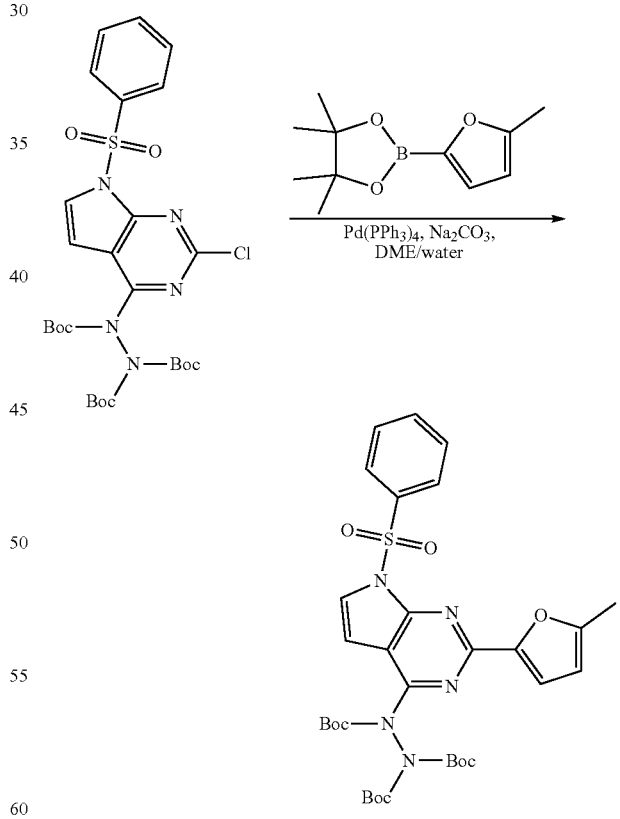

To a mixture of tert-butyl N-[7-(benzenesulfonyl)-2-chloro-pyrrolo[2,3-d]pyrimidin-4-yl]-N-[bis(tert-butoxycarbonyl)amino]carbamate (11.20 g, 17.95 mmol, 1.0 eq.) and 5-methylfuran-2-boronic acid pinacol ester (5.26 g, 25.30 mmol, 1.41 eq.) in DME (173 mL) and water (32 mL) were added Na$_2$CO$_3$ (4.56 g, 43.07 mmol, 2.40 eq.) and Pd(PPh$_3$)$_4$ (2.07 g, 1.79 mmol, 0.10 eq.). The resulting mixture was degassed and purged with nitrogen, then heated to 80° C. under nitrogen atmosphere and maintained stirring for 5 hours After the complete esterification was confirmed by LCMS, the reaction mixture was cooled to ambient temperature and partitioned with ethyl acetate (250 mL) and water (170 mL). The organic phase was collected by separation and the aqueous phase was extracted with ethyl acetate (130 mL×2). The combined organic extracts were washed with brine (250 mL), dried over anhydrous Na$_2$SO$_4$, filtered and concentrated under reduced pressure. The residue (17.6 g) was purified by column chromatography. Pure fractions were combined and concentrated under reduced pressure to afford tert-butyl N-[7-(benzenesulfonyl)-2-(5-methyl-2-furyl)pyrrolo[2,3-d]pyrimidin-4-yl]-N-[bis(tert-butoxycarbonyl)amino]carbamate (8.02 g, 93.02% calculated purity, 11.14 mmol, 62.1% yield) as a yellow solid. LCMS m/z 670.1 [M+H]$^+$; $^1$H NMR (CDCl$_3$ 400 MHz) δ 8.42-8.35 (m, 2H), 7.63-7.57 (m, 2H), 7.55-7.48 (m, 2H), 7.13 (d, J=2.8 Hz, 1H), 6.59 (d, J=4.0 Hz, 1H), 6.12 (dd, J=3.2, 0.8 Hz, 1H), 2.45 (s, 3H), 1.55 (s, 9H), 1.41 (s, 18H).

Step 5: Preparation of ethyl 7-(benzenesulfonyl)-4-[[bis(tert-butoxycarbonyl)amino]-tert-butoxycarbonyl-amino]-2-(5-methyl-2-furyl)pyrrolo[2,3-d]pyrimidine-6-carboxylate tion was stirred at −70° C. for 3 hours to form an orange suspension, to which a solution of ethyl chloroformate (399 mg, 3.57 mmol, 350.00 μL, 1.45 eq.) in anhydrous tetrahydrofuran (2.5 mL) was added dropwise. The reaction was continued stirring at −70° C. for 6 hours and then allowed to warm to 10° C. and stirred for additional 12 hours to form a dark red solution. After the complete conversion was confirmed by LCMS, the reaction was quenched by saturated NH$_4$Cl solution (10 mL) and diluted with water (15 mL), then extracted with ethyl acetate (20 mL×3). The combined organic layers were washed with brine (30 mL), dried over anhydrous Na$_2$SO$_4$, filtered and concentrated under reduced pressure. The residue was purified by column chromatography. Pure fractions were combined and concentrated under reduced pressure to afford ethyl 7-(benzenesulfonyl)-4-[[bis(tert-butoxycarbonyl)amino]-tert-butoxycarbonyl-amino]-2-(5-methyl-2-furyl)pyrrolo[2,3-d]pyrimidine-6-carboxylate (1.55 g, 66.8% yield) as an off-white foam. LCMS m/z 742.1 [M+H]$^+$; $^1$H NMR (CDCl$_3$ 400 MHz) δ 8.63-8.53 (m, 2H), 7.68-7.62 (m, 1H), 7.60-7.54 (m, 2H), 7.19 (d, J=3.2 Hz, 1H), 7.06 (s, 1H), 6.15 (d, J=2.8 Hz, 1H), 4.46 (q, J=7.2 Hz, 2H), 2.46 (s, 3H), 1.56 (s, 9H), 1.44 (t, J=7.2 Hz, 3H), 1.42 (s, 18H).

Step 6: Preparation of ethyl 7-(benzenesulfonyl)-4-hydrazino-2-(5-methyl-2-furyl)pyrrolo[2,3-d]pyrimidine-6-carboxylate

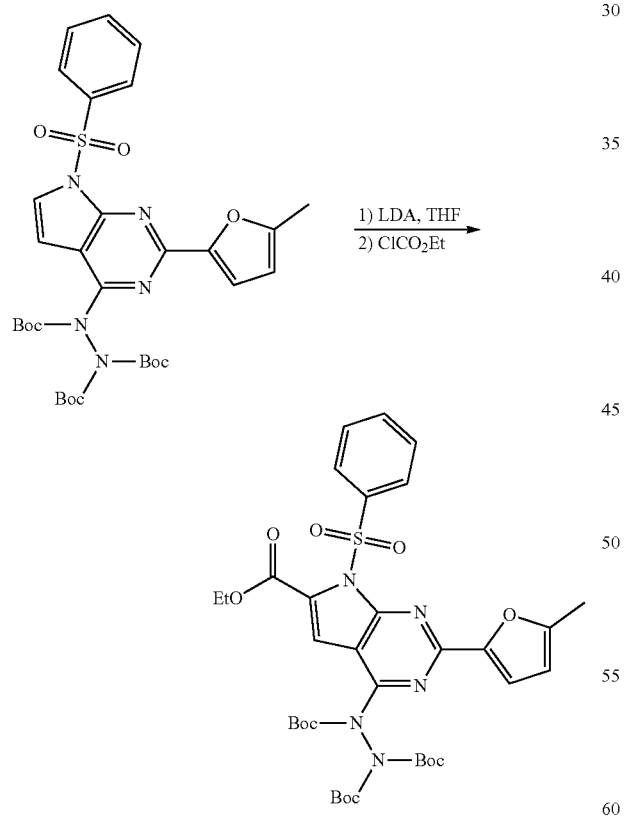
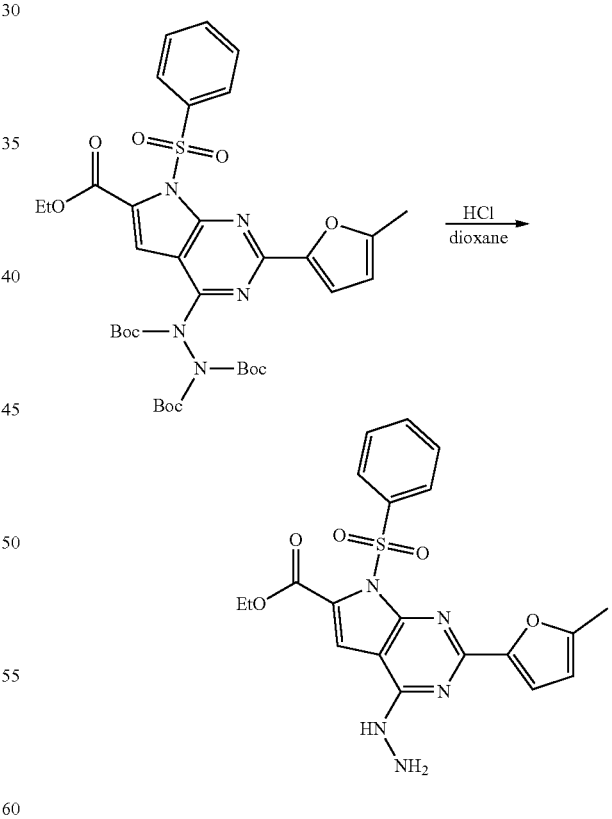

To a stirring solution of tert-butyl N-[7-(benzenesulfonyl)-2-(5-methyl-2-furyl)pyrrolo[2,3-d]pyrimidin-4-yl]-N-[bis(tert-butoxycarbonyl)amino]carbamate (1.90 g, 2.47 mmol, 1.0 eq.) in anhydrous tetrahydrofuran (16.0 mL) was added dropwise LDA (2.0 M, 2.00 mL, 1.62 eq.) at below −70° C. under nitrogen atmosphere. The resulting red solu- To a stirring solution of ethyl 7-(benzenesulfonyl)-4-[[bis(tert-butoxycarbonyl)amino]-tert-butoxycarbonyl-amino]-2-(5-methyl-2-furyl)pyrrolo[2,3-d]pyrimidine-6-carboxylate (1.55 g, 1.65 mmol, 1.0 eq.) in anhydrous dichloromethane (1.0 mL) was added dropwise 4 M HCl/dioxane solution (9.0 mL, 21.81 eq.) at 5° C. in a cooling bath. The mixture was then heated to 30° C. and maintained Step 7: Preparation of ethyl 7-(benzenesulfonyl)-4-[(2E)-2-ethylidenehydrazino]-2-(5-methyl-2-furyl)pyrrolo[2,3-d]pyrimidine-6-carboxylate

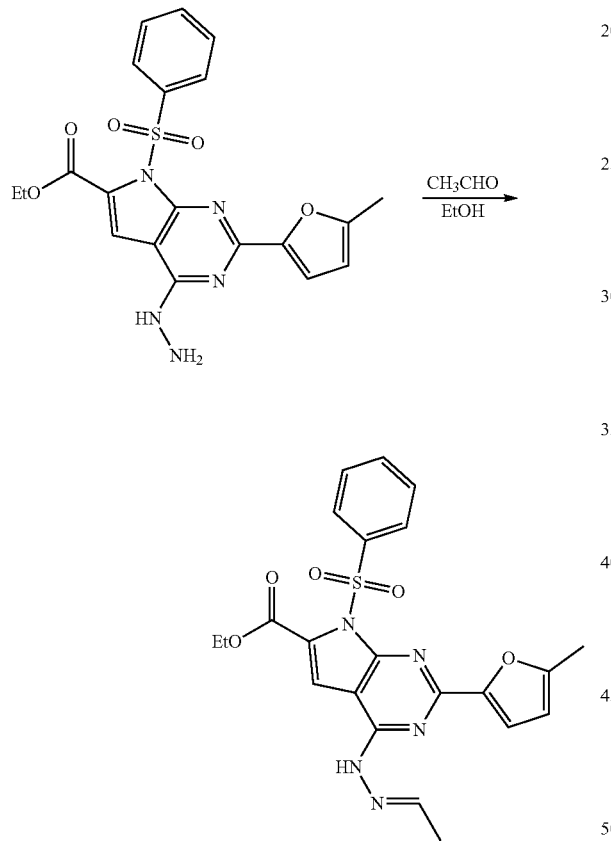

To a solution of ethyl 7-(benzenesulfonyl)-4-hydrazino-2-(5-methyl-2-furyl)pyrrolo[2,3-d]pyrimidine-6-carboxylate (1.14 g, 50.55% purity, 1.31 mmol, 1.0 eq.) in anhydrous ethanol (20 mL) was added dropwise acetaldehyde (400 µL, 7.06 mmol, 5.41 eq.). The resulting mixture was stirred at 10° C. for 20 minutes to form a brown solution. The reaction mixture was concentrated under reduced pressure to remove most of volatiles, then dried over vacuum to afford ethyl 7-(benzenesulfonyl)-4-[(2E)-2-ethylidenehydrazino]-2-(5-methyl-2-furyl)pyrrolo[2,3-d]pyrimidine-6-carboxylate (1.11 g, 1.18 mmol, 90.1% yield) as a green brown foam, which was used directly in the next step. LCMS m/z 467.9 [M+H]+.

Step 8: Preparation of ethyl 3-methyl-5-(5-methylfuran-2-yl)-7-(phenylsulfonyl)-7H-pyrrolo[3,2-e][1,2,4]triazolo[4,3-c]pyrimidine-8-carboxylate

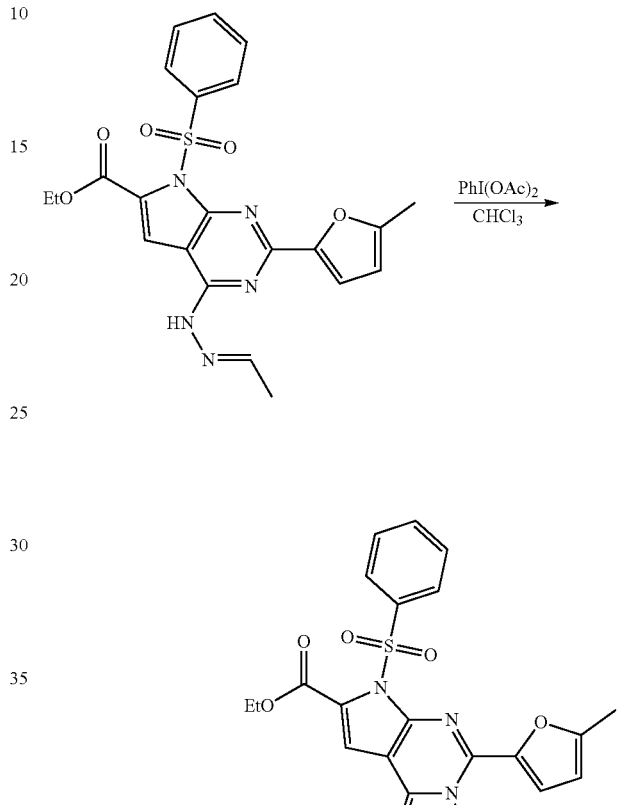

To a solution of ethyl 7-(benzenesulfonyl)-4-[(2E)-2-ethylidenehydrazino]-2-(5-methyl-2-furyl)pyrrolo[2,3-d]pyrimidine-6-carboxylate (1.11 g, 1.18 mmol, 1.0 eq.) in chloroform (20 mL) was added PhI(OAc)$_2$ (880 mg, 2.60 mmol, 2.21 eq.). The resulting mixture was heated to 50° C. and maintained stirring for 40 minutes to provide a red solution. After the complete conversion was confirmed by LCMS, the reaction mixture was quenched by a solution of Na$_2$SO$_3$ (6.3 g) and NaHCO$_3$ (8.4 g) in water (120 mL), then extracted with dichloromethane (70 mL×3). The combined organic extracts were washed with brine (100 mL), dried over anhydrous Na$_2$SO$_4$, filtered and concentrated under reduced pressure. The residue was purified by column chromatography to afford ethyl 3-methyl-5-(5-methylfuran-2-yl)-7-(phenylsulfonyl)-7H-pyrrolo[3,2-e][1,2,4]triazolo[4,3-c]pyrimidine-8-carboxylate (555 mg, 1.16 mmol, 70.5% yield) as a yellow foam. LCMS m/z 466.0 [M+H]+; $^1$H NMR (CDCl$_3$ 400 MHz) δ 8.47-8.41 (m, 2H), 7.70-7.64 (m, 1H), 7.61-7.53 (m, 2H), 7.51 (s, 1H), 7.16 (d, J=3.6 Hz, 1H), 6.35 (dd, J=3.6, 0.8 Hz, 1H), 4.47 (q, J=7.2 Hz, 2H), 2.62 (s, 3H), 2.48 (s, 3H), 1.45 (t, J=7.2 Hz, 3H).

Step 9: Preparation of 2-(3-methyl-5-(5-methyl-furan-2-yl)-7-(phenylsulfonyl)-7H-pyrrolo[3,2-e][1,2,4]triazolo[4,3-c]pyrimidin-8-yl)propan-2-ol

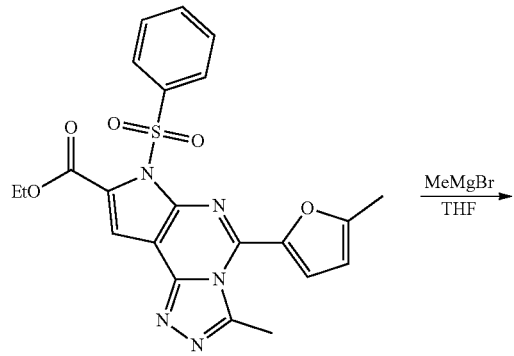

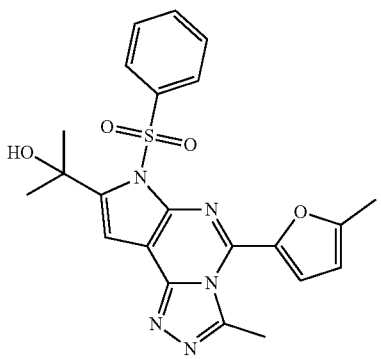

To a stirring solution of ethyl 3-methyl-5-(5-methylfuran-2-yl)-7-(phenylsulfonyl)-7H-pyrrolo[3,2-e][1,2,4]triazolo[4,3-c]pyrimidine-8-carboxylate (250 mg, 522.09 μmol, 1.0 eq.) in anhydrous tetrahydrofuran (7.8 mL) was added dropwise a solution of MeMgBr (3.0 M solution in diethyl ether, 950 μL, 5.46 eq.) at 0° C. under nitrogen atmosphere. The resulting mixture was allowed to warm to 20° C. and maintained stirring for 16 hours to form a dark red solution. After the complete conversion was confirmed by LCMS, the reaction mixture was quenched by saturated NH$_4$Cl solution (10 mL) and diluted with water (20 mL), then extracted with ethyl acetate (15 mL×3). The combined extracts were washed with brine (25 mL), dried over anhydrous Na$_2$SO$_4$, filtered and concentrated. The resulting mixture was purified by preparative TLC (acidic silica gel, methanol/ethyl acetate=1/15) to afford 2-(3-methyl-5-(5-methylfuran-2-yl)-7-(phenylsulfonyl)-7H-pyrrolo[3,2-e][1,2,4]triazolo[4,3-c]pyrimidin-8-yl)propan-2-ol (42.0 mg, 72.56 μmol) as a light yellow solid. LCMS m/z 452.1 [M+H]$^+$.

Step 10: Preparation of 2-(2-methyl-5-(5-methylfuran-2-yl)-7H-pyrrolo[3,2-e][1,2,4]triazolo[1,5-c]pyrimidin-8-yl)propan-2-ol (134)

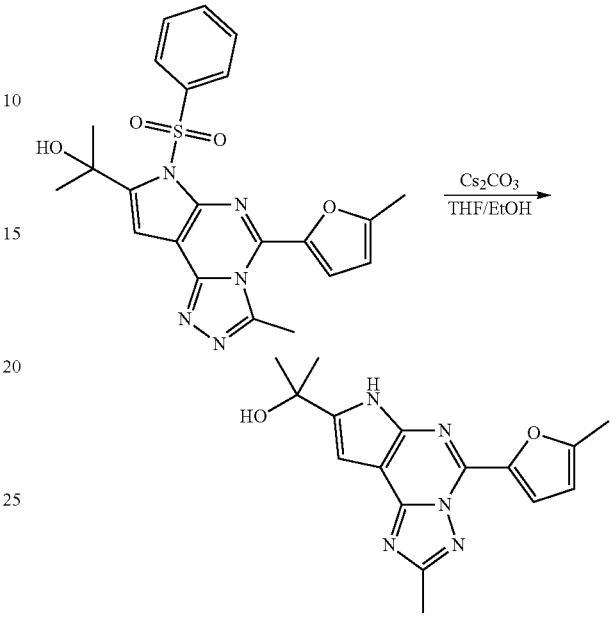

To a solution of 2-(3-methyl-5-(5-methylfuran-2-yl)-7-(phenylsulfonyl)-7H-pyrrolo[3,2-e][1,2,4]triazolo[4,3-c]pyrimidin-8-yl)propan-2-ol (42.0 mg, 72.5 μmol, 1.0 eq.) in tetrahydrofuran (600 μL) and ethanol (300 μL) was added cesium carbonate (74.0 mg, 227.12 μmol, 3.13 eq.) in portions. The resulting mixture was heated to 75° C. and maintained stirring for 14 hours to form an orange suspension. After the complete conversion was confirmed by LCMS, the reaction mixture was cooled and concentrated to remove most of volatiles. The residue was partitioned between ethyl acetate (5 mL) and water (2 mL). The organic phase was collected and washed with brine (3 mL), dried over anhydrous Na$_2$SO$_4$, filtered and concentrated under reduced pressure. The residue was purified by preparative TLC (acidic silica gel, methanol/ethyl acetate=1/25). Pure fraction was collected and concentrated under reduced pressure, then lyophilized to afford 2-(2-methyl-5-(5-methylfuran-2-yl)-7H-pyrrolo[3,2-e][1,2,4]triazolo[1,5-c]pyrimidin-8-yl)propan-2-ol (29.5 mg, 8.17% overall yield for totally 2 steps) as a light yellow solid. LCMS m/z 312.1 [M+H]$^+$; $^1$H NMR (Methanol-d$_4$ 400 MHz) δ 8.04 (d, J=3.2 Hz, 1H), 6.70 (s, 1H), 6.37 (d, J=2.8 Hz, 1H), 2.62 (s, 3H), 2.47 (s, 3H), 1.67 (s, 6H).

Example 8: Preparation of 2-methyl-5-(5-methylfuran-2-yl)pyrido[3,2-e][1,2,4]triazolo[1,5-c]pyrimidine (136)

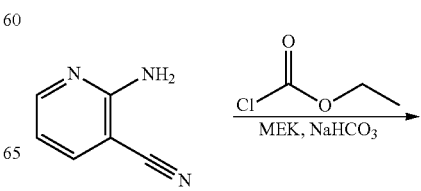

-continued

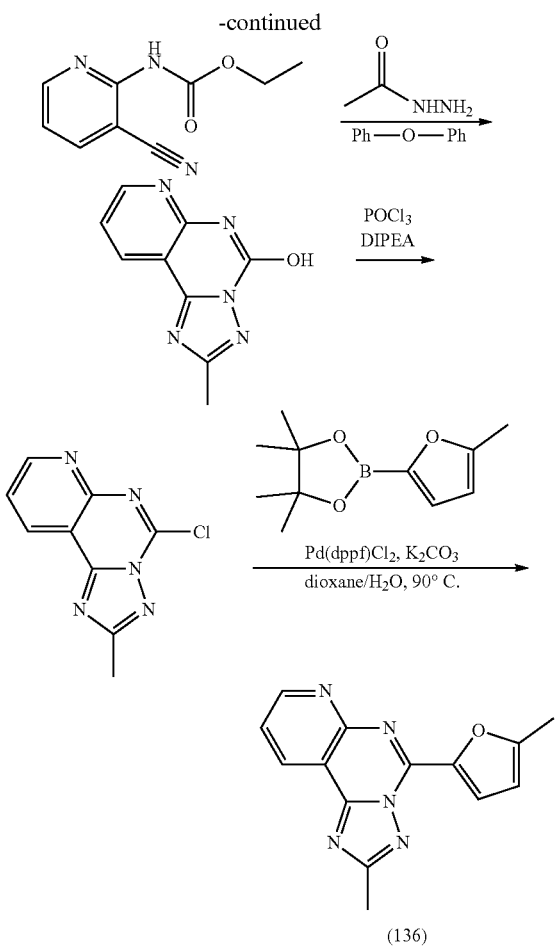

(136)

Step 1: Preparation of ethyl N-(3-cyano-2-pyridyl)carbamate

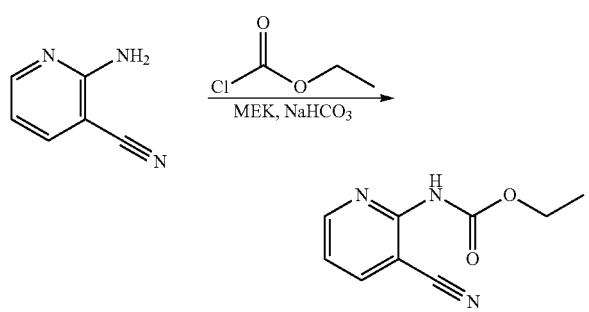

Ethyl carbonochloridate (11.40 g, 105.05 mmol, 10 mL, 6.26 eq.) was added to a suspension of 2-aminopyridine-3-carbonitrile (2 g, 16.79 mmol, 1 eq.) and NaHCO₃ (4.23 g, 50.39 mmol, 3 eq.) in 2-butanone (10 mL). The mixture was heated and stirred at 70° C. for 10 min. After cooling to room temperature, the mixture was diluted with CH₂Cl₂ (50 mL), filtered and the filtrate was concentrated under vacuum to give ethyl N-(3-cyano-2-pyridyl)carbamate (1.24 g, 31.1% yield,) as brown solid, which was used directly in the next step. LCMS m/z 192.1 [M+H]⁺.

Step 2: Preparation of 2-methylpyrido[3,2-e][1,2,4]triazolo[1,5-c]pyrimidin-5-ol

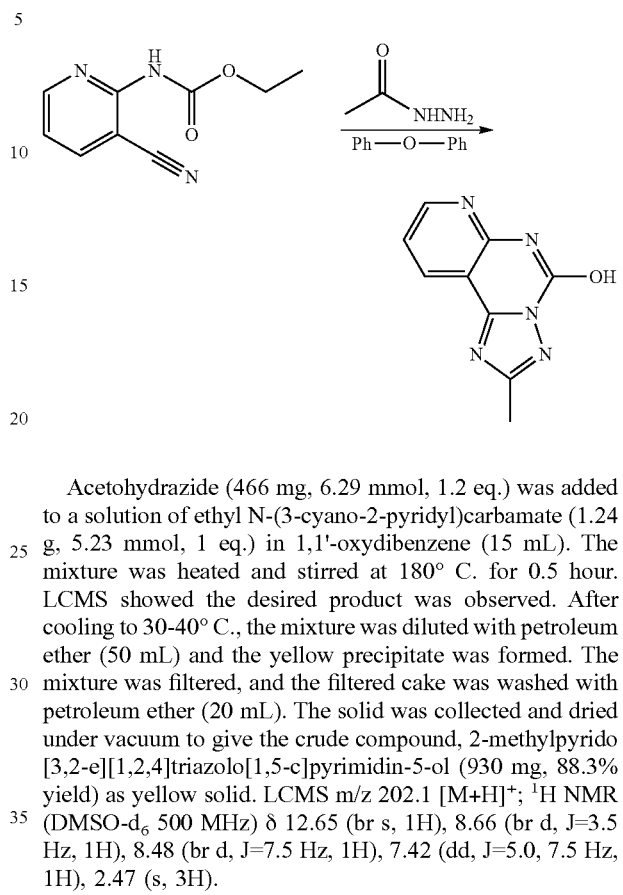

Acetohydrazide (466 mg, 6.29 mmol, 1.2 eq.) was added to a solution of ethyl N-(3-cyano-2-pyridyl)carbamate (1.24 g, 5.23 mmol, 1 eq.) in 1,1'-oxydibenzene (15 mL). The mixture was heated and stirred at 180° C. for 0.5 hour. LCMS showed the desired product was observed. After cooling to 30-40° C., the mixture was diluted with petroleum ether (50 mL) and the yellow precipitate was formed. The mixture was filtered, and the filtered cake was washed with petroleum ether (20 mL). The solid was collected and dried under vacuum to give the crude compound, 2-methylpyrido[3,2-e][1,2,4]triazolo[1,5-c]pyrimidin-5-ol (930 mg, 88.3% yield) as yellow solid. LCMS m/z 202.1 [M+H]⁺; ¹H NMR (DMSO-d₆ 500 MHz) δ 12.65 (br s, 1H), 8.66 (br d, J=3.5 Hz, 1H), 8.48 (br d, J=7.5 Hz, 1H), 7.42 (dd, J=5.0, 7.5 Hz, 1H), 2.47 (s, 3H).

Step 3: Preparation of 5-chloro-2-methylpyrido[3,2-e][1,2,4]triazolo[1,5-c]pyrimidine A mixture of 2-methylpyrido[3,2-e][1,2,4]triazolo[1,5-c]pyrimidin-5-ol (930 mg, 4.62 mmol, 1 eq.) and DIEA (1.79 g, 13.87 mmol, 2.42 mL, 3 eq.) in POCl₃ (10 mL) was heated and stirred at 100° C. for 17 hours. After cooling to room temperature, to the mixture was added aq. NaHCO₃, slowly, to provide a solution of pH=7-8. The mixture was extracted with EtOAc (50 mL×4), washed with water (100 mL) and brine (100 mL). The organic layer was dried over sodium sulfate, filtered and concentrated under vacuum to give 5-chloro-2-methylpyrido[3,2-e][1,2,4]triazolo[1,5-c]pyrimidine (500 mg, 49.25% yield) as yellow solid, which was used for next step directly. LCMS m/z 219.8 [M+H]⁺.

Step 4: Preparation of 2-methyl-5-(5-methylfuran-2-yl)pyrido[3,2-e][1,2,4]triazolo[1,5-c]pyrimidine (136)

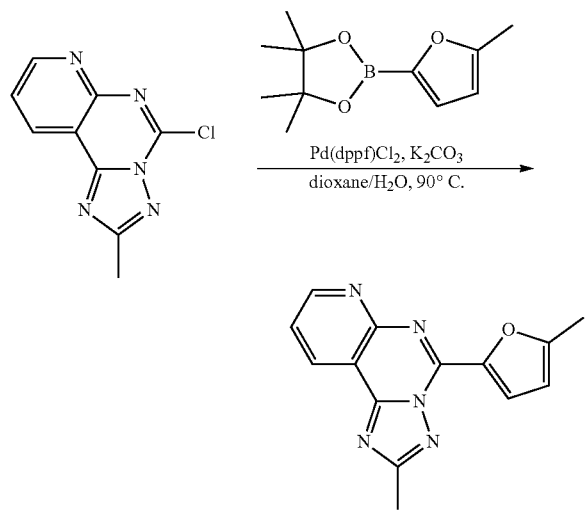

To a suspension of 5-chloro-2-methylpyrido[3,2-e][1,2,4]triazolo[1,5-c]pyrimidine (100 mg, 346.95 µmol, 1 eq.), 4,4,5,5-tetramethyl-2-(5-methyl-2-furyl)-1,3,2-dioxaborolane (110 mg, 528.69 µmol, 1.52 eq.) and $K_2CO_3$ (72 mg, 520.96 µmol, 1.50 eq.) in dioxane (10 mL) and $H_2O$ (0.5 mL) was added Pd(dppf)$Cl_2$ (26 mg, 35.53 µmol, 0.102 eq.) under nitrogen. The mixture was heated and stirred at 90° C. for 18 hours. After cooling to room temperature, the mixture was diluted with EtOAc (50 mL) and filtered through a pad of Celite®. The filtrate was washed with water (30 mL) and brine (30 mL), dried over sodium sulfate, filtered and concentrated under vacuum. The residue was purified by column chromatography on silica gel and lyophilizated to give 2-methyl-5-(5-methylfuran-2-yl)pyrido[3,2-e][1,2,4]triazolo[1,5-c]pyrimidine (44.2 mg, 48.0% yield) as yellow solid. LCMS m/z 266.1 [M+H]$^+$; $^1$H NMR (DMSO-$d_6$ 400 MHz) δ 9.10 (dd, J=1.6, 4.4 Hz, 1H), 8.80 (dd, J=2.0, 8.0 Hz, 1H), 8.21 (d, J=3.6 Hz, 1H), 7.74 (dd, J=4.8, 7.6 Hz, 1H), 6.63-6.54 (m, 1H), 2.65 (s, 3H), 2.53 (s, 3H).

The compounds in Table 1 were prepared in accordance with the synthetic protocols set forth in Examples 1-8 and general synthesis Schemes 1-4 by adjusting to the appropriate starting materials.

TABLE 1

| Compound No. | Structure | IUPAC Name | LC/MS | Purity |
|---|---|---|---|---|
| 1 | 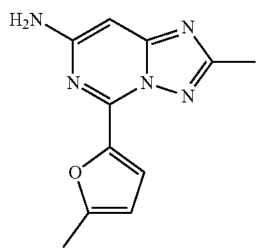 [SMILES: Cc1nc2cc(N)nc(-c3ccc(C)o3)n2n1] | 2-Methyl-5-(5-methylfuran-2-yl)-[1,2,4]triazolo[1,5-c]pyrimidin-7-amine | [MH+] = 229.9 | 99.6% |
| 2 | 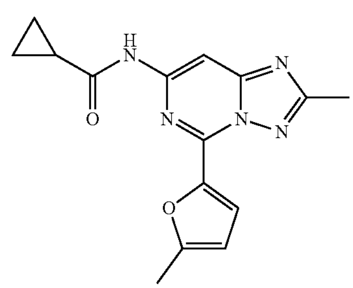 [SMILES: Cc1nc2cc(NC(=O)C3CC3)nc(-c3ccc(C)o3)n2n1] | N-[2-methyl-5-(5-methylfuran-2-yl)-[1,2,4]triazolo[1,5-c]pyrimidin-7-yl]cyclopropanecarboxamide | [MH+] = 297.9 | 99.0% |
| 3 | 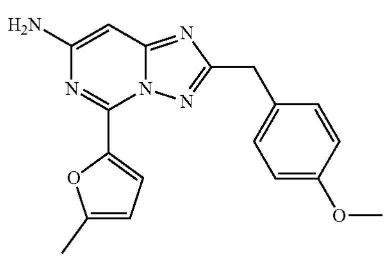 [SMILES: COc1ccc(Cc2nc3cc(N)nc(-c4ccc(C)o4)n3n2)cc1] | 2-[(4-methoxyphenyl)methyl]-5-(5-methylfuran-2-yl)-[1,2,4]triazolo[1,5-c]pyrimidin-7-amine | [MH+] = 336.0 | 99.0% |

TABLE 1-continued

| Compound No. | Structure | IUPAC Name | LC/MS | Purity |
|---|---|---|---|---|
| 4 | 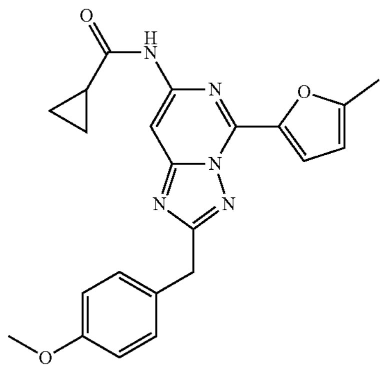 | N-2-[(4-methoxyphenyl)methyl]-5-(5-methylfuran-2-yl)-[1,2,4]triazolo[1,5-c]pyrimidin-7-yl]cyploroelpanecarboxamide | [MH+] = 404.1 | 99.0% |
| 5 | 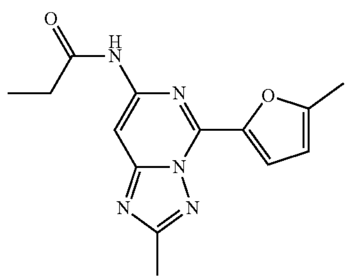 [SMILES: CCC(=O)Nc1cc2nc(C)nn2c(-c2ccc(C)o2)n1] | N-[2-methyl-5-(5-methylfuran-2-yl)-[1,2,4]triazolo[1,5-c]pyrimidin-7-yl]propanamide | [MH+] = 285.9 | 100.0% |
| 6 | 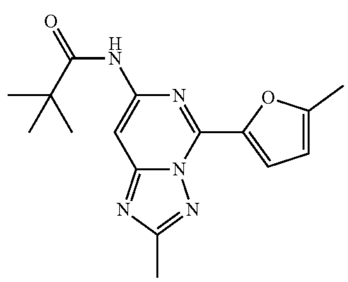 [SMILES: Cc1nc2cc(NC(=O)C(C)(C)C)nc(-c3ccc(C)o3)n2n1] | 2,2-dimethyl-N-[2-methyl-5-(5-methylfuran-2-yl)-[1,2,4]triazolo[1,5-c]pyrimidin-7-yl]propanamide | [MH+] = 313.9 | 100.0% |
| 7 | 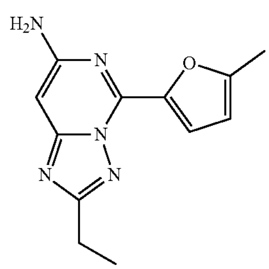 [SMILES: CCc1nc2cc(N)nc(-c3ccc(C)o3)n2n1] | 2-ethyl-5-(5-methylfuran-2-yl)-[1,2,4]triazolo[1,5-c]pyrimidin-7-amine | [MH+] = 243.8 | 100.0% |
| 8 | 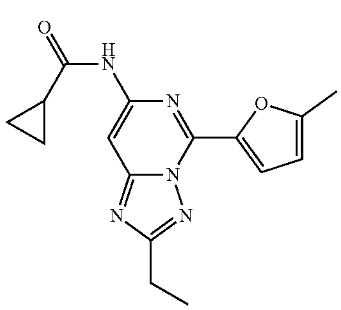 [SMILES: CCc1nc2cc(NC(=O)C3CC3)nc(-c3ccc(C)o3)n2n1] | N-[2-ethyl-5-(5-methylfuran-2-yl)-[1,2,4]triazolo[1,5-c]pyrimidin-7-yl]cyclopropanecarboxamide | [MH+] = 311.9 | 100.0% |

TABLE 1-continued

| Compound No. | Structure | IUPAC Name | LC/MS | Purity |
|---|---|---|---|---|
| 9 | 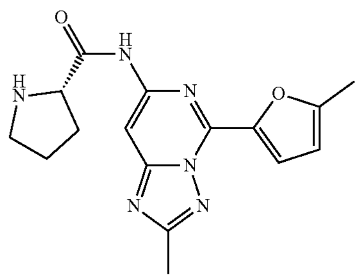 [SMILES: Cc1nc2cc(NC(=O)[C@@H]3CCCN3)nc(-c3ccc(C)o3)n2n1] | (2S)-N-[2-methyl-5-(5-methylfuran-2-yl)-[1,2,4]triazolo[1,5-c]pyrimidin-7-yl]pyrrolidine-2-carboxamide | [MH+] = 326.9 | 94.8% |
| 10 | 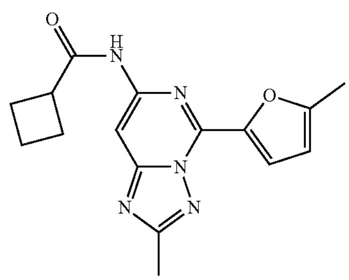 | N-[2-methyl-5-(5-methylfuran-2-yl)-[1,2,4]triazolo[1,5-c]pyrimidin-7-yl]cyclobutanecarboxamide | [MH+] = 311.9 | 99.3% |
| 11 | 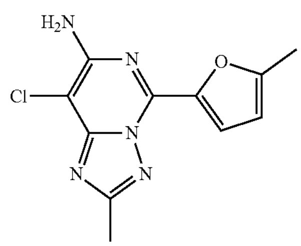 | 8-chloro-2-methyl-5-(5-methylfuran-2-yl)-[1,2,4]triazolo[1,5-c]pyrimidin-7-amine | [MH+] = 264.1 | 100.0% |
| 12 | 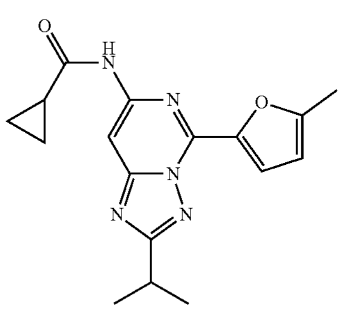 [SMILES: Cc1ccc(-c2nc(NC(=O)C3CC3)cc3nc(C(C)C)nn23)o1] | N-[5-(5-methylfuran-2-yl)-2-propan-2-yl-[1,2,4]triazolo[1,5-c]pyrimidin-7-yl]cyclopropanecarboxamide | [MH+] = 326.2 | 100.0% |
| 13 | 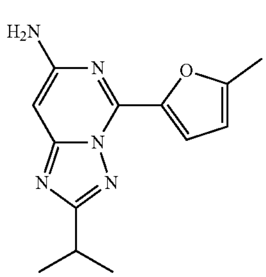 [SMILES: Cc1ccc(-c2nc(N)cc3nc(C(C)C)nn23)o1] | 5-(5-methylfuran-2-yl)-2-propan-2-yl-[1,2,4]triazolo[1,5-c]pyrimidin-7-amine | [MH+] = 258.1 | 99.3% |

TABLE 1-continued

| Compound No. | Structure | IUPAC Name | LC/MS | Purity |
|---|---|---|---|---|
| 14 | 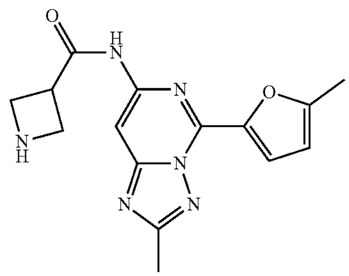 [SMILES: Cc1nc2cc(NC(=O)C3CNC3)nc(-c3ccc(C)o3)n2n1] | N-[2-methyl-5-(5-methylfuran-2-yl)-[1,2,4]triazolo[1,5-c]pyrimidin-7-yl]azetidine-3-carboxamide | [MH+] = 312.9 | 95.3% |
| 15 | 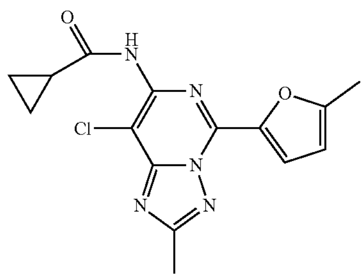 [SMILES: Cc1nc2c(Cl)c(NC(=O)C3CC3)nc(-c3ccc(C)o3)n2n1] | N-[8-chloro-2-methyl-5-(5-methylfuran-2-yl)-[1,2,4]triazolo[1,5-c]pyrimidin-7-yl]cyclopropanecarboxamide | [MH+] = 331.9 | 99.1% |
| 16 | 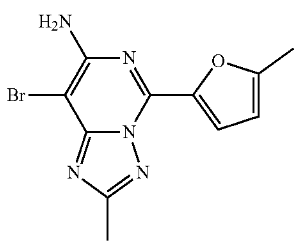 | 8-bromo-2-methyl-5-(5-methylfuran-2-yl)-[1,2,4]triazolo[1,5-c]pyrimidin-7-amine | [MH+] = 309.7 | 100.0% |
| 17 | 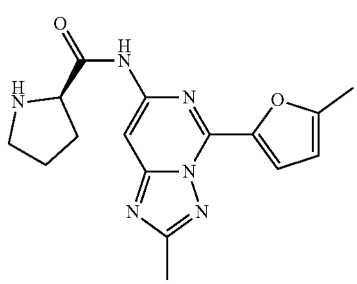 [SMILES: Cc1nc2cc(NC(=O)[C@H]3CCCN3)nc(-c3ccc(C)o3)n2n1] | (2R)-N-[2-methyl-5-(5-methylfuran-2-yl)-[1,2,4]triazolo[1,5-c]pyrimidin-7-yl]pyrrolidine-2-carboxamide | [MH+] = 327.1 | 97.2% |
| 18 | 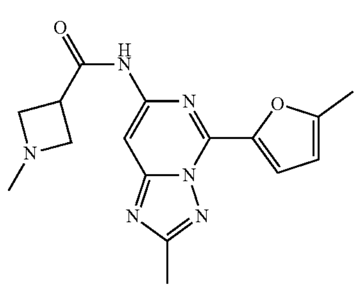 | 1-methyl-N-[2-methyl-5-(5-methylfuran-2-yl)-[1,2,4]triazolo[1,5-c]pyrimidin-7-yl]azetidine-3-carboxamide | [MH+] = 327.1 | 99.1% |

TABLE 1-continued

| Compound No. | Structure | IUPAC Name | LC/MS | Purity |
|---|---|---|---|---|
| 19 | 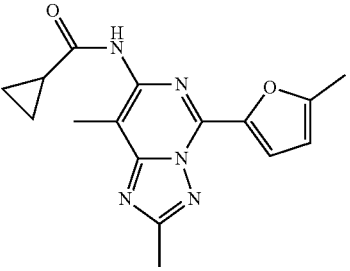 [SMILES: Cc1nc2c(C)c(NC(=O)C3CC3)nc(-c3ccc(C)o3)n2n1] | N-[2,8-dimethyl-5-(5-methylfuran-2-yl)-[1,2,4]triazolo[1,5-c]pyrimidin-7-yl]cyclopropanecarboxamide | [MH+] = 312.0 | 100.0% |
| 20 | 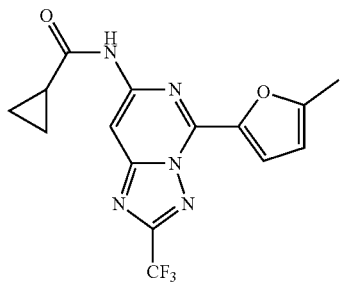 [SMILES: Cc1ccc(-c2nc(NC(=O)C3CC3)cc3nc(C(F)(F)F)nn23)o1] | N-[5-(5-methylfuran-2-yl)-2-(trifluoromethyl)-[1,2,4]triazolo[1,5-c]pyrimidin-7-yl]cyclopropanecarboxamide | [MH+] = 352.0 | 100.0% |
| 21 | 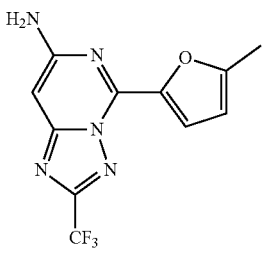 [SMILES: Cc1ccc(-c2nc(N)cc3nc(C(F)(F)F)nn23)o1] | 5-(5-methylfuran-2-yl)-2-(trifluoromethyl)-[1,2,4]triazolo[1,5-c]pyrimidin-7-amine | [MH+] = 283.9 | 99.5% |
| 22 | 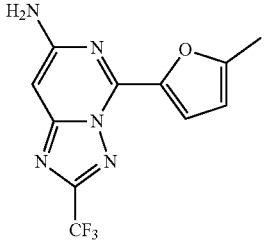 | 2,8-dimethyl-5-(5-methylfuran-2-yl)-[1,2,4]triazolo[1,5-c]pyrimidin-7-amine | [MH+] = 244.1 | 98.8% |
| 23 | 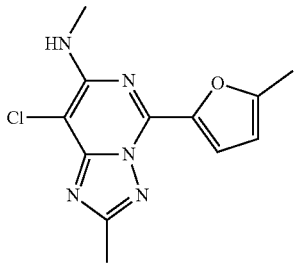 | 8-chloro-N,2-dimethyl-5-(5-methylfuran-2-yl)-[1,2,4]triazolo[1,5-c]pyrimidin-7-amine | [MH+] = 277.9 | 100.0% |

TABLE 1-continued

| Compound No. | Structure | IUPAC Name | LC/MS | Purity |
|---|---|---|---|---|
| 24 | 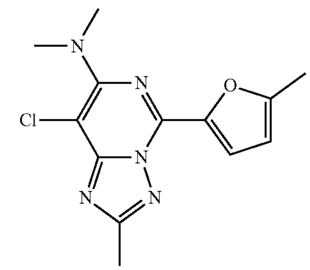 | 8-chloro-N,N,2-trimethyl-5-(5-methylfuran-2-yl)-[1,2,4]triazolo[1,5-c]pyrimidin-7-amine | [MH+] = 291.9 | 100.0% |
| 25 | 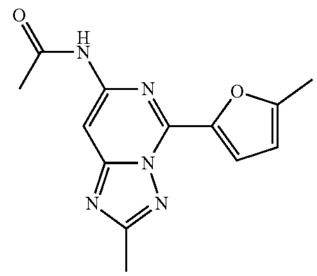 [SMILES: CC(=O)Nc1cc2nc(C)nn2c(-c2ccc(C)o2)n1] | N-[2-methyl-5-(5-methylfuran-2-yl)-[1,2,4]triazolo[1,5-c]pyrimidin-7-yl]acetamide | [MH+] = 271.9 | 100.0% |
| 26 | 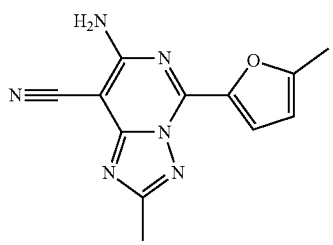 [SMILES: Cc1nc2c(C#N)c(N)nc(-c3ccc(C)o3)n2n1] | 7-amino-2-methyl-5-(5-methylfuran-2-yl)-[1,2,4]triazolo[1,5-c]pyrimidine-8-carbonitrile | [M + H] = 254.9 | 99.0% |
| 27 | 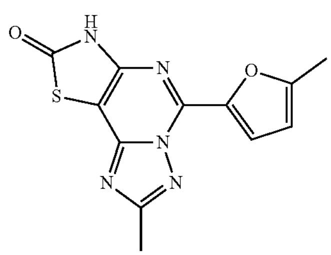 [SMILES: Cc1nc2c3sc(=O)[nH]c3nc(-c3ccc(C)o3)n2n1] | 4-methyl-7-(5-methylfuran-2-yl)-12-thia-3,5,6,8,10-pentazatricyclo[7.3.0.0$^{2,6}$]dodeca-1(9),2,4,7-tetraen-11-one | [M + H] = 287.9 | 100.0% |
| 28 | 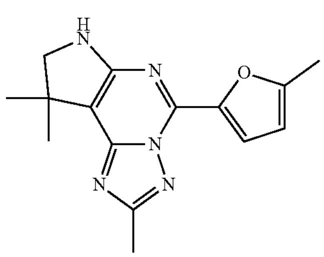 | 4,12,12-trimethyl-7-(5-methylfuran-2-yl)-3,5,6,8,10-pentazatricyclo[7.3.0.0$^{2,6}$]dodeca-1(9),2,4,7-tetraene | [M + H] = 284 | 92.0% |
| 29 | 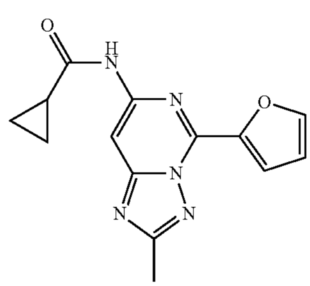 [SMILES: Cc1nc2cc(NC(=O)C3CC3)nc(-c3ccco3)n2n1] | N-[5-(furan-2-yl)-2-methyl-[1,2,4]triazolo[1,5-c]pyrimidin-7-yl]cyclopropanecarboxamide | [M + H] = 284 | 98.0% |

TABLE 1-continued

| Compound No. | Structure | IUPAC Name | LC/MS | Purity |
|---|---|---|---|---|
| 30 | 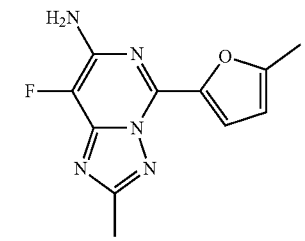 [SMILES: Cc1nc2c(F)c(N)nc(-c3ccc(C)o3)n2n1] | 8-fluoro-2-methyl-5-(5-methylfuran-2-yl)-[1,2,4]triazolo[1,5-c]pyrimidin-7-amine | [M + H] = 247.9 | 99.0% |
| 31 | 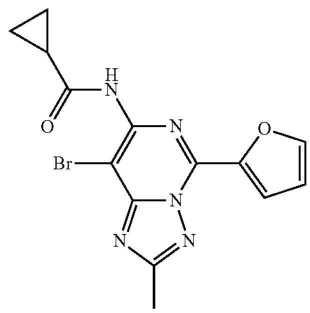 [SMILES: Cc1nc2c(Br)c(NC(=O)C3CC3)nc(-c3ccco3)n2n1] | N-[8-bromo-5-(furan-2-yl)-2-methyl-[1,2,4]triazolo[1,5-c]pyrimidin-7-yl]cyclopropanecarboxamide | [M+/M + 2] = | 100.0% |
| 32 | 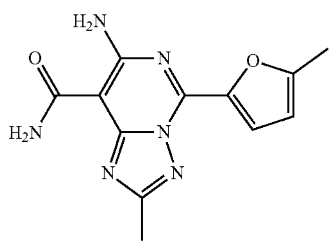 [SMILES: Cc1nc2c(C(N)=O)c(N)nc(-c3ccc(C)o3)n2n1] | 7-amino-2-methyl-5-(5-methylfuran-2-yl)-[1,2,4]triazolo[1,5-c]pyrimidine-8-carboxamide | [MH+] = 273.0 | 100.0% |
| 33 | 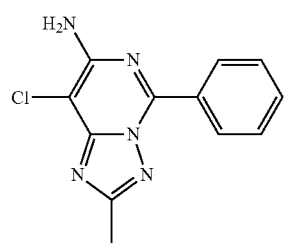 [SMILES: Cc1nc2c(Cl)c(N)nc(-c3ccccc3)n2n1] | 8-chloro-2-methyl-5-phenyl-[1,2,4]triazolo[1,5-c]pyrimidin-7-amine | [MH+] = 259.9 | 99.9% |
| 34 | 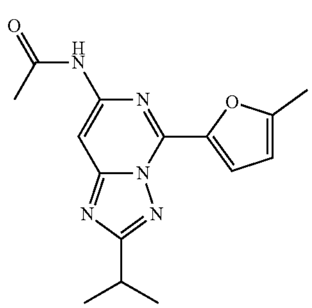 [SMILES: CC(=O)Nc1cc2nc(C(C)C)nn2c(-c2ccc(C)o2)n1] | N-[5-(5-methylfuran-2-yl)-2-propan-2-yl-[1,2,4]triazolo[1,5-c]pyrimidin-7-yl]acetamide | [MH+] = 300.0 | 92.1% |

TABLE 1-continued

| Compound No. | Structure | IUPAC Name | LC/MS | Purity |
|---|---|---|---|---|
| 35 | 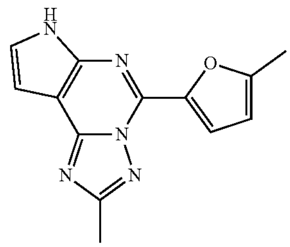 [SMILES: Cc1nc2c3cc[nH]c3nc(-c3ccc(C)o3)n2n1] | 4-methyl-7-(5-methylfuran-2-yl)-3,5,6,8,10-pentazatricyclo[7.3.0.0²,⁶]dodeca-1(9),2,4,7,11-pentaene | [MH+] = 254.2 | 98.9% |
| 36 | 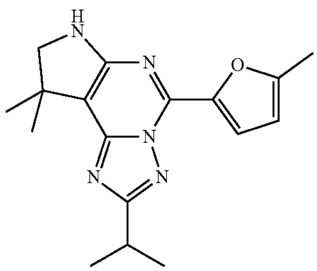 | 12,12-dimethyl-7-(5-methylfuran-2-yl)-4-propan-2-yl-3,5,6,8,10-pentazatricyclo[7.3.0.0²,⁶]dodeca-1(9),2,4,7-tetraene | [MH+] = 311.9 | 100.0% |
| 37 | 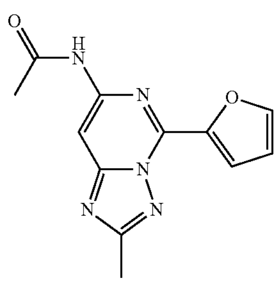 [SMILES: CC(=O)Nc1cc2nc(C)nn2c(-c2ccco2)n1] | N-[5-(furan-2-yl)-2-methyl-[1,2,4]triazolo[1,5-c]pyrimidin-7-yl]acetamide | [MH+] = 258.1 | 96.0% |
| 38 | 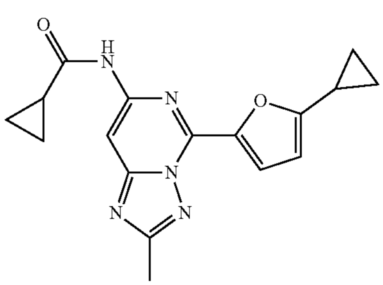 [SMILES: Cc1nc2cc(NC(=O)C3CC3)nc(-c3ccc(C4CC4)o3)n2n1] | N-[5-(5-cyclopropylfuran-2-yl)-2-methyl-[1,2,4]triazolo[1,5-c]pyrimidin-7-yl]cyclopropanecarboxamide | [MH+] = 323.9 | 99.0% |
| 39 | 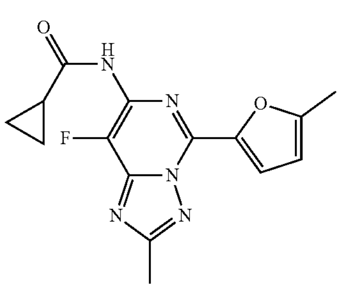 [SMILES: Cc1nc2c(F)c(NC(=O)C3CC3)nc(-c3ccc(C)o3)n2n1] | N-[8-fluoro-2-methyl-5-(5-methylfuran-2-yl)-[1,2,4]triazolo[1,5-c]pyrimidin-7-yl]cyclopropanecarboxamide | [MH+] = 315.9 | 100.0% |

TABLE 1-continued

| Compound No. | Structure | IUPAC Name | LC/MS | Purity |
|---|---|---|---|---|
| 40 | 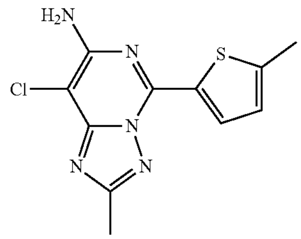 [SMILES: Cc1nc2c(Cl)c(N)nc(-c3ccc(C)s3)n2n1] | 8-chloro-2-methyl-5-(5-methylthiophen-2-yl)-[1,2,4]triazolo[1,5-c]pyrimidin-7-amine | [MH+] = 279.8 | 99.1% |
| 41 | 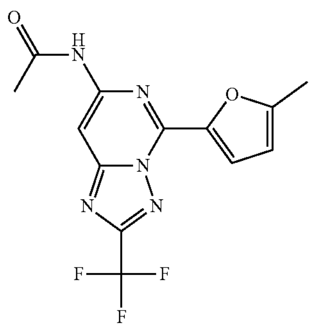 [SMILES: CC(=O)Nc1cc2nc(C(F)(F)F)nn2c(-c2ccc(C)o2)n1] | N-[5-(5-methylfuran-2-yl)-2-(trifluoromethyl)-[1,2,4]triazolo[1,5-c]pyrimidin-7-yl]acetamide | [MH+] = 326.0 | 100.0% |
| 42 | 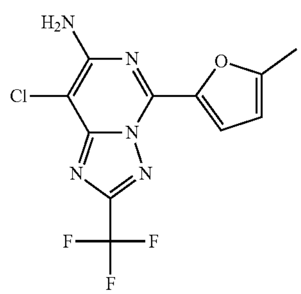 [SMILES: Cc1ccc(-c2nc(N)c(Cl)c3nc(C(F)(F)F)nn23)o1] | 8-chloro-5-(5-methylfuran-2-yl)-2-(trifluoromethyl)-[1,2,4]triazolo[1,5-c]pyrimidin-7-amine | [MH+] = 318.0 | 98.0% |
| 43 | 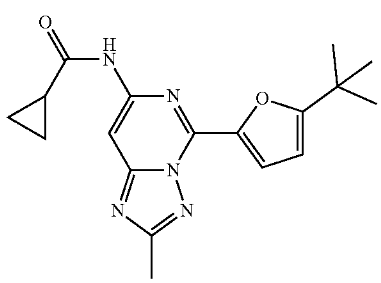 [SMILES: Cc1nc2cc(NC(=O)C3CC3)nc(-c3ccc(C(C)(C)C)o3)n2n1] | N-[5-(5-tert-butylfuran-2-yl)-2-methyl-[1,2,4]triazolo[1,5-c]pyrimidin-7-yl]cyclopropanecarboxamide | [MH+] = 340.1 | 95.6% |
| 44 | 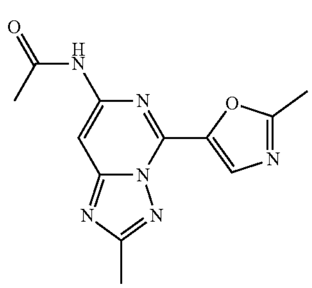 [SMILES: CC(=O)Nc1cc2nc(C)nn2c(-c2cnc(C)o2)n1] | N-[2-methyl-5-(2-methyl-1,3-oxazol-5-yl)-[1,2,4]triazolo[1,5-c]pyrimidin-7-yl]acetamide | 273.1 | 98.9% |

TABLE 1-continued

| Compound No. | Structure | IUPAC Name | LC/MS | Purity |
|---|---|---|---|---|
| 45 | 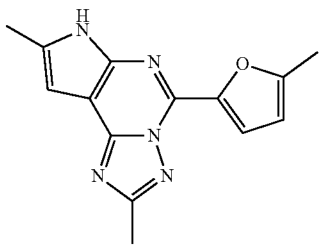 | 4,11-dimethyl-7-(5-methylfuran-2-yl)-3,5,6,8,10-pentazatricyclo[7.3.0.0$^{2,6}$]dodeca-1(9),2,4,7,11-pentaene | 268.1 | 97.0% |
| 46 | 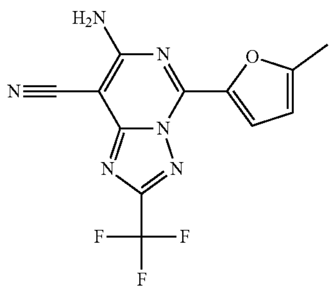 [SMILES: Cc1ccc(-c2nc(N)c(C#N)c3nc(C(F)(F)F)nn23)o1] | 7-amino-5-(5-methylfuran-2-yl)-2-(trifluoromethyl)-[1,2,4]triazolo[1,5-c]pyrimidine-8-carbonitrile | [MH+] = 326.1 | 100.0% |
| 47 | 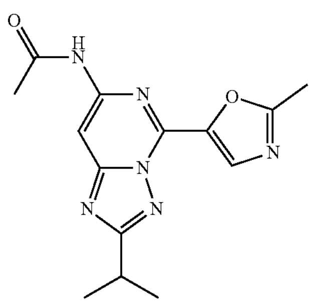 [SMILES: CC(=O)Nc1cc2nc(C(C)C)nn2c(-c2cnc(C)o2)n1] | N-[5-(2-methyl-1,3-oxazol-5-yl)-2-propan-2-yl-[1,2,4]triazolo[1,5-c]pyrimidin-7-yl]acetamide | [MH+] = 301.1 | 100.0% |
| 48 | 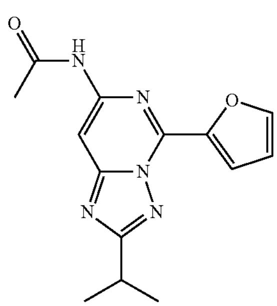 [SMILES: CC(=O)Nc1cc2nc(C(C)C)nn2c(-c2ccco2)n1] | N-[5-(furan-2-yl)-2-propan-2-yl-[1,2,4]triazolo[1,5-c]pyrimidin-7-yl]acetamide | [MH+] = 286.1 | 100.0% |
| 49 | 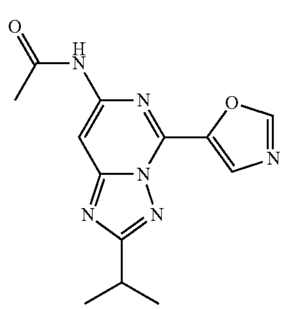 [SMILES: CC(=O)Nc1cc2nc(C(C)C)nn2c(-c2cnco2)n1] | N-[5-(1,3-oxazol-5-yl)-2-propan-2-yl-[1,2,4]triazolo[1,5-c]pyrimidin-7-yl]acetamide | [MH+] = 287.1 | 99.4% |

TABLE 1-continued

| Compound No. | Structure | IUPAC Name | LC/MS | Purity |
|---|---|---|---|---|
| 50 | 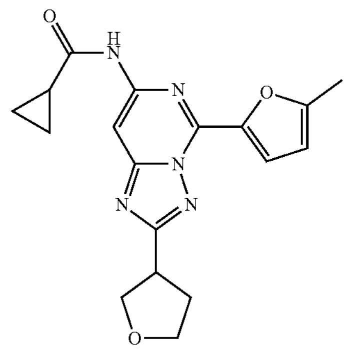 [SMILES: Cc1ccc(-c2nc(NC(=O)C3CC3)cc3nc(C4CCOC4)nn23)o1] | N-[5-(5-methylfuran-2-yl)-2-(oxolan-3-yl)-[1,2,4]triazolo[1,5-c]pyrimidin-7-yl]cyclopropanecarboxamide | [MH+] = 354.35, 95% | 91.0% |
| 51 | 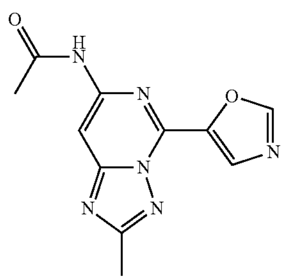 [SMILES: CC(=O)Nc1cc2nc(C)nn2c(-c2cnco2)n1] | N-[2-methyl-5-(1,3-oxazol-5-yl)-[1,2,4]triazolo[1,5-c]pyrimidin-7-yl]acetamide | [MH+] = 259.1 | 98.7% |
| 52 | 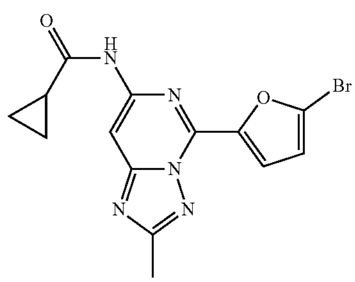 [SMILES: Cc1nc2cc(NC(=O)C3CC3)nc(-c3ccc(Br)o3)n2n1] | N-[5-(5-bromofuran-2-yl)-2-methyl-[1,2,4]triazolo[1,5-c]pyrimidin-7-yl]cyclopropanecarboxamide | [M+] = 362.0/364.0 | 93.4% |
| 53 | 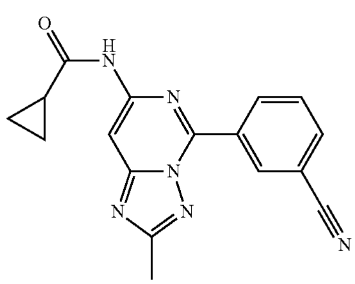 [SMILES: Cc1nc2cc(NC(=O)C3CC3)nc(-c3cccc(C#N)c3)n2n1] | N-[5-(3-cyanophenyl)-2-methyl-[1,2,4]triazolo[1,5-c]pyrimidin-7-yl]cyclopropanecarboxamide | [MH+] = 319.6 | 95.0% |
| 54 | 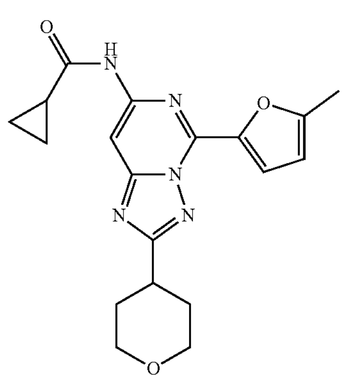 [SMILES: Cc1ccc(-c2nc(NC(=O)C3CC3)cc3nc(C4CCOCC4)nn23)o1] | N-[5-(5-methylfuran-2-yl)-2-(oxan-4-yl)-[1,2,4]triazolo[1,5-c]pyrimidin-7-yl]cyclopropanecarboxamide | [MH+] = 368.4 | 95.0% |

TABLE 1-continued

| Compound No. | Structure | IUPAC Name | LC/MS | Purity |
|---|---|---|---|---|
| 55 | 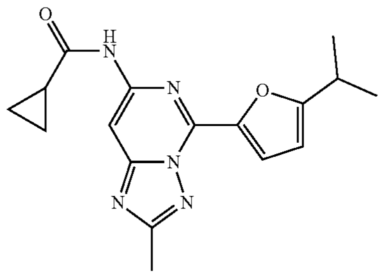 [SMILES: Cc1nc2cc(NC(=O)C3CC3)nc(-c3ccc(C(C)C)o3)n2n1] | N-[2-methyl-5-(5-propan-2-ylfuran-2-yl)-[1,2,4]triazolo[1,5-c]pyrimidin-7-yl]cyclopropanecarboxamide | [M + H] = 326.1 | 99.8% |
| 56 | 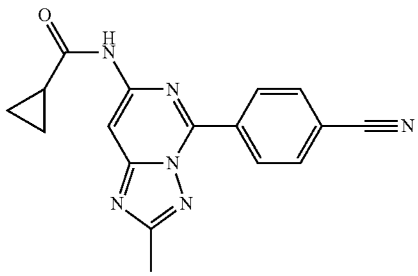 [SMILES: Cc1nc2cc(NC(=O)C3CC3)nc(-c3ccc(C#N)cc3)n2n1] | N-[5-(4-cyanophenyl)-2-methyl-[1,2,4]triazolo[1,5-c]pyrimidin-7-yl]cyclopropanecarboxamide | [MH+] = 319.3 | 96.0% |
| 57 | 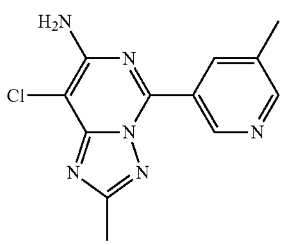 [SMILES: Cc1cncc(-c2nc(N)c(Cl)c3nc(C)nn23)c1] | 8-chloro-2-methyl-5-(5-methylpyridin-3-yl)-[1,2,4]triazolo[1,5-c]pyrimidin-7-amine | [MH+] = 275.1 | 100.0% |
| 58 | 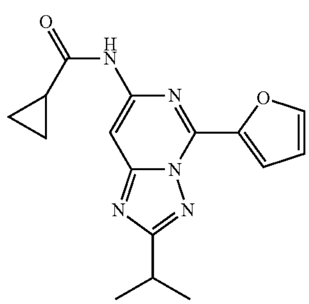 [SMILES: CC(C)c1nc2cc(NC(=O)C3CC3)nc(-c3ccco3)n2n1] | N-[5-(furan-2-yl)-2-propan-2-yl-[1,2,4]triazolo[1,5-c]pyrimidin-7-yl]cyclopropanecarboxamide | [MH+] = 312.4 | 100.0% |
| 59 | 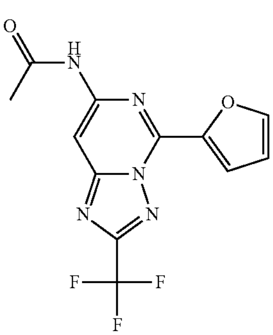 [SMILES: CC(=O)Nc1cc2nc(C(F)(F)F)nn2c(-c2ccco2)n1] | N-[5-(furan-2-yl)-2-(trifluoromethyl)-[1,2,4]triazolo[1,5-c]pyrimidin-7-yl]acetamide | [MH+] = 312.0 | 99.6% |

TABLE 1-continued

| Compound No. | Structure | IUPAC Name | LC/MS | Purity |
|---|---|---|---|---|
| 60 | 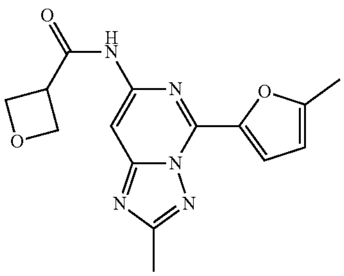 [SMILES: Cc1nc2cc(NC(=O)C3COC3)nc(-c3ccc(C)o3)n2n1] | N-[2-methyl-5-(5-methylfuran-2-yl)-[1,2,4]triazolo[1,5-c]pyrimidin-7-yl]oxetane-3-carboxamide | [MH+] = 314.1 | 96.8% |
| 61 | 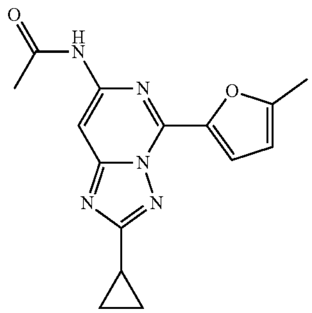 [SMILES: CC(=O)Nc1cc2nc(C3CC3)nn2c(-c2ccc(C)o2)n1] | N-[2-cyclopropyl-5-(5-methylfuran-2-yl)-[1,2,4]triazolo[1,5-c]pyrimidin-7-yl]acetamide | [M + H] = 298.3 | 95.0% |
| 62 | 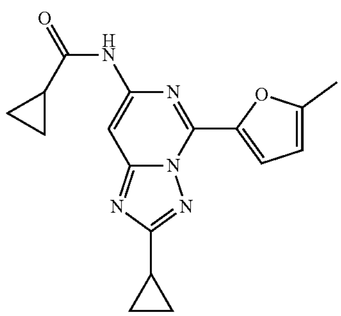 [SMILES: Cc1ccc(-c2nc(NC(=O)C3CC3)cc3nc(C4CC4)nn23)o1] | N-[2-cyclopropyl-5-(5-methylfuran-2-yl)-[1,2,4]triazolo[1,5-c]pyrimidin-7-yl]cyclopropanecarboxamide | [MH+] = 324.3 | 95.0% |
| 63 | 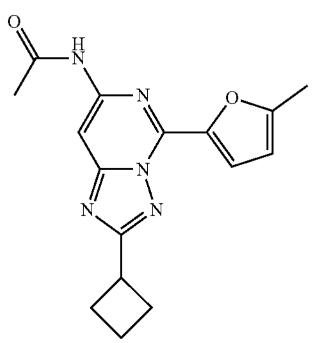 [SMILES: CC(=O)Nc1cc2nc(C3CCC3)nn2c(-c2ccc(C)o2)n1] | N-[2-cyclobutyl-5-(5-methylfuran-2-yl)-[1,2,4]triazolo[1,5-c]pyrimidin-7-yl]acetamide | [MH+] = 312.3 | 95.0% |
| 64 | 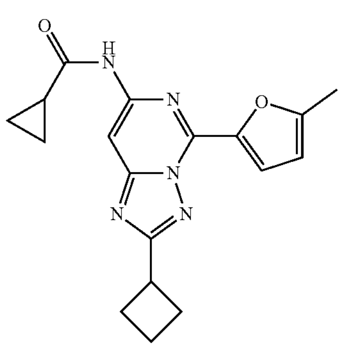 [SMILES: Cc1ccc(-c2nc(NC(=O)C3CC3)cc3nc(C4CCC4)nn23)o1] | N-[2-cyclobutyl-5-(5-methylfuran-2-yl)-[1,2,4]triazolo[1,5-c]pyrimidin-7-yl]cyclopropanecarboxamide | [MH+] = 338.3 | 95.0% |

TABLE 1-continued

| Compound No. | Structure | IUPAC Name | LC/MS | Purity |
|---|---|---|---|---|
| 65 | 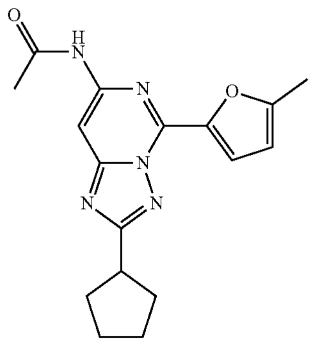 [SMILES: CC(=O)Nc1cc2nc(C3CCCC3)nn2c(-c2ccc(C)o2)n1] | N-[2-cyclopentyl-5-(5-methylfuran-2-yl)-[1,2,4]triazolo[1,5-c]pyrimidin-7-yl]acetamide | [MH+] = 326.3 | 95.0% |
| 66 | 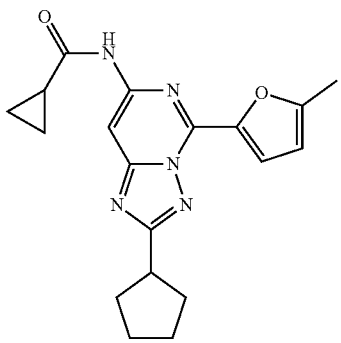 [SMILES: Cc1ccc(-c2nc(NC(=O)C3CC3)cc3nc(C4CCCC4)nn23)o1] | N-[2-cyclopentyl-5-(5-methylfuran-2-yl)-[1,2,4]triazolo[1,5-c]pyrimidin-7-yl]cyclopropanecarboxamide | [MH+] = 352.3 | 95.0% |
| 67 | 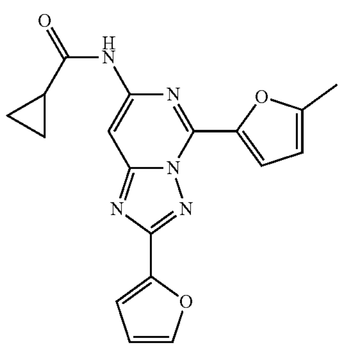 [SMILES: Cc1ccc(-c2nc(NC(=O)C3CC3)cc3nc(-c4ccco4)nn23)o1] | N-[2-(furan-2-yl)-5-(5-methylfuran-2-yl)-[1,2,4]triazolo[1,5-c]pyrimidin-7-yl]cyclopropanecarboxamide | [MH+] = 350.3 | 95.0% |
| 68 | 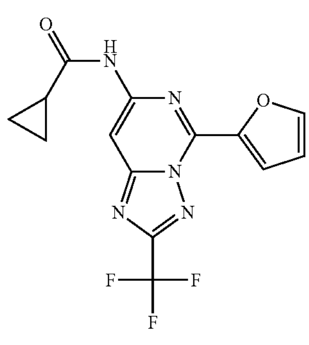 [SMILES: O=C(Nc1cc2nc(C(F)(F)F)nn2c(-c2ccco2)n1)C1CC1] | N-[5-(furan-2-yl)-2-(trifluoromethyl)-[1,2,4]triazolo[1,5-c]pyrimidin-7-yl]cyclopropanecarboxamide | [MH+] = 338.4 | 98.7% |

TABLE 1-continued

| Compound No. | Structure | IUPAC Name | LC/MS | Purity |
|---|---|---|---|---|
| 69 | 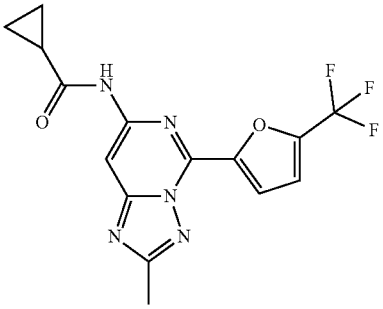 [SMILES: Cc1nc2cc(NC(=O)C3CC3)nc(-c3ccc(C(F)(F)F)o3)n2n1] | N-[2-methyl-5-[5-(trifluoromethyl)furan-2-yl]-[1,2,4]triazolo[1,5-c]pyrimidin-7-yl]cyclopropanecarboxamide | [MH+] = 352.1 | 98.8% |
| 70 | 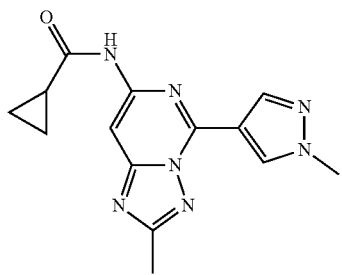 [SMILES: Cc1nc2cc(NC(=O)C3CC3)nc(-c3cnn(C)c3)n2n1] | N-[2-methyl-5-(1-methylpyrazol-4-yl)-[1,2,4]triazolo[1,5-c]pyrimidin-7-yl]cyclopropanecarboxamide | [MH+] = 298.35 | 95.0% |
| 71 | 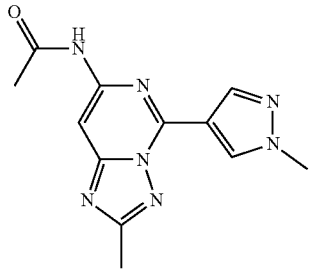 [SMILES: CC(=O)Nc1cc2nc(C)nn2c(-c2cnn(C)c2)n1] | N-[2-methyl-5-(1-methylpyrazol-4-yl)-[1,2,4]triazolo[1,5-c]pyrimidin-7-yl]acetamide | [MH+] = 272.3 | 95.0% |
| 72 | 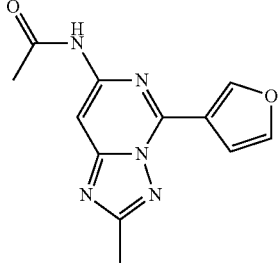 [SMILES: CC(=O)Nc1cc2nc(C)nn2c(-c2ccoc2)n1] | N-[5-(furan-3-yl)-2-methyl-[1,2,4]triazolo[1,5-c]pyrimidin-7-yl]acetamide | [MH+] = 258.3 | 95.0% |
| 73 | 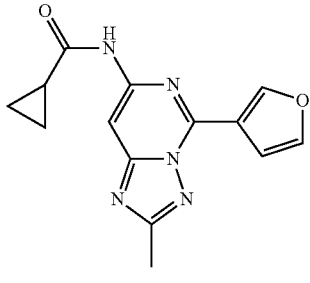 [SMILES: Cc1nc2cc(NC(=O)C3CC3)nc(-c3ccoc3)n2n1] | N-[5-(furan-3-yl)-2-methyl-[1,2,4]triazolo[1,5-c]pyrimidin-7-yl]cyclopropanecarboxamide | [MH+] = 284.3 | 95.0% |

TABLE 1-continued

| Compound No. | Structure | IUPAC Name | LC/MS | Purity |
|---|---|---|---|---|
| 74 | 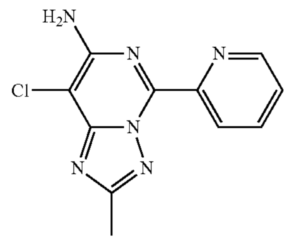 [SMILES: Cc1nc2c(Cl)c(N)nc(-c3ccccn3)n2n1] | 8-chloro-2-methyl-5-pyridin-2-yl-[1,2,4]triazolo[1,5-c]pyrimidin-7-amine | [M + H] = 261.3 | 100.0% |
| 75 | 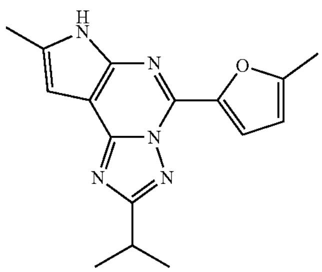 | 11-methyl-7-(5-methylfuran-2-yl)-4-propan-2-yl-3,5,6,8,10-pentazatricyclo[7.3.0.0$^{2,6}$]dodeca-1(9),2,4,7,11-pentaene | [MH+] = 296.1 | 98.2% |
| 76 | 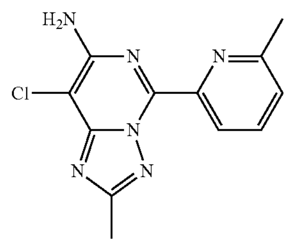 [SMILES: Cc1cccc(-c2nc(N)c(Cl)c3nc(C)nn23)n1] | 8-chloro-2-methyl-5-(6-methylpyridin-2-yl)-[1,2,4]triazolo[1,5-c]pyrimidin-7-amine | [MH+] = 274.9 | 99.4% |
| 77 | 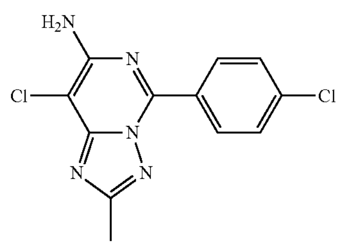 [SMILES: Cc1nc2c(Cl)c(N)nc(-c3ccc(Cl)cc3)n2n1] | 8-chloro-5-(4-chlorophenyl)-2-methyl-[1,2,4]triazolo[1,5-c]pyrimidin-7-amine | [M+/M + 2] = 294.0/296.0 | 99.7% |
| 78 | 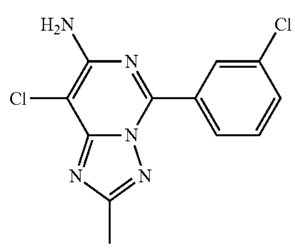 [SMILES: Cc1nc2c(Cl)c(N)nc(-c3cccc(Cl)c3)n2n1] | 8-chloro-5-(3-chlorophenyl)-2-methyl-[1,2,4]triazolo[1,5-c]pyrimidin-7-amine | [M+/M + 2] = 294.0/296.0 | 96.1% |
| 79 | 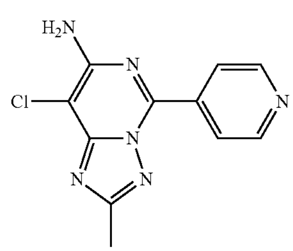 [SMILES: Cc1nc2c(Cl)c(N)nc(-c3ccncc3)n2n1] | 8-chloro-2-methyl-5-pyridin-4-yl-[1,2,4]triazolo[1,5-c]pyrimidin-7-amine | [M + H] = 261.0 | 99.5% |

TABLE 1-continued

| Compound No. | Structure | IUPAC Name | LC/MS | Purity |
|---|---|---|---|---|
| 80 | 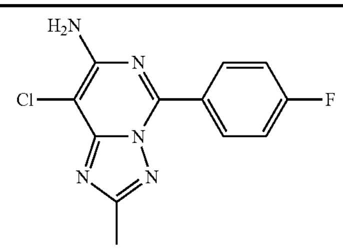 | 8-chloro-5-(4-fluorophenyl)-2-methyl-[1,2,4]triazolo[1,5-c]pyrimidin-7-amine | [M + H] = 278.0 | 99.6% |
| 81 | 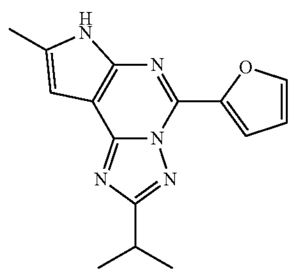 [SMILES: Cc1cc2c(nc(-c3ccco3)n3nc(C(C)C)nc23)[nH]1] | 7-(furan-2-yl)-11-methyl-4-propan-2-yl-3,5,6,8,10-pentazatricyclo[7.3.0.0$^{2,6}$]dodeca-1(9),2,4,7,11-pentaene | [M + H] = 282.1 | 97.6% |
| 82 | 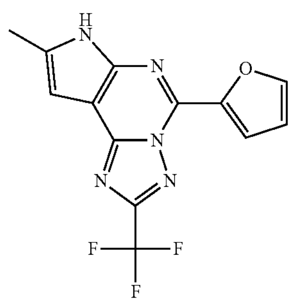 [SMILES: Cc1cc2c(nc(-c3ccco3)n3nc(C(F)(F)F)nc23)[nH]1] | 7-(furan-2-yl)-11-methyl-4-(trifluoromethyl)-3,5,6,8,10-pentazatricyclo[7.3.0.0$^{2,6}$]dodeca-1(9),2,4,7,11-pentaene | [MH+] = 308.0 | 100.0% |
| 83 | 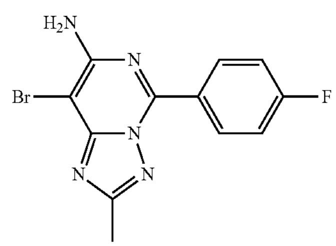 | 8-bromo-5-(4-fluorophenyl)-2-methyl-[1,2,4]triazolo[1,5-c]pyrimidin-7-amine | [M+/M + 2] = 322/324 | 100.0% |
| 84 | 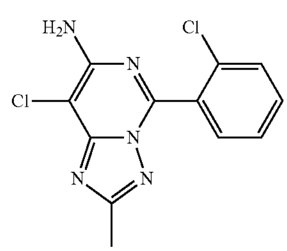 [SMILES: Cc1nc2c(Cl)c(N)nc(-c3ccccc3Cl)n2n1] | 8-chloro-5-(2-chlorophenyl)-2-methyl-[1,2,4]triazolo[1,5-c]pyrimidin-7-amine | [M+/M + 2] = 294.0/296.0 | 99.6% |
| 85 | 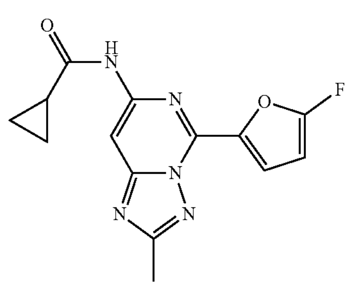 [SMILES: Cc1nc2cc(NC(=O)C3CC3)nc(-c3ccc(F)o3)n2n1] | N-[5-(5-fluorofuran-2-yl)-2-methyl-[1,2,4]triazolo[1,5-c]pyrimidin-7-yl]cyclopropanecarboxamide | [M + H] = 302.1 | 100.0% |

TABLE 1-continued

| Compound No. | Structure | IUPAC Name | LC/MS | Purity |
|---|---|---|---|---|
| 86 | 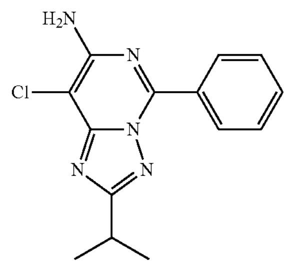 [SMILES: CC(C)c1nc2c(Cl)c(N)nc(-c3ccccc3)n2n1] | 8-chloro-5-phenyl-2-propan-2-yl-[1,2,4]triazolo[1,5-c]pyrimidin-7-amine | [M + H] = 288.1 | 99.3% |
| 87 | 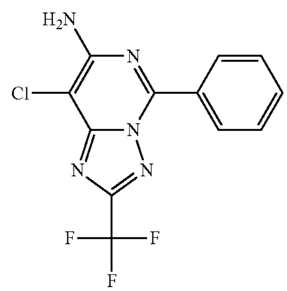 [SMILES: Nc1nc(-c2ccccc2)n2nc(C(F)(F)F)nc2c1Cl] | 8-chloro-5-phenyl-2-(trifluoromethyl)-[1,2,4]triazolo[1,5-c]pyrimidin-7-amine | [M + H] = 314.0 | 100.0% |
| 88 | 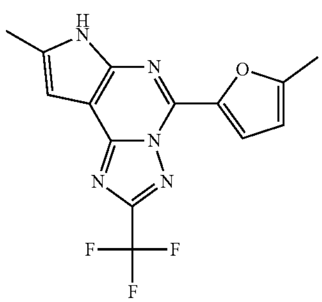 | 11-methyl-7-(5-methylfuran-2-yl)-4-(trifluoromethyl)-3,5,6,8,10-pentazatricyclo[7.3.0.0$^{2,6}$]dodeca-1(9),2,4,7,11-pentaene | [MH+] = 322.0 | 98.2% |
| 89 | 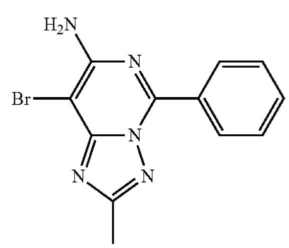 | 8-bromo-2-methyl-5-phenyl-[1,2,4]triazolo[1,5-c]pyrimidin-7-amine | [M+/M + 2] = 304.0/306.0 | 100.0% |
| 90 | 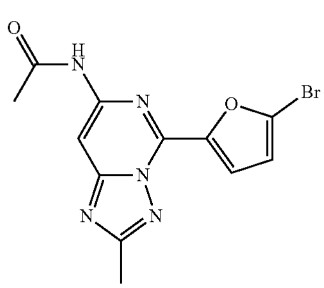 [SMILES: CC(=O)Nc1cc2nc(C)nn2c(-c2ccc(Br)o2)n1] | N-[5-(5-bromofuran-2-yl)-2-methyl-[1,2,4]triazolo[1,5-c]pyrimidin-7-yl]acetamide | [M+/M + 2] = 335.8 | 95.2% |

TABLE 1-continued

| Compound No. | Structure | IUPAC Name | LC/MS | Purity |
|---|---|---|---|---|
| 91 | 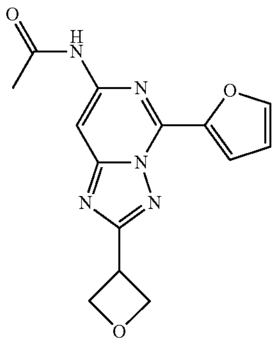 [SMILES: CC(=O)Nc1cc2nc(C3COC3)nn2c(-c2ccco2)n1] | N-[5-(furan-2-yl)-2-(oxetan-3-yl)-[1,2,4]triazolo[1,5-c]pyrimidin-7-yl]acetamide | [M + H] = 300.1 | 100.0% |
| 92 | 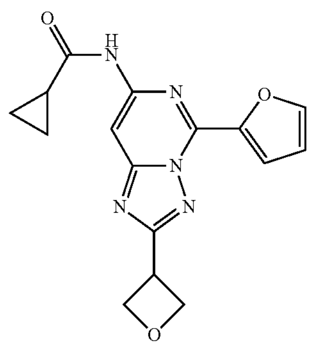 [SMILES: O=C(Nc1cc2nc(C3COC3)nn2c(-c2ccco2)n1)C1CC1] | N-[5-(furan-2-yl)-2-(oxetan-3-yl)-[1,2,4]triazolo[1,5-c]pyrimidin-7-yl]cyclopropanecarboxamide | [M + H] = 326.1 | 100.0% |
| 93 | 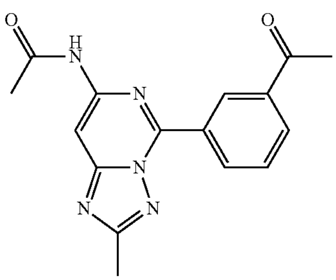 [SMILES: CC(=O)Nc1cc2nc(C)nn2c(-c2cccc(C(C)=O)c2)n1] | N-[5-(3-acetylphenyl)-2-methyl-[1,2,4]triazolo[1,5-c]pyrimidin-7-yl]acetamide | [M + H] = 310.3 | 96.0% |
| 94 | 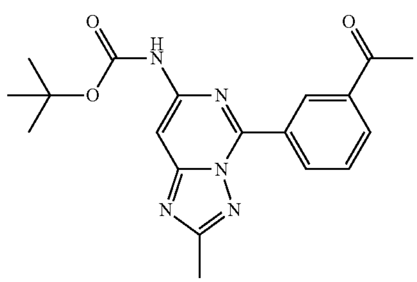 [SMILES: CC(=O)c1cccc(-c2nc(NC(=O)OC(C)(C)C)cc3nc(C)nn23)c1] | tert-butyl N-[5-(3-acetylphenyl)-2-methyl-[1,2,4]triazolo[1,5-c]pyrimidin-7-yl]carbamate | [M + H] = 368.40 | 95.0% |
| 95 | 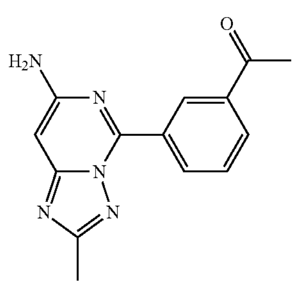 [SMILES: CC(=O)c1cccc(-c2nc(N)cc3nc(C)nn23)c1] | 1-[3-(7-amino-2-methyl-[1,2,4]triazolo[1,5-c]pyrimidin-5-yl)phenyl]ethanone | [M + H] = 268.35 | 95.0% |

TABLE 1-continued

| Compound No. | Structure | IUPAC Name | LC/MS | Purity |
|---|---|---|---|---|
| 96 | 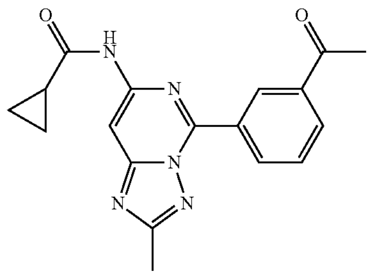 [SMILES: CC(=O)c1cccc(-c2nc(NC(=O)C3CC3)cc3nc(C)nn23)c1] | N-[5-(3-acetylphenyl)-2-methyl-[1,2,4]triazolo[1,5-c]pyrimidin-7-yl]cyclopropanecarboxamide | [M + H] = 336.4 | 97.5% |
| 97 | 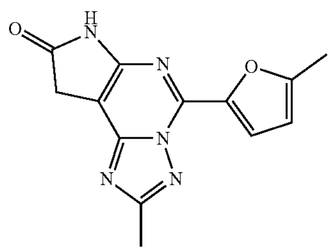 [SMILES: Cc1nc2c3c(nc(-c4ccc(C)o4)n2n1)NC(=O)C3] | 4-methyl-7-(5-methylfuran-2-yl)-3,5,6,8,10-pentazatricyclo[7.3.0.0$^{2,6}$]dodeca-1(9),2,4,7-tetraen-11-one | [M + H] = 270.0 | 96.0% |
| 98 | 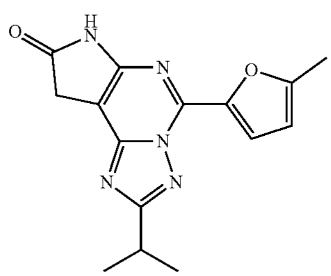 [SMILES: Cc1ccc(-c2nc3c(c4nc(C(C)C)nn24)CC(=O)N3)o1] | 7-(5-methylfuran-2-yl)-4-propan-2-yl-3,5,6,8,10-pentazatricyclo[7.3.0.0$^{2,6}$]dodeca-1(9),2,4,7-tetraen-11-one | [M + H] = 298.0 | 93.4% |
| 99 | 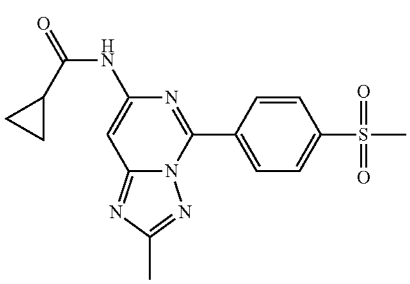 [SMILES: Cc1nc2cc(NC(=O)C3CC3)nc(-c3ccc(S(C)(=O)=O)cc3)n2n1] | A-[2-methyl-5-(4-methylsulfonylphenyl)-[1,2,4]triazolo[1,5-c]pyrimidin-7-yl]cyclopropanecarboxamide | [M + H] = 372.1 | 99.0% |
| 100 | 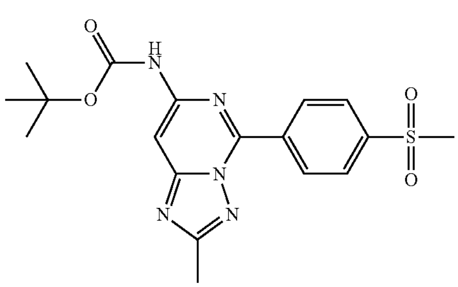 [SMILES: Cc1nc2cc(NC(=O)OC(C)(C)C)nc(-c3ccc(S(C)(=O)=O)cc3)n2n1] | tert-butyl N-[2-methyl-5-(4-methylsulfonylphenyl)-[1,2,4]triazolo[1,5-c]pyrimidin-7-yl]carbamate | [M + H] = 404.3 | 99.0% |

TABLE 1-continued

| Compound No. | Structure | IUPAC Name | LC/MS | Purity |
|---|---|---|---|---|
| 101 | 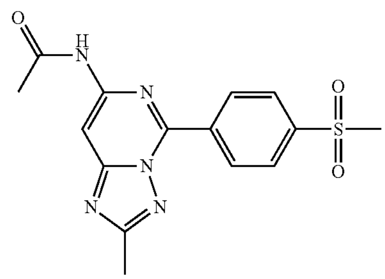 [SMILES: CC(=O)Nc1cc2nc(C)nn2c(-c2ccc(S(C)(=O)=O)cc2)n1] | N-[2-methyl-5-(4-methylsulfonylphenyl)-[1,2,4]triazolo[1,5-c]pyrimidin-7-yl]acetamide | [M + H] = 346.2 | 99.0% |
| 102 | 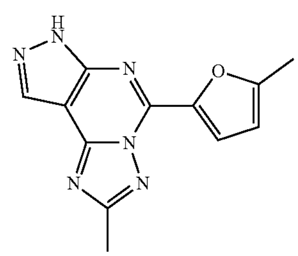 [SMILES: Cc1nc2c3cn[nH]c3nc(-c3ccc(C)o3)n2n1] | 4-methyl-7-(5-methylfuran-2-yl)-3,5,6,8,10,11-hexazatricyclo[7.3.0.0$^{2,6}$]dodeca-1(9),2,4,7,11-pentaene | [M + H] = 255.1 | 98.6% |
| 103 | 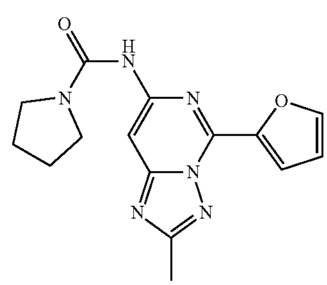 [SMILES: Cc1nc2cc(NC(=O)N3CCCC3)nc(-c3ccco3)n2n1] | N-[5-(furan-2-yl)-2-methyl-[1,2,4]triazolo[1,5-c]pyrimidin-7-yl]pyrrolidine-1-carboxamide | [M + H] = 313.1 | 100.0% |
| 104 | 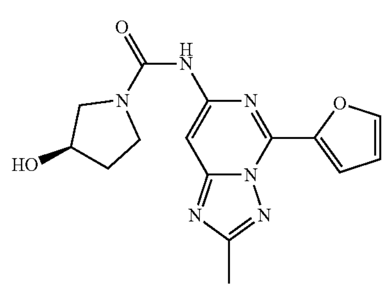 [SMILES: Cc1nc2cc(NC(=O)N3CC[C@@H](O)C3)nc(-c3ccco3)n2n1] | (3R)-N-[5-(furan-2-yl)-2-methyl-[1,2,4]triazolo[1,5-c]pyrimidin-7-yl]-3-hydroxypyrrolidine-1-carboxamide | [M + H] = 329.1 | 100.0% |
| 105 | 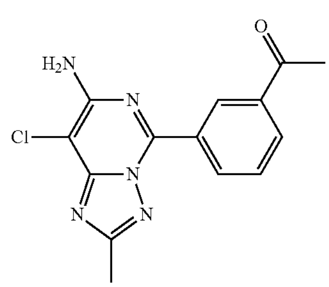 [SMILES: CC(=O)c1cccc(-c2nc(N)c(Cl)c3nc(C)nn23)c1] | 1-[3-(7-amino-8-chloro-2-methyl-[1,2,4]triazolo[1,5-c]pyrimidin-5-yl)phenyl]ethanone | [M + H] = 302.2 | 98.0% |

TABLE 1-continued

| Compound No. | Structure | IUPAC Name | LC/MS | Purity |
|---|---|---|---|---|
| 106 | 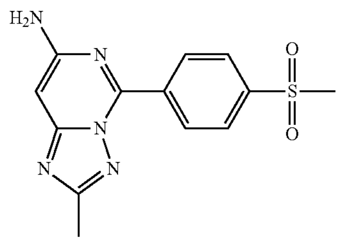 [SMILES: Cc1nc2cc(N)nc(-c3ccc(S(C)(=O)=O)cc3)n2n1] | 2-methyl-5-(4-methylsulfonylphenyl)-[1,2,4]triazolo[1,5-c]pyrimidin-7-amine | [M + H] = 304.3 | 95.0% |
| 107 | 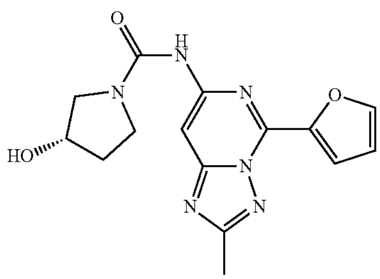 [SMILES: Cc1nc2cc(NC(=O)N3CC[C@H](O)C3)nc(-c3ccco3)n2n1] | (3S)-N-[5-(furan-2-yl)-2-methyl-[1,2,4]triazolo[1,5-c]pyrimidin-7-yl]-3-hydroxypyrrolidine-1-carboxamide | [M + H] = 329.1 | 100.0% |
| 108 | 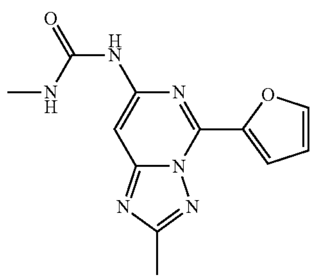 [SMILES: CNC(=O)Nc1cc2nc(C)nn2c(-c2ccco2)n1] | 1-[5-(furan-2-yl)-2-methyl-[1,2,4]triazolo[1,5-c]pyrimidin-7-yl]-3-methylurea | [M + H] = 273.1 | 100.0% |
| 109 | 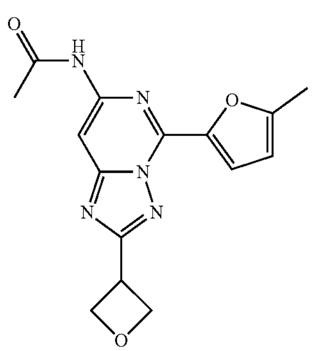 [SMILES: CC(=O)Nc1cc2nc(C3COC3)nn2c(-c2ccc(C)o2)n1] | N-[5-(5-methylfuran-2-yl)-2-(oxetan-3-yl)-[1,2,4]triazolo[1,5-c]pyrimidin-7-yl]acetamide | [M + H] = 314.1 | 100.0% |
| 110 | 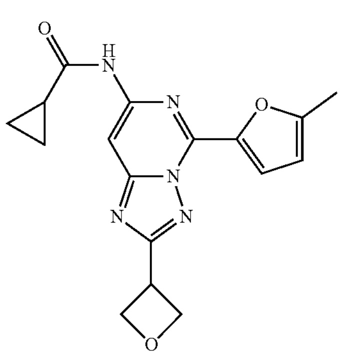 [SMILES: Cc1ccc(-c2nc(NC(=O)C3CC3)cc3nc(C4COC4)nn23)o1] | N-[5-(5-methylfuran-2-yl)-2-(oxetan-3-yl)-[1,2,4]triazolo[1,5-c]pyrimidin-7-yl]cyclopropanecarboxamide | [M + H] = 340.1 | 100.0% |

TABLE 1-continued

| Compound No. | Structure | IUPAC Name | LC/MS | Purity |
|---|---|---|---|---|
| 111 | 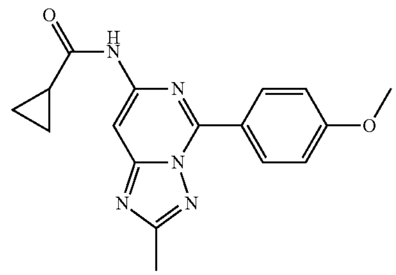 [SMILES: COc1ccc(-c2nc(NC(=O)C3CC3)cc3nc(C)nn23)cc1] | N-[5-(4-methoxyphenyl)-2-methyl-[1,2,4]triazolo[1,5-c]pyrimidin-7-yl]cyclopropanecarboxamide | [M + H] = 324.3 | 98.0% |
| 112 | 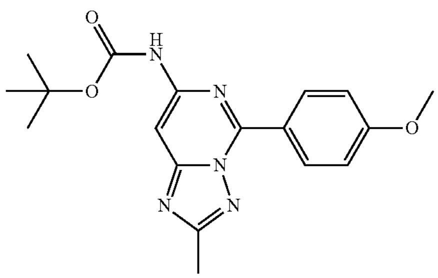 [SMILES: COc1ccc(-c2nc(NC(=O)OC(C)(C)C)cc3nc(C)nn23)cc1] | tert-butyl N-[5-(4-methoxyphenyl)-2-methyl-[1,2,4]triazolo[1,5-c]pyrimidin-7-yl]carbamate | [M + H] = 356.4 | 98.0% |
| 113 | 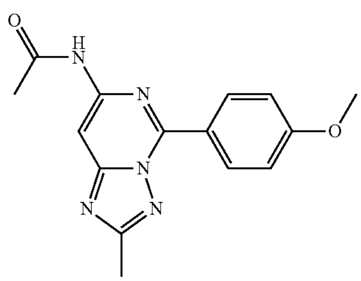 [SMILES: COc1ccc(-c2nc(NC(C)=O)cc3nc(C)nn23)cc1] | N-[5-(4-methoxyphenyl)-2-methyl-[1,2,4]triazolo[1,5-c]pyrimidin-7-yl]acetamide | [M + H] = 298.3 | 95.0% |
| 114 | 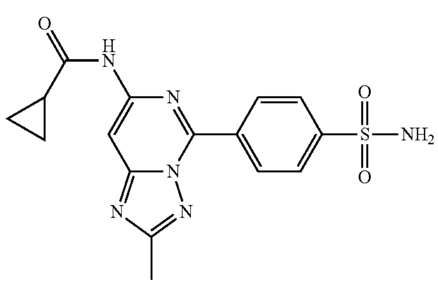 [SMILES: Cc1nc2cc(NC(=O)C3CC3)nc(-c3ccc(S(N)(=O)=O)cc3)n2n1] | N-[2-methyl-5-(4-sulfamoylphenyl)-[1,2,4]triazolo[1,5-c]pyrimidin-7-yl]cyclopropanecarboxamide | [M + H] = 373.3 | 96.0% |
| 115 | 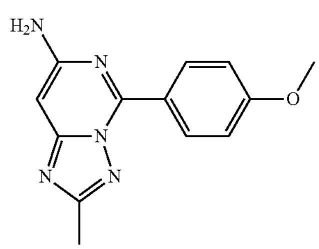 [SMILES: COc1ccc(-c2nc(N)cc3nc(C)nn23)cc1] | 5-(4-methoxyphenyl)-2-methyl-[1,2,4]triazolo[1,5-c]pyrimidin-7-amine | [M + H] = 256.3 | 97.0% |

TABLE 1-continued

| Compound No. | Structure | IUPAC Name | LC/MS | Purity |
|---|---|---|---|---|
| 116 | 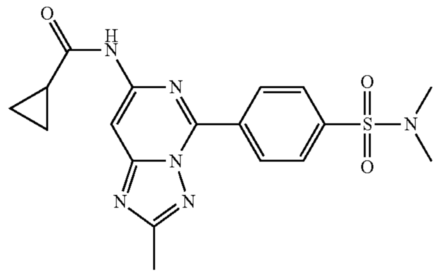 [SMILES: Cc1nc2cc(NC(=O)C3CC3)nc(-c3ccc(S(=O)(=O)N(C)C)cc3)n2n1] | N-[5-[4-(dimethylsulfamoyl)phenyl]-2-methyl-[1,2,4]triazolo[1,5-c]pyrimidin-7-yl]cyclopropanecarboxamide | [M + H] = 401.2 | 97.0% |
| 117 | 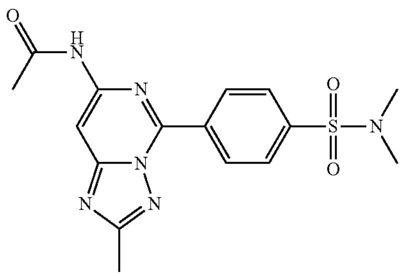 [SMILES: CC(=O)Nc1cc2nc(C)nn2c(-c2ccc(S(=O)(=O)N(C)C)cc2)n1] | N-[5-[4-(dimethylsulfamoyl)phenyl]-2-methyl-[1,2,4]triazolo[1,5-c]pyrimidin-7-yl]acetamide | [M + H] = 375.3 | 97.0% |
| 118 | 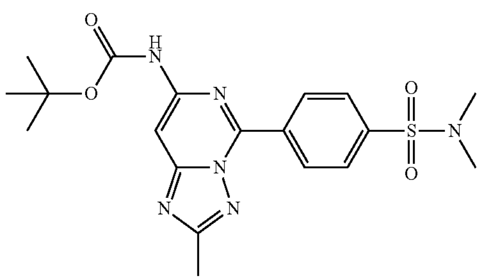 [SMILES: Cc1nc2cc(NC(=O)OC(C)(C)C)nc(-c3ccc(S(=O)(=O)N(C)C)cc3)n2n1] | tert-butyl N-[5-[4-(dimethylsulfamoyl)phenyl]-2-methyl-[1,2,4]triazolo[1,5-c]pyrimidin-7-yl]carbamate | [M + H] = 433.3 | 97.0% |
| 119 | 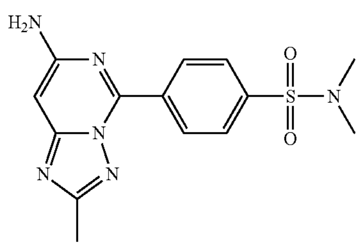 [SMILES: Cc1nc2cc(N)nc(-c3ccc(S(=O)(=O)N(C)C)cc3)n2n1] | 4-(7-amino-2-methyl-[1,2,4]triazolo[1,5-c]pyrimidin-5-yl)-N,N-dimethylbenzenesulfonamide | [M + H] = 333.2 | 97.0% |
| 120 | 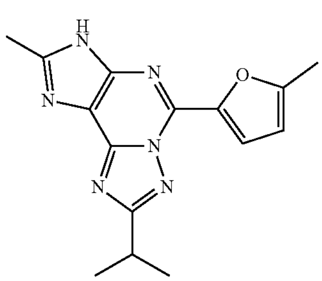 | 2-methyl-5-(5-methylfuran-2-yl)-8-propan-2-yl-3H-[1,2,4]triazolo[5,1-f]purine | [M + H] = 297.1 | 100.0% |

TABLE 1-continued

| Compound No. | Structure | IUPAC Name | LC/MS | Purity |
|---|---|---|---|---|
| 121 | 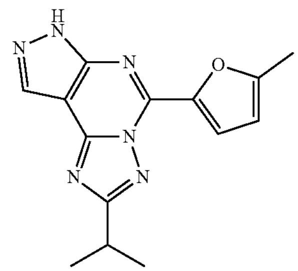 [SMILES: Cc1ccc(-c2nc3[nH]ncc3c3nc(C(C)C)nn23)o1] | 7-(5-methylfuran-2-yl)-4-propan-2-yl-3,5,6,8,10,11-hexazatricyclo[7.3.0.0²,⁶]dodeca-1(9),2,4,7,11-pentaene | [M + H] = 283.1 | 98.7% |
| 122 | 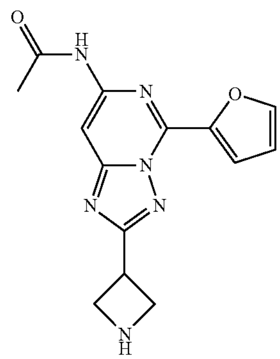 [SMILES: CC(=O)Nc1cc2nc(C3CNC3)nn2c(-c2ccco2)n1] | N-[2-(azetidin-3-yl)-5-(furan-2-yl)-[1,2,4]triazolo[1,5-c]pyrimidin-7-yl]acetamide | [M + H] = 299.1 | 100.0% |
| 123 | 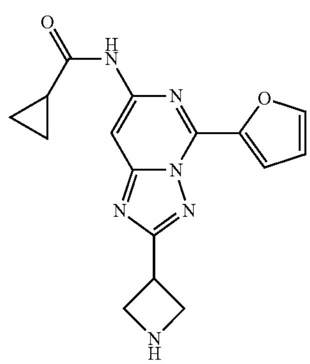 [SMILES: O=C(Nc1cc2nc(C3CNC3)nn2c(-c2ccco2)n1)C1CC1] | N-[2-(azetidin-3-yl)-5-(furan-2-yl)-[1,2,4]triazolo[1,5-c]pyrimidin-7-yl]cyclopropanecarboxamide | [M + H] = 325.1 | 100.0% |
| 124 | 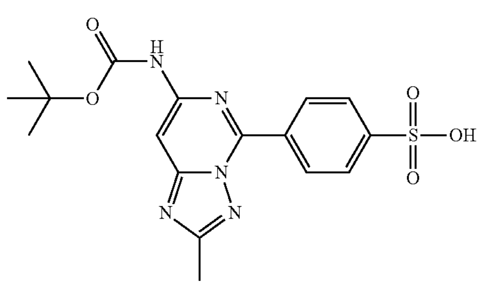 [SMILES: Cc1nc2cc(NC(=O)OC(C)(C)C)nc(-c3ccc(S(=O)(=O)O)cc3)n2n1] | 4-[2-methyl-7-[(2-methylpropan-2-yl)oxycarbonylamino]-[1,2,4]triazolo[1,5-c]pyrimidin-5-yl]benzenesulfonic acid | [M + H] = 406.3 | 95.0% |
| 125 | 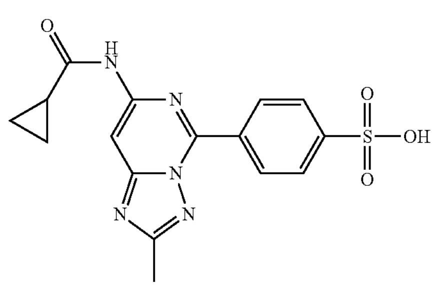 [SMILES: Cc1nc2cc(NC(=O)C3CC3)nc(-c3ccc(S(=O)(=O)O)cc3)n2n1] | 4-[7-(cyclopropanecarbonylamino)-2-methyl-[1,2,4]triazolo[1,5-c]pyrimidin-5-yl]benzenesulfonic acid | [M + H] = 374.3 | 95.0% |

TABLE 1-continued

| Compound No. | Structure | IUPAC Name | LC/MS | Purity |
|---|---|---|---|---|
| 126 | 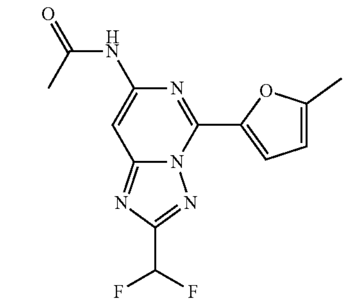 [SMILES: CC(=O)Nc1cc2nc(C(F)F)nn2c(-c2ccc(C)o2)n1] | N-[2-(difluoromethyl)-5-(5-methylfuran-2-yl)-[1,2,4]triazolo[1,5-c]pyrimidin-7-yl]acetamide | [M + H] = 308.1 | 99.5% |
| 127 | 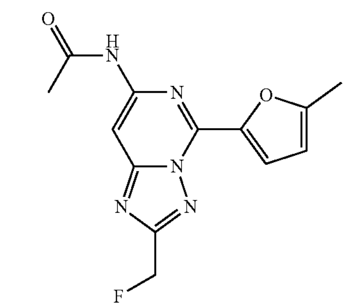 [SMILES: CC(=O)Nc1cc2nc(CF)nn2c(-c2ccc(C)o2)n1] | N-[2-(fluoromethyl)-5-(5-methylfuran-2-yl)-[1,2,4]triazolo[1,5-c]pyrimidin-7-yl]acetamide | [M + H] = 290.1 | 100.0% |
| 128 | 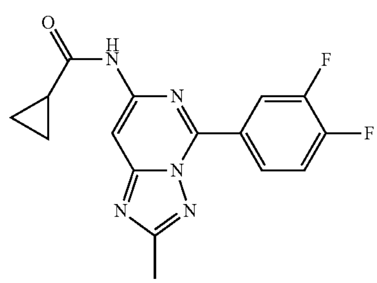 [SMILES: Cc1nc2cc(NC(=O)C3CC3)nc(-c3ccc(F)c(F)c3)n2n1] | N-[5-(3,4-difluorophenyl)-2-methyl-[1,2,4]triazolo[1,5-c]pyrimidin-7-yl]cyclopropanecarboxamide | [M + H] = 330.3 | 97.0% |
| 129 | 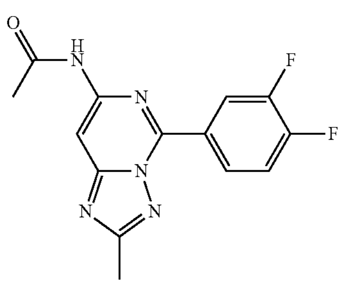 [SMILES: CC(=O)Nc1cc2nc(C)nn2c(-c2ccc(F)c(F)c2)n1] | N-[5-(3,4-difluorophenyl)-2-methyl-[1,2,4]triazolo[1,5-c]pyrimidin-7-yl]acetamide | [M + H] = 304.2 | 97.0% |
| 130 | 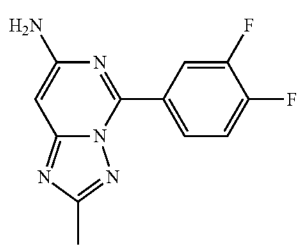 [SMILES: Cc1nc2cc(N)nc(-c3ccc(F)c(F)c3)n2n1] | 5-(3,4-difluorophenyl)-2-methyl-[1,2,4]triazolo[1,5-c]pyrimidin-7-amine | [M + H] = 262.2 | 97.0% |

TABLE 1-continued

| Compound No. | Structure | IUPAC Name | LC/MS | Purity |
|---|---|---|---|---|
| 131 | 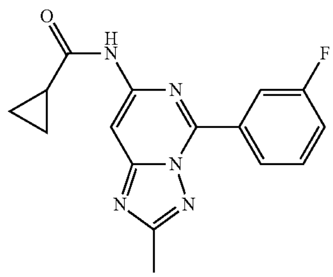 [SMILES: Cc1nc2cc(NC(=O)C3CC3)nc(-c3cccc(F)c3)n2n1] | N-[5-(3-fluorophenyl)-2-methyl-[1,2,4]triazolo[1,5-c]pyrimidin-7-yl]cyclopropanecarboxamide | [M + H] = 312.3 | 97.0% |
| 132 | 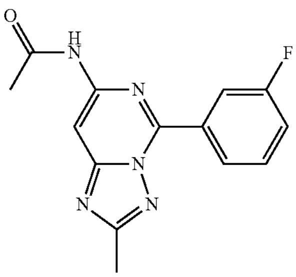 [SMILES: CC(=O)Nc1cc2nc(C)nn2c(-c2cccc(F)c2)n1] | N-[5-(3-fluorophenyl)-2-methyl-[1,2,4]triazolo[1,5-c]pyrimidin-7-yl]acetamide | [M + H] = 286.3 | 97.0% |
| 133 | 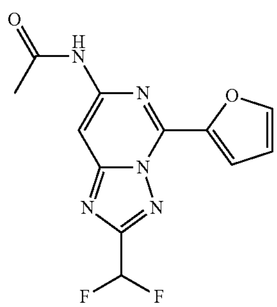 [SMILES: CC(=O)Nc1cc2nc(C(F)F)nn2c(-c2ccco2)n1] | N-[2-(difluoromethyl)-5-(furan-2-yl)-[1,2,4]triazolo[1,5-c]pyrimidin-7-yl]acetamide | [M + H] = 294.0 | 100.0% |
| 134 | 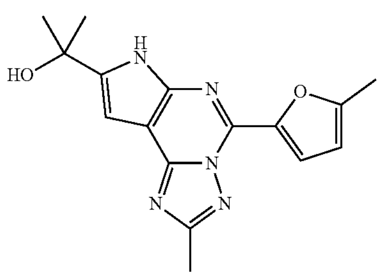 [SMILES: Cc1nc2c3cc(C(C)(C)O)[nH]c3nc(-c3ccc(C)o3)n2n1] | 2-[4-methyl-7-(5-methylfuran-2-yl)-3,5,6,8,10-pentazatricyclo[7.3.0.0$^{2,6}$]dodeca-1(9),2,4,7,11-pentaen-11-yl]propan-2-ol | [M + H] = 312.1 | 100.0% |
| 135 | 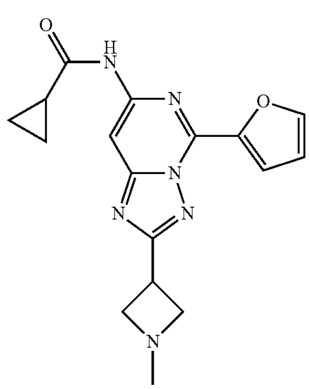 [SMILES: CN1CC(c2nc3cc(NC(=O)C4CC4)nc(-c4ccco4)n3n2)C1] | N-[5-(furan-2-yl)-2-(1-methylazetidin-3-yl)-[1,2,4]triazolo[1,5-c]pyrimidin-7-yl]cyclopropanecarboxamide | [M + H] = 339.1 | 98.1% |

… TABLE 1-continued

| Compound No. | Structure | IUPAC Name | LC/MS | Purity |
|---|---|---|---|---|
| 136 | 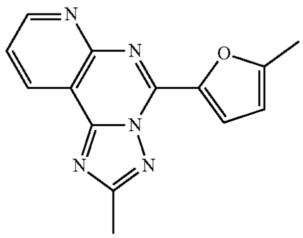 [SMILES: Cc1nc2c3cccnc3nc(-c3ccc(C)o3)n2n1] | 4-methyl-7-(5-methylfuran-2-yl)-3,5,6,8,10-pentazatricyclo[7.4.0.0²,⁶]trideca-1(9),2,4,7,10,12-hexaene | [M + H] = 266.1 | 99.5% |
| 137 | 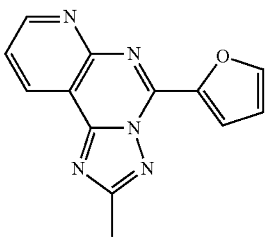 [SMILES: Cc1nc2c3cccnc3nc(-c3ccco3)n2n1] | 7-(furan-2-yl)-4-methyl-3,5,6,8,10-pentazatricyclo[7.4.0.0²,⁶]trideca-1(9),2,4,7,10,12-hexaene | [M + H] = 252.1 | 100.0% |
| 138 | 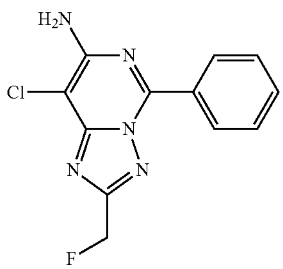 [SMILES: Nc1nc(-c2ccccc2)n2nc(CF)nc2c1Cl] | 8-chloro-2-(fluoromethyl)-5-phenyl-[1,2,4]triazolo[1,5-c]pyrimidin-7-amine | [M + H] = 278.0 | 100.0% |
| 139 | 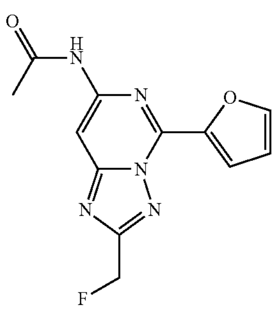 [SMILES: CC(=O)Nc1cc2nc(CF)nn2c(-c2ccco2)n1] | N-[2-(fluoromethyl)-5-(furan-2-yl)-[1,2,4]triazolo[1,5-c]pyrimidin-7-yl]acetamide | [M + H] = 276.1 | 100.0% |
| 140 | 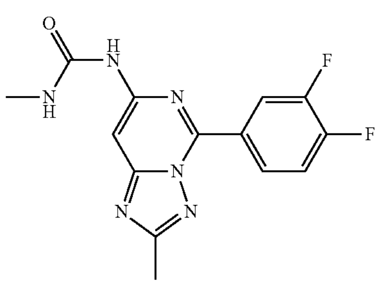 [SMILES: CNC(=O)Nc1cc2nc(C)nn2c(-c2ccc(F)c(F)c2)n1] | 1-[5-(3,4-difluorophenyl)-2-methyl-[1,2,4]triazolo[1,5-c]pyrimidin-7-yl]-3-methylurea | [M + H] = 319.2 | 95.0% |
| 141 | 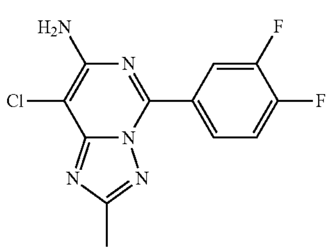 [SMILES: Cc1nc2c(Cl)c(N)nc(-c3ccc(F)c(F)c3)n2n1] | 8-chloro-5-(3,4-difluorophenyl)-2-methyl-[1,2,4]triazolo[1,5-c]pyrimidin-7-amine | [M + H] = 296.2 | 95.0% |

TABLE 1-continued

| Compound No. | Structure | IUPAC Name | LC/MS | Purity |
|---|---|---|---|---|
| 142 | 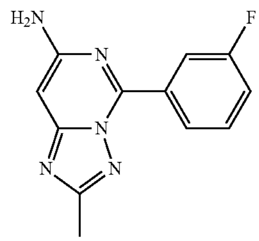 [SMILES: Cc1nc2cc(N)nc(-c3cccc(F)c3)n2n1] | 5-(3-fluorophenyl)-2-methyl-[1,2,4]triazolo[1,5-c]pyrimidin-7-amine | [M + H] = 244.3 | 97.0% |
| 143 | 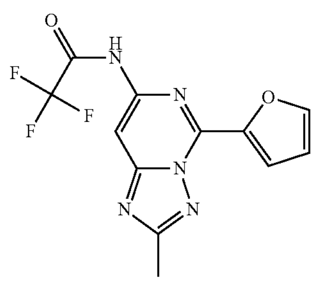 [SMILES: Cc1nc2cc(NC(=O)C(F)(F)F)nc(-c3ccco3)n2n1] | 2,2,2-trifluoro-N-[5-(furan-2-yl)-2-methyl-[1,2,4]triazolo[1,5-c]pyrimidin-7-yl]acetamide | [M + H] = 312.2 | 97.0% |
| 144 | 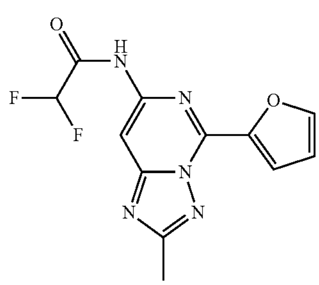 [SMILES: Cc1nc2cc(NC(=O)C(F)F)nc(-c3ccco3)n2n1] | 2,2-difluoro-N-[5-(furan-2-yl)-2-methyl-[1,2,4]triazolo[1,5-c]pyrimidin-7-yl]acetamide | [M + H] = 294.2 | 95.0% |
| 145 | 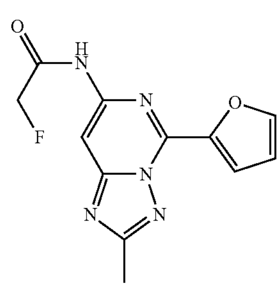 [SMILES: Cc1nc2cc(NC(=O)CF)nc(-c3ccco3)n2n1] | 2-fluoro-N-[5-(furan-2-yl)-2-methyl-[1,2,4]triazolo[1,5-c]pyrimidin-7-yl]acetamide | [M + H] = 275.3 | 95.0% |
| 146 | 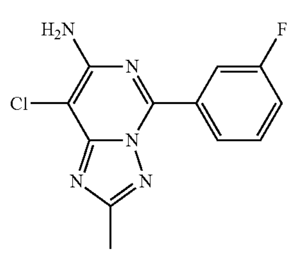 [SMILES: Cc1nc2c(Cl)c(N)nc(-c3cccc(F)c3)n2n1] | 8-chloro-5-(3-fluorophenyl)-2-methyl-[1,2,4]triazolo[1,5-c]pyrimidin-7-amine | [M + H] = 278.3 | 97.0% |

TABLE 1-continued

| Compound No. | Structure | IUPAC Name | LC/MS | Purity |
|---|---|---|---|---|
| 147 | 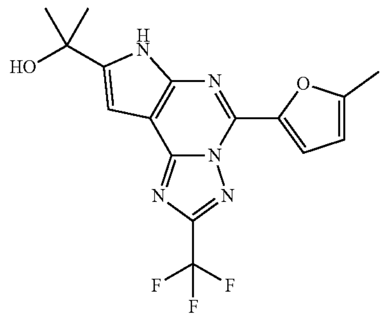 [SMILES: Cc1ccc(-c2nc3[nH]c(C(C)(C)O)cc3c3nc(C(F)(F)F)nn23)o1] | 2-[7-(5-methylfuran-2-yl)-4-(trifluoromethyl)-3,5,6,8,10-pentazatricyclo[7.3.0.0²,⁶]dodeca-1(9),2,4,7,11-pentaen-11-yl]propan-2-ol | [M + H] = 366.0 | 97.3% |
| 148 | 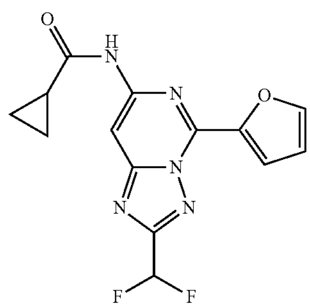 [SMILES: O=C(Nc1cc2nc(C(F)F)nn2c(-c2ccco2)n1)C1CC1] | N-[2-(difluoromethyl)-5-(furan-2-yl)-[1,2,4]triazolo[1,5-c]pyrimidin-7-yl]cyclopropanecarboxamide | [M + H] = 320.1 | 100.0% |
| 149 | 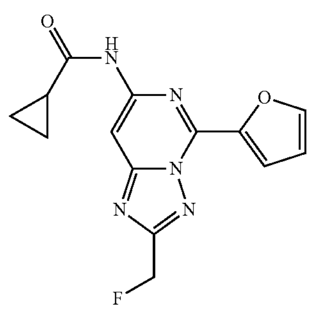 [SMILES: O=C(Nc1cc2nc(CF)nn2c(-c2ccco2)n1)C1CC1] | N-[2-(fluoromethyl)-5-(furan-2-yl)-[1,2,4]triazolo[1,5-c]pyrimidin-7-yl]cyclopropanecarboxamide | [M + H] = 302.1 | 99.4% |
| 150 | 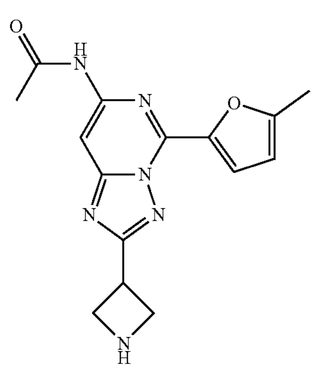 [SMILES: CC(=O)Nc1cc2nc(C3CNC3)nn2c(-c2ccc(C)o2)n1] | N-[2-(azetidin-3-yl)-5-(5-methylfuran-2-yl)-[1,2,4]triazolo[1,5-c]pyrimidin-7-yl]acetamide | [M + H] = 313.1 | 98.9% |

TABLE 1-continued

| Compound No. | Structure | IUPAC Name | LC/MS | Purity |
|---|---|---|---|---|
| 151 | 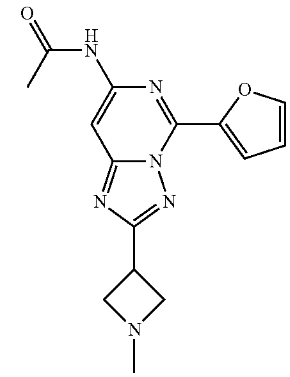 [SMILES: CC(=O)Nc1cc2nc(C3CN(C)C3)nn2c(-c2ccco2)n1] | N-[5-(furan-2-yl)-2-(1-methylazetidin-3-yl)-[1,2,4]triazolo[1,5-c]pyrimidin-7-yl]acetamide | [M + H] = 313.1 | 99.6% |
| 152 | 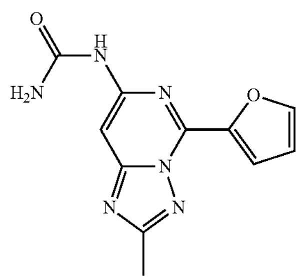 [SMILES: Cc1nc2cc(NC(N)=O)nc(-c3ccco3)n2n1] | [5-(furan-2-yl)-2-methyl-[1,2,4]triazolo[1,5-c]pyrimidin-7-yl]urea | [M + H] = 259.1 | 100.0% |
| 153 | 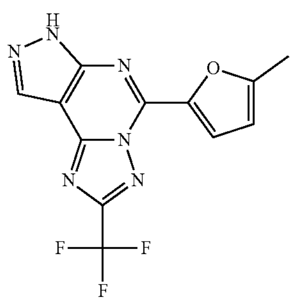 [SMILES: Cc1ccc(-c2nc3[nH]ncc3c3nc(C(F)(F)F)nn23)o1] | 7-(5-methylfuran-2-yl)-4-(trifluoromethyl)-3,5,6,8,10,11-hexazatricyclo[7.3.0.0$^{2,6}$]dodeca-1(9),2,4,7,11-pentaene | [M + H] = 309.0 | 96.1% |
| 154 | 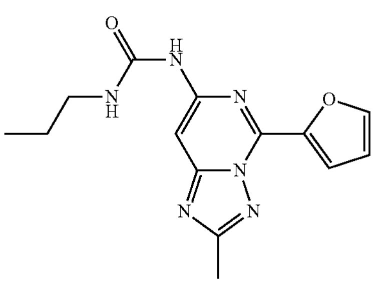 [SMILES: CCCNC(=O)Nc1cc2nc(C)nn2c(-c2ccco2)n1] | 1-[5-(furan-2-yl)-2-methyl-[1,2,4]triazolo[1,5-c]pyrimidin-7-yl]-3-propylurea | [M + H] = 301.1 | 98.8% |
| 155 | 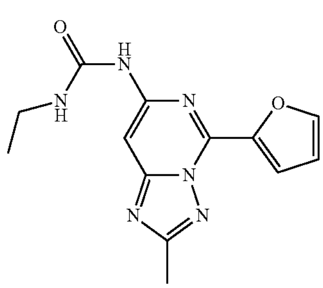 [SMILES: CCNC(=O)Nc1cc2nc(C)nn2c(-c2ccco2)n1] | 1-ethyl-3-[5-(furan-2-yl)-2-methyl-[1,2,4]triazolo[1,5-c]pyrimidin-7-yl]urea | [M + H] = 287.1 | 99.0% |

TABLE 1-continued

| Compound No. | Structure | IUPAC Name | LC/MS | Purity |
|---|---|---|---|---|
| 156 | 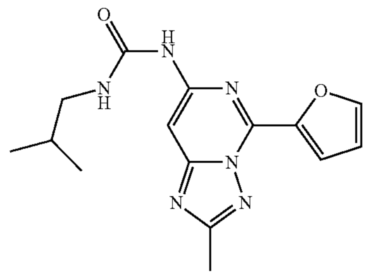 [SMILES: Cc1nc2cc(NC(=O)NCC(C)C)nc(-c3ccco3)n2n1] | 1-[5-(furan-2-yl)-2-methyl-[1,2,4]triazolo[1,5-c]pyrimidin-7-yl]-3-(2-methylpropyl)urea | [M + H] = 315.1 | 99.0% |
| 157 | 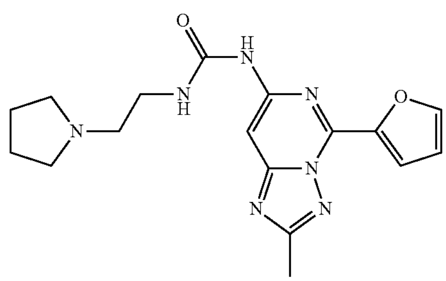 [SMILES: Cc1nc2cc(NC(=O)NCCN3CCCC3)nc(-c3ccco3)n2n1] | 1-[5-(furan-2-yl)-2-methyl-[1,2,4]triazolo[1,5-c]pyrimidin-7-yl]-3-(2-pyrrolidin-1-ylethyl)urea | 356.1 | 99.7% |
| 158 | 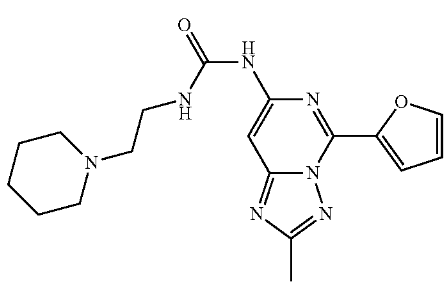 [SMILES: Cc1nc2cc(NC(=O)NCCN3CCCCC3)nc(-c3ccco3)n2n1] | 1-[5-(furan-2-yl)-2-methyl-[1,2,4]triazolo[1,5-c]pyrimidin-7-yl]-3-(2-piperidin-1-ylethyl)urea | 370.1 | 100.0% |
| 159 | 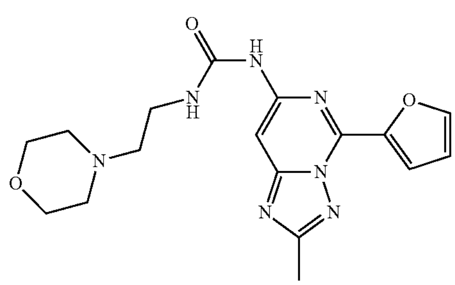 [SMILES: Cc1nc2cc(NC(=O)NCCN3CCOCC3)nc(-c3ccco3)n2n1] | 1-[5-(furan-2-yl)-2-methyl-[1,2,4]triazolo[1,5-c]pyrimidin-7-yl]-3-(2-morpholin-4-ylethyl)urea | [M + H] = 372.1 | 96.5% |
| 160 | 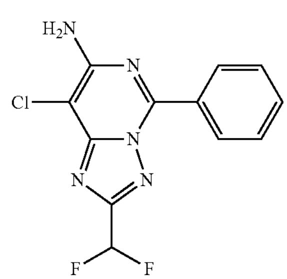 [SMILES: Nc1nc(-c2ccccc2)n2nc(C(F)F)nc2c1Cl] | 8-chloro-2-(difluoromethyl)-5-phenyl-[1,2,4]triazolo[1,5-c]pyrimidin-7-amine | [M + H] = 296.0 | 99.4% |

TABLE 1-continued

| Compound No. | Structure | IUPAC Name | LC/MS | Purity |
|---|---|---|---|---|
| 161 | 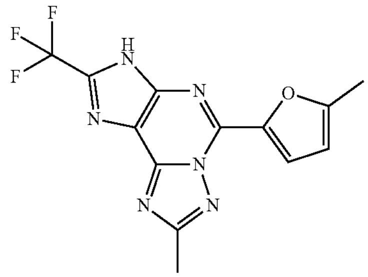 [SMILES: Cc1nc2c3nc(C(F)(F)F)[nH]c3nc(-c3ccc(C)o3)n2n1] | 8-methyl-5-(5-methylfuran-2-yl)-2-(trifluoromethyl)-3H-[1,2,4]triazolo[5,1-f]purine | [M + H] = 323.0 | 100.0% |
| 162 | 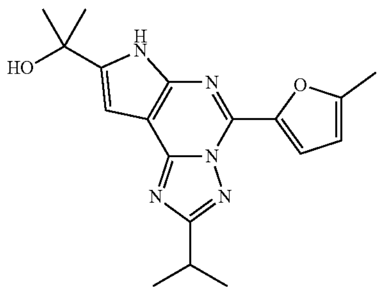 [SMILES: Cc1ccc(-c2nc3[nH]c(C(C)(C)O)cc3c3nc(C(C)C)nn23)o1] | 2-[7-(5-methylfuran-2-yl)-4-propan-2-yl-3,5,6,8,10-pentazatricyclo[7.3.0.0$^{2,6}$]dodeca-1(9),2,4,7,11-pentaen-11-yl]propan-2-ol | [M + H] = 340.1 | 97.0% |
| 163 | 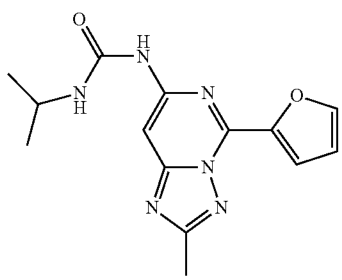 [SMILES: Cc1nc2cc(NC(=O)NC(C)C)nc(-c3ccco3)n2n1] | 1-[5-(furan-2-yl)-2-methyl-[1,2,4]triazolo[1,5-c]pyrimidin-7-yl]-3-propan-2-ylurea | [M + H] = 301.1 | 96.5% |
| 164 | 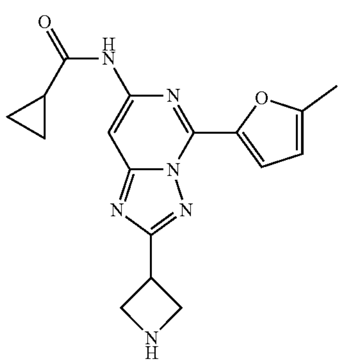 [SMILES: Cc1ccc(-c2nc(NC(=O)C3CC3)cc3nc(C4CNC4)nn23)o1] | N-[2-(azetidin-3-yl)-5-(5-methylfuran-2-yl)-[1,2,4]triazolo[1,5-c]pyrimidin-7-yl]cyclopropanecarboxamide | [M + H] = 339.1 | 99.3% |
| 165 | 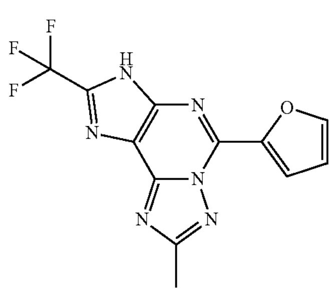 [SMILES: Cc1nc2c3nc(C(F)(F)F)[nH]c3nc(-c3ccco3)n2n1] | 5-(furan-2-yl)-8-methyl-2-(trifluoromethyl)-3H-[1,2,4]triazolo[5,1-f]purine | [M + H] = 309.0 | 98.6% |

Part II: Preparation of Triazolopyrazine Adenosine Antagonists

Example 9: Preparation of 8-(5-methylfuran-2-yl)-[1,2,4]triazolo[1,5-a]pyrazin-6-amine (166)

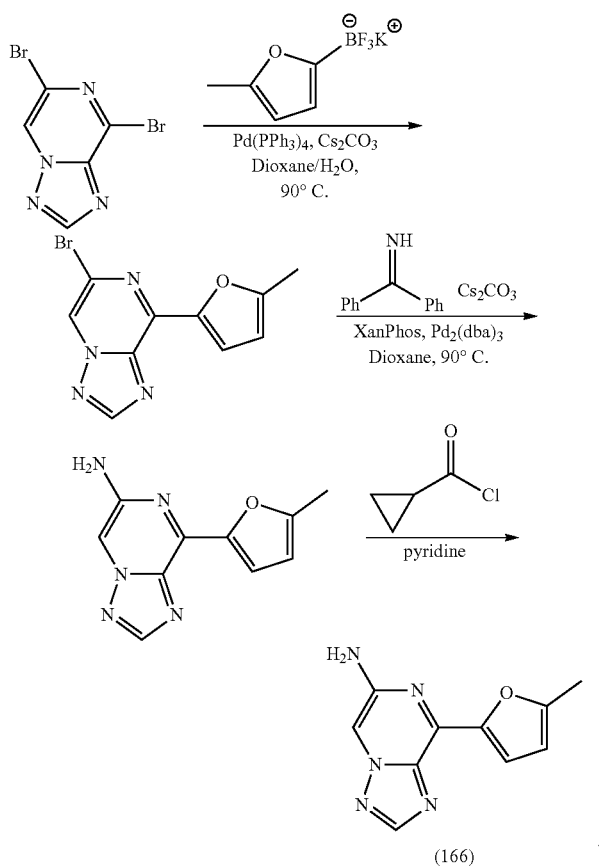

(166)

Step 1: Preparation of 6-bromo-8-(5-methylfuran-2-yl)-[1,2,4]triazolo[1,5-a]pyrazine

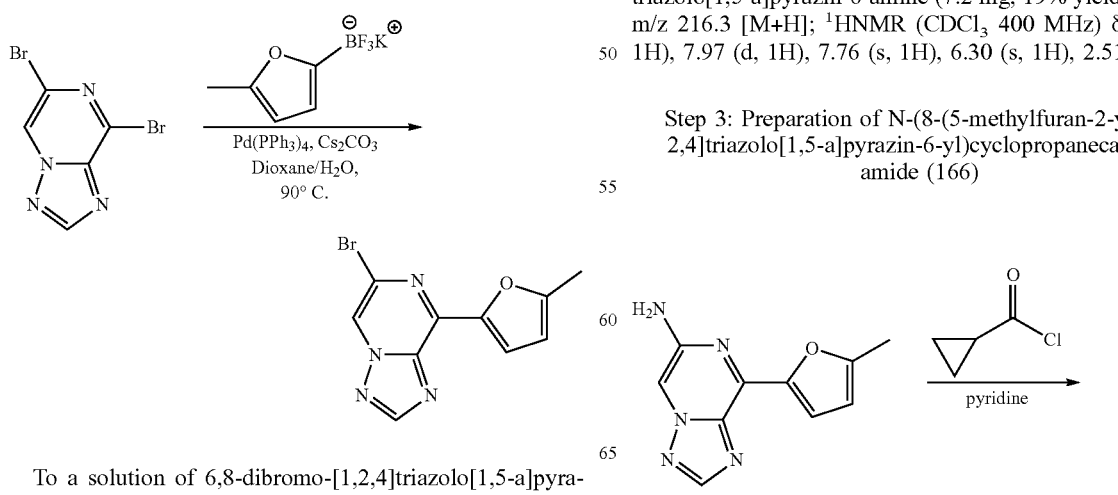

To a solution of 6,8-dibromo-[1,2,4]triazolo[1,5-a]pyrazine (70 mg, 0.252 mmol, 1.0 eq.), potassium trifluoro(5-methylfuran-2-yl)borate (47 mg, 0.252 mmol, 1.0 eq.) and $Cs_2CO_3$ (205 mg, 0.629 mmol, 2.5 eq.) in dioxane-water (6 mL, 3:1) was added $Pd(PPh_3)_4$ (28 mg, 0.025 mmol, 0.1 eq.) under $N_2$ atmosphere. The resulting mixture was heated at 97° C. for 5 h. The mixture was monitored by LCMS. After completion, the mixture was poured into the separatory funnel and washed with water (10 mL), followed by ethyl acetate (20 mL×3). The combined organic layers were washed with brine, dried over $MgSO_4$, filtered and concentrated by reduced pressure. The crude material was purified by column chromatography to give 6-bromo-8-(5-methylfuran-2-yl)-[1,2,4]triazolo[1,5-a]pyrazine (49 mg, 70% yield). LCMS m/z 279.1/281.2 [M+/M+2]

Step 2: Preparation of 8-(5-methylfuran-2-yl)-[1,2,4]triazolo[1,5-a]pyrazin-6-amine

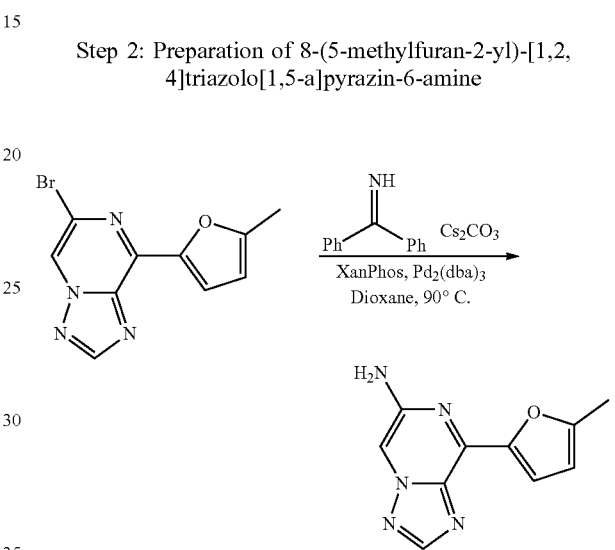

A mixture of 6-bromo-8-(5-methylfuran-2-yl)-[1,2,4]triazolo[1,5-a]pyrazine (49 mg, 0.176 mmol, 1.0 eq.), diphenylmethanimine (48 mg, 0.265 mmol, 1.5 eq.), $Cs_2CO_3$ (115 mg, 0.352 mmol, 2.0 eq.), Xantphos (21 mg, 0.035 mmol, 0.2 eq.), tris(dibenzylideneacetone)dipalladium(0) (16 mg, 0.02 mmol, 0.1 eq.) were dissolved in degassed dioxane (5 mL) and heated to 100° C. for 6 hours. The reaction mixture was filtered over Celite®, washed with ethyl acetate and concentrated by reduced pressure. The crude material was purified by preparative HPLC to give 8-(furan-2-yl)-[1,2,4]triazolo[1,5-a]pyrazin-6-amine (7.2 mg, 19% yield). LCMS m/z 216.3 [M+H]; $^1$HNMR (CDCl$_3$ 400 MHz) δ 8.30 (s, 1H), 7.97 (d, 1H), 7.76 (s, 1H), 6.30 (s, 1H), 2.51 (s, 3H).

Step 3: Preparation of N-(8-(5-methylfuran-2-yl)-[1,2,4]triazolo[1,5-a]pyrazin-6-yl)cyclopropanecarboxamide (166)

-continued

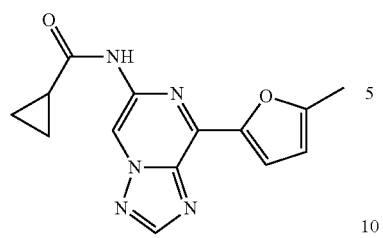

To a solution of 8-(furan-2-yl)-[1,2,4]triazolo[1,5-a]pyrazin-6-amin (22 mg, 0.102 mmol, 1.0 eq) in pyridine (1 mL) was added slowly cyclopropanecarbonyl chloride (11 umL, 0.113 mmol, 1.1 eq) at 0° C. The reaction mixture was heated at 70° C. for 1 hour. The mixture was concentrated by reduced pressure and purified by column chromatography to give N-(8-(5-methylfuran-2-yl)-[1,2,4]triazolo[1,5-a]pyrazin-6-yl)cyclopropanecarboxamide (6.9 mg, 23.8% yield). LCMS m/z 284.3 [M+H]; HNMR (CDCl₃ 400 MHz) δ 9.40 (s, 1H), 8.41 (s, 1H), 9.25 (s, 1H), 8.03 (d, 1H), 6.32 (s, 1H), 2.53 (s, 3H), 1.25 (m, 1H), 1.15 (m, 2H), 0.95 (m, 2H).

Example 10: Preparation of N-(2-methyl-8-(5-methylfuran-2-yl)-triazolo[1,5-a]pyrazin-6-yl)cyclopropanecarboxamide (169)

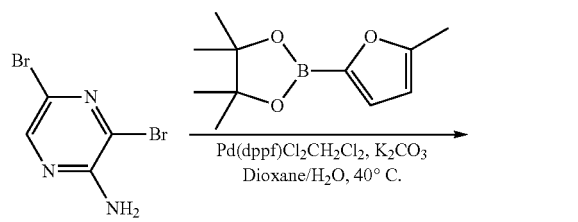

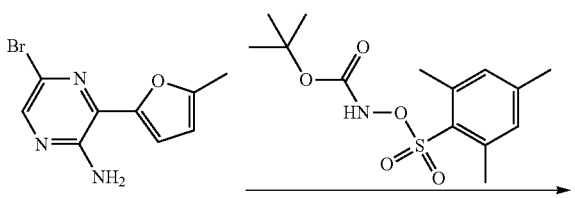

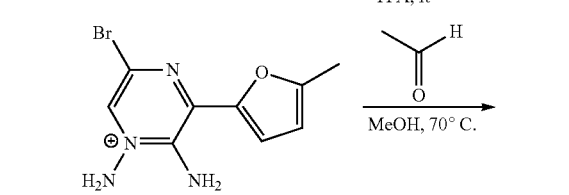

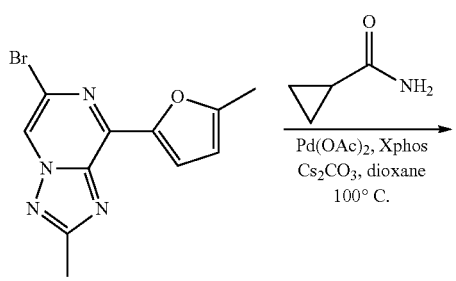

-continued

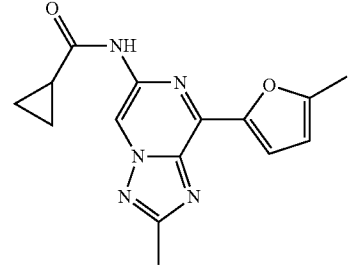

(169)

Step 1: Preparation of 5-bromo-3-(5-methyl-2-furyl)pyrazin-2-amine

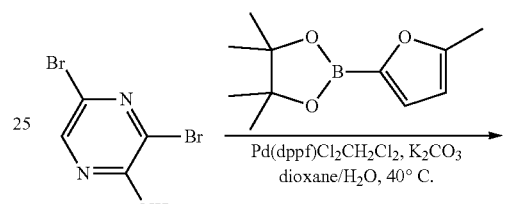

A mixture of 3,5-dibromopyrazin-2-amine (5 g, 19.77 mmol, 1 eq.), 4,4,5,5-tetramethyl-2-(5-methyl-2-furyl)-1,3,2-dioxaborolane (4.11 g, 19.77 mmol, 1 eq.), Pd(dppf)Cl₂·CH₂Cl₂ (1.61 g, 1.98 mmol, 0.1 eq.) and K₂CO₃ (8.20 g, 59.31 mmol, 3 eq.) in dioxane (50 mL) and H₂O (2 mL) was stirred at 40° C. for 4 hours under N₂. The reaction was monitored by LCMS. After complete, the reaction mixture was poured into H₂O (80 mL). The mixture was extracted with ethyl acetate (90 mL×3). The organic phase was washed with brine (35 mL), dried over anhydrous Na₂SO₄, concentrated in vacuo. The crude material was purified by flash silica gel chromatography to afford 5-bromo-3-(5-methyl-2-furyl)pyrazin-2-amine (2.3 g, 45.7% yield) as a light yellow solid. LCMS m/z 256.3 [M+H]⁺; ¹HNMR (CDCl₃ 400 MHz) δ 7.94 (s, 1H), 7.09 (d, J=3.2 Hz, 1H), 6.20-6.19 (m, 1H), 5.56 (s, 2H), 2.42 (s, 3H).

Step 2: Preparation of 5-bromo-3-(5-methyl-2-furyl)pyrazin-1-ium-1,2-diamine

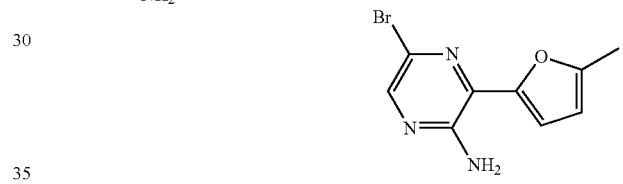

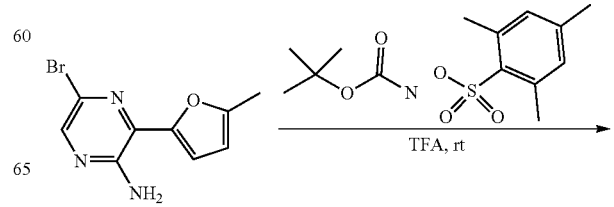

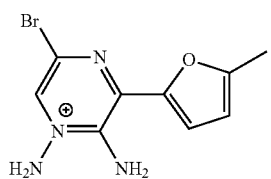

To a solution of TFA (4.62 g, 40.52 mmol, 3 mL, 17.16 eq.), (tert-butoxycarbonylamino) 2,4,6-trimethylbenzenesulfonate (1.0 g, 3.17 mmol, 1.34 eq.) was added in small portions at 0° C. The reaction was stirred at 0° C. for 1.5 hours under $N_2$, then poured into crushed ice. The white precipitate formed was filtered and washed with water. The solid was transferred to a round bottom flask while wet, and immediately dissolved in $CH_2Cl_2$ (50 mL). The organic layer was dried over $Na_2SO_4$, filtered and concentrated. The crude material was dissolved in $CH_2Cl_2$ (15 mL) and the above solution was then added to a solution of 5-bromo-3-(5-methyl-2-furyl)pyrazin-2-amine (600 mg, 2.36 mmol, 1 eq.) in $CH_2Cl_2$ (3 mL) slowly at 0° C. The reaction mixture was then stirred at 25-28° C. for 12 hours. The reaction was monitored by LCMS. After complete the reaction, the mixture was cooled at 0° C. and the white precipitate was filtered, washed with cold $CH_2Cl_2$ (5 mL). The crude material was dried in vacuo to yield 1,2-diamino-5-bromo-3-(5-methylfuran-2-yl)pyrazin-1-ium (600 mg, crude, 2,4,6-trimethylbenzenesulfonic acid salt) as a yellow solid, which was used into the next step without further purification. LCMS m/z 271.2 [M+H]⁺.

Step 3: Preparation of 6-bromo-2-methyl-8-(5-methyl-2-furyl)-[1,2,4]triazolo[1,5-a]pyrazine

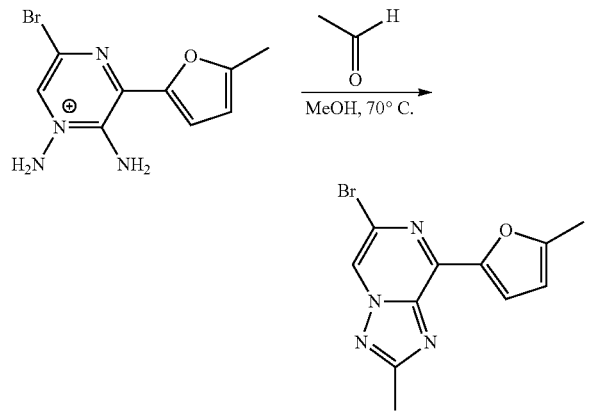

To a mixture of 5-bromo-3-(5-methyl-2-furyl)pyrazin-1-ium-1,2-diamine (600 mg, 2.22 mmol, 1 eq., 2,4,6-trimethylbenzenesulfonic acid salt) and acetaldehyde (489.28 mg, 11.11 mmol, 623.29 µL, 5 eq.) in MeOH (10 mL) was stirred at 70° C. for 12 hours. The reaction was monitored by LCMS. The solvent was removed under pressure to give a residue and the residue was purified by flash silica gel chromatography to afford 6-bromo-2-methyl-8-(5-methyl-2-furyl)-[1,2,4]triazolo[1,5-a]pyrazine (300 mg, 1.02 mmol, 46.0% yield) as a yellow solid. LCMS m/z 295.3 [M+H]⁺

Step 4: Preparation of N-[2-methyl-8-(5-methyl-2-furyl)-[1,2,4]triazolo[1,5-a]pyrazin-6-yl]cyclopropanecarboxamide (169)

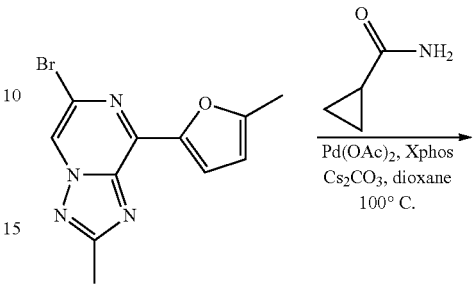

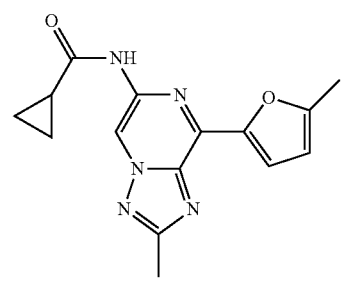

6-Bromo-2-methyl-8-(5-methyl-2-furyl)-[1,2,4]triazolo[1,5-a]pyrazine (150 mg, 511.74 µmol, 1 eq.), cyclopropanecarboxamide (90.00 mg, 1.06 mmol, 2.07 eq.), $Pd(OAc)_2$ (15 mg, 66.81 µmol, 1.31e-1 eq.), $Cs_2CO_3$ (330 mg, 1.01 mmol, 1.98 eq.) and XPhos (65.00 mg, 136.35 µmol, 0.266 eq.) in dioxane (4 mL) was de-gassed and then heated to 100° C. for 2 hours under $N_2$. The reaction was monitored by LCMS. After completion, the reaction mixture was partitioned between water (80 mL) and ethyl acetate (100 mL×2). The organic phase was separated, washed with brine (20 mL), dried with anhydrous $Na_2SO_4$, filtration and concentrated. The residue was purified by flash silica gel chromatography to give N-[2-methyl-8-(5-methyl-2-furyl)-[1,2,4]triazolo[1,5-a]pyrazin-6-yl]cyclopropanecarboxamide (31.2 mg, 20.2% yield, 98.4% purity) as a white solid. LCMS m/z 298.4 [M+H]⁺; ¹HNMR (CDCl₃, 400 MHz) δ 9.30 (s, 1H), 8.21 (s, 1H), 8.01 (d, J=3.2 Hz 1H), 6.32 (d, J=2.4 Hz, 1H), 2.66 (s, 3H), 2.52 (s, 3H), 1.56-1.54 (m, 1H), 1.16-1.14 (m, 2H), 0.96-0.92 (m, 2H).

Example 11: Preparation of 5-chloro-2-methyl-8-phenyl-[1,2,4]triazolo[1,5-a]pyrazin-6-amine (168) and 5-bromo-2-methyl-8-phenyl-[1,2,4]triazolo[1,5-a]pyrazin-6-amine (172)

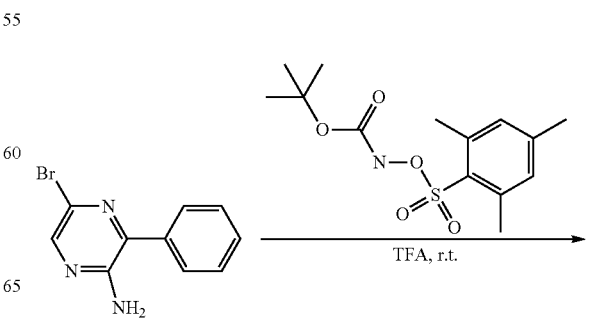

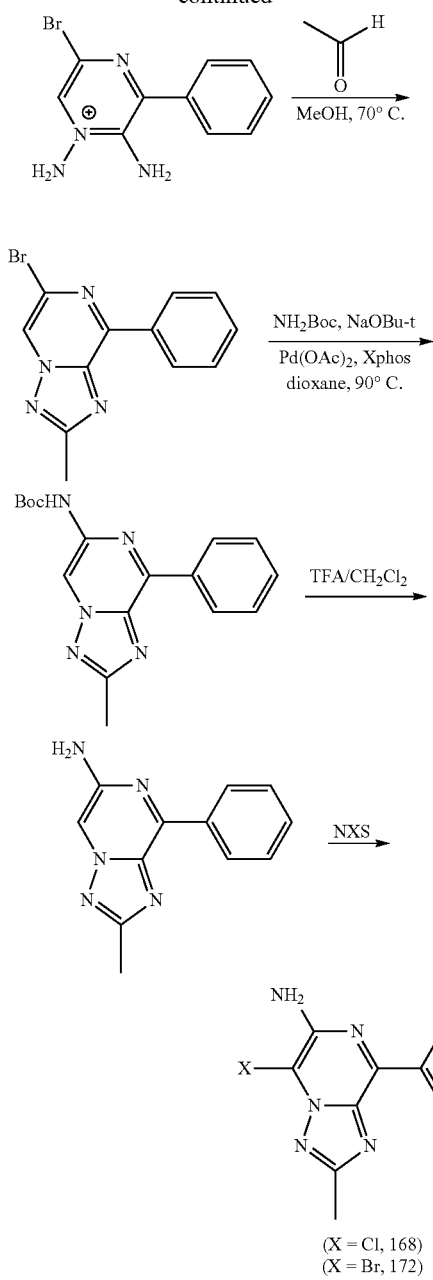

Step 1: Preparation of
1,2-diamino-5-bromo-3-phenylpyrazin-1-ium,
2,4,6-trimethyl benzenesulfonic

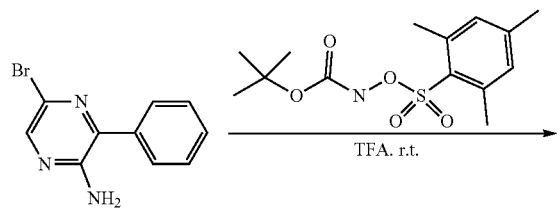

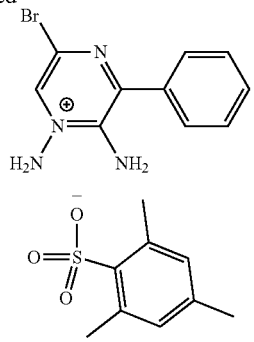

To a 2,2,2-trifluoroacetic acid (54.03 mmol, 4.00 mL, 13.51 eq.) was added (tert-butoxycarbonylamino) 2,4,6-trimethylbenzenesulfonate (2.02 g, 6.40 mmol, 1.6 eq.) in portions at 0° C. The reaction mixture was stirred at 0° C. for 1.5 hours under $N_2$, then poured into crushed ice. The resulting white precipitate was filtered and washed with water, transferred to a round bottom flask while wet, and immediately dissolved in $CH_2C_2$ (15 mL). Trace amount of water was removed via separatory funnel and the organic layer was dried over $Na_2SO_4$ and filtered. The above $CH_2C_2$ solution was then added to a solution of 5-bromo-3-phenyl-pyrazin-2-amine (1 g, 4.00 mmol, 1 eq.) in $CH_2Cl_2$ (5 mL) slowly at 0° C. The reaction mixture was then stirred at 5° C. for 20 hours. The reaction mixture was cooled to 0° C. and filtered. The filtered cake was washed with $CH_2C_2$ (5 mL) and concentrated under reduce pressure to obtain 1,2-diamino-5-bromo-3-phenylpyrazin-1-ium, 2,4,6-trimethylbenzenesulfonic acid salt (0.8 g, 1.55 mmol, 38.6% yield) as a yellow solid, which was used without further purification. $^1$HNMR (CDCl$_3$, 400 MHz) δ 8.18-8.06 (m, 1H), 7.60-7.43 (m, 4H), 7.25-7.22 (m, 1H), 6.72-6.60 (m, 2H), 3.21-3.19 (m, 6H), 2.13-2.00 (m, 3H).

Step 2: Preparation of 6-bromo-2-methyl-8-phenyl-[1,2,4]triazolo[1,5-a]pyrazine

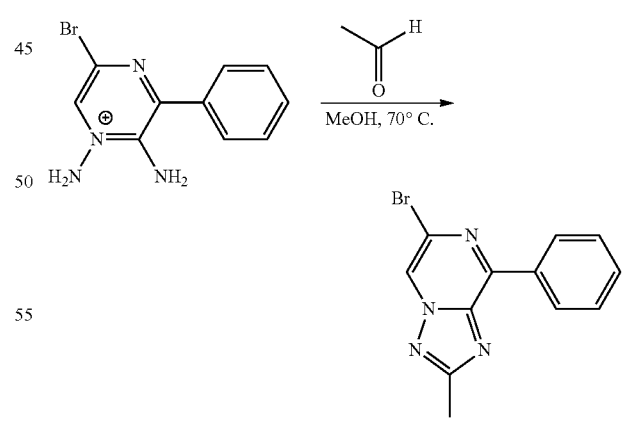

The solution of 1,2-diamino-5-bromo-3-phenylpyrazin-1-ium, 2,4,6-trimethylbenzenesulfonic acid salt (0.8 g, 1.72 mmol, 1 eq.) and acetaldehyde (378.65 mg, 8.60 mmol, 482.36 μL, 5 eq.) in MeOH (10 mL) was stirred at 70° C. for 40 hours. The reaction was monitored by LCMS. The reaction mixture was concentrated under reduce pressure after completion. The residue was poured into aqueous NaHCO₃ (30 mL), and extracted with ethyl acetate (15 mL×3). The combined organic layers were washed with brine (20 mL), dried over Na₂SO₄, filtered and concentrated under reduced pressure to give a residue. The residue was purified by flash silica gel chromatography to afford 6-bromo-2-methyl-8-phenyl-[1,2,4]triazolo[1,5-a]pyrazine (450 mg, 1.40 mmol, 81.4% yield) as a yellow solid. LCMS m/z 288.8 [M+]⁺290.7 [M+H+2]⁺; ¹HNMR (CDCl₃, 400 MHz) δ 8.80-8.71 (m, 2H), 8.56 (s, 1H), 7.62-7.50 (m, 3H), 2.71 (s, 3H).

Step 3: Preparation of tert-butyl N-(2-methyl-8-phenyl-[1,2,4]triazolo[1,5-a]pyrazin-6-yl)carbamate

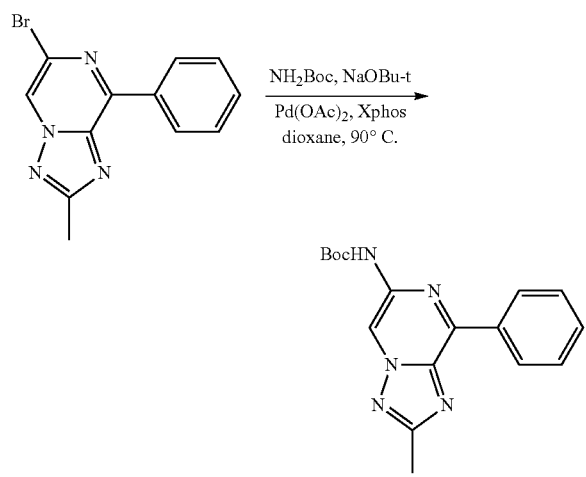

A mixture of 6-bromo-2-methyl-8-phenyl-[1,2,4]triazolo[1,5-a]pyrazine (300.00 mg, 1.04 mmol, 1 eq.), NH₂Boc (182.33 mg, 1.56 mmol, 1.5 eq.), XPhos (98.93 mg, 207.52 μmol, 0.2 eq.), t-BuONa (199.43 mg, 2.08 mmol, 2 eq.) and Pd(OAc)₂ (23.30 mg, 103.76 μmol, 0.1 eq.) in dioxane (10 mL) was degassed and purged with N₂, and then the mixture was stirred at 90° C. for 16 hours under N₂ atmosphere. After completion, the reaction mixture was filtered and concentrated under reduce pressure. The residue was purified by flash silica gel chromatography to give tert-butyl N-(2-methyl-8-phenyl-[1,2,4]triazolo[1,5-a]pyrazin-6-yl)carbamate (280 mg, 757.30 μmol, 72.9% yield) as a yellow solid. LCMS m/z 326.1 [M+H]⁺; ¹HNMR (CDCl₃, 400 MHz) δ 9.10 (s, 1H), 8.69-8.67 (m, 2H), 7.61-7.47 (m, 3H), 7.19 (s, 1H), 2.68 (s, 3H), 1.56 (s, 9H)

Step 4: Preparation of 2-methyl-8-phenyl-[1,2,4]triazolo[1,5-a]pyrazin-6-amine

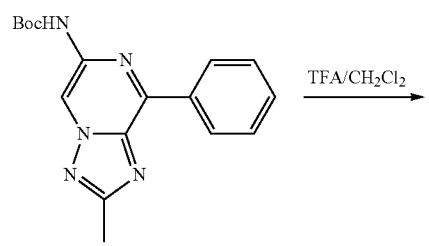

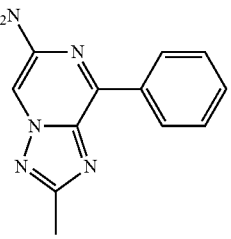

To a solution of tert-butyl N-(2-methyl-8-phenyl-[1,2,4]triazolo[1,5-a]pyrazin-6-yl)carbamate (280 mg, 714.28 μmol, 1 eq.) in anhydrous CH₂Cl₂ (3 mL) was added 2,2,2-trifluoroacetic acid (1.54 g, 13.51 mmol, 1 mL, 18.91 eq.). The resulted mixture was stirred at 5° C. for 16 hours. The reaction was monitored by LCMS. The resulting reaction mixture was adjusted to pH=8-9 with aq. NaHCO₃, and extracted with ethyl acetate (15 mL×3). The combined organic layers were washed with brine (20 mL), dried over Na₂SO₄, filtered and concentrated under reduced pressure to give a residue. The residue was purified by flash silica gel chromatography to provide 2-methyl-8-phenyl-[1,2,4]triazolo[1,5-a]pyrazin-6-amine (105 mg, 419.54 μmol, 58.7% yield) as yellow solid. LCMS m/z 226.1 [M+H]⁺; ¹HNMR (CDCl₃, 400 MHz) δ 8.76-8.59 (m, 2H), 7.84-7.78 (m, 1H), 7.59-7.46 (m, 3H), 4.28 (br s, 2H), 2.64 (s, 3H).

Step 5: Procedure for preparation of 5-chloro-2-methyl-8-phenyl-[1,2,4]triazolo[1,5-a]pyrazin-6-amine (168)

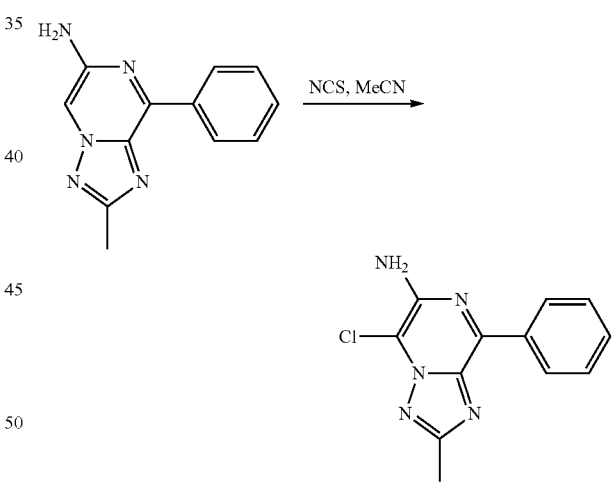

(168)

A mixture of 2-methyl-8-phenyl-[1,2,4]triazolo[1,5-a]pyrazin-6-amine (50 mg, 221.98 μmol, 1 eq.), NCS (35.57 mg, 266.37 μmol, 1.2 eq.) in CH₃CN (0.5 mL) was stirred at 5° C. for 60 hours LCMS showed the starting material was consumed. The reaction mixture was poured into aq. Na₂SO₃ (10 mL), and extracted with ethyl acetate (5 mL×2). The combined organic phase was washed with brine (20 mL), dried with anhydrous Na₂SO₄, filtered and concentrated in vacuum. The residue was purified by flash silica gel chromatography and lyophilized to obtained 5-chloro-2-methyl-8-phenyl-[1,2,4]triazolo[1,5-a]pyrazin-6-amine (25.2 mg, 43.4% yield) as a yellow solid. LCMS m/z 260.0

[M+H]⁺; ¹HNMR (CDCl₃, 400 MHz) δ=8.64 (dd, J=1.6, 8.0 Hz, 2H), 7.59-7.46 (m, 3H), 4.59 (s, 2H), 2.70 (s, 3H).

Step 5: Preparation of 5-bromo-2-methyl-8-phenyl-[1,2,4]triazolo[1,5-a]pyrazin-6-amine (172)

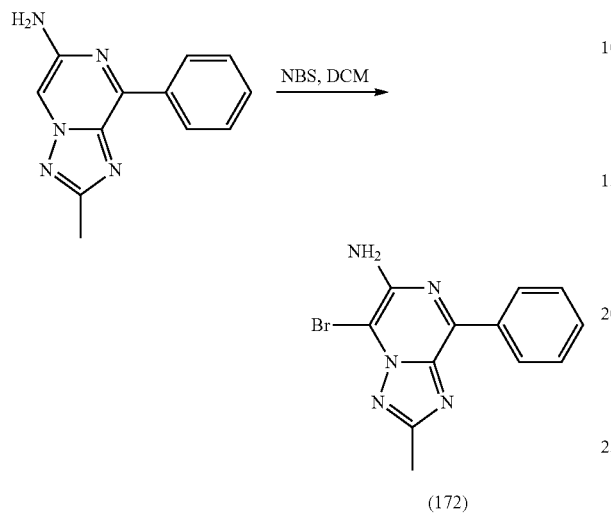

(172)

A mixture of 2-methyl-8-phenyl-[1,2,4]triazolo[1,5-a]pyrazin-6-amine (40 mg, 177.58 μmol, 1 eq.), NBS (37.93 mg, 213.10 μmol, 1.2 eq.) in CH₂Cl₂ (0.5 mL) was stirred at 5° C. for 10 min. LCMS showed the starting material was consumed. The reaction mixture was poured into aqueous Na₂SO₃ (10 mL) and extracted with ethyl acetate (5 mL×2). The combined organic phase was washed with brine (20 mL), dried with anhydrous Na₂SO₄, filtered and concentrated in vacuum. The residue was purified by flash silica gel chromatography and lyophilized to obtained 5-bromo-2-methyl-8-phenyl-[1,2,4]triazolo[1,5-a]pyrazin-6-amine (23.8 mg, 43.7% yield) as a yellow solid. LCMS m/z 304.0 [M+]*, 306.0 [M+H+2]⁺; ¹HNMR (CDCl₃, 400 MHz) δ 8.65 (dd, J=2.0, 8.0 Hz, 2H), 7.58-7.48 (m, 3H), 4.63 (s, 2H), 2.70 (s, 3H).

Example 12: Preparation of N-(2-bromo-8-(5-methylfuran-2-yl)-triazolo[1,5-a]pyrazin-6-yl)cyclopropanecarboxamide (190)

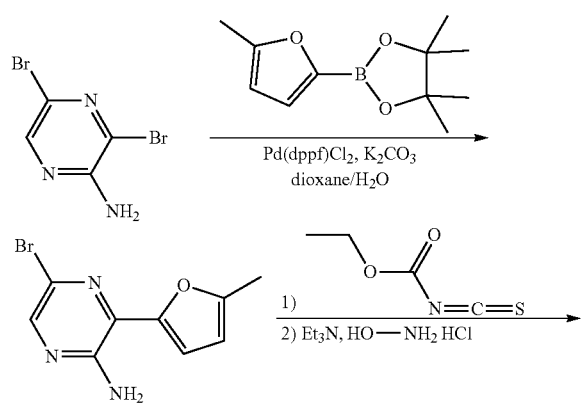

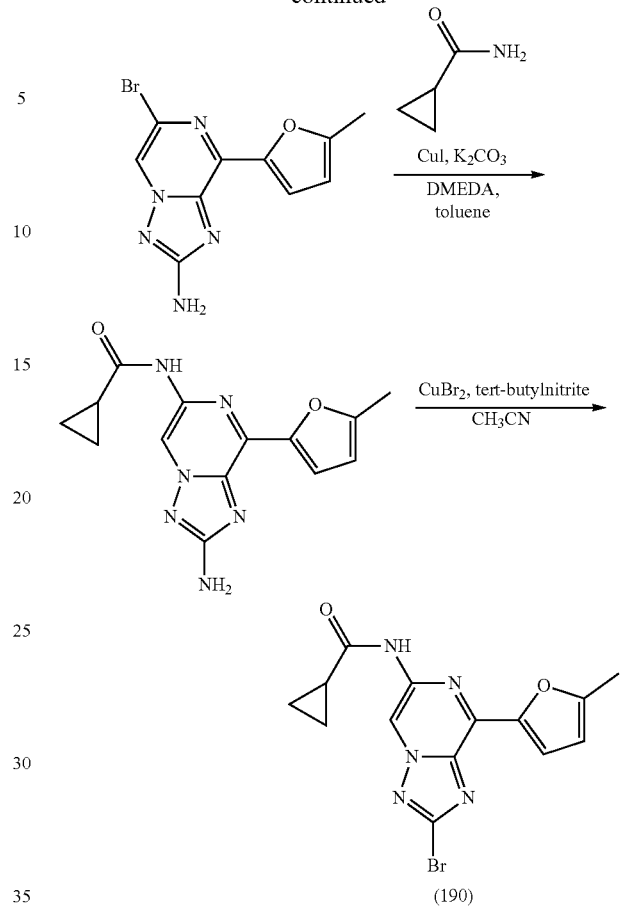

(190)

Step 1: Preparation of 5-bromo-3-(5-methyl-2-furyl)pyrazin-2-amine

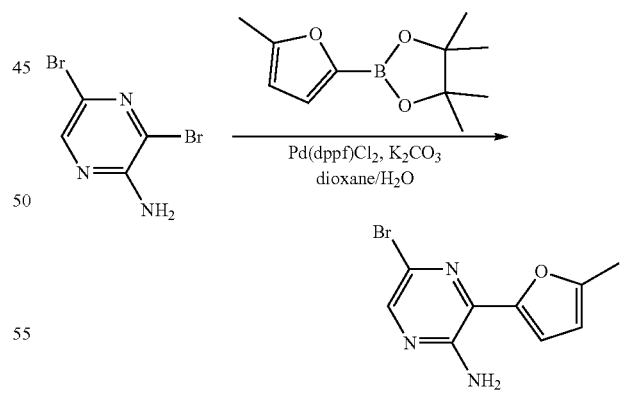

To a mixture of 3,5-dibromopyrazin-2-amine (6.5 g, 25.70 mmol, 1 eq.), 4,4,5,5-tetramethyl-2-(5-methyl-2-furyl)-1,3,2-dioxaborolane (4.81 g, 23.13 mmol, 0.9 eq.) and K₂CO₃ (7.10 g, 51.40 mmol, 2 eq.) in 1,4-dioxane (100 mL) and H₂O (50 mL) was added Pd(dppf)Cl₂ (1.88 g, 2.57 mmol, 0.1 eq.) at 10° C. under nitrogen atmosphere. Then the mixture was stirred for 1 hour at 100° C. under nitrogen atmosphere. The reaction was monitored by LCMS. After cooled to room temperature, the reaction was diluted with brine (100 mL), extracted with EtOAc (60 mL×3). The combined extracts were dried over anhydrous sodium sulfate, filtered and concentrated. The residue was purified by flash column chromatography to afford 5-bromo-3-(5-methyl-2-furyl)pyrazin-2-amine (3.60 g, 44.1% yield) as yellow solid. LCMS m/z 253.9 [M+H]$^+$, 255.9 [M+H+2]$^+$; $^1$HNMR (CDCl$_3$, 400 MHz) δ 7.94 (s, 1H), 7.09 (d, J=3.2 Hz, 1H), 6.19 (dd, J=0.8, 3.2 Hz, 1H), 5.52 (s, 2H), 2.42 (s, 3H).

Step 2: Preparation of 6-bromo-8-(5-methyl-2-furyl)-[1,2,4]triazolo[1,5-a]pyrazin-2-amine

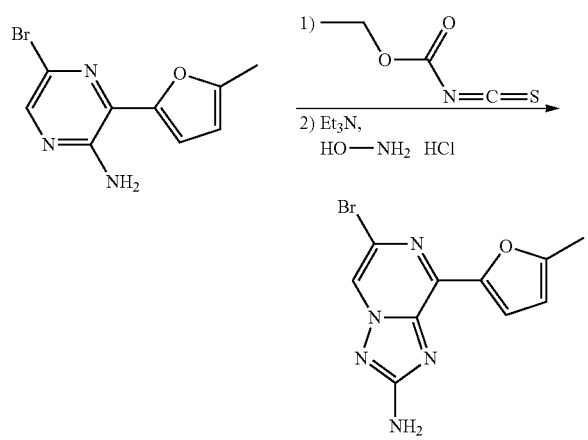

To a solution of 5-bromo-3-(5-methyl-2-furyl)pyrazin-2-amine (500 mg, 1.97 mmol, 1 eq.) in dioxane (6 mL) was added ethyl N-(thioxomethylene)carbamate (387.14 mg, 2.95 mmol, 1.5 eq.) dropwise at 0° C. The mixture was stirred at 20° C. for 20 hours LCMS showed the starting material was consumed. The resulting mixture was concentrated by reduced pressure and Et$_3$N (597.38 mg, 5.90 mmol, 821.71 µL, 3 eq.) and hydroxylamine hydrochloride (546.99 mg, 7.87 mmol, 4 eq.) in MeOH (4 mL)/EtOH (4 mL) were added to the suspension. The mixture was heated at 80° C. for 12 hours. The mixture was cooled to room temperature and concentrated in vacuum. The crude product was triturated with 95% ethanol to give 6-bromo-8-(5-methyl-2-furyl)-[1,2,4]triazolo[1,5-a]pyrazin-2-amine (500 mg, 60.47% yield) as brown solid; $^1$HNMR (DMSO-d$_6$ 400 MHz) δ 10.06 (br s, 2H), 8.93 (s, 1H), 7.67 (d, J=3.2 Hz, 1H), 6.44 (d, J=3.2 Hz, 1H), 2.45 (s, 3H).

Step 3: Preparation of N-[2-amino-8-(5-methyl-2-furyl)-[1,2,4]triazolo[1,5-a]pyrazin-6-yl]cyclopropanecarboxamide

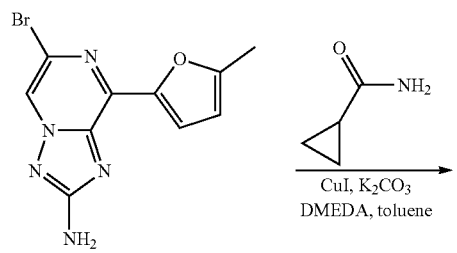

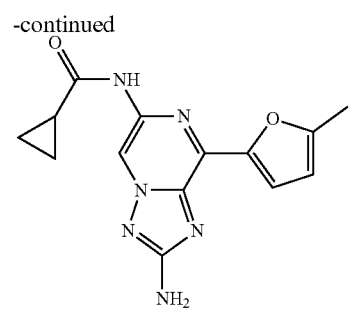

To a mixture of 6-bromo-8-(5-methyl-2-furyl)-[1,2,4]triazolo[1,5-a]pyrazin-2-amine (100 mg, 340.01 µmol, 1 eq.) and cyclopropanecarboxamide (144.68 mg, 1.70 mmol, 5 eq.) in toluene (5 mL) was added CuI (64.76 mg, 340.01 µmol, 1 eq.) and K$_2$CO$_3$ (93.98 mg, 680.02 µmol, 2 eq.) in one portion at 20° C. under N$_2$ atmosphere. DMEDA (119.89 mg, 1.36 mmol, 146.39 µL, 4 eq.) was added. The reaction mixture was stirred at 20° C. for 30 min, then heated to 90° C. and stirred for 12 hours. The reaction was monitored by LCMS. The mixture was concentrated by rotary evaporator and the residue was purified by flash silica gel chromatography and triturated with MeOH (10 mL) and filtered to afford N-[2-amino-8-(5-methyl-2-furyl)-[1,2,4] triazolo[1,5-a]pyrazin-6-yl]cyclopropanecarboxamide (14 mg, 13.1% yield) as a yellow solid. LCMS m/z 299.1 [M+H]$^+$; $^1$HNMR (CDCl$_3$, 400 MHz) δ 9.16 (s, 1H), 8.18 (br s, 1H), 7.83 (d, J=3.2 Hz, 1H), 6.28 (d, J=3.2 Hz, 1H), 4.64 (s, 2H), 2.51 (s, 3H), 1.54 (m, 1H), 1.17-1.08 (m, 2H), 0.93 (dd, J=3.2, 7.6 Hz, 2H)

Step 4: Preparation of N-[2-bromo-8-(5-methyl-2-furyl)-[1,2,4]triazolo[1,5-a]pyrazin-6-yl]cyclopropanecarboxamide (190)

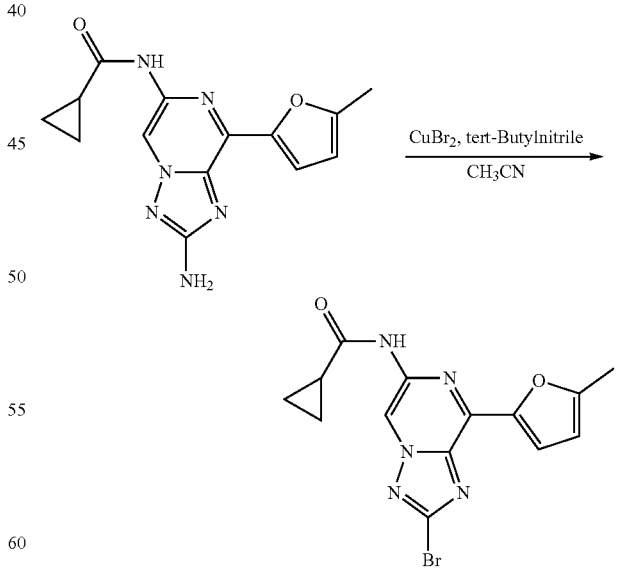

To a solution of tert-butylnitrite (20.74 mg, 201.14 µmol, 23.92 µL, 1.5 eq.) in dry acetonitrile (2 mL) was added copper (II) bromide (44.93 mg, 201.14 µmol, 9.42 µL, 1.5 eq.) under an N$_2$ atmosphere and heated to 60° C. for 10 min. The N-[2-amino-8-(5-methyl-2-furyl)-[1,2,4]triazolo[1,5-a]

pyrazin-6-yl]cyclopropanecarboxamide (40 mg, 134.09 μmol, 1 eq.) in acetonitrile (3 mL) was added at 60° C. The reaction mixture was stirred at 75° C. for 2 hours and then cooled to room temperature. LCMS showed the starting material was consumed completely. Water (10 mL) was added and the aqueous phase was extracted with dichloromethane (10 mL×2). The combined organic layers were dried over sodium sulfate, filtered and evaporated. The residue was purified by preparative to afford N-[2-bromo-8-(5-methyl-2-furyl)-[1,2,4]triazolo[1,5-a]pyrazin-6-yl]cyclopropanecarboxamide (13.9 mg, 27.2% yield) as yellow solid. LCMS m/z 364.0 [M+H]$^+$; $^1$HNMR (CDCl$_3$, 400 MHz) δ 9.32 (s, 1H), 8.22 (s, 1H), 8.02 (d, J=3.2 Hz, 1H), 6.33 (d, J=3.2 Hz, 1H), 2.53 (s, 3H), 1.60 (m, 1H), 1.22-1.11 (m, 2H), 0.96 (m, 2H)

The compounds in Table 2 were prepared in accordance with the synthetic protocols set forth in Examples 9-12 and general synthesis Schemes 5 and 6 by adjusting to the appropriate starting materials.

TABLE 2

| Compound No. | Structure | IUPAC Name | LC/MS | Purity |
|---|---|---|---|---|
| 166 | 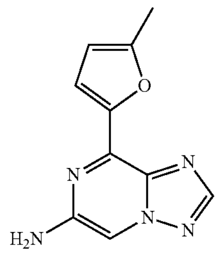 | 8-(5-methylfuran-2-yl)-[1,2,4]triazolo[1,5-a]pyrazin-6-amine | [MH+] = 216.3 | 97.0% |
| 167 | 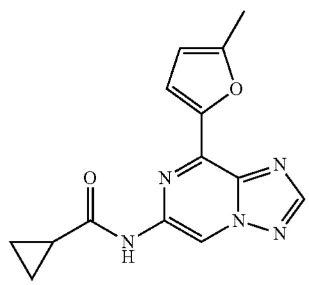 [SMILES: Cc1ccc(-c2nc(NC(=O)C3CC3)cn3ncnc23)o1] | N-[8-(5-methylfuran-2-yl)-[1,2,4]triazolo[1,5-a]pyrazin-6-yl]cyclopropanecarboxamide | [MH+] = 284.3 | 98.0% |
| 168 | 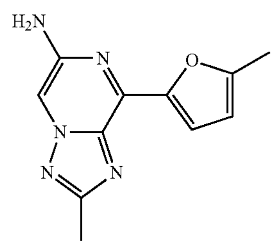 [SMILES: Cc1nc2c(-c3ccc(C)o3)nc(N)cn2n1] | 2-methyl-8-(5-methylfuran-2-yl)-[1,2,4]triazolo[1,5-a]pyrazin-6-amine | [MH+] = 229.9 | 95.0% |
| 169 | 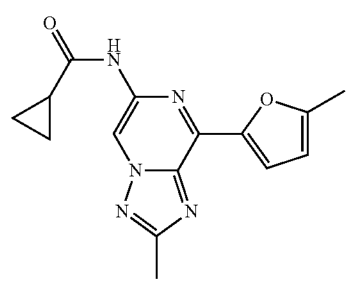 [SMILES: Cc1nc2c(-c3ccc(C)o3)nc(NC(=O)C3CC3)cn2n1] | N-[2-methyl-8-(5-methlfuran-2-yl)-[1,2,4]triazolo[1,5-a]pyrazin-6-yl]cyclopropanecarboxamide | [MH+] = 297.9, [M + Na] = 319.8 | 99.0% |
| 170 | 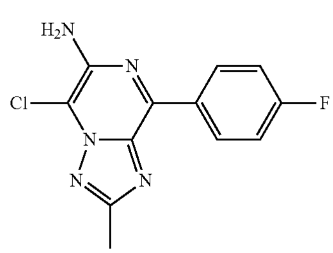 | 5-chloro-8-(4-fluorophenyl)-2-methyl-[1,2,4]triazolo[1,5-a]pyrazin-6-amine | [MH+] = 278.0 | 99.8% |

TABLE 2-continued

| Compound No. | Structure | IUPAC Name | LC/MS | Purity |
|---|---|---|---|---|
| 171 | 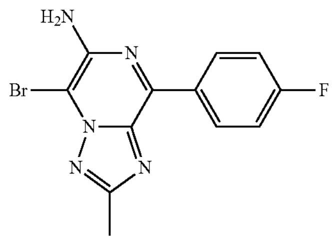 | 5-bromo-8-(4-fluorophenyl)-2-methyl-[1,2,4]triazolo[1,5-a]pyrazin-6-amine | [M+/M + 2] = 322.0/324.0 | 99.4% |
| 172 | 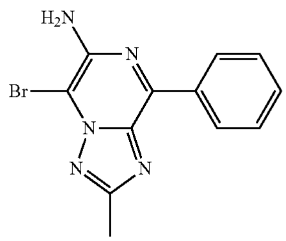 [SMILES: Cc1nc2c(-c3ccccc3)nc(N)c(Br)n2n1] | 5-bromo-2-methyl-8-phenyl-[1,2,4]triazolo[1,5-a]pyrazin-6-amine | [M+/M + 2] = 304.0/306.0 | 99.7% |
| 173 | 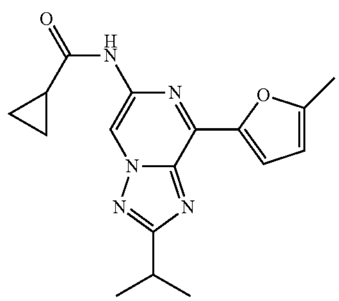 [SMILES: Cc1ccc(-c2nc(NC(=O)C3CC3)cn3nc(C(C)C)nc23)o1] | N-[8-(5-methylfuran-2-yl)-2-propan-2-yl-[1,2,4]triazolo[1,5-a]pyrazin-6-yl]cyclopropanecarboxamide | [M + H] = 326.1 | 97.5% |
| 174 | 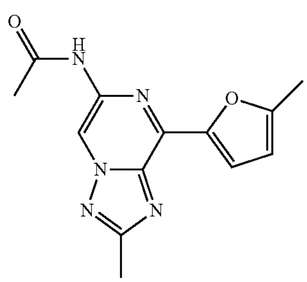 [SMILES: CC(=O)Nc1cn2nc(C)nc2c(-c2ccc(C)o2)n1] | N-[2-methyl-8-(5-methylfuran-2-yl)-[1,2,4]triazolo[1,5-a]pyrazin-6-yl]acetamide | [M + H] = 272.1 | 100.0% |
| 175 | 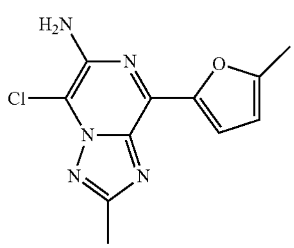 [SMILES: Cc1nc2c(-c3ccc(C)o3)nc(N)c(Cl)n2n1] | 5-chloro-2-methyl-8-(5-methylfuran-2-yl)-[1,2,4]triazolo[1,5-a]pyrazin-6-amine | [M + H] = 264.1 | 99.3% |
| 176 | 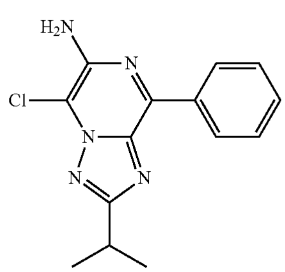 | 5-chloro-2-methyl-8-phenyl-[1,2,4]triazolo[1,5-a]pyrazin-6-amine | [M + H] = 260.1 | 99.6% |

TABLE 2-continued

| Compound No. | Structure | IUPAC Name | LC/MS | Purity |
|---|---|---|---|---|
| 177 | 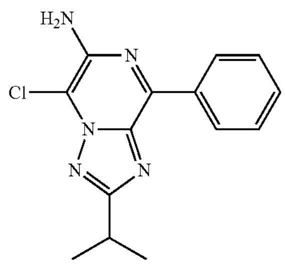 [SMILES: CC(C)c1nc2c(-c3ccccc3)nc(N)c(Cl)n2n1] | 5-chloro-8-phenyl-2-propan-2-yl-[1,2,4]triazolo[1,5-a]pyrazin-6-amine | [M + H] = 288.1 | 98.9% |
| 178 | 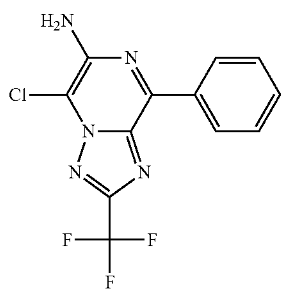 [SMILES: Nc1nc(-c2ccccc2)c2nc(C(F)(F)F)nn2c1Cl] | 5-chloro-8-phenyl-2-(trifluoromethyl)-[1,2,4]triazolo[1,5-a]pyrazin-6-amine | [M + H] = 314.1 | 94.0% |
| 179 | 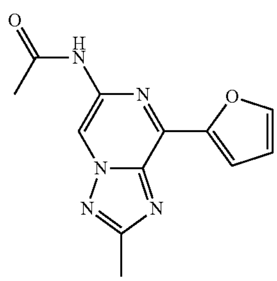 [SMILES: CC(=O)Nc1cn2nc(C)nc2c(-c2ccco2)n1] | N-[8-(furan-2-yl)-2-methyl-[1,2,4]triazolo[1,5-a]pyrazin-6-yl]acetamide | [M + H] = 258.2 | 100.0% |
| 180 | 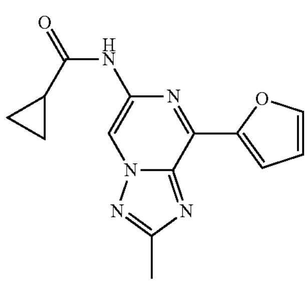 [SMILES: Cc1nc2c(-c3ccco3)nc(NC(=O)C3CC3)cn2n1] | N-[8-(furan-2-yl)-2-methyl-[1,2,4]triazolo[1,5-a]pyrazin-6-yl]cyclopropanecarboxamide | [M + H] = 284.0 | 99.7% |
| 181 | 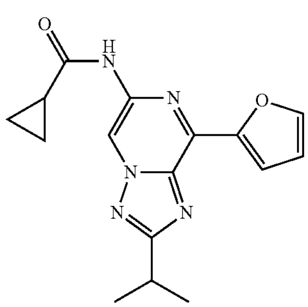 [SMILES: CC(C)c1nc2c(-c3ccco3)nc(NC(=O)C3CC3)cn2n1] | N-[8-(furan-2-yl)-2-propan-2-yl-[1,2,4]triazolo[1,5-a]pyrazin-6-yl]cyclopropanecarboxamide | [M + H] = 312.1 | 100.0% |

TABLE 2-continued

| Compound No. | Structure | IUPAC Name | LC/MS | Purity |
|---|---|---|---|---|
| 182 | 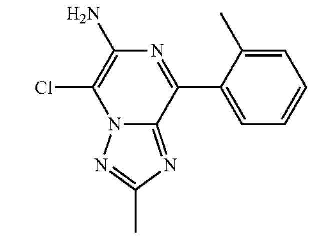 [SMILES: Cc1nc2c(-c3ccccc3C)nc(N)c(Cl)n2n1] | 5-chloro-2-methyl-8-(2-methylphenyl)-[1,2,4]triazolo[1,5-a]pyrazin-6-amine | [M + H] = 274.0 | 95.6% |
| 183 | 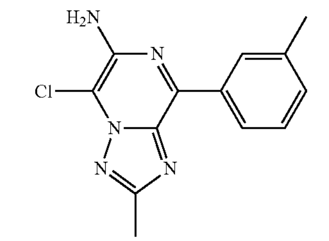 [SMILES: Cc1cccc(-c2nc(N)c(Cl)n3nc(C)nc23)c1] | 5-chloro-2-methyl-8-(3-methylphenyl)-[1,2,4]triazolo[1,5-a]pyrazin-6-amine | [M + H] = 274.1 | 100.0% |
| 184 | 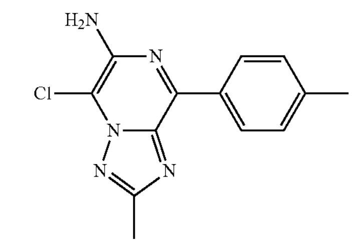 [SMILES: Cc1ccc(-c2nc(N)c(Cl)n3nc(C)nc23)cc1] | 5-chloro-2-methyl-8-(4-methylphenyl)-[1,2,4]triazolo[1,5-a]pyrazin-6-amine | [MH+] = 274.0 | 100.0% |
| 185 | 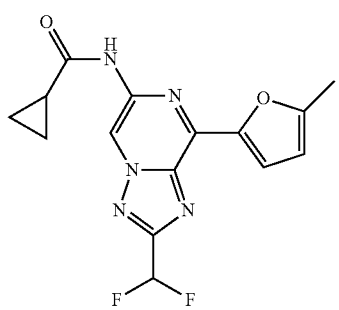 [SMILES: Cc1ccc(-c2nc(NC(=O)C3CC3)cn3nc(C(F)F)nc23)o1] | N-[2-(difluoromethyl)-8-(5-methylfuran-2-yl)-[1,2,4]triazolo[1,5-a]pyrazin-6-yl]cyclopropanecarboxamide | [M + H] = 334.0 | 100.0% |
| 186 | 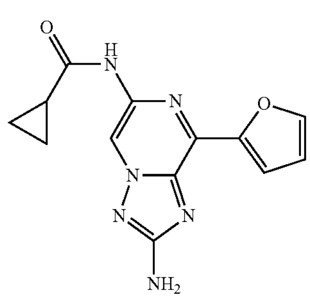 [SMILES: Nc1nc2c(-c3ccco3)nc(NC(=O)C3CC3)cn2n1] | N-[2-amino-8-(furan-2-yl)-[1,2,4]triazolo[1,5-a]pyrazin-6-yl]cyclopropanecarboxamide | [M + H] = 284.1 | 100.0% |

TABLE 2-continued

| Compound No. | Structure | IUPAC Name | LC/MS | Purity |
|---|---|---|---|---|
| 187 | 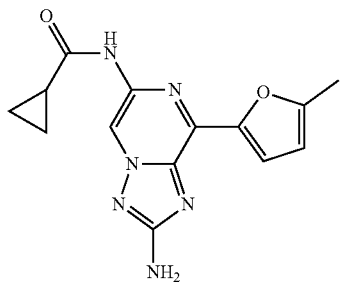 [SMILES: Cc1ccc(-c2nc(NC(=O)C3CC3)cn3nc(N)nc23)o1] | N-[2-amino-8-(5-methylfuran-2-yl)-[1,2,4]triazolo[1,5-a]pyrazin-6-yl]cyclopropanecarboxamide | [M + H] = 299.1 | 95.9% |
| 188 | 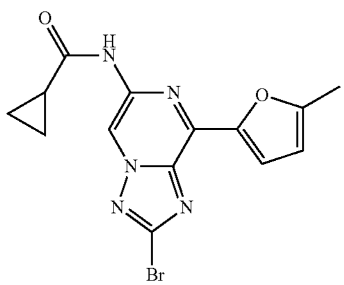 [SMILES: Cc1ccc(-c2nc(NC(=O)C3CC3)cn3nc(Br)nc23)o1] | N-[2-bromo-8-(5-methylfuran-2-yl)-[1,2,4]triazolo[1,5-a]pyrazin-6-yl]cyclopropanecarboxamide | [M+/M + 2] = 362.0/364.0 | 97.6% |
| 189 | 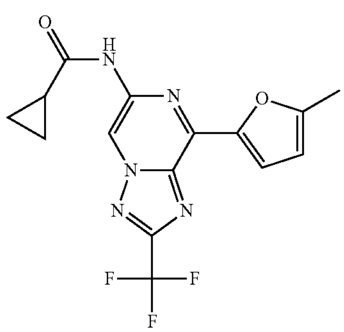 [SMILES: Cc1ccc(-c2nc(NC(=O)C3CC3)cn3nc(C(F)(F)F)nc23)o1] | N-[8-(5-methylfuran-2-yl)-2-(trifluoromethyl)-[1,2,4]triazolo[1,5-a]pyrazin-6-yl]cyclopropanecarboxamide | [M + H] = 352.0 | 98.6% |
| 190 | 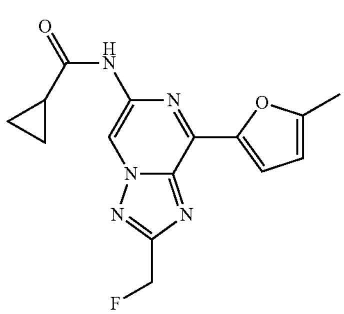 [SMILES: Cc1ccc(-c2nc(NC(=O)C3CC3)cn3nc(CF)nc23)o1] | N-[2-(fluoromethyl)-8-(5-methylfuran-2-yl)-[1,2,4]triazolo[1,5-a]pyrazin-6-yl]cyclopropanecarboxamide | [M + H] = 316.0 | 100.0% |

Part III: Preparation of Imidazolopyrazine Adenosine Antagonists

Example 13: Preparation of 5-bromo-2-methyl-8-phenylimidazo[1,2-a]pyrazin-6-amine (210) and 5-chloro-2-methyl-8-phenylimidazo[1,2-a]pyrazin-6-amine (211)

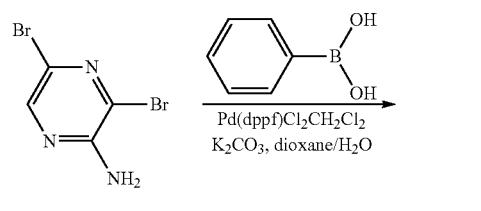

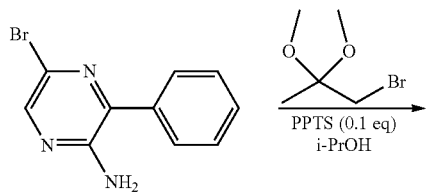

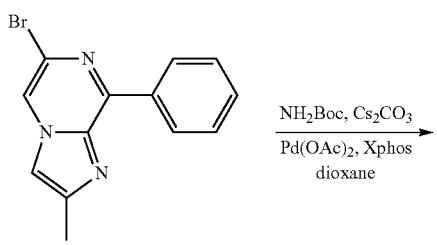

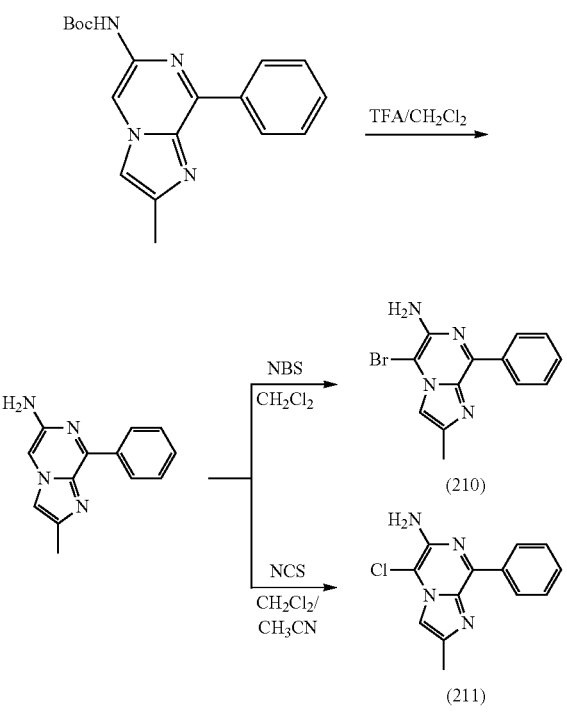

Step 1: Preparation of 5-bromo-3-phenyl-pyrazin-2-amine

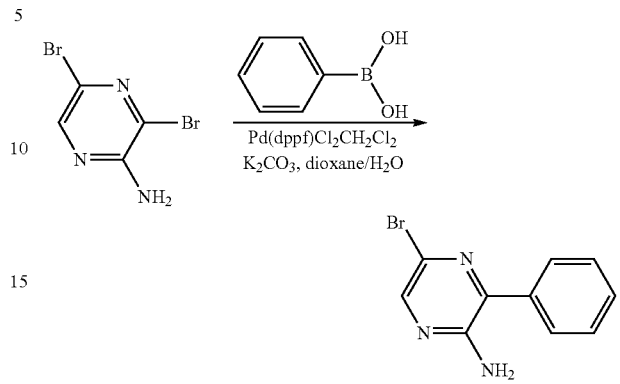

To a solution of 3,5-dibromopyrazin-2-amine (4 g, 15.82 mmol, 1 eq.) in dioxane (10 mL) were added Pd(dppf)Cl$_2$·CH$_2$Cl$_2$ (1.29 g, 1.58 mmol, 0.1 eq.), K$_2$CO$_3$ (4.37 g, 31.63 mmol, 2 eq.), phenylboronic acid (1.93 g, 15.82 mmol, 1 eq.) and H$_2$O (2 mL). The mixture was heated at 78° C. for 12 hours. The reaction was monitored by LCMS that showed the starting material was consumed. The mixture was concentrated in vacuo. The reaction mixture was added to water (20 mL) and extracted with DCM (25 mL×3). The organic layer was dried over anhydrous sodium sulfate, filtered and concentrated by rotary evaporator to give the crude material. The residue was purified by column chromatography to afford 5-bromo-3-phenyl-pyrazin-2-amine (2 g, 50.56% yield) as yellow solid. LCMS m/z 249.8 and 251.8 [M+H]$^+$; $^1$HNMR (DMSO-d$_6$ 400 MHz) δ 8.08 (s, 1H), 7.68 (dd, J=1.4, 7.9 Hz, 2H), 7.54-7.44 (m, 3H), 6.44 (br s, 2H)

Step 2: Preparation of 6-bromo-2-methyl-8-phenyl-imidazo[1,2-a]pyrazine

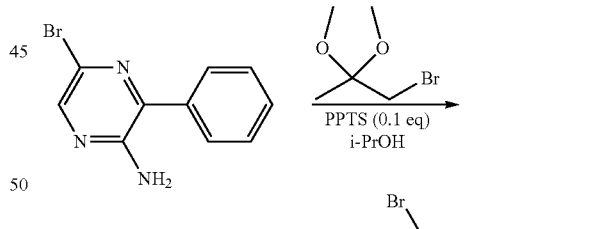

To a mixture of 5-bromo-3-phenyl-pyrazin-2-amine (900 mg, 3.60 mmol, 1 eq.) and 1-bromo-2,2-dimethoxy-propane (988.06 mg, 5.40 mmol, 726.52 μL, 1.5 eq.) in i-PrOH (25 mL) was added pyridinium p-toluenesulfonate (PPTS) (90.43 mg, 359.86 μmol, 0.1 eq.) in one portion at 25° C. The mixture was stirred at 90° C. for 3 hours. The mixture was diluted with ethyl acetate (20 mL) and added aqueous NaHCO₃. The aqueous layer was extracted with ethyl acetate (20 mL×2) and the combined organic layers were dried with anhydrous Na₂SO₄, filtered and concentrated in vacuo. The residue was purified by silica gel chromatography to afford 6-bromo-2-methyl-8-phenyl-imidazo[1,2-a]pyrazine (600 mg, 49.18% yield) as brown solid. LCMS m/z 287.9 and 289.9 [M+H]⁺; HNMR (DMSO d₆, 400 MHz) δ 8.89 (s, 1H), 8.76-8.67 (m, 2H), 7.96 (s, 1H), 7.64-7.49 (m, 3H), 2.48 (s, 3H).

Step 3: Preparation of tert-butyl N-(2-methyl-8-phenyl-imidazo[1,2-a]pyrazin-6-yl)carbamate

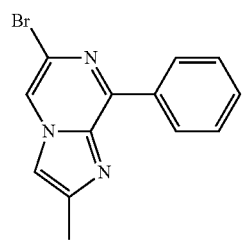

NH₂Boc, Cs₂CO₃
———————————→
Pd(OAc)₂, Xphos
dioxane

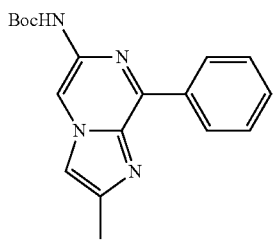

To a solution of 6-bromo-2-methyl-8-phenyl-imidazo[1,2-a]pyrazine (600 mg, 2.08 mmol, 1 eq.) in dioxane (25 mL) were added tert-butyl carbamate (731.80 mg, 6.25 mmol, 3 eq.), Cs₂CO₃ (1.70 g, 5.21 mmol, 2.5 eq.), Pd(OAc)₂ (46.75 mg, 208.23 μmol, 0.1 eq.) and XPhos (198.53 mg, 416.46 μmol, 0.2 eq.). The mixture was heated at 110° C. for 12 hours and monitored by LCMS. The reaction mixtures were added water (20 mL) was added and extracted with ethyl acetate (25 mL×3). The organic phase was dried over anhydrous sodium sulfate, filtered and concentrated in vacuo to give tert-butyl N-(2-methyl-8-phenyl-imidazo[1,2-a]pyrazin-6-yl)carbamate (240 mg, 30.20% yield, 85% purity) as yellow solid. LCMS m/z 325.2 [M+H]⁺; HNMR (DMSO d₆, 400 MHz) δ 9.77 (s, 1H), 8.85-8.77 (m, 3H), 8.02 (s, 1H), 7.61-7.50 (m, 3H), 2.44 (s, 3H), 1.51 (s, 9H).

Step 4: Preparation of 2-methyl-8-phenyl-imidazo[1,2-a]pyrazin-6-amine

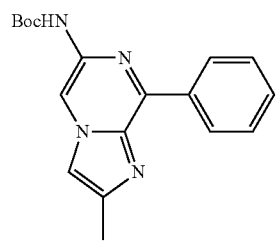

TFA/CH₂Cl₂
——————→

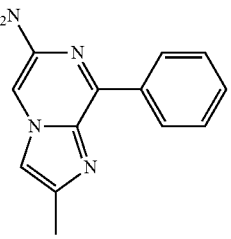

To a solution of tert-butyl N-(2-methyl-8-phenyl-imidazo[1,2-a]pyrazin-6-yl) carbamate (240 mg, 739.88 μmol, 1 eq.) in DCM (4 mL) was added TFA (843.64 mg, 7.40 mmol, 547.82 μL, 10 eq.). The mixture was stirred at 15° C. for 1 hour After completion, the mixture was concentrated by reduced pressure to give 2-methyl-8-phenyl-imidazo[1,2-a]pyrazin-6-amine (250 mg, 79.9% yield) as yellow TFA salt. LCMS m/z 225.1 [M+H]⁺

Step 5: Preparation of 5-bromo-2-methyl-8-phenyl-imidazo[1,2-a]pyrazin-6-amine (210)

To a solution 2-methyl-8-phenyl-imidazo[1,2-a]pyrazin-6-amine (90 mg, 266.05 μmol, 1 eq., TFA) in CH₂Cl₂ (1.5 mL) was added NBS (47.35 mg, 266.05 μmol, 1 eq.). The mixture was stirred at −20° C. for 1 hour. Water (20 mL) was added to the reaction mixture, which was extracted with CH₂Cl₂ (25 mL×3). The obtained organic phase was dried over anhydrous sodium sulfate, filtered, and concentrated in vacuo to give the residue. The residue was purified by chromatography to give 5-bromo-2-methyl-8-phenyl-imidazo[1,2-a]pyrazin-6-amine (16 mg, 18.25% yield) as green solid. LCMS m/z 305.0 [M+H]⁺; ¹HNMR (CDCl₃ 400 MHz) 5=8.58-8.46 (m, 2H), 7.51-7.35 (m, 4H), 4.51-4.01 (br, 2H), 2.46 (s, 3H).

Step 5: Preparation of 5-chloro-2-methyl-8-phenyl-imidazo[1,2-a]pyrazin-6-amine (211)

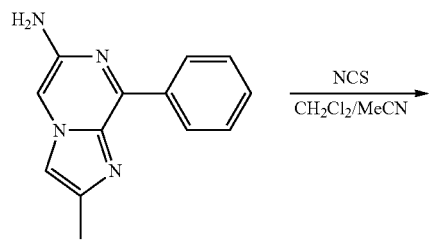

1 hour. The reaction mixture was added water (20 mL) and extracted with DCM (25 mL×3). The organic phase was dried over anhydrous sodium sulfate, filtered, and concentrated in vacuo to give the crude product. The crude product was purified by chromatographed to give 5-chloro-2-methyl-8-phenyl-imidazo[1,2-a]pyrazin-6-amine (22.1 mg, 35.25% yield) as green solid. LCMS m/z 259.0 [M+H]$^+$; $^1$HNMR (DMSO-$d_6$ 400 MHz) δ 8.69 (dd, J=1.3, 8.0 Hz, 2H), 7.79 (s, 1H), 7.62-7.45 (m, 3H), 5.80 (br s, 2H), 2.43 (s, 3H).

Example 14: Preparation of methyl (8-(furan-2-yl)-2-methylimidazo[1,2-a]pyrazin-6-yl)carbamate (224) and 1-(8-(furan-2-yl)-2-methylimidazo[1,2-a]pyrazin-6-yl)-3-methylurea (225)

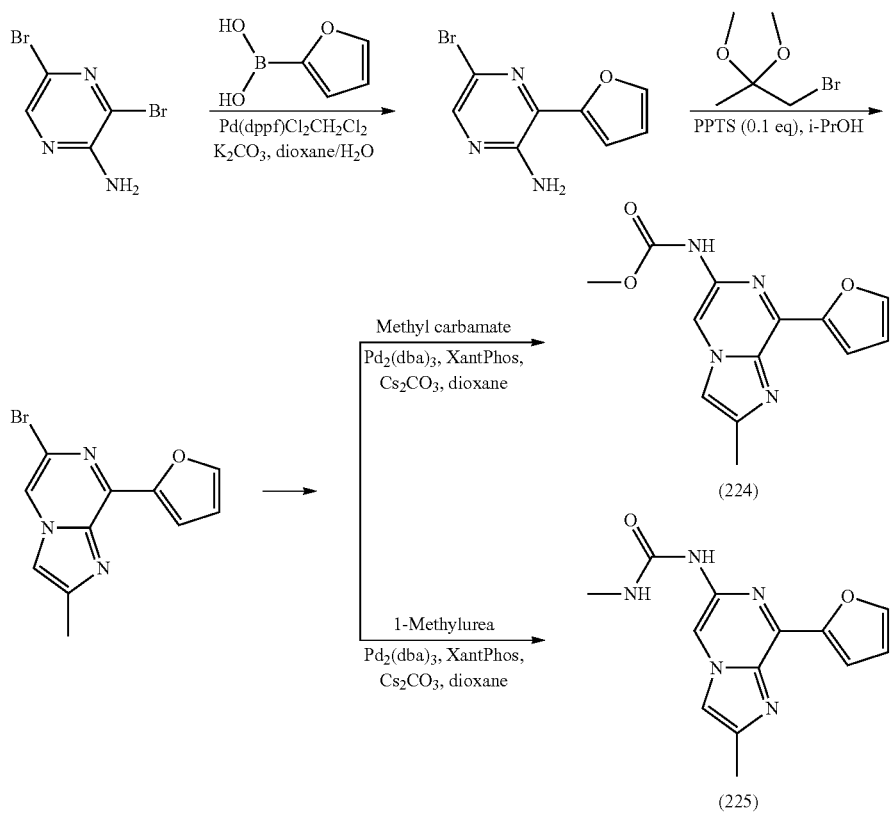

-continued

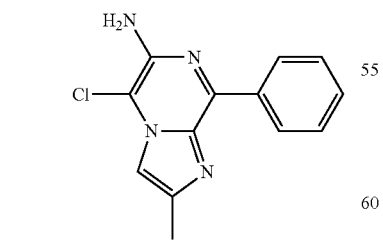

To a solution 2-methyl-8-phenyl-imidazo[1,2-a]pyrazin-6-amine (50 mg, 222.95 μmol, 1 eq.) in CH$_2$Cl$_2$ (2 mL) as added a solution of NCS (23.82 mg, 178.36 μmol, 0.8 eq.) in CH$_3$CN (0.5 mL). The mixture was stirred at 25° C. for Step 1: Preparation of 5-bromo-3-(2-furyl)pyrazin-2-amine

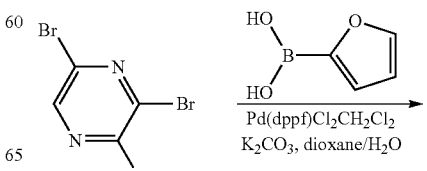

-continued

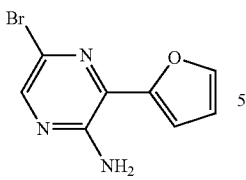

The a mixtures of 2-furylboronic acid (3.50 g, 31.28 mmol, 7.91e-1 eq.), 3,5-dibromopyrazin-2-amine (10 g, 39.54 mmol, 1 eq.) in dioxane (100 mL) and H$_2$O (20 mL) were added Pd(dppf)Cl$_2$·CH$_2$Cl$_2$ (3.23 g, 3.95 mmol, 0.1 eq.) and K$_2$CO$_3$ (16.39 g, 118.63 mmol, 3 eq.) at 40° C. under N$_2$. The mixture was stirred at 40° C. for 2 hours After completion, the reaction mixture was filtered and concentrated under reduced pressure to give a crude product, 5-bromo-3-(2-furyl)pyrazin-2-amine (7 g, 73.74% yield) as a yellow solid, which was used into the next step without further purification. LCMS m/z 283.0 [M+MeCN]$^+$.

Step 2: Preparation of 6-bromo-8-(2-furyl)-2-methyl-imidazo[1,2-a]pyrazine

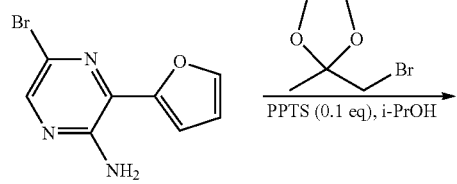

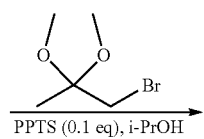

To a solution of 5-bromo-3-(2-furyl)pyrazin-2-amine (1 g, 4.17 mmol, 1 eq.) and 1-bromo-2,2-dimethoxy-propane (915 mg, 5.00 mmol, 672.79 μL, 1.2 eq.) in i-PrOH (10 mL) was added PPTS (104.68 mg, 416.57 μmol, 0.1 eq.). The reaction mixture was heated to 90° C. for 30 hours. The mixture was quenched with saturated NaHCO$_3$ and extracted with ethyl acetate (20 mL×3). The combined organic layers were dried over sodium sulfate, filtered and concentrated. The residue was purified by flash chromatography to give 6-bromo-8-(2-furyl)-2-methyl-imidazo[1,2-a]pyrazine (682 mg, 2.13 mmol, 51.22% yield) as brown solid. LCMS m/z 277.9 [M+H]$^+$; $^1$HNMR (DMSO-d$_6$ 400 MHz) δ=8.80 (s, 1H), 8.05 (s, 1H), 7.99 (d, J=3.6 Hz, 1H), 7.91 (s, 1H), 6.78-6.80 (m, 1H), 2.47 (s, 3H).

Step 3: Preparation of methyl N-[8-(2-furyl)-2-methyl-imidazo[1,2-a]pyrazin-6-yl]carbamate (224)

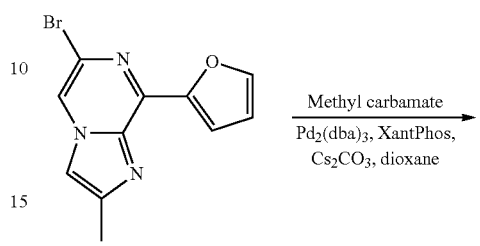

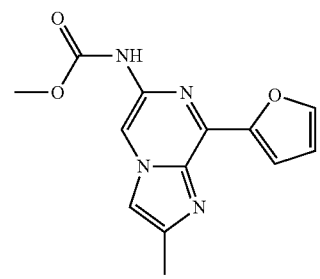

To a solution of 6-bromo-8-(2-furyl)-2-methyl-imidazo[1,2-a]pyrazine (120 mg, 431.49 μmol, 1 eq.) and methyl carbamate (97.17 mg, 1.29 mmol, 3 eq.) in dioxane (3 mL) were added Cs$_2$CO$_3$ (281.18 mg, 862.99 μmol, 2 eq.), Pd$_2$(dba)$_3$ (39.51 mg, 43.15 μmol, 0.1 eq.) and Xantphos (49.93 mg, 86.30 μmol, 0.2 eq.). Then the mixture was heated to 100° C. for 3 hours under N$_2$. The reaction was completed by LCMS. The mixture was filtered with Celite®. The filtrate was concentrated and purified by flash silica gel chromatography, followed by preparative HPLC to give methyl N-[8-(2-furyl)-2-methyl-imidazo[1,2-a]pyrazin-6-yl]carbamate (10.1 mg, 37.10 μmol, 8.60% yield) as a white solid. LCMS m/z 273.0 [M+H]$^+$; $^1$H NMR (DMSO-d$_6$ 400 MHz) δ 10.22 (s, 1H), 8.80 (s, 1H), 8.02 (s, 2H), 7.99 (d, J=3.6 Hz, 1H), 6.78 (dd, J=1.6, 3.2 Hz, 1H), 3.69 (s, 3H), 2.43 (s, 3H).

Step 3: Procedure for preparation of 1-[8-(2-furyl)-2-methyl-imidazo[1,2-a]pyrazin-6-yl]-3-methyl-urea (225)

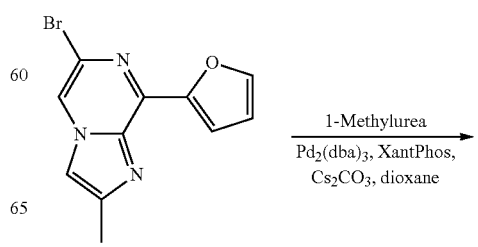

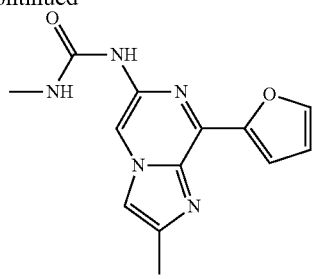

To a solution of 6-bromo-8-(2-furyl)-2-methyl-imidazo[1,2-a]pyrazine (160 mg, 575.32 μmol, 1 eq.) and methylurea (127.86 mg, 1.73 mmol, 3 eq.) in dioxane (3 mL) were added Cs₂CO₃ (374.90 mg, 1.15 mmol, 2 eq.), Pd₂(dba)₃ (52.68 mg, 57.53 μmol, 0.1 eq.) and Xantphos (66.58 mg, 115.06 μmol, 0.2 eq.). The mixture was heated to 100° C. for 2 hours under N₂ atmosphere. The reaction was monitored by LCMS. After completion, the mixture was filtered through Celite® and concentrated. The residue was purified by flash chromatography, followed by preparative HPLC to afford 1-[8-(2-furyl)-2-methyl-imidazo[1,2-a]pyrazin-6-yl]-3-methyl-urea (8.2 mg) as a white solid. LCMS m/z 272.1 [M+H]⁺; ¹H NMR (DMSO-d₆ 400 MHz) δ 9.08 (s, 1H), 8.78 (s, 1H), 7.96-7.99 (m, 3H), 6.77 (dd, J=2.0, 3.2 Hz, 1H), 6.35-6.36 (m, 1H), 2.68 (d, J=4.8 Hz, 3H), 2.41 (s, 3H).

The compounds in Table 3 were prepared in accordance with the synthetic protocols set forth in Examples 13 and 14 and general synthesis Scheme 7 by adjusting to the appropriate starting materials.

TABLE 3

| Compound No. | Structure | IUPAC Name | LC/MS | Purity |
|---|---|---|---|---|
| 191 | 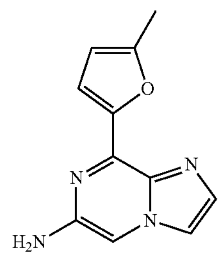 [SMILES: Cc1ccc(-c2nc(N)cn3ccnc23)o1] | 8-(5-methylfuran-2-yl)imidazo[1,2-a]pyrazin-6-amine | [MH+] = 215.2 | 92.0% |
| 192 | 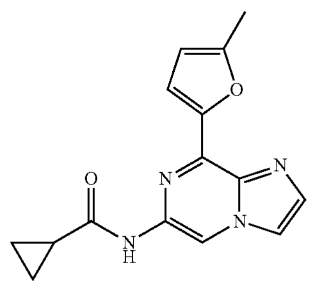 [SMILES: Cc1ccc(-c2nc(NC(=O)C3CC3)cn3ccnc23)o1] | N-[8-(5-methylfuran-2-yl)imidazo[1,2-a]pyrazin-6-yl]cyclopropanecarboxamide | [MH+] = 283.1, >96% purity | 96.0% |
| 193 | 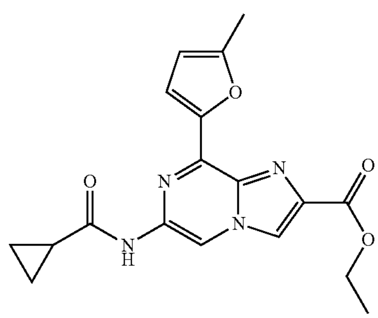 [SMILES: CCOC(=O)c1cn2cc(NC(=O)C3CC3)nc(-c3ccc(C)o3)c2n1] | ethyl 6-(cyclopropanecarbonylamino)-8-(5-methylfuran-2-yl)imidazo[1,2-a]pyrazine-2-carboxylate | [MH+] = 355.4 | 95.0% |
| 194 | 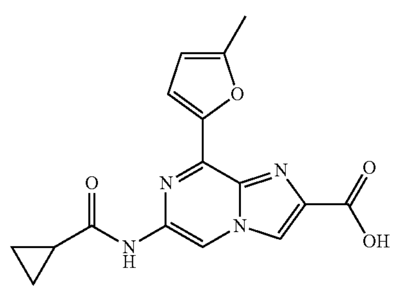 [SMILES: Cc1ccc(-c2nc(NC(=O)C3CC3)cn3cc(C(=O)O)nc23)o1] | 6-(cyclopropanecarbonylamino)-8-(5-methylfuran-2-yl)imidazo[1,2-a]pyrazine-2-carboxylic acid | [MH+] = 327.2 | 95.0% |

TABLE 3-continued

| Compound No. | Structure | IUPAC Name | LC/MS | Purity |
|---|---|---|---|---|
| 195 | 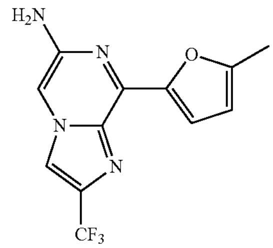 [SMILES: Cc1ccc(-c2nc(N)cn3cc(C(F)(F)F)nc23)o1] | 8-(5-methylfuran-2-yl)-2-(trifluoromethyl)imidazo[1,2-a]pyrazin-6-amine | [MH+] = 282.9 | 100% |
| 196 | 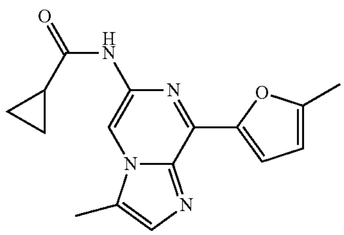 [SMILES: Cc1ccc(-c2nc(NC(=O)C3CC3)cn3c(C)cnc23)o1] | N-[3-methyl-8-(5-methylfuran-2-yl)imidazo[1,2-a]pyrazin-6-yl]cyclopropanecarboxamide | [MH+] = 296.9 | 100% |
| 197 | 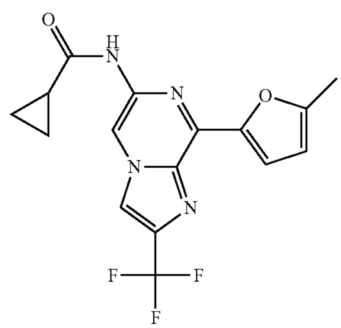 [SMILES: Cc1ccc(-c2nc(NC(=O)C3CC3)cn3cc(C(F)(F)F)nc23)o1] | N-[8-(5-methylfuran-2-yl)-2-(trifluoromethyl)imidazo[1,2-a]pyrazin-6-yl]cyclopropanecarboxamide | [M + H] = 351 | 99% |
| 198 | 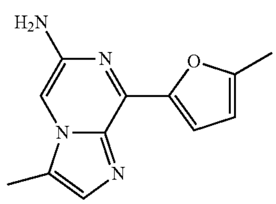 | 3-methyl-8-(5-methylfuran-2-yl)imidazo[1,2-a]pyrazin-6-amine | [M + H] = 229 | 97% |
| 199 | 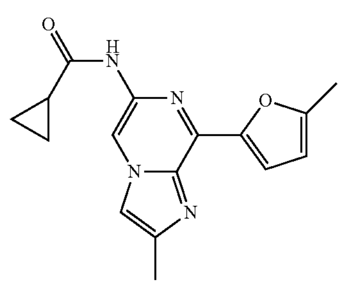 [SMILES: Cc1cn2cc(NC(=O)C3CC3)nc(-c3ccc(C)o3)c2n1] | N-[2-methyl-8-(5-methylfuran-2-yl)imidazo[1,2-a]pyrazin-6-yl]cyclopropanecarboxamide | [MH+] = 297.0 | 99.6% |
| 200 | 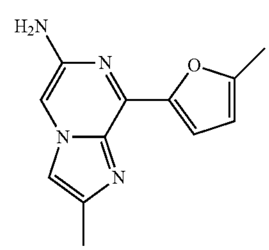 [SMILES: Cc1cn2cc(N)nc(-c3ccc(C)o3)c2n1] | 2-methyl-8-(5-methylfuran-2-yl)imidazo[1,2-a]pyrazin-6-amine | [MH+] = 228.9 | 97.6% |

TABLE 3-continued

| Compound No. | Structure | IUPAC Name | LC/MS | Purity |
|---|---|---|---|---|
| 201 | 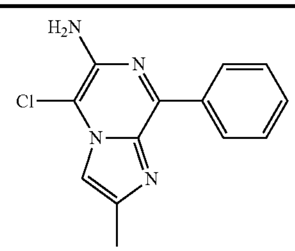 | 5-chloro-2-methyl-8-phenylimidazo[1,2-a]pyrazin-6-amine | [M + H] = 259.0 | 93.8% |
| 202 | 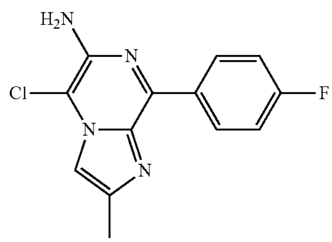 [SMILES: Cc1cn2c(Cl)c(N)nc(-c3ccc(F)cc3)c2n1] | 5-chloro-8-(4-fluorophenyl)-2-methylimidazo[1,2-a]pyrazin-6-amine | [MH+] = 277.0 | 98.3% |
| 203 | 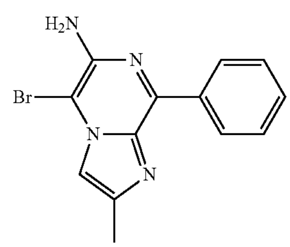 [SMILES: Cc1cn2c(Br)c(N)nc(-c3ccccc3)c2n1] | 5-bromo-2-methyl-8-phenylimidazo[1,2-a]pyrazin-6-amine | [M+/M + 2] = 303.0/305.0 | 91.5% |
| 204 | 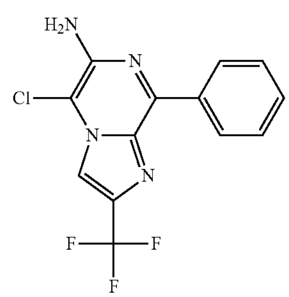 [SMILES: Nc1nc(-c2ccccc2)c2nc(C(F)(F)F)cn2c1Cl] | 5-chloro-8-phenyl-2-(trifluoromethyl)imidazo[1,2-a]pyrazin-6-amine | [M + H] = 313.0 | 99.6% |
| 205 | 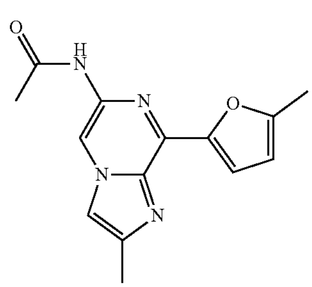 [SMILES: CC(=O)Nc1cn2cc(C)nc2c(-c2ccc(C)o2)n1] | N-[2-methyl-8-(5-methylfuran-2-yl)imidazo[1,2-a]pyrazin-6-yl]acetamide | [M + H] = 271.1 | 98.5% |
| 206 | 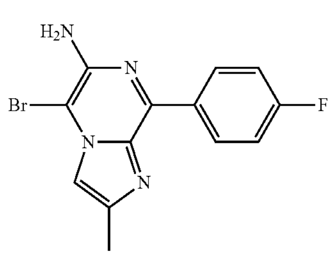 | 5-bromo-8-(4-fluorophenyl)-2-methylimidazo[1,2-a]pyrazin-6-amine | [M+/M + 2] = 321.0/323.0 | 98.6% |

TABLE 3-continued

| Compound No. | Structure | IUPAC Name | LC/MS | Purity |
|---|---|---|---|---|
| 207 | 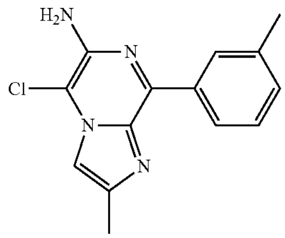 [SMILES: Cc1cccc(-c2nc(N)c(Cl)n3cc(C)nc23)c1] | 5-chloro-2-methyl-8-(3-methylphenyl)imidazo[1,2-a]pyrazin-6-amine | [M + H] = 273.1 | 91.3% |
| 208 | 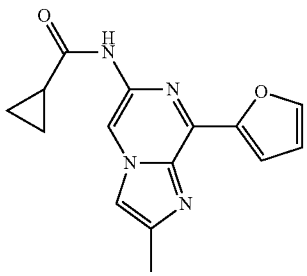 [SMILES: Cc1cn2cc(NC(=O)C3CC3)nc(-c3ccco3)c2n1] | N-[8-(furan-2-yl)-2-methylimidazo[1,2-a]pyrazin-6-yl]cyclopropanecarboxamide | [M + H] = 283.1 | 98.8% |
| 209 | 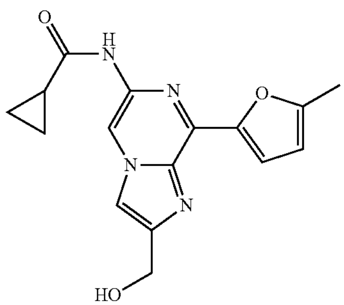 [SMILES: Cc1ccc(-c2nc(NC(=O)C3CC3)cn3cc(CO)nc23)o1] | N-[2-(hydroxymethyl)-8-(5-methylfuran-2-yl)imidazo[1,2-a]pyrazin-6-yl]cyclopropanecarboxamide | [M + H] = 313.3 | 96.5% |
| 210 | 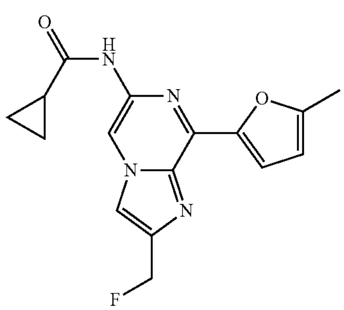 [SMILES: Cc1ccc(-c2nc(NC(=O)C3CC3)cn3cc(CF)nc23)o1] | N-[2-(fluoromethyl)-8-(5-methylfuran-2-yl)imidazo[1,2-a]pyrazin-6-yl]cyclopropanecarboxamide | [M + H] = 315.35 | 99% |
| 211 | 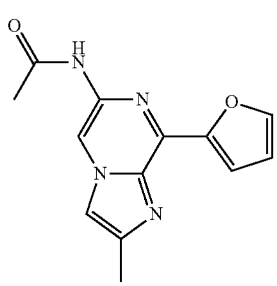 [SMILES: CC(=O)Nc1cn2cc(C)nc2c(-c2ccco2)n1] | N-[8-(furan-2-yl)-2-methylimidazo[1,2-a]pyrazin-6-yl]acetamide | [M + H] = 257.1 | 96.5% |

TABLE 3-continued

| Compound No. | Structure | IUPAC Name | LC/MS | Purity |
|---|---|---|---|---|
| 212 | 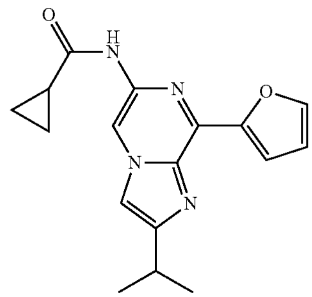 [SMILES: CC(C)c1cn2cc(NC(=O)C3CC3)nc(-c3ccco3)c2n1] | N-[8-(furan-2-yl)-2-propan-2-ylimidazo[1,2-a]pyrazin-6-yl]cyclopropanecarboxamide | [M + H] = 311.1 | 97.3% |
| 213 | 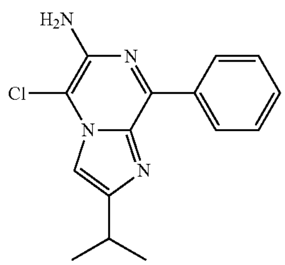 [SMILES: CC(C)c1cn2c(Cl)c(N)nc(-c3ccccc3)c2n1] | 5-chloro-8-phenyl-2-propan-2-ylimidazo[1,2-a]pyrazin-6-amine | [M + H] = 287.1 | 98.6% |
| 214 | 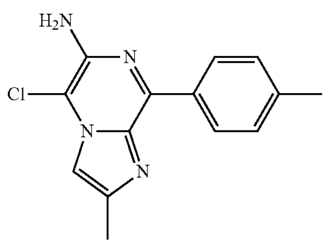 | 5-chloro-2-methyl-8-(4-methylphenyl)imidazo[1,2-a]pyrazin-6-amine | [M + H] = 273.1 | 95.0% |
| 215 | 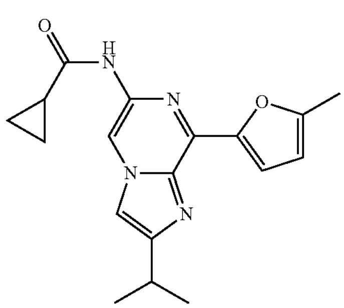 [SMILES: Cc1ccc(-c2nc(NC(=O)C3CC3)cn3cc(C(C)C)nc23)o1] | N-[8-(5-methylfuran-2-yl)-2-propan-2-ylimidazo[1,2-a]pyrazin-6-yl]cyclopropanecarboxamide | [M + H] = 325.1 | 100% |
| 216 | 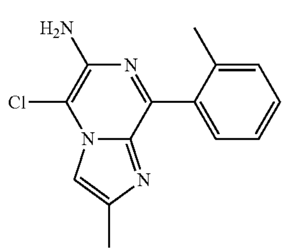 [SMILES: Cc1cn2c(Cl)c(N)nc(-c3ccccc3C)c2n1] | 5-chloro-2-methyl-8-(2-methylphenyl)imidazo[1,2-a]pyrazin-6-amine | [M + H] = 273.0 | 93.5% |

TABLE 3-continued

| Compound No. | Structure | IUPAC Name | LC/MS | Purity |
|---|---|---|---|---|
| 217 | 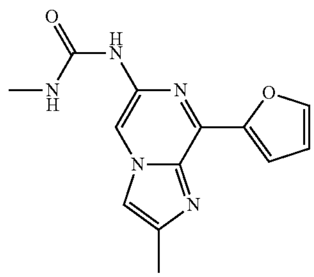 [SMILES: CNC(=O)Nc1cn2cc(C)nc2c(-c2ccco2)n1] | 1-[8-(furan-2-yl)-2-methylimidazo[1,2-a]pyrazin-6-yl]-3-methylurea | [M + H] = 272.1 | 99.2% |
| 218 | 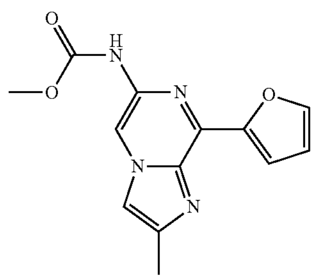 | methyl N-[8-(furan-2-yl)-2-methylimidazo[1,2-a]pyrazin-6-yl]carbamate | [M + H] = 273.1 | 99.0% |
| 219 | 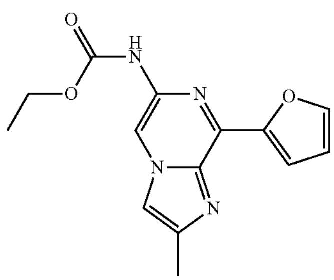 [SMILES: CCOC(=O)Nc1cn2cc(C)nc2c(-c2ccco2)n1] | ethyl N-[8-(furan-2-yl)-2-methylimidazo[1,2-a]pyrazin-6-yl]carbamate | [M + H] = 287.2 | 95% |
| 220 | 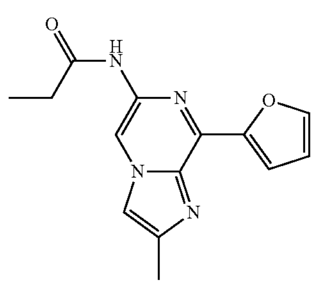 [SMILES: CCC(=O)Nc1cn2cc(C)nc2c(-c2ccco2)n1] | N-[8-(furan-2-yl)-2-methylimidazo[1,2-a]pyrazin-6-yl]propanamide | [M + H] = 271.2 | 95% |
| 221 | 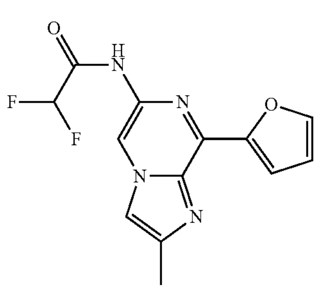 [SMILES: Cc1cn2cc(NC(=O)C(F)F)nc(-c3ccco3)c2n1] | 2,2-difluoro-N-[8-(furan-2-yl)-2-methylimidazo[1,2-a]pyrazin-6-yl]acetamide | [M + H] = 293.2 | 95% |

TABLE 3-continued

| Compound No. | Structure | IUPAC Name | LC/MS | Purity |
|---|---|---|---|---|
| 222 | 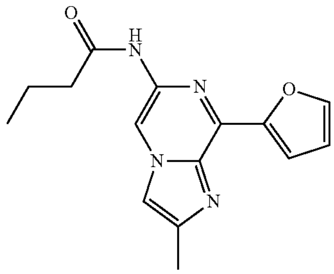 [SMILES: CCCC(=O)Nc1cn2cc(C)nc2c(-c2ccco2)n1] | N-[8-(furan-2-yl)-2-methylimidazo[1,2-a]pyrazin-6-yl]butanamide | [M + H] = 285.2 | 95% |
| 223 | 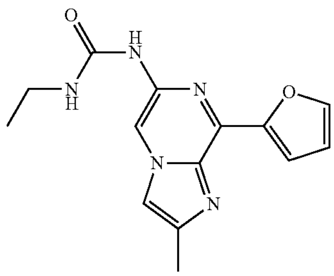 [SMILES: CCNC(=O)Nc1cn2cc(C)nc2c(-c2ccco2)n1] | 1-ethyl-3-[8-(furan-2-yl)-2-methylimidazo[1,2-a]pyrazin-6-yl]urea | [M + H] = 286.30 | 95% |
| 224 | 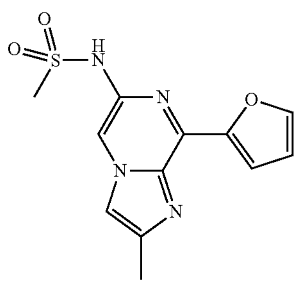 [SMILES: Cc1cn2cc(NS(C)(=O)=O)nc(-c3ccco3)c2n1] | N-[8-(furan-2-yl)-2-methylimidazo[1,2-a]pyrazin-6-yl]methanesulfonamide | [M + H] = 293.20 | 95% |
| 225 | 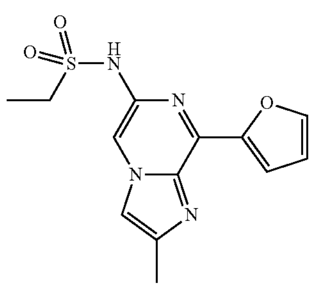 [SMILES: CCS(=O)(=O)Nc1cn2cc(C)nc2c(-c2ccco2)n1] | N-[8-(furan-2-yl)-2-methylimidazo[1,2-a]pyrazin-6-yl]ethanesulfonamide | [M + H] = 307.25 | 95% |

BIOLOGICAL EXAMPLES

ADORA1A and ADORA2A Receptor Binding Assay

2 μL of each compound (test compounds, high control compound, low control compound) was transferred into individual wells of an assay plate. Also to each individual well, 98 μL of Adenosine A1a membrane stock (for ADORA1A Receptor Binding Assay) or Adenosine A2a membrane stock (for ADORA2A Receptor Binding Assay) was dispensed, followed by 100 μL of radio-labeled ligand. Plates were then sealed, and incubated at room temperature for 1 hour (for ADORA1A Receptor Binding Assay) or 2 hours (for ADORA2A Receptor Binding Assay). Unifilter-96 GF/C filter plates were pre-soaked with 50 μL of 0.3% PEI per well for at least 30 min at room temperature. When binding assays were completed, reaction mixtures were filtered through GF/C plates using a Perkin Elmer Filtermate Harvester, and then each plate was washed 4× with cold wash buffer. Filter plates were then dried for 1 hour at 50° C. After drying, the bottom of the filter plate wells was sealed using Perkin Elmer Unifilter-96 backing seal tape. 50 μL of Perkin Elmer Microscint 20 cocktail was then added, and the top of the filter plate was then sealed using Perkin Elmer TopSeal-A sealing film. $^3$H trapped on the filter was counted using a Perkin Elmer MicroBeta2 Reader. Data analysis was performed using GraphPad Prism 5 software, and the "Inhibition [% Control]" was calculated using the following equation: % Inh=(1-Background subtracted Assay value/Background subtracted HC value)*100.

ADORA2B Receptor Binding Assay

100 μL of Adenosine A2B membrane stock was dispensed into individual wells of an assay plate. 1 μL of each compound (test compounds, high control compound, low control compound) was then transferred into individual wells, followed by 100 μL of radio-labeled ligand. Plates were then sealed, and incubated at room temperature for 1 hour. Unifilter-96 GF/C filter plates were pre-soaked with 50 μL of 0.5% BSA per well for at least 30 min at room temperature. When binding assays were completed, reaction mixtures were filtered through GF/C plates using a Perkin Elmer Filtermate Harvester, and then each plate was washed 4× with cold wash buffer. Filter plates were then dried for 1 hour at 50° C. After drying, the bottom of the filter plate wells was sealed using Perkin Elmer Unifilter-96 backing seal tape. 50 μL of Perkin Elmer Microscint 20 cocktail was then added, and the top of the filter plate was then sealed using Perkin Elmer TopSeal-A sealing film. $^3$H trapped on the filter was counted using a Perkin Elmer MicroBeta2 Reader. Data analysis was performed using GraphPad Prism 5 software, and the "Inhibition [% Control]" was calculated using the following equation: % Inh=(1-Background subtracted Assay value/Background subtracted HC value)*100.

Table 4 provides the binding data for the compounds of the invention. In Table 4, an $IC_{50}$ concentration of less than 10 nM is indicated by "**", an $IC_{50}$ concentration of 10 nM or greater, but less than 100 nM is indicated by "*", an $IC_{50}$ concentration of 100 nM or greater, but less than 1000 nM is indicated by "**", and an $IC_{50}$ concentration of greater than 1000 nM is indicated by "*". ND indicates "not determined".

TABLE 4

50% Inhibitory concentrations ($IC_{50}$) for the compounds of the invention.

| Compound No. | A2A (binding) $IC_{50}$ (nM) | A2B (binding) $IC_{50}$ (nM) |
| --- | --- | --- |
| 1 | **** | *** |
| 2 | **** | **** |
| 3 | *** | ** |
| 4 | **** | **** |
| 5 | **** | *** |
| 6 | **** | * |
| 7 | **** | ** |
| 8 | **** | *** |
| 9 | *** | nd |
| 10 | **** | *** |
| 11 | **** | **** |
| 12 | **** | **** |
| 13 | **** | ** |
| 14 | **** | *** |
| 15 | **** | ** |
| 16 | **** | **** |
| 17 | **** | nd |
| 18 | **** | *** |
| 19 | *** | ** |
| 20 | **** | **** |
| 21 | **** | *** |
| 22 | **** | *** |
| 23 | ** | * |
| 24 | * | * |
| 25 | **** | **** |
| 26 | **** | **** |
| 27 | *** | *** |
| 28 | *** | ** |
| 29 | **** | **** |
| 30 | **** | *** |
| 31 | *** | nd |
| 32 | ** | ** |
| 33 | **** | *** |
| 34 | **** | **** |
| 35 | **** | **** |
| 36 | *** | ** |
| 37 | **** | *** |
| 38 | **** | *** |
| 39 | **** | *** |
| 40 | **** | **** |
| 41 | **** | **** |
| 42 | **** | **** |
| 43 | *** | * |
| 44 | *** | *** |
| 45 | **** | **** |
| 46 | **** | **** |
| 47 | **** | *** |
| 48 | **** | **** |
| 49 | *** | ** |
| 50 | **** | *** |
| 51 | ** | * |
| 52 | **** | **** |
| 53 | *** | ** |
| 54 | **** | ** |
| 55 | **** | ** |
| 56 | ** | * |
| 57 | * | * |
| 58 | **** | **** |
| 59 | **** | *** |
| 60 | **** | *** |
| 61 | **** | *** |
| 62 | **** | *** |
| 63 | **** | *** |
| 64 | **** | *** |
| 65 | **** | *** |
| 66 | **** | *** |
| 67 | **** | *** |
| 68 | **** | **** |
| 69 | **** | *** |
| 70 | ** | * |
| 71 | * | * |
| 72 | ** | * |
| 73 | *** | ** |
| 74 | *** | * |
| 75 | **** | *** |
| 76 | *** | * |
| 77 | *** | *** |
| 78 | **** | *** |
| 79 | *** | ** |
| 80 | *** | ** |
| 81 | **** | *** |
| 82 | **** | **** |
| 83 | *** | ** |
| 84 | * | * |
| 85 | **** | **** |
| 86 | **** | *** |
| 87 | **** | *** |
| 88 | **** | **** |
| 89 | *** | *** |
| 90 | **** | **** |
| 91 | **** | *** |
| 92 | **** | *** |
| 93 | * | * |
| 94 | * | * |
| 95 | * | * |
| 96 | ** | ** |
| 97 | **** | *** |
| 98 | *** | ** |
| 99 | * | * |
| 100 | * | * |
| 101 | * | * |
| 102 | *** | *** |
| 103 | *** | ** |
| 104 | ** | * |
| 105 | *** | ** |
| 106 | * | * |
| 107 | * | * |
| 108 | **** | **** |
| 109 | **** | *** |
| 110 | **** | *** |
| 111 | *** | *** |
| 112 | * | * |

TABLE 4-continued

50% Inhibitory concentrations (IC$_{50}$) for the compounds of the invention.

| Compound No. | A2A (binding) IC$_{50}$ (nM) | A2B (binding) IC$_{50}$ (nM) |
|---|---|---|
| 113 | ** | ** |
| 114 | * | * |
| 115 | ** | * |
| 116 | * | * |
| 117 | * | * |
| 118 | * | * |
| 119 | * | * |
| 120 | **** | *** |
| 121 | **** | *** |
| 122 | ** | * |
| 123 | *** | * |
| 124 | ** | * |
| 125 | * | * |
| 126 | **** | **** |
| 127 | **** | **** |
| 128 | *** | ** |
| 129 | *** | * |
| 130 | *** | ** |
| 131 | **** | *** |
| 132 | *** | ** |
| 133 | **** | **** |
| 134 | **** | **** |
| 135 | **** | * |
| 136 | * | * |
| 137 | * | * |
| 138 | **** | *** |
| 139 | **** | *** |
| 140 | *** | ** |
| 141 | *** | ** |
| 142 | *** | ** |
| 143 | *** | ** |
| 144 | **** | **** |
| 145 | *** | *** |
| 146 | **** | *** |
| 147 | **** | **** |
| 148 | **** | **** |
| 149 | **** | *** |
| 150 | ** | * |
| 151 | *** | * |
| 152 | *** | *** |
| 153 | **** | *** |
| 154 | *** | *** |
| 155 | *** | *** |
| 156 | **** | *** |
| 157 | **** | *** |
| 158 | **** | *** |
| 159 | **** | *** |
| 160 | **** | *** |
| 161 | ** | ** |
| 162 | **** | *** |
| 163 | **** | *** |
| 164 | *** | * |
| 165 | * | * |
| 166 | ** | ** |
| 167 | **** | **** |
| 168 | **** | *** |
| 169 | **** | **** |
| 170 | **** | *** |
| 171 | **** | *** |
| 172 | **** | **** |
| 173 | **** | **** |
| 174 | **** | **** |
| 175 | **** | **** |
| 176 | **** | **** |
| 177 | **** | **** |
| 178 | **** | **** |
| 179 | **** | **** |
| 180 | **** | **** |
| 181 | **** | **** |
| 182 | ** | ** |
| 183 | **** | *** |
| 184 | **** | **** |
| 185 | **** | **** |
| 186 | **** | **** |
| 187 | **** | **** |
| 188 | **** | **** |
| 189 | **** | **** |
| 190 | **** | **** |
| 191 | ** | nd |
| 192 | *** | *** |
| 193 | *** | nd |
| 194 | * | nd |
| 195 | *** | ** |
| 196 | *** | *** |
| 197 | **** | **** |
| 198 | * | * |
| 199 | **** | *** |
| 200 | ** | ** |
| 201 | *** | ** |
| 202 | ** | ** |
| 203 | ** | ** |
| 204 | *** | *** |
| 205 | **** | *** |
| 206 | ** | ** |
| 207 | ** | ** |
| 208 | **** | *** |
| 209 | **** | *** |
| 210 | **** | *** |
| 211 | *** | *** |
| 212 | **** | *** |
| 213 | *** | ** |
| 214 | ** | ** |
| 215 | **** | *** |
| 216 | * | * |
| 217 | *** | *** |
| 218 | *** | ** |
| 219 | *** | ** |
| 220 | **** | *** |
| 221 | **** | *** |
| 222 | *** | ** |
| 223 | **** | *** |
| 224 | ** | * |
| 225 | ** | ** |

OTHER EMBODIMENTS

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A method of treating a disease or disorder in a patient, the method comprising administering to the patient a therapeutically effective amount of a compound of formula I:

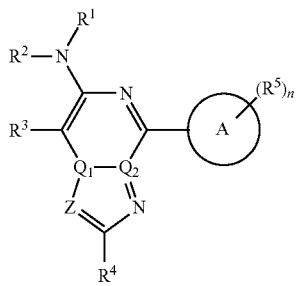

or a pharmaceutically acceptable salt thereof, wherein:
Ring A is heteroaryl or aryl, provided that Ring A is furanyl when $R^4$ is H, aryl, or heteroaryl;
$R^1$ is H or alkyl optionally substituted with 1, 2, 3, or 4 independently selected $R^a$ substituents;
$R^2$ is H, alkyl, —COR''', —CONR'R'', —COOR', —SO$_2$R', —SO$_2$NR'R'', or —SO$_2$OR', wherein the alkyl of $R^2$ is optionally substituted with 1, 2, 3, or 4 independently selected $R^a$ substituents;
$R^3$ is H, alkyl, halo, —CN, or —CONR'R'', wherein the alkyl of $R^3$ is optionally substituted with 1, 2, 3, or 4 independently selected $R^a$ substituents;
$R^4$ is H, alkyl, halo, haloalkyl, —NR'R'', —COR', —CONR'R'', —COOR', SO$_2$R', —SO$_2$NR'R'', —SO$_2$OR', cycloalkyl, heterocycloalkyl, aryl, heteroaryl, or —C$_{1-4}$ alkylene-R$^b$, wherein R$^b$ is cycloalkyl, heterocycloalkyl, aryl or heteroaryl, and wherein the alkyl, cycloalkyl, heterocycloalkyl, aryl, heteroaryl, or —C$_{1-4}$ alkylene-R$^b$ of $R^4$ is optionally substituted with 1, 2, 3, or 4 independently selected $R^a$ substituents;
each $R^5$ is independently H, alkyl, halo, haloalkyl, alkoxy, —CN, —COR', —CONR'R'', —COOR', —SO$_2$R', —SO$_2$NR'R'', —SO$_2$OR', cycloalkyl, heterocycloalkyl, aryl, or heteroaryl wherein the alkyl, alkoxy, cycloalkyl, heterocycloalkyl, aryl, or heteroaryl of $R^5$ is optionally substituted with 1, 2, 3, or 4 independently selected $R^a$ substituents;
n is 0, 1, 2, 3, 4, or 5;
one of Q$_1$ and Q$_2$ is N and the other is C;
Z is N or CR$^6$;
$R^6$ is H or alkyl, wherein the alkyl of $R^6$ is optionally substituted with 1, 2, 3, or 4 independently selected $R^a$ substituents;
R' and R'' are each independently H or alkyl, wherein each alkyl of R' and R'' is optionally substituted with 1, 2, 3, or 4 independently selected $R^a$ substituents;
R''' is alkyl, haloalkyl, cycloalkyl, or heterocycloalkyl, wherein the alkyl, cycloalkyl or heterocycloalkyl of R''' is optionally substituted with 1, 2, 3, or 4 independently selected $R^a$ substituents; and
each $R^a$ is independently alkyl, halo, haloalkyl, hydroxy, alkoxy, hydroxyalkyl, cycloalkyl, or heterocycloalkyl, wherein each cycloalkyl and heterocycloalkyl of $R^a$ is optionally and independently further substituted with 1, 2, or 3 of C$_{1-4}$ alkyl, halo, C$_{1-4}$ haloalkyl, hydroxy, or C$_{1-4}$ alkoxy;
wherein the disease or disorder is associated with abnormal expression of A2A or A2B receptors, and wherein the disease or disorder is:
a cancer selected from the group consisting of lung cancer, non-small cell lung cancer, melanoma, malignant melanoma, renal cell cancer, triple negative breast cancer, colorectal cancer, bladder cancer, metastatic castration resistant prostate, cervical cancer, ovarian cancer, colorectal cancer, pancreatic cancer, esophageal cancer, prostate cancer, kidney cancer, skin cancer, thyroid cancer, liver cancer, and uterine cancer;
an inflammatory disease selected from the group consisting of a respiratory disorder, sepsis, reperfusion injury, and thrombosis;
a cardiovascular disease selected from the group consisting of coronary artery-disease, cerebrovascular disease, peripheral artery disease, aortic atherosclerosis, and aneurysm; or
Parkinson's disease.

2. The method of claim 1, wherein $R^1$ is H or C$_{1-4}$ alkyl.

3. The method of claim 1, wherein $R^2$ is H, C$_{1-4}$ alkyl, —C(O)—C$_{1-4}$ alkyl, —C(O)—C$_{1-4}$ haloalkyl, —C(O)-cycloalkyl, —C(O)-heterocycloalkyl, —CONH$_2$, —CONH—C$_{1-4}$ alkyl, —COO—C$_{1-4}$ alkyl, —SO$_2$—C$_{1-6}$ alkyl or —CONH—C$_{1-4}$ alkylene-heterocycloalkyl, and wherein $R^2$ is optionally substituted with 1 or 2 independently selected $R^a$ substituents.

4. The method of claim 3, wherein $R^2$ is H or methyl, acetyl, or —C(O)-cyclopropyl.

5. The method of claim 1, wherein $R^3$ is H, C$_{1-4}$ alkyl, halo, —CN, or —CONH$_2$.

6. The method of claim 1, wherein $R^4$ is H, C$_{1-4}$ alkyl, C$_{1-4}$ hydroxyalkyl, halo, C$_{1-4}$ haloalkyl, —NH$_2$, —COOH, or —COO—C$_{1-4}$ alkyl.

7. The method of claim 1, wherein $R^4$ is benzyl, heterocycloalkyl, heteroaryl, or cycloalkyl, wherein the benzyl, heterocycloalkyl, heteroaryl, or cycloalkyl are optionally substituted with 1, 2 or 3 substituents independently selected from C$_{1-4}$ alkyl, halo, C$_{1-4}$ haloalkyl, hydroxy, and C$_{1-4}$ alkoxy.

8. The method of claim 1, wherein n is 0, 1, or 2 and wherein each $R^5$ is independently H, C$_{1-4}$ alkyl, halo, C$_{1-4}$ haloalkyl, C$_{1-4}$ alkoxy, —CN, acetyl, SO$_2$NH$_2$, SO$_2$N(CH$_3$)$_2$, SO$_2$OH, or SO$_2$CH$_3$.

9. The method of claim 1, wherein Q$_1$ is N, and Z is N or CR$^6$; or Q$_2$ is N, and Z is N.

10. The method of claim 1, wherein the compound of formula I is a compound of formula IA, IB, or IC:

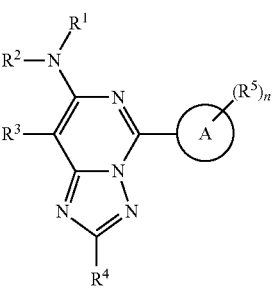

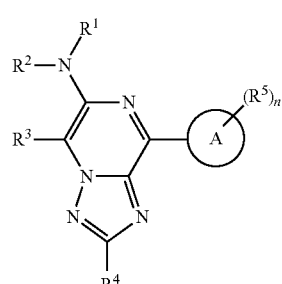

IC

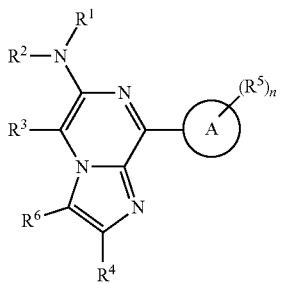

or a pharmaceutically acceptable salt thereof.

11. The method of claim 10, wherein the compound of formula I is a compound of formula IA or a pharmaceutically acceptable salt thereof, wherein $R^2$ is H, methyl, acetyl or —C(O)-cyclopropyl; and $R^4$ is $C_{1-4}$ alkyl, haloalkyl, cycloalkyl or heterocycloalkyl.

12. The method of claim 10, wherein the compound of formula I is a compound of formula IB or a pharmaceutically acceptable salt thereof, wherein $R^2$ is H, acetyl or —C(O)-cyclopropyl; and $R^4$ is $C_{1-4}$ alkyl, haloalkyl, halo or amino.

13. The method of claim 10, wherein the compound of formula I is a compound of formula IC or a pharmaceutically acceptable salt thereof, wherein $R^2$ is H or —C(O)-cyclopropyl; and one of $R^4$ and $R^6$ is H and the other is $C_{1-4}$ alkyl.

14. The method of claim 1, wherein the compound of formula I is a compound of formula IVA, IVB, or IVC:

IVA

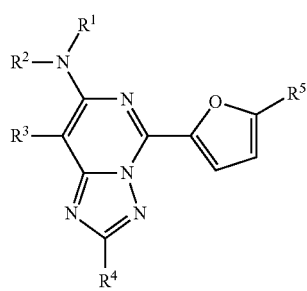

IVB

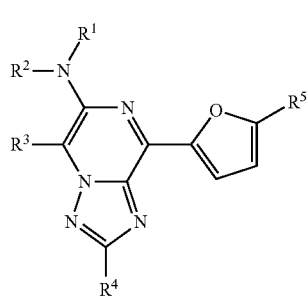

IVC

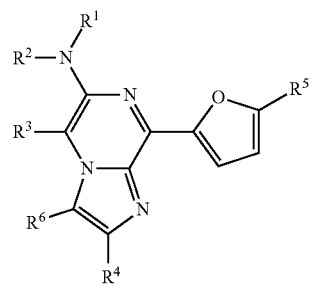

or a pharmaceutically acceptable salt thereof.

15. The method of claim 1, wherein the compound of formula I is selected from the group consisting of:

2-Methyl-5-(5-methylfuran-2-yl)-[1,2,4]triazolo[1,5-c]pyrimidin-7-amine,
N-[2-methyl-5-(5-methylfuran-2-yl)-[1,2,4]triazolo[1,5-c]pyrimidin-7-yl]cyclopropanecarboxamide,
2-[(4-methoxyphenyl)methyl]-5-(5-methylfuran-2-yl)-[1,2,4]triazolo[1,5-c]pyrimidin-7-amine,
N-[2-[(4-methoxyphenyl)methyl]-5-(5-methylfuran-2-yl)-[1,2,4]triazolo[1,5-c]pyrimidin-7-yl]cyclopropanecarboxamide,
N-[2-methyl-5-(5-methylfuran-2-yl)-[1,2,4]triazolo[1,5-c]pyrimidin-7-yl]propanamide,
2,2-dimethyl-N-[2-methyl-5-(5-methylfuran-2-yl)-[1,2,4]triazolo[1,5-c]pyrimidin-7-yl]propanamide,
2-ethyl-5-(5-methylfuran-2-yl)-[1,2,4]triazolo[1,5-c]pyrimidin-7-amine,
N-[2-ethyl-5-(5-methylfuran-2-yl)-[1,2,4]triazolo[1,5-c]pyrimidin-7-yl]cyclopropanecarboxamide,
(2S)-N-[2-methyl-5-(5-methylfuran-2-yl)-[1,2,4]triazolo[1,5-c]pyrimidin-7-yl]pyrrolidine-2-carboxamide,
N-[2-methyl-5-(5-methylfuran-2-yl)-[1,2,4]triazolo[1,5-c]pyrimidin-7-yl]cyclobutanecarboxamide,
8-chloro-2-methyl-5-(5-methylfuran-2-yl)-[1,2,4]triazolo[1,5-c]pyrimidin-7-amine,
N-[5-(5-methylfuran-2-yl)-2-propan-2-yl-[1,2,4]triazolo[1,5-c]pyrimidin-7-yl]cyclopropanecarboxamide,
5-(5-methylfuran-2-yl)-2-propan-2-yl-[1,2,4]triazolo[1,5-c]pyrimidin-7-amine,
N-[2-methyl-5-(5-methylfuran-2-yl)-[1,2,4]triazolo[1,5-c]pyrimidin-7-yl]azetidine-3-carboxamide,
N-[8-chloro-2-methyl-5-(5-methylfuran-2-yl)-[1,2,4]triazolo[1,5-c]pyrimidin-7-yl]cyclopropanecarboxamide,
8-bromo-2-methyl-5-(5-methylfuran-2-yl)-[1,2,4]triazolo[1,5-c]pyrimidin-7-amine,
(2R)-N-[2-methyl-5-(5-methylfuran-2-yl)-[1,2,4]triazolo[1,5-c]pyrimidin-7-yl]pyrrolidine-2-carboxamide,
1-methyl-N-[2-methyl-5-(5-methylfuran-2-yl)-[1,2,4]triazolo[1,5-c]pyrimidin-7-yl]azetidine-3-carboxamide,
N-[2,8-dimethyl-5-(5-methylfuran-2-yl)-[1,2,4]triazolo[1,5-c]pyrimidin-7-yl]cyclopropanecarboxamide,
N-[5-(5-methylfuran-2-yl)-2-(trifluoromethyl)-[1,2,4]triazolo[1,5-c]pyrimidin-7-yl]cyclopropanecarboxamide,
5-(5-methylfuran-2-yl)-2-(trifluoromethyl)-[1,2,4]triazolo[1,5-c]pyrimidin-7-amine,
2,8-dimethyl-5-(5-methylfuran-2-yl)-[1,2,4]triazolo[1,5-c]pyrimidin-7-amine,
8-chloro-N,2-dimethyl-5-(5-methylfuran-2-yl)-[1,2,4]triazolo[1,5-c]pyrimidin-7-amine,
8-chloro-N,N,2-trimethyl-5-(5-methylfuran-2-yl)-[1,2,4]triazolo[1,5-c]pyrimidin-7-amine, N-[2-methyl-5-(5-methylfuran-2-yl)-[1,2,4]triazolo[1,5-c]pyrimidin-7-yl]acetamide,
7-amino-2-methyl-5-(5-methylfuran-2-yl)-[1,2,4]triazolo[1,5-c]pyrimidine-8-carbonitrile,
N-[5-(furan-2-yl)-2-methyl-[1,2,4]triazolo[1,5-c]pyrimidin-7-yl]cyclopropanecarboxamide,
8-fluoro-2-methyl-5-(5-methylfuran-2-yl)-[1,2,4]triazolo[1,5-c]pyrimidin-7-amine,
N-[8-bromo-5-(furan-2-yl)-2-methyl-[1,2,4]triazolo[1,5-c]pyrimidin-7-yl]cyclopropanecarboxamide,
7-amino-2-methyl-5-(5-methylfuran-2-yl)-[1,2,4]triazolo[1,5-c]pyrimidine-8-carboxamide,
8-chloro-2-methyl-5-phenyl-[1,2,4]triazolo[1,5-c]pyrimidin-7-amine,
N-[5-(5-methylfuran-2-yl)-2-propan-2-yl-[1,2,4]triazolo[1,5-c]pyrimidin-7-yl]acetamide,
N-[5-(furan-2-yl)-2-methyl-[1,2,4]triazolo[1,5-c]pyrimidin-7-yl]acetamide,
N-[5-(5-cyclopropylfuran-2-yl)-2-methyl-[1,2,4]triazolo[1,5-c]pyrimidin-7-yl]cyclopropanecarboxamide,
N-[8-fluoro-2-methyl-5-(5-methylfuran-2-yl)-[1,2,4]triazolo[1,5-c]pyrimidin-7-yl]cyclopropanecarboxamide,
8-chloro-2-methyl-5-(5-methylthiophen-2-yl)-[1,2,4]triazolo[1,5-c]pyrimidin-7-amine,
N-[5-(5-methylfuran-2-yl)-2-(trifluoromethyl)-[1,2,4]triazolo[1,5-c]pyrimidin-7-yl]acetamide,
8-chloro-5-(5-methylfuran-2-yl)-2-(trifluoromethyl)-[1,2,4]triazolo[1,5-c]pyrimidin-7-amine,
N-[5-(5-tert-butylfuran-2-yl)-2-methyl-[1,2,4]triazolo[1,5-c]pyrimidin-7-yl]cyclopropanecarboxamide,
N-[2-methyl-5-(2-methyl-1,3-oxazol-5-yl)-[1,2,4]triazolo[1,5-c]pyrimidin-7-yl]acetamide,
7-amino-5-(5-methylfuran-2-yl)-2-(trifluoromethyl)-[1,2,4]triazolo[1,5-c]pyrimidine-8-carbonitrile,
N-[5-(2-methyl-1,3-oxazol-5-yl)-2-propan-2-yl-[1,2,4]triazolo[1,5-c]pyrimidin-7-yl]acetamide,
N-[5-(furan-2-yl)-2-propan-2-yl-[1,2,4]triazolo[1,5-c]pyrimidin-7-yl]acetamide,
N-[5-(1,3-oxazol-5-yl)-2-propan-2-yl-[1,2,4]triazolo[1,5-c]pyrimidin-7-yl]acetamide,
N-[5-(5-methylfuran-2-yl)-2-(oxolan-3-yl)-[1,2,4]triazolo[1,5-c]pyrimidin-7-yl]cyclopropanecarboxamide,
N-[2-methyl-5-(1,3-oxazol-5-yl)-[1,2,4]triazolo[1,5-c]pyrimidin-7-yl]acetamide,
N-[5-(5-bromofuran-2-yl)-2-methyl-[1,2,4]triazolo[1,5-c]pyrimidin-7-yl]cyclopropanecarboxamide,
N-[5-(3-cyanophenyl)-2-methyl-[1,2,4]triazolo[1,5-c]pyrimidin-7-yl]cyclopropanecarboxamide,
N-[5-(5-methylfuran-2-yl)-2-(oxan-4-yl)-[1,2,4]triazolo[1,5-c]pyrimidin-7-yl]cyclopropanecarboxamide,
N-[2-methyl-5-(5-propan-2-ylfuran-2-yl)-[1,2,4]triazolo[1,5-c]pyrimidin-7-yl]cyclopropanecarboxamide,
N-[5-(4-cyanophenyl)-2-methyl-[1,2,4]triazolo[1,5-c]pyrimidin-7-yl]cyclopropanecarboxamide,
8-chloro-2-methyl-5-(5-methylpyridin-3-yl)-[1,2,4]triazolo[1,5-c]pyrimidin-7-amine,
N-[5-(furan-2-yl)-2-propan-2-yl-[1,2,4]triazolo[1,5-c]pyrimidin-7-yl]cyclopropanecarboxamide,
N-[5-(furan-2-yl)-2-(trifluoromethyl)-[1,2,4]triazolo[1,5-c]pyrimidin-7-yl]acetamide,
N-[2-methyl-5-(5-methylfuran-2-yl)-[1,2,4]triazolo[1,5-c]pyrimidin-7-yl]oxetane-3-carboxamide,
N-[2-cyclopropyl-5-(5-methylfuran-2-yl)-[1,2,4]triazolo[1,5-c]pyrimidin-7-yl]acetamide,
N-[2-cyclopropyl-5-(5-methylfuran-2-yl)-[1,2,4]triazolo[1,5-c]pyrimidin-7-yl]cyclopropanecarboxamide,
N-[2-cyclobutyl-5-(5-methylfuran-2-yl)-[1,2,4]triazolo[1,5-c]pyrimidin-7-yl]acetamide,
N-[2-cyclobutyl-5-(5-methylfuran-2-yl)-[1,2,4]triazolo[1,5-c]pyrimidin-7-yl]cyclopropanecarboxamide,
N-[2-cyclopentyl-5-(5-methylfuran-2-yl)-[1,2,4]triazolo[1,5-c]pyrimidin-7-yl]acetamide,
N-[2-cyclopentyl-5-(5-methylfuran-2-yl)-[1,2,4]triazolo[1,5-c]pyrimidin-7-yl]cyclopropanecarboxamide,
N-[2-(furan-2-yl)-5-(5-methylfuran-2-yl)-[1,2,4]triazolo[1,5-c]pyrimidin-7-yl]cyclopropanecarboxamide,
N-[5-(furan-2-yl)-2-(trifluoromethyl)-[1,2,4]triazolo[1,5-c]pyrimidin-7-yl]cyclopropanecarboxamide,
N-[2-methyl-5-[5-(trifluoromethyl)furan-2-yl]-[1,2,4]triazolo[1,5-c]pyrimidin-7-yl]cyclopropanecarboxamide,
N-[2-methyl-5-(1-methylpyrazol-4-yl)-[1,2,4]triazolo[1,5-c]pyrimidin-7-yl]cyclopropanecarboxamide,
N-[2-methyl-5-(1-methylpyrazol-4-yl)-[1,2,4]triazolo[1,5-c]pyrimidin-7-yl]acetamide,
N-[5-(furan-3-yl)-2-methyl-[1,2,4]triazolo[1,5-c]pyrimidin-7-yl]acetamide,
N-[5-(furan-3-yl)-2-methyl-[1,2,4]triazolo[1,5-c]pyrimidin-7-yl]cyclopropanecarboxamide,
8-chloro-2-methyl-5-pyridin-2-yl-[1,2,4]triazolo[1,5-c]pyrimidin-7-amine,
8-chloro-2-methyl-5-(6-methylpyridin-2-yl)-[1,2,4]triazolo[1,5-c]pyrimidin-7-amine,
8-chloro-5-(4-chlorophenyl)-2-methyl-[1,2,4]triazolo[1,5-c]pyrimidin-7-amine,
8-chloro-5-(3-chlorophenyl)-2-methyl-[1,2,4]triazolo[1,5-c]pyrimidin-7-amine,
8-chloro-2-methyl-5-pyridin-4-yl-[1,2,4]triazolo[1,5-c]pyrimidin-7-amine,
8-chloro-5-(4-fluorophenyl)-2-methyl-[1,2,4]triazolo[1,5-c]pyrimidin-7-amine,
8-bromo-5-(4-fluorophenyl)-2-methyl-[1,2,4]triazolo[1,5-c]pyrimidin-7-amine,
8-chloro-5-(2-chlorophenyl)-2-methyl-[1,2,4]triazolo[1,5-c]pyrimidin-7-amine,
N-[5-(5-fluorofuran-2-yl)-2-methyl-[1,2,4]triazolo[1,5-c]pyrimidin-7-yl]cyclopropanecarboxamide,
8-chloro-5-phenyl-2-propan-2-yl-[1,2,4]triazolo[1,5-c]pyrimidin-7-amine,
8-chloro-5-phenyl-2-(trifluoromethyl)-[1,2,4]triazolo[1,5-c]pyrimidin-7-amine,
8-bromo-2-methyl-5-phenyl-[1,2,4]triazolo[1,5-c]pyrimidin-7-amine,
N-[5-(5-bromofuran-2-yl)-2-methyl-[1,2,4]triazolo[1,5-c]pyrimidin-7-yl]acetamide,
N-[5-(furan-2-yl)-2-(oxetan-3-yl)-[1,2,4]triazolo[1,5-c]pyrimidin-7-yl]acetamide,
N-[5-(furan-2-yl)-2-(oxetan-3-yl)-[1,2,4]triazolo[1,5-c]pyrimidin-7-yl]cyclopropanecarboxamide,
N-[5-(3-acetylphenyl)-2-methyl-[1,2,4]triazolo[1,5-c]pyrimidin-7-yl]acetamide,
tert-butyl N-[5-(3-acetylphenyl)-2-methyl-[1,2,4]triazolo[1,5-c]pyrimidin-7-yl]carbamate,
1-[3-(7-amino-2-methyl-[1,2,4]triazolo[1,5-c]pyrimidin-5-yl)phenyl]ethanone,
N-[5-(3-acetylphenyl)-2-methyl-[1,2,4]triazolo[1,5-c]pyrimidin-7-yl]cyclopropanecarboxamide,
N-[2-methyl-5-(4-methylsulfonylphenyl)-[1,2,4]triazolo[1,5-c]pyrimidin-7-yl]cyclopropanecarboxamide,
tert-butyl N-[2-methyl-5-(4-methylsulfonylphenyl)-[1,2,4]triazolo[1,5-c]pyrimidin-7-yl]carbamate,
N-[2-methyl-5-(4-methylsulfonylphenyl)-[1,2,4]triazolo[1,5-c]pyrimidin-7-yl]acetamide, N-[5-(furan-2-yl)-2-methyl-[1,2,4]triazolo[1,5-c]pyrimidin-7-yl]pyrrolidine-1-carboxamide,
(3R)-N-[5-(furan-2-yl)-2-methyl-[1,2,4]triazolo[1,5-c]pyrimidin-7-yl]-3-hydroxypyrrolidine-1-carboxamide,
1-[3-(7-amino-8-chloro-2-methyl-[1,2,4]triazolo[1,5-c]pyrimidin-5-yl)phenyl]ethanone,
2-methyl-5-(4-methylsulfonylphenyl)-[1,2,4]triazolo[1,5-c]pyrimidin-7-amine,
(3S)-N-[5-(furan-2-yl)-2-methyl-[1,2,4]triazolo[1,5-c]pyrimidin-7-yl]-3-hydroxypyrrolidine-1-carboxamide,
1-[5-(furan-2-yl)-2-methyl-[1,2,4]triazolo[1,5-c]pyrimidin-7-yl]-3-methylurea,
N-[5-(5-methylfuran-2-yl)-2-(oxetan-3-yl)-[1,2,4]triazolo[1,5-c]pyrimidin-7-yl]acetamide,
N-[5-(5-methylfuran-2-yl)-2-(oxetan-3-yl)-[1,2,4]triazolo[1,5-c]pyrimidin-7-yl]cyclopropanecarboxamide,
N-[5-(4-methoxyphenyl)-2-methyl-[1,2,4]triazolo[1,5-c]pyrimidin-7-yl]cyclopropanecarboxamide,
tert-butyl N-[5-(4-methoxyphenyl)-2-methyl-[1,2,4]triazolo[1,5-c]pyrimidin-7-yl]carbamate,
N-[5-(4-methoxyphenyl)-2-methyl-[1,2,4]triazolo[1,5-c]pyrimidin-7-yl]acetamide,
N-[2-methyl-5-(4-sulfamoylphenyl)-[1,2,4]triazolo[1,5-c]pyrimidin-7-yl]cyclopropanecarboxamide,
5-(4-methoxyphenyl)-2-methyl-[1,2,4]triazolo[1,5-c]pyrimidin-7-amine,
N-[5-[4-(dimethylsulfamoyl)phenyl]-2-methyl-[1,2,4]triazolo[1,5-c]pyrimidin-7-yl]cyclopropanecarboxamide,
N-[5-[4-(dimethylsulfamoyl)phenyl]-2-methyl-[1,2,4]triazolo[1,5-c]pyrimidin-7-yl]acetamide,
tert-butyl N-[5-[4-(dimethylsulfamoyl)phenyl]-2-methyl-[1,2,4]triazolo[1,5-c]pyrimidin-7-yl]carbamate,
4-(7-amino-2-methyl-[1,2,4]triazolo[1,5-c]pyrimidin-5-yl)-N,N-dimethylbenzenesulfonamide,
N-[2-(azetidin-3-yl)-5-(furan-2-yl)-[1,2,4]triazolo[1,5-c]pyrimidin-7-yl]acetamide,
N-[2-(azetidin-3-yl)-5-(furan-2-yl)-[1,2,4]triazolo [1,5-c]pyrimidin-7-yl]cyclopropanecarboxamide,
4-[2-methyl-7-[(2-methylpropan-2-yl)oxycarbonylamino]-[1,2,4]triazolo[1,5-c]pyrimidin-5-yl]benzenesulfonic acid,
4-[7-(cyclopropanecarbonylamino)-2-methyl-[1,2,4]triazolo[1,5-c]pyrimidin-5-yl]benzenesulfonic acid,
N-[2-(difluoromethyl)-5-(5-methylfuran-2-yl)-[1,2,4]triazolo[1,5-c]pyrimidin-7-yl]acetamide,
N-[2-(fluoromethyl)-5-(5-methylfuran-2-yl)-[1,2,4]triazolo[1,5-c]pyrimidin-7-yl]acetamide,
N-[5-(3,4-difluorophenyl)-2-methyl-[1,2,4]triazolo[1,5-c]pyrimidin-7-yl]cyclopropanecarboxamide,
N-[5-(3,4-difluorophenyl)-2-methyl-[1,2,4]triazolo[1,5-c]pyrimidin-7-yl]acetamide,
5-(3,4-difluorophenyl)-2-methyl-[1,2,4]triazolo[1,5-c]pyrimidin-7-amine,
N-[5-(3-fluorophenyl)-2-methyl-[1,2,4]triazolo[1,5-c]pyrimidin-7-yl]cyclopropanecarboxamide,
N-[5-(3-fluorophenyl)-2-methyl-[1,2,4]triazolo[1,5-c]pyrimidin-7-yl]acetamide,
N-[2-(difluoromethyl)-5-(furan-2-yl)-[1,2,4]triazolo[1,5-c]pyrimidin-7-yl]acetamide,
N-[5-(furan-2-yl)-2-(1-methylazetidin-3-yl)-[1,2,4]triazolo[1,5-c]pyrimidin-7-yl]cyclopropanecarboxamide,
8-chloro-2-(fluoromethyl)-5-phenyl-[1,2,4]triazolo[1,5-c]pyrimidin-7-amine,
N-[2-(fluoromethyl)-5-(furan-2-yl)-[1,2,4]triazolo[1,5-c]pyrimidin-7-yl]acetamide,
1-[5-(3,4-difluorophenyl)-2-methyl-[1,2,4]triazolo[1,5-c]pyrimidin-7-yl]-3-methylurea,
8-chloro-5-(3,4-difluorophenyl)-2-methyl-[1,2,4]triazolo[1,5-c]pyrimidin-7-amine,
5-(3-fluorophenyl)-2-methyl-[1,2,4]triazolo[1,5-c]pyrimidin-7-amine,
2,2,2-trifluoro-N-[5-(furan-2-yl)-2-methyl-[1,2,4]triazolo[1,5-c]pyrimidin-7-yl]acetamide,
2,2-difluoro-N-[5-(furan-2-yl)-2-methyl-[1,2,4]triazolo[1,5-c]pyrimidin-7-yl]acetamide,
2-fluoro-N-[5-(furan-2-yl)-2-methyl-[1,2,4]triazolo[1,5-c]pyrimidin-7-yl]acetamide,
8-chloro-5-(3-fluorophenyl)-2-methyl-[1,2,4]triazolo[1,5-c]pyrimidin-7-amine,
N-[2-(difluoromethyl)-5-(furan-2-yl)-[1,2,4]triazolo[1,5-c]pyrimidin-7-yl]cyclopropanecarboxamide,
N-[2-(fluoromethyl)-5-(furan-2-yl)-[1,2,4]triazolo[1,5-c]pyrimidin-7-yl]cyclopropanecarboxamide,
N-[2-(azetidin-3-yl)-5-(5-methylfuran-2-yl)-[1,2,4]triazolo[1,5-c]pyrimidin-7-yl]acetamide,
N-[5-(furan-2-yl)-2-(1-methylazetidin-3-yl)-[1,2,4]triazolo[1,5-c]pyrimidin-7-yl]acetamide,
[5-(furan-2-yl)-2-methyl-[1,2,4]triazolo[1,5-c]pyrimidin-7-yl]urea,
1-[5-(furan-2-yl)-2-methyl-[1,2,4]triazolo[1,5-c]pyrimidin-7-yl]-3-propylurea,
1-ethyl-3-[5-(furan-2-yl)-2-methyl-[1,2,4]triazolo[1,5-c]pyrimidin-7-yl]urea,
1-[5-(furan-2-yl)-2-methyl-[1,2,4]triazolo[1,5-c]pyrimidin-7-yl]-3-(2-methylpropyl)urea,
1-[5-(furan-2-yl)-2-methyl-[1,2,4]triazolo[1,5-c]pyrimidin-7-yl]-3-(2-pyrrolidin-1-ylethyl)urea,
1-[5-(furan-2-yl)-2-methyl-[1,2,4]triazolo[1,5-c]pyrimidin-7-yl]-3-(2-piperidin-1-ylethyl)urea,
1-[5-(furan-2-yl)-2-methyl-[1,2,4]triazolo[1,5-c]pyrimidin-7-yl]-3-(2-morpholin-4-ylethyl)urea,
8-chloro-2-(difluoromethyl)-5-phenyl-[1,2,4]triazolo[1,5-c]pyrimidin-7-amine,
1-[5-(furan-2-yl)-2-methyl-[1,2,4]triazolo[1,5-c]pyrimidin-7-yl]-3-propan-2-ylurea,
N-[2-(azetidin-3-yl)-5-(5-methylfuran-2-yl)-[1,2,4]triazolo[1,5-c]pyrimidin-7-yl]cyclopropanecarboxamide,
8-(5-methylfuran-2-yl)-[1,2,4]triazolo[1,5-a]pyrazin-6-amine,
N-[8-(5-methylfuran-2-yl)-[1,2,4]triazolo[1,5-a]pyrazin-6-yl]cyclopropanecarboxamide,
2-methyl-8-(5-methylfuran-2-yl)-[1,2,4]triazolo[1,5-a]pyrazin-6-amine,
N-[2-methyl-8-(5-methylfuran-2-yl)-[1,2,4]triazolo [1,5-a]pyrazin-6-yl]cyclopropanecarboxamide,
5-chloro-8-(4-fluorophenyl)-2-methyl-[1,2,4]triazolo[1,5-a]pyrazin-6-amine,
5-bromo-8-(4-fluorophenyl)-2-methyl-[1,2,4]triazolo[1,5-a]pyrazin-6-amine,
5-bromo-2-methyl-8-phenyl-[1,2,4]triazolo[1,5-a]pyrazin-6-amine,
N-[8-(5-methylfuran-2-yl)-2-propan-2-yl-[1,2,4]triazolo[1,5-a]pyrazin-6-yl]cyclopropanecarboxamide,
N-[2-methyl-8-(5-methylfuran-2-yl)-[1,2,4]triazolo[1,5-a]pyrazin-6-yl]acetamide,
5-chloro-2-methyl-8-(5-methylfuran-2-yl)-[1,2,4]triazolo[1,5-a]pyrazin-6-amine,
5-chloro-2-methyl-8-phenyl-[1,2,4]triazolo[1,5-a]pyrazin-6-amine,
5-chloro-8-phenyl-2-propan-2-yl-[1,2,4]triazolo[1,5-a]pyrazin-6-amine,
5-chloro-8-phenyl-2-(trifluoromethyl)-[1,2,4]triazolo[1,5-a]pyrazin-6-amine, N-[8-(furan-2-yl)-2-methyl-[1,2,4]triazolo[1,5-a]pyrazin-6-yl]acetamide,
N-[8-(furan-2-yl)-2-methyl-[1,2,4]triazolo[1,5-a]pyrazin-6-yl]cyclopropanecarboxamide,
N-[8-(furan-2-yl)-2-propan-2-yl-[1,2,4]triazolo[1,5-a]pyrazin-6-yl]cyclopropanecarboxamide,
5-chloro-2-methyl-8-(2-methylphenyl)-[1,2,4]triazolo[1,5-a]pyrazin-6-amine,
5-chloro-2-methyl-8-(3-methylphenyl)-[1,2,4]triazolo[1,5-a]pyrazin-6-amine,
5-chloro-2-methyl-8-(4-methylphenyl)-[1,2,4]triazolo[1,5-a]pyrazin-6-amine,
N-[2-(difluoromethyl)-8-(5-methylfuran-2-yl)-[1,2,4]triazolo[1,5-a]pyrazin-6-yl]cyclopropanecarboxamide,
N-[2-amino-8-(furan-2-yl)-[1,2,4]triazolo[1,5-a]pyrazin-6-yl]cyclopropanecarboxamide,
N-[2-amino-8-(5-methylfuran-2-yl)-[1,2,4]triazolo[1,5-a]pyrazin-6-yl]cyclopropanecarboxamide,
N-[2-bromo-8-(5-methylfuran-2-yl)-[1,2,4]triazolo[1,5-a]pyrazin-6-yl]cyclopropanecarboxamide,
N-[8-(5-methylfuran-2-yl)-2-(trifluoromethyl)-[1,2,4]triazolo[1,5-a]pyrazin-6-yl]cyclopropanecarboxamide,
N-[2-(fluoromethyl)-8-(5-methylfuran-2-yl)-[1,2,4]triazolo[1,5-a]pyrazin-6-yl]cyclopropanecarboxamide,
8-(5-methylfuran-2-yl)imidazo[1,2-a]pyrazin-6-amine,
N-[8-(5-methylfuran-2-yl)imidazo[1,2-a]pyrazin-6-yl]cyclopropanecarboxamide,
ethyl 6-(cyclopropanecarbonylamino)-8-(5-methylfuran-2-yl)imidazo[1,2-a]pyrazine-2-carboxylate,
6-(cyclopropanecarbonylamino)-8-(5-methylfuran-2-yl)imidazo[1,2-a]pyrazine-2-carboxylic acid,
8-(5-methylfuran-2-yl)-2-(trifluoromethyl)imidazo[1,2-a]pyrazin-6-amine,
N-[3-methyl-8-(5-methylfuran-2-yl)imidazo[1,2-a]pyrazin-6-yl]cyclopropanecarboxamide,
N-[8-(5-methylfuran-2-yl)-2-(trifluoromethyl)imidazo[1,2-a]pyrazin-6-yl]cyclopropanecarboxamide,
3-methyl-8-(5-methylfuran-2-yl)imidazo[1,2-a]pyrazin-6-amine,
N-[2-methyl-8-(5-methylfuran-2-yl)imidazo[1,2-a]pyrazin-6-yl]cyclopropanecarboxamide,
2-methyl-8-(5-methylfuran-2-yl)imidazo[1,2-a]pyrazin-6-amine,
5-chloro-2-methyl-8-phenylimidazo[1,2-a]pyrazin-6-amine,
5-chloro-8-(4-fluorophenyl)-2-methylimidazo[1,2-a]pyrazin-6-amine,
5-bromo-2-methyl-8-phenylimidazo[1,2-a]pyrazin-6-amine,
5-chloro-8-phenyl-2-(trifluoromethyl)imidazo[1,2-a]pyrazin-6-amine,
N-[2-methyl-8-(5-methylfuran-2-yl)imidazo[1,2-a]pyrazin-6-yl]acetamide,
5-bromo-8-(4-fluorophenyl)-2-methylimidazo[1,2-a]pyrazin-6-amine,
5-chloro-2-methyl-8-(3-methylphenyl)imidazo[1,2-a]pyrazin-6-amine,
N-[8-(furan-2-yl)-2-methylimidazo[1,2-a]pyrazin-6-yl]cyclopropanecarboxamide,
N-[2-(hydroxymethyl)-8-(5-methylfuran-2-yl)imidazo[1,2-a]pyrazin-6-yl]cyclopropanecarboxamide,
N-[2-(fluoromethyl)-8-(5-methylfuran-2-yl)imidazo[1,2-a]pyrazin-6-yl]cyclopropanecarboxamide,
N-[8-(furan-2-yl)-2-methylimidazo[1,2-a]pyrazin-6-yl]acetamide,
N-[8-(furan-2-yl)-2-propan-2-ylimidazo[1,2-a]pyrazin-6-yl]cyclopropanecarboxamide,
5-chloro-8-phenyl-2-propan-2-ylimidazo[1,2-a]pyrazin-6-amine,
5-chloro-2-methyl-8-(4-methylphenyl)imidazo[1,2-a]pyrazin-6-amine,
N-[8-(5-methylfuran-2-yl)-2-propan-2-ylimidazo[1,2-a]pyrazin-6-yl]cyclopropanecarboxamide,
5-chloro-2-methyl-8-(2-methylphenyl)imidazo[1,2-a]pyrazin-6-amine,
1-[8-(furan-2-yl)-2-methylimidazo[1,2-a]pyrazin-6-yl]-3-methylurea,
methyl N-[8-(furan-2-yl)-2-methylimidazo[1,2-a]pyrazin-6-yl]carbamate,
ethyl N-[8-(furan-2-yl)-2-methylimidazo[1,2-a]pyrazin-6-yl]carbamate,
N-[8-(furan-2-yl)-2-methylimidazo[1,2-a]pyrazin-6-yl]propanamide,
2,2-difluoro-N-[8-(furan-2-yl)-2-methylimidazo[1,2-a]pyrazin-6-yl]acetamide,
N-[8-(furan-2-yl)-2-methylimidazo[1,2-a]pyrazin-6-yl]butanamide,
1-ethyl-3-[8-(furan-2-yl)-2-methylimidazo[1,2-a]pyrazin-6-yl]urea,
N-[8-(furan-2-yl)-2-methylimidazo[1,2-a]pyrazin-6-yl]methanesulfonamide, and
N-[8-(furan-2-yl)-2-methylimidazo[1,2-a]pyrazin-6-yl]ethanesulfonamide,
and pharmaceutically acceptable salts thereof.

16. The method of claim 1, wherein the disease or disorder is a cancer selected from the group consisting of lung cancer, non-small cell lung cancer, melanoma, malignant melanoma, renal cell cancer, triple negative breast cancer, colorectal cancer, bladder cancer, metastatic castration resistant prostate, cervical cancer, ovarian cancer, colorectal cancer, pancreatic cancer, esophageal cancer, prostate cancer, kidney cancer, skin cancer, thyroid cancer, liver cancer, and uterine cancer.

17. The method of claim 1, wherein the disease or disorder is an inflammatory disease selected from the group consisting of a respiratory disorder, sepsis, reperfusion injury, and thrombosis.

18. The method of claim 1, wherein the disease or disorder is a cardiovascular disease selected from the group consisting of coronary artery-disease, cerebrovascular disease, peripheral artery disease, aortic atherosclerosis, and aneurysm.

19. The method of claim 1, wherein the disease or disorder is Parkinson's disease.

20. A pharmaceutical composition comprising a compound of formula I:

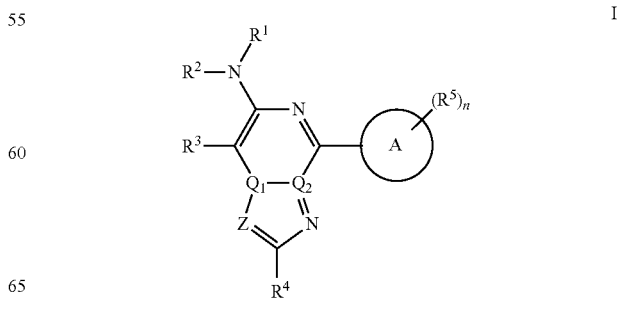

or a pharmaceutically acceptable salt thereof, and a pharmaceutically acceptable carrier or excipient, wherein:

Ring A is heteroaryl or aryl, provided that Ring A is furanyl when $R^4$ is H, aryl, or heteroaryl;

$R^1$ is H or alkyl optionally substituted with 1, 2, 3, or 4 independently selected $R^a$ substituents;

$R^2$ is H, alkyl, —COR''', —CONR'R", —COOR', —SO$_2$R', —SO$_2$NR'R", or —SO$_2$OR', wherein the alkyl of $R^2$ is optionally substituted with 1, 2, 3, or 4 independently selected $R^a$ substituents;

$R^3$ is H, alkyl, halo, —CN, or —CONR'R", wherein the alkyl of $R^3$ is optionally substituted with 1, 2, 3, or 4 independently selected $R^a$ substituents;

$R^4$ is H, alkyl, halo, haloalkyl, —NR'R", —COR', —CONR'R", —COOR', SO$_2$R', —SO$_2$NR'R", —SO$_2$OR', cycloalkyl, heterocycloalkyl, aryl, heteroaryl, or —C$_{1-4}$ alkylene-R$^b$, wherein R$^b$ is cycloalkyl, heterocycloalkyl, aryl or heteroaryl, and wherein the alkyl, cycloalkyl, heterocycloalkyl, aryl, heteroaryl, or —C$_{1-4}$ alkylene-R$^b$ of $R^4$ is optionally substituted with 1, 2, 3, or 4 independently selected $R^a$ substituents;

each $R^5$ is independently H, alkyl, halo, haloalkyl, alkoxy, —CN, —COR', —CONR'R", —COOR', —SO$_2$R', —SO$_2$NR'R", —SO$_2$OR', cycloalkyl, heterocycloalkyl, aryl, or heteroaryl wherein the alkyl, alkoxy, cycloalkyl, heterocycloalkyl, aryl, or heteroaryl of $R^5$ is optionally substituted with 1, 2, 3, or 4 independently selected $R^a$ substituents;

n is 0, 1, 2, 3, 4, or 5;

one of $Q_1$ and $Q_2$ is N and the other is C;

Z is N or CR$^6$;

$R^6$ is H or alkyl, wherein the alkyl of $R^6$ is optionally substituted with 1, 2, 3, or 4 independently selected $R^a$ substituents;

R' and R" are each independently H or alkyl, wherein each alkyl of R' and R" is optionally substituted with 1, 2, 3, or 4 independently selected $R^a$ substituents;

R''' is alkyl, haloalkyl, cycloalkyl, or heterocycloalkyl, wherein the alkyl, cycloalkyl or heterocycloalkyl of R''' is optionally substituted with 1, 2, 3, or 4 independently selected $R^a$ substituents; and each $R^a$ is independently alkyl, halo, haloalkyl, hydroxy, alkoxy, hydroxyalkyl, cycloalkyl, or heterocycloalkyl, wherein each cycloalkyl and heterocycloalkyl of $R^a$ is optionally and independently further substituted with 1, 2, or 3 of C$_{1-4}$ alkyl, halo, C$_{1-4}$ haloalkyl, hydroxy, or C$_{1-4}$ alkoxy.

* * * * *